United States Patent [19]

Sasaki et al.

[11] Patent Number: 5,494,790
[45] Date of Patent: Feb. 27, 1996

[54] α-3 SIALYLTRANSFERASE

[75] Inventors: Katsutoshi Sasaki, Machida; Etsuyo Watanabe, Kawasaki; Tatsunari Nishi, Machide; Susumu Sekine; Nobuo Hanai, both of Sagimihara; Mamoru Hasegawa, Kawasaki, all of Japan

[73] Assignee: Kyowa Hakko Kogyo Co., Ltd., Tokyo, Japan

[21] Appl. No.: 309,985

[22] Filed: Sep. 20, 1994

Related U.S. Application Data

[62] Division of Ser. No. 991,587, Dec. 16, 1992, Pat. No. 5,384,249.

[30] Foreign Application Priority Data

Dec. 17, 1991 [JP] Japan ..................... 3-333661
Apr. 10, 1992 [JP] Japan ..................... 4-091044

[51] Int. Cl.$^6$ .............. C12Q 1/68; C12N 9/10; C12N 15/54
[52] U.S. Cl. .............. 435/6; 435/85; 435/193; 435/252.33; 435/320.1; 536/23.2
[58] Field of Search ............. 536/23.2; 435/320.1, 435/193, 252.33, 85, 6

[56] References Cited

U.S. PATENT DOCUMENTS 5,047,335 9/1991 Paulson et al. ................. 435/69.1

FOREIGN PATENT DOCUMENTS

| 475354 | 3/1992 | European Pat. Off. . |
| WO91-12340 | 2/1991 | WIPO . |
| WO91-06635 | 8/1991 | WIPO . |
| 12340 | 8/1991 | WIPO . |

OTHER PUBLICATIONS

Ripka, et al, Biochem. Biophys. Acfa., vol. 159, No. 2 (1989) 554–60.
Paulson, et al., FASEB J., vol. 4, No. 7 (1990) A1862.
Gillespie, et al., FASEB J., vol. 4, No. 7 (1990) A2068.
Joziasse, et al., J. Biol. Chem., vol. 260, No. 8 (1985) 4941–51.
Weinstein et al., J. Biol. Chem. vol. 262, No. 36 pp. 17735–17743 (1987).
Weinstein et al., J. Biol. Chem. vol. 257, No. 22 pp. 13835–13844 (1982).
Wen et al., J. Biol. Chem., vol. 267 (Oct. 1992) pp. 21011–21019.
Kanani et al., Cancer Research, vol. 50 (Aug. 1990) pp. 5003–5007.
Sadler et al., J. Biol. Chem., vol. 254, No. 11 (Jun. 1979) pp. 4434–4443.
Saitoh et al., Cancer Research, vol. 51 (Jun. 1991) 2854–2862.
Phillips et al., Science, vol. 250 (Nov. 1990) pp. 1130–1132.
Sabesan et al. J. Am. Chem. Soc., vol. 108, No. 8 (1986) pp. 2068–2080.

*Primary Examiner*—Charles L. Patterson, Jr.
*Attorney, Agent, or Firm*—Fitzpatrick, Cella, Harper & Scinto

[57] ABSTRACT

There are provided a novel α2→3 sialyltransferase expressed by a cloned gene from animal cells, a cDNA encoding the α2→3 sialyltransferase, a method for detecting or suppressing the expression of an α2→3 sialyltransferase by use of said cDNA, a recombinant vector containing said cDNA, a cell containing said vector, and their production processes.

22 Claims, 29 Drawing Sheets

StuI Parial Digestion

BamHI Linker
(5' pCCGGATCCGG 3')

BamHI

T4-DNA Ligase

Ball

ScaI Linker
(5' pAAGTACTT 3')

T4-DNA Ligase

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 1919
        ( B ) TYPE: nucleic acid
        ( C ) STRANDEDNESS: double
        ( D ) TOPOLOGY: linear ( i i ) MOLECULE TYPE: cDNA to mRNA ( i i i ) ORIGINAL SOURCE:
        ( A ) ORGANISM: human
        ( B ) CELL LINE: TYH cell
        ( C ) CELL TYPE: histiocytoma cell ( i v ) SEQUENCE DESCRIPTION: SEQ ID NO: 1:

```
GTCGGGGCGC CTAACGGATC GGAGCTGCGC GCGGATTTAC CTCGCCCCGC CCCGCTCCAC        60

CCGCGAGGGT GGCCCGAGGC AGCCGGGATG ACACTTCTCC CCAGGAACCC TGCTATCTGC       120

TGAGAAAC ATG ACC AGC AAA TCT CAC TGG AAG CTC CTG GCC CTG GCT CTG        170
         Met Thr Ser Lys Ser His Trp Lys Leu Leu Ala Leu Ala Leu
          1               5                      10

GTC CTT GTT GTT GTC ATG GTG TGG TAT TCC ATC TCC CGA GAA GAT AGG         218
Val Leu Val Val Val Met Val Trp Tyr Ser Ile Ser Arg Glu Asp Arg
 15              20                  25                      30

TAC ATT GAG TTC TTT TAT TTT CCC ATC TCA GAG AAG AAA GAG CCA TGC         266
Tyr Ile Glu Phe Phe Tyr Phe Pro Ile Ser Glu Lys Lys Glu Pro Cys
                 35                  40                  45

TTC CAG GGT GAG GCA GAG AGA CAG GCC TCT AAG ATT TTT GGC AAC CGT         314
Phe Gln Gly Glu Ala Glu Arg Gln Ala Ser Lys Ile Phe Gly Asn Arg
             50                  55                  60

TCT AGG GAC CAG CCC ATC TTT CTG CAG CTT AAG GAT TAT TTC TGG GTA         362
Ser Arg Asp Gln Pro Ile Phe Leu Gln Leu Lys Asp Tyr Phe Trp Val
             65                  70                  75

AAG ACG CCA TCC ACC TAT GAG CTG CCC TTT GGG ACT AAA GGA AGT GAA         410
Lys Thr Pro Ser Thr Tyr Glu Leu Pro Phe Gly Thr Lys Gly Ser Glu
         80                  85                  90

GAC CTT CTT CTC CGG GTG CTG GCC ATC ACT AGC TAT TCT ATA CCT GAG         458
Asp Leu Leu Leu Arg Val Leu Ala Ile Thr Ser Tyr Ser Ile Pro Glu
 95             100                 105                     110

AGC ATA AAG AGC CTG GAG TGT CGT CGC TGT GTT GTG GTG GGA AAT GGG         506
Ser Ile Lys Ser Leu Glu Cys Arg Arg Cys Val Val Val Gly Asn Gly
                115                 120                 125

CAC CGG TTG CGG AAC AGC TCG CTG GGC GGT GTC ATC AAC AAG TAC GAC         554
His Arg Leu Arg Asn Ser Ser Leu Gly Gly Val Ile Asn Lys Tyr Asp
            130                 135                 140

GTG GTC ATC AGA TTG AAC AAT GCT CCT GTG GCT GGC TAC GAG GGA GAT         602
Val Val Ile Arg Leu Asn Asn Ala Pro Val Ala Gly Tyr Glu Gly Asp
            145                 150                 155

GTG GGC TCC AAG ACC ACC ATA CGT CTC TTC TAT CCT GAG TCG GCC CAC         650
Val Gly Ser Lys Thr Thr Ile Arg Leu Phe Tyr Pro Glu Ser Ala His
    160                 165                 170

TTT GAC CCT AAA ATA GAA AAC AAC CCA GAC ACG CTC TTG GTC CTG GTA         698
Phe Asp Pro Lys Ile Glu Asn Asn Pro Asp Thr Leu Leu Val Leu Val
175                 180                 185                 190

GCT TTC AAG GCG ATG GAC TTC CAC TGG ATT GAG ACC ATC TTG AGT GAT         746
Ala Phe Lys Ala Met Asp Phe His Trp Ile Glu Thr Ile Leu Ser Asp
                195                 200                 205
```

| | | | | | | | | | | | | | | | | |
|---|---|---|---|---|---|---|---|---|---|---|---|---|---|---|---|---|
| AAG | AAG | CGG | GTG | CGA | AAA | GGC | TTC | TGG | AAA | CAG | CCT | CCC | CTC | ATC | TGG | 794 |
| Lys | Lys | Arg | Val 210 | Arg | Lys | Gly | Phe | Trp 215 | Lys | Gln | Pro | Pro | Leu 220 | Ile | Trp | |
| GAT | GTC | AAC | CCC | AAA | CAG | GTC | CGG | ATT | CTA | AAC | CCC | TTC | TTT | ATG | GAG | 842 |
| Asp | Val | Asn 225 | Pro | Lys | Gln | Val | Arg 230 | Ile | Leu | Asn | Pro | Phe 235 | Phe | Met | Glu | |
| ATT | GCA | GCA | GAC | AAG | CTC | CTG | AGC | CTG | CCC | ATA | CAA | CAG | CCT | CGA | AAG | 890 |
| Ile | Ala 240 | Ala | Asp | Lys | Leu | Leu 245 | Ser | Leu | Pro | Ile | Gln 250 | Gln | Pro | Arg | Lys | |
| ATC | AAG | CAG | AAG | CCA | ACC | ACG | GGT | CTG | CTA | GCC | ATC | ACC | TTG | GCT | CTA | 938 |
| Ile 255 | Lys | Gln | Lys | Pro | Thr 260 | Thr | Gly | Leu | Leu | Ala 265 | Ile | Thr | Leu | Ala | Leu 270 | |
| CAC | CTC | TGC | GAC | TTA | GTG | CAC | ATT | GCT | GGC | TTT | GGC | TAT | CCA | GAT | GCC | 986 |
| His | Leu | Cys | Asp | Leu 275 | Val | His | Ile | Ala | Gly 280 | Phe | Gly | Tyr | Pro | Asp 285 | Ala | |
| TCC | AAC | AAG | AAG | CAG | ACC | ATC | CAC | TAC | TAT | GAA | CAG | ATC | ACA | CTT | AAG | 1034 |
| Ser | Asn | Lys | Lys 290 | Gln | Thr | Ile | His | Tyr 295 | Tyr | Glu | Gln | Ile | Thr 300 | Leu | Lys | |
| TCT | ATG | GCG | GGA | TCA | GGC | CAT | AAT | GTC | TCC | CAA | GAG | GCT | ATC | GCC | ATC | 1082 |
| Ser | Met | Ala 305 | Gly | Ser | Gly | His | Asn 310 | Val | Ser | Gln | Glu | Ala 315 | Ile | Ala | Ile | |
| AAG | CGG | ATG | CTA | GAG | ATG | GGA | GCT | GTC | AAG | AAC | CTC | ACA | TAC | TTC | TGA | 1130 |
| Lys | Arg 320 | Met | Leu | Glu | Met | Gly 325 | Ala | Val | Lys | Asn | Leu 330 | Thr | Tyr | Phe | TER | |
| CTTGGATGGG | AGCTGTAACA | CCTTGGTTCC | CTACTTTGCC | ATCTGAGTAG | GCCCTGTCTA | | | | | | | | | | | 1190 |
| CAGCTTAGGG | GTTCCTGGTG | CCAGTACAAT | CCAATTGAAC | TCACCCTCAA | TGGAGAGGGT | | | | | | | | | | | 1250 |
| GTTCTGGGGC | TGTCCAGGTC | TCCAGAGAGG | CTATGTCCCT | GCCTACTTTG | GTGGATTTCA | | | | | | | | | | | 1310 |
| AATCCAGACA | GGGTAGTCAC | ACCAGGCTAC | AGGAGCCTGG | CTAAAGGGG | GGGGGGGGCT | | | | | | | | | | | 1370 |
| GTTACTGTGG | CATCCCCTCT | CTCAGCCAGC | ACAAGAGCT | GTTTTGTTTT | GTTTGTTTT | | | | | | | | | | | 1430 |
| GTTTTGTTTT | GTTTCGTTTT | GTTTCGTTTT | GTTTTGTCTT | GTATTGTTGG | TGGTGGTTGG | | | | | | | | | | | 1490 |
| TTGGGTTTTG | TTTGTTTGTT | TTTGTTTGCT | TTGTTTTGTT | CTTGAGACAG | GGTCTGACTG | | | | | | | | | | | 1550 |
| TGAAACCCTG | GCTAATCTGG | AACTCACTAT | GTAGACCAGA | CTGGTCTTGA | ACTCACAGAG | | | | | | | | | | | 1610 |
| ATCCAACTGC | CTTTGCCTCC | CAAGTGTTGG | GATGAAAGGC | ATGTACTACG | CCTGGCCCCA | | | | | | | | | | | 1670 |
| ACACCAAGAG | ATTATTTAAC | ATTCTATTTA | ATTAAGGGGT | AGGAAAATGA | ATGGGCTGGT | | | | | | | | | | | 1730 |
| CCCAGGATGT | TCATGAAAGG | GACACAATAC | AGTGTTCTGC | CCACTTTTTA | ATAAAATTTA | | | | | | | | | | | 1790 |
| CATGTGATTG | GCCTGTTAAG | GCCCAATTCT | AGAGCTGGCC | TCCCAGAAAG | ATGGAGGCAT | | | | | | | | | | | 1850 |
| CAAGAGTGGG | AGGGTGTCCT | CCAGAGAGGG | GTTGCTACTT | CCCAGCAGGC | ATGGGGGGAG | | | | | | | | | | | 1910 |
| CATTGACAA | | | | | | | | | | | | | | | | 1919 |

( 2 ) INFORMATION FOR SEQ ID NO: 2:

( i ) SEQUENCE CHARACTERISTICS:
        ( A ) LENGTH: 333
        ( B ) TYPE: amino acid
        ( C ) TOPOLOGY: linear ( i i ) MOLECULE TYPE: protein ( i i i ) ORIGINAL SOURCE:
        ( A ) ORGANISM: human
        ( B ) CELL LINE: TYH cell
        ( C ) CELL TYPE: histiocytoma cell ( i v ) SEQUENCE DESCRIPTION: SEQ ID NO: 2:

| | | | | | | | | | | | | | | |
|---|---|---|---|---|---|---|---|---|---|---|---|---|---|---|
| Met | Thr | Ser | Lys | Ser | His | Trp | Lys | Leu | Leu | Ala | Leu | Ala | Leu | Val | Leu |
| 1 | | | | 5 | | | | | 10 | | | | | 15 | |

```
Val  Val  Val  Met  Val  Trp  Tyr  Ser  Ile  Ser  Arg  Glu  Asp  Arg  Tyr  Ile
               20                       25                  30

Glu  Phe  Phe  Tyr  Phe  Pro  Ile  Ser  Glu  Lys  Lys  Glu  Pro  Cys  Phe  Gln
          35                       40                       45

Gly  Glu  Ala  Glu  Arg  Gln  Ala  Ser  Lys  Ile  Phe  Gly  Asn  Arg  Ser  Arg
     50                       55                  60

Asp  Gln  Pro  Ile  Phe  Leu  Gln  Leu  Lys  Asp  Tyr  Phe  Trp  Val  Lys  Thr
65                            70                  75                       80

Pro  Ser  Thr  Tyr  Glu  Leu  Pro  Phe  Gly  Thr  Lys  Gly  Ser  Glu  Asp  Leu
               85                       90                       95

Leu  Leu  Arg  Val  Leu  Ala  Ile  Thr  Ser  Tyr  Ser  Ile  Pro  Glu  Ser  Ile
               100                      105                      110

Lys  Ser  Leu  Glu  Cys  Arg  Arg  Cys  Val  Val  Val  Gly  Asn  Gly  His  Arg
          115                      120                      125

Leu  Arg  Asn  Ser  Ser  Leu  Gly  Gly  Val  Ile  Asn  Lys  Tyr  Asp  Val  Val
     130                      135                 140

Ile  Arg  Leu  Asn  Asn  Ala  Pro  Val  Ala  Gly  Tyr  Glu  Gly  Asp  Val  Gly
145                      150                      155                      160

Ser  Lys  Thr  Thr  Ile  Arg  Leu  Phe  Tyr  Pro  Glu  Ser  Ala  His  Phe  Asp
               165                      170                      175

Pro  Lys  Ile  Glu  Asn  Asn  Pro  Asp  Thr  Leu  Leu  Val  Leu  Val  Ala  Phe
               180                      185                      190

Lys  Ala  Met  Asp  Phe  His  Trp  Ile  Glu  Thr  Ile  Leu  Ser  Asp  Lys  Lys
          195                      200                      205

Arg  Val  Arg  Lys  Gly  Phe  Trp  Lys  Gln  Pro  Pro  Leu  Ile  Trp  Asp  Val
     210                      215                      220

Asn  Pro  Lys  Gln  Val  Arg  Ile  Leu  Asn  Pro  Phe  Phe  Met  Glu  Ile  Ala
225                      230                      235                      240

Ala  Asp  Lys  Leu  Leu  Ser  Leu  Pro  Ile  Gln  Gln  Pro  Arg  Lys  Ile  Lys
               245                      250                      255

Gln  Lys  Pro  Thr  Thr  Gly  Leu  Leu  Ala  Ile  Thr  Leu  Ala  Leu  His  Leu
               260                      265                      270

Cys  Asp  Leu  Val  His  Ile  Ala  Gly  Phe  Gly  Tyr  Pro  Asp  Ala  Ser  Asn
          275                      280                      285

Lys  Lys  Gln  Thr  Ile  His  Tyr  Tyr  Glu  Gln  Ile  Thr  Leu  Lys  Ser  Met
     290                      295                      300

Ala  Gly  Ser  Gly  His  Asn  Val  Ser  Gln  Glu  Ala  Ile  Ala  Ile  Lys  Arg
305                      310                      315                      320

Met  Leu  Glu  Met  Gly  Ala  Val  Lys  Asn  Leu  Thr  Tyr  Phe
                    325                      330
```

( 2 ) INFORMATION FOR SEQ ID NO: 3:

( i ) SEQUENCE CHARACTERISTICS:
        ( A ) LENGTH: 52
        ( B ) TYPE: nucleic acid
        ( C ) STRANDEDNESS: double
        ( D ) TOPOLOGY: linear ( i i ) MOLECULE TYPE: Other nucleic acid synthetic DNA ( i i i ) SEQUENCE DESCRIPTION: SEQ ID NO: 3:

```
TCGACAAGCT TGATATCGGC CTGTGAGGCC TCACTGGCCG CGGCCGCGGT AC          52
```

( 2 ) INFORMATION FOR SEQ ID NO: 4:

( i ) SEQUENCE CHARACTERISTICS:

(A) LENGTH: 44
(B) TYPE: nucleic acid
(C) STRANDEDNESS: double
(D) TOPOLOGY: linear (ii) MOLECULE TYPE: Other nucleic acid synthetic DNA (iii) SEQUENCE DESCRIPTION: SEQ ID NO: 4:

CGCG GCCGCGGCCA GTGAGGCCTC ACAGGCCGAT ATCAAGCTTG    44

(2) INFORMATION FOR SEQ ID NO: 5:

(i) SEQUENCE CHARACTERISTICS:
(A) LENGTH: 11
(B) TYPE: nucleic acid
(C) STRANDEDNESS: double
(D) TOPOLOGY: linear (ii) MOLECULE TYPE: Other nucleic acid synthetic DNA (iii) SEQUENCE DESCRIPTION: SEQ ID NO:5:

CTTTAGAGCA C    11

(2) INFORMATION FOR SEQ ID NO: 6:

(i) SEQUENCE CHARACTERISTICS:
(A) LENGTH: 1766
(B) TYPE: nucleic acid
(C) STRANDEDNESS: double
(D) TOPOLOGY: linear (ii) MOLECULE TYPE: cDNA to mRNA (iii) ORIGINAL SOURCE:
(A) ORGANISM: human
(B) CELL LINE: WM266-4 cell
(C) CELL TYPE: melanoma (iv) SEQUENCE DESCRIPTION:SEQ ID NO:6:

```
CGGTCAGGTC CAGCACTTGG GAGCTGACTG TGCTGGAGGT GACAGGCTTT GCGGGGTCCG        60

CCTGTGTGCA GGAGTCGCAA GGTCGCTGAG CAGGACCCAA AGGTGGCCCG AGGCAGCCGG       120

GATGACAGCT CTCCCCAGGA ATCCTGCTGC CTGCTGAGAA AC ATG GTC AGC AAG          174
                                                Met Val Ser Lys
                                                  1

TCC CGC TGG AAG CTC CTG GCC ATG TTG GCT CTG GTC CTG GTC GTC ATG         222
Ser Arg Trp Lys Leu Leu Ala Met Leu Ala Leu Val Leu Val Val Met
  5              10              15              20

GTG TGG TAT TCC ATC TCC CGG GAA GAC AGT TTT TAT TTT CCC ATC CCA         270
Val Trp Tyr Ser Ile Ser Arg Glu Asp Ser Phe Tyr Phe Pro Ile Pro
                  25              30              35

GAG AAG AAG GAG CCG TGC CTC CAG GGT GAG GCA GAG AGC AAG GCC TCT         318
Glu Lys Lys Glu Pro Cys Leu Gln Gly Glu Ala Glu Ser Lys Ala Ser
              40              45              50

AAG CTC TTT GGC AAC TAC TCC CGG GAT CAG CCC ATC TTC CTG CGG CTT         366
Lys Leu Phe Gly Asn Tyr Ser Arg Asp Gln Pro Ile Phe Leu Arg Leu
          55              60              65

GAG GAT TAT TTC TGG GTC AAG ACG CCA TCT GCT TAC GAG CTG CCC TAT         414
Glu Asp Tyr Phe Trp Val Lys Thr Pro Ser Ala Tyr Glu Leu Pro Tyr
      70              75              80

GGG ACC AAG GGG AGT GAG GAT CTG CTC CTC CGG GTG CTA GCC ATC ACC         462
Gly Thr Lys Gly Ser Glu Asp Leu Leu Leu Arg Val Leu Ala Ile Thr
 85              90              95             100

AGC TCC TCC ATC CCC AAG AAC ATC CAG AGC CTC AGG TGC CGC CGC TGT         510
Ser Ser Ser Ile Pro Lys Asn Ile Gln Ser Leu Arg Cys Arg Arg Cys
             105             110             115
```

```
GTG GTC GTG GGG AAC GGG CAC CGG CTG CGG AAC AGC TCA CTG GGA GAT          558
Val Val Val Gly Asn Gly His Arg Leu Arg Asn Ser Ser Leu Gly Asp
            120                 125                 130

GCC ATC AAC AAG TAC GAT GTG GTC ATC AGA TTG AAC AAT GCC CCA GTG          606
Ala Ile Asn Lys Tyr Asp Val Val Ile Arg Leu Asn Asn Ala Pro Val
        135                 140                 145

GCT GGC TAT GAG GGT GAC GTG GGC TCC AAG ACC ACC ATG CGT CTC TTC          654
Ala Gly Tyr Glu Gly Asp Val Gly Ser Lys Thr Thr Met Arg Leu Phe
150                 155                 160

TAC CCT GAA TCT GCC CAC TTC GAC CCC AAA GTA GAA AAC AAC CCA GAC          702
Tyr Pro Glu Ser Ala His Phe Asp Pro Lys Val Glu Asn Asn Pro Asp
165                 170                 175                 180

ACA CTC CTC GTC CTG GTA GCT TTC AAG GCA ATG GAC TTC CAC TGG ATT          750
Thr Leu Leu Val Leu Val Ala Phe Lys Ala Met Asp Phe His Trp Ile
                185                 190                 195

GAG ACC ATC CTG AGT GAT AAG AAG CGG GTG CGA AAG GGT TTC TGG AAA          798
Glu Thr Ile Leu Ser Asp Lys Lys Arg Val Arg Lys Gly Phe Trp Lys
            200                 205                 210

CAG CCT CCC CTC ATC TGG GAT GTC AAT CCT AAA CAG ATT CGG ATT CTC          846
Gln Pro Pro Leu Ile Trp Asp Val Asn Pro Lys Gln Ile Arg Ile Leu
        215                 220                 225

AAC CCC TTC TTC ATG GAG ATT GCA GCT GAC AAA CTG CTG AGC CTG CCA          894
Asn Pro Phe Phe Met Glu Ile Ala Ala Asp Lys Leu Leu Ser Leu Pro
    230                 235                 240

ATG CAA CAG CCA CGG AAG ATT AAG CAG AAG CCC ACC ACG GGC CTG TTG          942
Met Gln Gln Pro Arg Lys Ile Lys Gln Lys Pro Thr Thr Gly Leu Leu
245                 250                 250                 260

GCC ATC ACG CTG GCC CTC CAC CTC TGT GAC TTG GTG CAC ATT GCC GGC          990
Ala Ile Thr Leu Ala Leu His Leu Cys Asp Leu Val His Ile Ala Gly
                265                 270                 275

TTT GGC TAC CCA GAC GCC TAC AAC AAG AAG CAG ACC ATT CAC TAC TAT         1038
Phe Gly Tyr Pro Asp Ala Tyr Asn Lys Lys Gln Thr Ile His Tyr Tyr
            280                 285                 290

GAG CAG ATC ACG CTC AAG TCC ATG GCG GGG TCA GGC CAT AAT GTC TCC         1086
Glu Gln Ile Thr Leu Lys Ser Met Ala Gly Ser Gly His Asn Val Ser
        295                 300                 305

CAA GAG GCC CTG GCC ATT AAG CGG ATG CTG GAG ATG GGA GCT ATC AAG         1134
Gln Glu Ala Leu Ala Ile Lys Arg Met Leu Glu Met Gly Ala Ile Lys
    310                 315                 320

AAC CTC ACG TCC TGC TGA CCTGGGCAAG AGCTGTAGCC TGTCGGTTGC                 1182
Asn Leu Thr Ser Phe TER
325             329

CTACTCTGCT GTCTGGGTGA CCCCCATGCG TGGCTGTGGG GGTGGCTGGT GCCAGTATGA       1242

CCCACTTGGA CTCACCCCCT CTTGGGGAGG GAGTTCTGGG CCTGGCCAGG TCTGAGATGA       1302

GGCCATGCCC CTGGCTGCTC TTATGGAGCC GAGATCCAGT CAGGGTGGGG GCGCTGGAGC       1362

AAGAGATTAT TTAATGGGCT ATTTAATTAA GGGGTAGGAA GGTGCTGTGG GCTGGTCCCA       1482

CACATCCAGG AAAGAGGCCA GTAGAGAATT CTGCCCACTT TTTATAAAAA CTTACAGCGA       1542

TGGCCCCACC AAGGCCTAGA CACGGCACTG GCCTCCCAGG AGGGCAGGGG CATTGGGAAT       1602

GGGTGGGTGC CCTCCAGAGA GGGGCTGCTA CCTCCCAGCA GGCATGGGAA GAGCACTGGT       1662

ACTATTTTTC CTAAAACGGA AAAAAAAAA AAAAAAAAA AAAA                          1766
```

( 2 ) INFORMATION FOR SEQ ID NO: 7:

( A ) LENGTH: 329
    ( B ) TYPE: amino acid
    ( C ) TOPOLOGY: linear ( i i ) MOLECULE TYPE: protein (iii) ORIGINAL SOURCE:
    (A) ORGANISM: human
    (B) CELL LINE: WM266-4 cell
    (C) CELL TYPE: melanoma (iv) SEQUENCE DESCRIPTION: SEQ ID NO: 7:

| Met 1 | Val | Ser | Lys | Ser 5 | Arg | Trp | Lys | Leu | Leu 10 | Ala | Met | Leu | Ala | Val 15 |
|---|---|---|---|---|---|---|---|---|---|---|---|---|---|---|
| Leu | Val | Val | Met 20 | Val | Trp | Tyr | Ser | Ile 25 | Ser | Arg | Glu | Asp | Ser 30 | Phe | Tyr |
| Phe | Pro | Ile 35 | Pro | Glu | Lys | Lys | Glu 40 | Pro | Cys | Leu | Gln | Gly 45 | Glu | Ala | Glu |
| Ser | Lys 50 | Ala | Ser | Lys | Leu | Phe 55 | Gly | Asn | Tyr | Ser | Arg 60 | Asp | Gln | Pro | Ile |
| Phe 65 | Leu | Arg | Leu | Glu | Asp 70 | Tyr | Phe | Trp | Val | Lys 75 | Thr | Pro | Ser | Ala | Tyr 80 |
| Glu | Leu | Pro | Tyr | Gly 85 | Thr | Lys | Gly | Ser | Glu 90 | Asp | Leu | Leu | Leu | Arg 95 | Val |
| Leu | Ala | Ile | Thr 100 | Ser | Ser | Ser | Ile | Pro 105 | Lys | Asn | Ile | Gln | Ser 110 | Leu | Arg |
| Cys | Arg | Arg 115 | Cys | Val | Val | Val | Gly 120 | Asn | Gly | His | Arg | Leu 125 | Arg | Asn | Ser |
| Ser | Leu 130 | Gly | Asp | Ala | Ile | Asn 135 | Lys | Tyr | Asp | Val | Val 140 | Ile | Arg | Leu | Asn |
| Asn 145 | Ala | Pro | Val | Ala | Gly 150 | Tyr | Glu | Gly | Asp | Val 155 | Gly | Ser | Lys | Thr | Thr 160 |
| Met | Arg | Leu | Phe | Tyr 165 | Pro | Glu | Ser | Ala | His 170 | Phe | Asp | Pro | Lys | Val 175 | Glu |
| Asn | Asn | Pro | Asp 180 | Thr | Leu | Leu | Val | Leu 185 | Val | Ala | Phe | Lys | Ala 190 | Met | Asp |
| Phe | His | Trp 195 | Ile | Glu | Thr | Ile | Leu 200 | Ser | Asp | Lys | Lys | Arg 205 | Val | Arg | Lys |
| Gly | Phe 210 | Trp | Lys | Gln | Pro | Pro 215 | Leu | Ile | Trp | Asp | Val 220 | Asn | Pro | Lys | Gln |
| Ile 225 | Arg | Ile | Leu | Asn | Pro 230 | Phe | Phe | Met | Glu | Ile 235 | Ala | Ala | Asp | Lys | Leu 240 |
| Leu | Ser | Leu | Pro | Met 245 | Gln | Gln | Pro | Arg | Lys 250 | Ile | Lys | Gln | Lys | Pro 255 | Thr |
| Thr | Gly | Leu | Leu 260 | Ala | Ile | Thr | Leu | Ala 265 | Leu | His | Leu | Cys | Asp 270 | Leu | Val |
| His | Ile | Ala 275 | Gly | Phe | Gly | Tyr | Pro 280 | Asp | Ala | Tyr | Asn | Lys 285 | Lys | Gln | Thr |
| Ile | His 290 | Tyr | Tyr | Glu | Gln | Ile 295 | Thr | Leu | Lys | Ser | Met 300 | Ala | Gly | Ser | Gly |
| His 305 | Asn | Val | Ser | Gln | Glu 310 | Ala | Leu | Ala | Ile | Lys 315 | Arg | Met | Leu | Glu | Met 320 |
| Gly | Ala | Ile | Lys | Asn 325 | Leu | Thr | Ser | Phe 329 | | | | | | | |

α-3 SIALYLTRANSFERASE

This application is a division of application Ser. No. 07/991,587, filed Dec. 16, 1992, now U.S. Pat. No. 5,384,249.

FIELD OF THE INVENTION

The present invention relates to a novel α2→3 sialyltransferase, DNA encoding the α2→3 sialyltransferase, recombinant vector in which the DNA is incorporated and a cell containing the recombinant vector as well as a process for producing them. Further, the present invention relates to a process for producing a sugar chain using the α2→3 sialyltransferase and a process for producing a sugar chain by expressing the α2→3 sialyltransferase in a transformed cell. Further, the present invention relates to a method for detecting or inhibiting the expression of α2→3 sialyltransferase using cDNA encoding the α2→3 sialyltransferase of the present invention. The α2→3 sialyltransferase of the present invention is useful for producing a sugar chain or modification thereof having useful physiological activity and improving a sugar chain which is attached to a useful physiologically active protein.

BACKGROUND OF THE INVENTION

While proteins produced by a procaryote such as *Escherichia coli* and the like have no sugar chain, the proteins and lipids produced by an eucaryote such as yeast, fungi, plant cells, animal cells and the like have an attached sugar chain in many cases.

As a sugar chain in animal cells, N-linked sugar chain (also called as N-glycan) which binds to asparagine (Asn) residue in proteins, and O-linked sugar chain (also called as O-glycan) which binds to serine (Ser) or threonine (Thr) residue are known to be added to glycoproteins. There has been recently revealed that a certain lipids containing a sugar chain are bound covalently to a number of proteins and the proteins are attached to the cell membrane via those lipids. Those lipids containing a sugar chain are called as glycosyl phosphatidylinositol anchor.

The other example of a sugar chain in animal cells is glycosaminoglycan. A compound wherein a protein and a glycosaminoglycan are covalently bound is called as proteoglycan. Although glycosaminoglycan which is a component of sugar chain of proteoglycan has similar structure to that of O-glycan which is glycoprotein sugar chain, glycosaminoglycan-has-chemical properties different from those of O-glycan. Glycosaminoglycan has the characteristic structure composed of disaccharide unit repeats containing glucosamine or galactosamine and uronic acid (except that keratan sulfate has no uronic acid), wherein the sulfate groups are covalently bound thereto (except that hyaluronic acid has no sulfate groups).

Furthermore, as a sugar chain in animal cells, there is a sugar chain contained in glycolipid. As glycolipid in animal cells, there are known sphingoglycolipid in which sugar, long chain fatty acid and sphingosine which is long chain base are covalently bound, and glyceroglycolipid in which sugar chain is covalently bound to glycerol.

Recently, elucidation on the function of a sugar chain has been rapidly advanced together with advance in molecular biology and cell biology, and a variety of functions of a sugar chain have been revealed. Firstly, a sugar chain play an important role on clearance of glycoprotein in blood. Erythropoietin obtained by transferring a gene in *Escherichia coli* manifests in vitro its activity, but is known to be rapidly in vivo clearanced [Dordal et al.: Endocrinology, 116, 2293 (1985) and Browne et al.: Cold Spr. Harb. Symp. Quant. Biol., 51, 693, 1986]. Human granulocyte-macrophage colony stimulating factor (hGM-CSF) has naturally two N-linked sugar chains, but it is known that, as the-number of sugar chains is decreased, the clearance rate in rat plasma is raised proportionally thereto [Donahue et al.: Cold Spr. Harb. Symp. Quant. Biol., 51, 685 (1986)]. The clearance rate and clearanced places vary depending upon the structure of a sugar chain. It is known that, while hGM-CSF to which sialic acid is added is clearanced in kidney, hGM-CSF from which sialic acid is removed is raised in the clearance rate and is clearanced in liver. Additionally, the clearance rates in rat plasma and rat perfusion liquid were studied with respect α1-acid glycoproteins having different sugar chain which were biosynthesized by rat liver primary culture in the presence of various N-linked sugar chain biosynthesis inhibitors. In both cases, the clearance rates were slower in descending order of high mannose type, sugar chain deficient type, hybrid type and complex type (natural type). It is also known that the clearance in blood of tissue-type plasminogen activator (t-PA) used as a fibrinolytic agent is significantly influenced by the structure of a sugar chain.

It is also known that a sugar chain endows a protein with the protease resistance. For example, when formation of sugar chain of fibronectin is inhibited by zunicamycin, the resulting sugar chain deficient fibronectin is promoted in the intracellular degrading rate. It is also known that addition of a sugar chain increases the heat stability and anti-freezing properties. It is also known that a sugar chain makes a contribution to increase the solubility of protein.

A sugar chain also makes a contribution to holding the correct steric structure of proteins. It is known that, although the removal of two N-linked sugar chains naturally present in membrane-bound glycoprotein of vesicular stomatitis virus inhibits the transport of proteins to cell surface, new addition of a sugar chain to said proteins recovers the transport. In this case, it has been revealed that the removal of a sugar chain induces the association between protein molecules via disulfide bond and, as the result, the transport of proteins is inhibited. Since the correct steric structure is retained due to inhibition of this association by new addition of sugar chain, the transport of proteins becomes possible. It is shown that the position to which new sugar chain is added is considerably flexible. To the contrary, it has been revealed that the transport of proteins having natural sugar chains is completely inhibited, in some cases, depending upon the introduction site of the additional sugar chain.

There is known the case where a sugar chain masks antigen site on polypeptide. From the experiments using polyclonal antibody or monoclonal antibody reacting with a particular region on polypeptide in hGM-CSF, prolactin, interferon-γ, Rauscher leukemia virus gp70 and influenza hemagglutinin, it is considered that a sugar chain of the above proteins inhibits a reaction with antibody. There is also known the case where a sugar chain itself has direct relationship with manifestation of the activity of glycoprotein. For example, a sugar chain is considered to participate in manifestation of the activity of glycoprotein hormones such as luteinizing hormone, follicule stimulating hormone, chorionic gonadotropin and the like.

In addition, EP-A 0370205 discloses that granulocyte colony-stimulating factor (G-CSF), pro-urokinase (pro-UK) and the like can be improved in the properties by artificially and intentionally introducing a sugar chain into the proteins using recombinant DNA techniques.

Furthermore, as an important function of a sugar chain, there is participation in recognition phenomena between cells, between proteins or between cells and proteins. For example, it is known that the place where a sugar chain is clearanced in the living body is different depending upon the difference in the structure of a sugar chain. In addition, it has been found that a ligand of ELAM-1 which is inflammatory response-specifically expressed on blood vessel endothelial cell and promotes adhesion to neutrophil is a sugar chain called as Sialyl-Le$^x$ [NeuAc α2→3Gal β1→4 (Fuc α1→3)GlcNAc:NeuAc, sialic acid; Gal, galactose; Fuc, fucose; GlcNAc, N-acetylglucosamine]. As the result, there has risen the possibility that a sugar chain itself or-modification thereof is used in pharmaceuticals and the like [Phillips et al.: Science 250, 1130 (1990), Goelz et al.: Trends in Glycoscience and Glycotechnology 4, 14 (1992)]. Further, it is suggested that L-selectin which is expressed in a part of T lymphocytes and neutrophil and GMP-140 (also called as P-selectin) which is expressed in the membrane surface of platelet and blood vessel endothelial cell by inflammatory stimulation participate in inflammatory response as same as ELAM-1, and ligands thereof are also sugar chains similar to Sialyl-Le$^x$ sugar chain which is a ligand of ELAM-1 [Rosen et al.: Trends in Glycoscience and Glycotechnology 4, 1 (1992), Larsen et al.: Trends in Glycoscience and Glycotechnology) 4, 25 (1992), Aruffo et al.: Trends in Glycoscience and Glycotechnology 4, 146 (1992)].

Also in metastasis of cancer as in the inflammatory response, it is suggested that ELAM-1 and GMP-140 promote metastasis of cancer by causing adhesion of cancer cells to inner wall of blood vessel or aggregation between cancer cells and platelets [Goelz et al.: Trends in Glycoscience and Glycotechnology) 4, 14 (1992), Larsen et al.: Trends in Glycoscience and Glycotechnology) 4, 25 (1992)]. These suggestions are consistent with the findings that expression of Sialyl-Le$^x$ sugar chain is high in cancer cells having high metastasis ability [Irimura et al.: Experimental Medicine 6, 33 (1988)].

From these findings, it is expected that Sialyl-Le$^x$ sugar chain or derivatives thereof manifest the excellent anti-inflammatory effects and anti-metastatic effects by binding to ELAM-1, L-selectin or GMP-140.

Additionally, in view of the mechanism of the above-described inflammatory response and metastasis of cancer, inflammatory response could be inhibited and metastasis of cancer could be prevented by inhibiting the expression of glycosyltransferase which controls synthesis of ligand sugar chain recognized by ELAM-1, L-selectin or GMP-140. Antisense RNA/antisense DNA techniques [Tokuhisa: Bioscience and Industry 50, 322 (1992), Murakami: Chemistry 46, 681 (1991)] or Triple helix techniques [Chubb and Hogan: Trends in Biotechnology 10, 132 (1992)] are useful for inhibiting the expression of some particular genes. Since information on those gene or nucleotide sequence of those gene is necessary in order to inhibit the expression of desired glycosyltransferase using this antisense RNA/DNA techniques, the cloning of a gene of desired glycosyltransferase and analysis of the information on the nucleotide sequence are important.

Further, diagnosis of malignancy in inflammatory diseases or cancer can be also performed by investigating the expression of the particular glycosyltransferase in inflammatory lymphocyte and cancer cells. For investigating the expression of desired glycosyltransferase, Northern hybridization method which uses as a probe the relevant gene labelled with radioactivity and the like [Sambrook, Fritsch, Maniatis, Molecular Cloning, A laboratory manual, 2nd edition, Cold Spring Harbor Laboratory Press, 1989] and Polymerase Chain Reaction method (abbreviated as PCR method hereinafter) [Innis et al.: PCR Protocols, Academic Press, 1990] are useful. For applying these methods, the information on desired glycosyltransferase gene or nucleotide sequence thereof is necessary. Also from this respect, the cloning of desired glycosyltransferase gene and analysis of information of that nucleotide sequence are important.

As described above, alteration in the structure of glycoprotein and mass production of the particular sugar chain or modification thereof are industrially extremely important themes.

The means by which the structure of a sugar chain is altered have recently advanced remarkably. In particular, the structure of a sugar chain can be altered by a high specific enzyme (exoglycosidase) which successively dissociates a sugar chain or glycopeptidase and endo-type glycosidase which cleavages a bonding between peptide chain and sugar chain without changing both peptide chain and sugar chain. As the result, the biological role of a sugar chain can be studied in detail. Further, endoglycoceramidase which cleavages between a sugar chain of glycolipid and ceramide has been recently found [Ito and Yamagata: J. Biol. Chem. 261, 14278 (1986)]. This finding has not only facilitated the preparation of a sugar chain of glycolipid but also advanced the study on the function of cell surface glycolipid. In addition, new addition of sugar chain has been possible by using glycosyltransferase. For example, sialic acid can be newly added to the end of sugar chain by using sialyltransferase [Sabesan and Paulson: J. Am. Chem. Soc. 108, 2068 (1986)]. A sugar chain to be added can be varied by using other various glycosyltransferases or glycosidase inhibitors [Alan et al.: Annu. Rev. Biochem. 56, 497 (1097)]. However, mass production of glycosyltransferase used in synthesis of a sugar chain is extremely difficult. For that reason, it is desired that glycosyltransferase is produced in a large amount by cloning glycosyltransferase using recombinant DNA techniques and effectively expressing glycosyltransferase in a host cell.

As a method for cloning glycosyltransferase, there are known a method by purifying a protein, producing an antibody reacting with it and performing immunoscreening using the antibody [Weinstein et al.: J. Biol. Chem. 262, 17735 (1987)], and a method by purifying a protein, determining amino acid sequence thereof, producing synthetic DNA which corresponds thereto and performing hybridization using the DNA as a probe [Narimatsu et al.: Proc. Natl. Acad. Sci., USA, 83, 4720 (1986)]. A method is also known where hybridization is performed using cloned glycosyltransferase gene as a probe and thereby glycosyltransferase gene having homology with the glycosyltransferase is cloned [John. B. Lowe et al.: J. Biol. Chem. 266, 17467 (1991)]. In addition, there is known a cloning method by direct expression cloning using panning method as screening method, in which antibody or lectin reacting with a sugar chain is employed [John. B. Lowe et al.: Proc. Natl. Acad. Sci.,USA, 86, 8227 (1989), John. B. Lowe et al.: Genes Develop., 4, 1288 (1990)].

There is no case where glycosyltransferase can be cloned using lectin-resistance as an index. From the studies on various lectin-resistant mutants of CHO cell, it has been revealed that there are cases where new glycosyltransferase is expressed, where the activity of a certain glycosyltransferase disappears, and where synthesis of sugar nucleotide or its transfer to Golgi body is inhibited [Pamela Stanley et al.: Methods in Enzymology, 96, 157]. Therefore, it is considered that cloning of glycosyltransferase can be performed using lectin-resistance as index by introducing a gene derived from a cell expressing glycosyltransferase to be cloned into CHO cell or lectin-resistant mutants of CHO cell [Ravindra Kumar et al.: Mol. Cell. Biol., 9, 5713 (1989)]. James Ripka et al. have tried to clone N-acetylglucosaminyltransferase I by introducing human genomic DNA derived from A431 cell into lectin-resistant mutants of CHO cell (Lec1) using resistance to lectin concanavalin A as an index. However, they could not clone glycosyltransferase by the screening method using lectin-resistance as an index [James Ripka et al.: Biochem. Biophys. Res. Commun., 159, 554 (1989)]. Heffernan et al. have cloned mouse sialic acid hydroxylase using resistance to lectin WGA (wheat germ agglutinin) as an index by introducing cDNA library into CHO cell [Michael Heffernan et al.: Nucleic Acids Res., 19, 85 (1991)] which was made to produce large T antigen of polyoma [Michael Heffernan et al.: Glycoconjugate J., 8, 154 (1991)]. However, there is no report in which glycosyltransferase could be cloned in a screening system using the lectin-resistance as an index. In addition, with respect to hosts, Stanley, Ripka, Heffernan et al. all used CHO cell or lectin-resistant mutants of CHO cell as a host.

With respect to sialyltransferase, a cDNA encoding an enzyme having βgalactoside α2→6 sialyltransferase activity has been isolated and nucleotide sequence thereof has been revealed [Weinstein et al.: J. Biol. Chem., 262, 17735 (1987)]. With respect to an enzyme having βgalactoside α2→3 sialyltransferase activity, Gillespie et al. have reported cloning of a gene encoding an enzyme which adds sialic acid to galactose in O-linked sugar chain of glycoprotein (sugar chain which is added to serine or threonine residue), but base sequence thereof has not been revealed [Gillespie et al.: Glycoconjugate J., 7, 469 (1990)]. In addition, Weinstein et al. have been reported a method for purifying an enzyme having βgalactoside α2→3 sialyltransferase activity from rat liver [Weistein et al.: J. Biol. Chem., 257, 13835 (1982)]. However, desired enzyme can be obtained in an extremely small amount. Hitherto, there have been no reports in which sialic acid is added in α2→3 linkage to desired position on sugar chain of glycoprotein, glycolipid, oligosaccharide and the like using recombinant DNA techniques.

OBJECTS OF THE INVENTION

The main object of the present invention is to provide novel α2→3 sialyltransferase which effectively alters a sugar chain of protein and produces a particular sugar chain, cDNA encoding said α2→3 sialyltransferase and a vector containing said cDNA.

These objects as well as other objects and advantages of the present invention will become apparent to those skilled in the art from the following description with reference to the accompanying drawings.

SUMMARY OF THE INVENTION

The present inventors constructed cDNA library by incorporating cDNA which was synthesized using mRNA extracted from animal cells as a template into expression cloning vector, introduced said cDNA library into a cell, the resultant cell was cultured in the presence of lectin having the activity which inhibits growth of said cell, and growing cells were isolated to obtain a cloned gene which was introduced in a host cell to express. As the result, we found that novel α2→3 sialyltransferase was expressed, resulting in completion of the present invention.

According to the present invention, there is provided novel α2→3 sialyltransferase having amino acid sequence shown by SEQUENCE IDENTIFIER NUMBER (Seq. ID:) 2 or 7, cDNA encoding said α2→3 sialyltransferase, and a recombinant vector containing said DNA. α2→3 Sialyltransferase of the present invention is glycosyltransferase having the βgalactoside α2→3 sialyltransferase activity, and has the activity which adds sialic acid to end of substrate sugar chain in α2→3 linkage.

Figure 1:
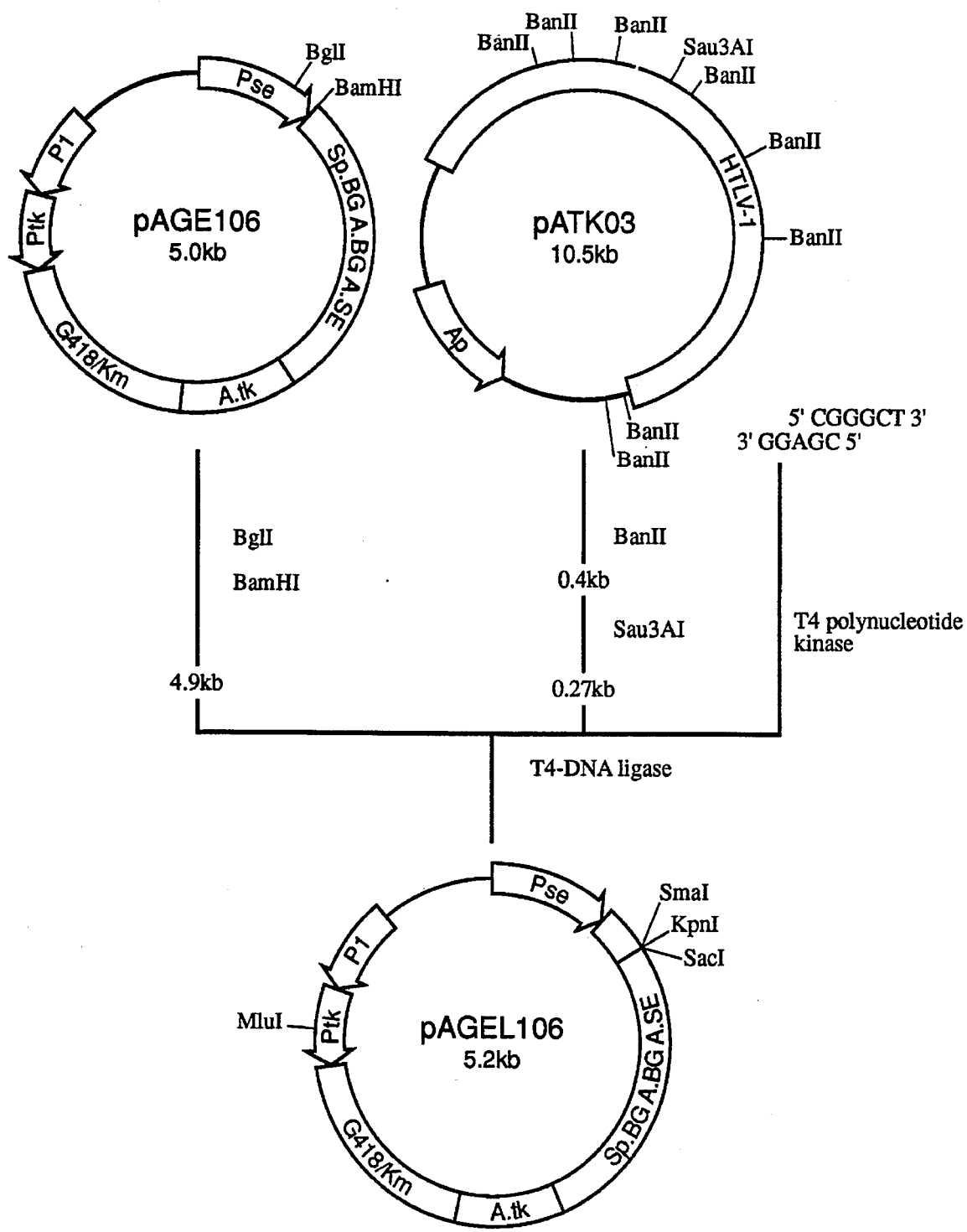
FIG. 1 is a flow sheet showing construction of plasmid pAGEL106.

The abbreviations used herein have the following meanings.

dhfr: dihydrofolate reductase gene hG-CSF: human granulocyte colony stimulating factor gene bp: base pairs kb: kilobase pairs G418/Km: G418 and kanamycin resistance gene derived from transposon 5 (Tn5)

hyg: hygromycin resistance gene

Ap: ampicillin resistance gene derived from pBR322

Tc: tetracycline resistance gene derived from pBR322

P1: P1 promoter derived from pBR322

Pkt: Herpes simplex virus (HSV) thymidine kinase (tk) gene promoter

Sp. βG: rabbit βglobin gene splicing signal

A. βG: rabbit βglobin gene poly A addition signal

A. SE: simian virus 40 (SV40) early gene poly A addition signal

Atk: Herpes simplex virus (HSV) thymidine kinase (tk) gene poly A addition signal Pse: simian virus 40 (SV40) early gene promoter Pmo: Moloney murine leukemia virus long terminal repeat (LTR) promoter HTLV-1: human T-cell leukemia virus type-1 (HTLV-1) gene EBNA-1: Epstein-Barr virus EBNA-1 gene oriP: Epstein-Barr virus replication gene ori: pUCl19 replication gene lac'Z: a part of *Escherichia coli* βgalctosidase gene IG: intergenic region of M13 phage DNA

DETAILED DESCRIPTION OF THE INVENTION cDNA encoding $\alpha 2 \rightarrow 3$ sialyltransferase of the present invention include (a) DNA having nucleotide sequence shown in Seq. ID: 1 or 6, (b) DNA having nucleotide sequence different from that shown in Seq. ID: 1 or 6 due to presence of a plurality of genetic codes relative to one amino acid, or due to natural mutation which occurs in individual animal including human being, (c) DNA in which mutations such as substitution, deletion, insertion and the like are introduced in the DNA defined by (a) or (b) without losing the activity of $\alpha 2 \rightarrow 3$ sialyltransferase activity of the present invention, for example, DNA having such homology with $\alpha 2 \rightarrow 3$ sialyltransferase encoded by DNA defined by (a) or (b) as can be isolated by hybridization method. $\alpha 2 \rightarrow 3$ Sialylytransferase of the present invention includes all of $\alpha 2 \rightarrow 3$ sialyltransferases encoded by DNA defined in the above (a), (b) or (c).

A process for producing cDNA which encodes $\alpha 2 \rightarrow 3$ sialyltransferase of the present invention is explained below by exemplifying a process for producing cDNA defined in the above (a).

cDNA library is constructed by incorporating cDNA synthesized using mRNA extracted from animal cells as a template into expression cloning vector. This cDNA library is introduced in animal or insect cells, and the cells are cultured in the presence of lectin which inhibits the growth of the cells. A cell transfected with cDNA encoding appropriate glycosyltransferases which change the structure of sugar chain recognized by lectin grows in the presence of lectin. This cell is isolated, and cDNA encoding desired $\alpha 2 \rightarrow 3$ sialyltransferase is obtained from the cell.

As an animal cell used in the above method, any animal cell can be used so long as cDNA encoding $\alpha 2 \rightarrow 3$ sialyltransferase of the present invention can be expressed in the animal cell. For example, human histiocytic leukemia cell line TYH [Haranaka et al.: Int. J. Cancer, 36, 313 (1985)], human melanoma cell line WM266-4 (ATCC CRL1676) and the like are used. As a vector in which cDNA synthesized using mRNA extracted from these cells as a template is incorporated, any vectors can be used in which said cDNA can be incorporated and expressed. For example, pAMoERC3Sc and the like are used. As an animal or insect cell in which cDNA library constructed using said vector is introduced, any cells can be used in which said cDNA library can be introduced and expressed. For example, human Namalwa cell [Hosoi et al.: Cytotechnology, 1, 151 (1988)] and the like can be used. As lectin to be used in the present invention, any lectins can be used which can inhibit the growth of cell in which cDNA is introduced. For example, *Ricinus communis* 120 lectin and the like are used. After resistance of host cell to lectin is determined, the lectin is used in such the concentration as can inhibit the growth of host cell. Plasmid having cDNA encoding $\alpha 2 \rightarrow 3$ sialyltransferase of the present invention or DNA fragment containing the cDNA part is recovered from cells which grow in the presence of lectin by the known method, for example, Hirt method [Robert F. Margolskee et al.: Mol. Cell. Biol., 8, 2837 (1988)]. As a plasmid having cDNA encoding the enzyme of the present invention, there are, for example, pUC119-LEC, pUC119-WM17 and the like. *Escherichia coli* HB101/pUC119-LEC containing pUC119-LEC and *Escherichia coli* HB101/pUC119-WM17 have been deposited with Fermentation Research Institute, Agency of Industrial Science and Technology, 1-3, Higashi 1 chome Tsukuba-shi Ibaraki-ken 305, Japan on Oct. 29, 1991 and on Sep. 22, 1992 under the Budapest Treaty, and have been assigned the accession number FERM BP-3625 and FERM BP-4013, respectively.

DNA defined by the above (b) and (c) can be prepared by well known recombinant DNA techniques such as hybridization method, and a method introducing mutations in DNA and the like, based on cDNA encoding α2→3 sialyltransferase obtained by the above process. Alternatively, cDNA encoding α2→3 sialyltransferase of the present invention can be prepared using chemosynthetic method.

DNA encoding α2→3 sialyltransferase of the present invention obtained in the above process is inserted downstream of appropriate promoter to construct recombinant vector which is introduced in a host cell, and the resulting cell is cultured to obtain α2→3 sialyltransferase of the present invention. As a host cell, any host cells can be used to which recombinant DNA techniques have been applied such as procaryotic cells, animal cells, yeasts, fungi, insect cells and the like. For example, there are *Escherichia coli* cell as procaryotic cell, CHO cell which is Chinese hamster ovary cell, COS cell which is monkey cell, Namalwa cell which is human cell and the like as animal cell. In particular, direct expression system using Namalwa cell as a host cell is suitably used due to such the advantages that efficiency which introduces cDNA library in Namalwa cell as a host cell is extremely high, the introduced plasmid (cDNA library) can exist extrachromosomally, and plasmid is easily recovered from the resultant lectin resistant strain.

As a vector for introducing DNA encoding the present α2→3 sialyltransferase therein, there can be used any vectors in which DNA encoding the α2→3 sialyltransferase can be incorporated and which can be expressed in a host cell. For example, there are pAGE107 [JP-A 3-22979, Miyaji et al.: Cytotechnology, 3, 133 (1990)], pAS3-3 [EP-A 0370205], pAMoERC3Sc, CDM8 [Brian Seed et al.: Nature, 329, 840 (1987)] and the like. For expressing the cDNA encoding the enzyme of the present invention in *Escherichia coli*, it is preferred that there is used a plasmid wherein foreign DNA can be inserted downstream of promoter having the strong transcription activity such as trp promoter and the like and the distance between Shine-Dalgarno sequence (abbreviated as SD sequence hereinafter) and initiation codon is appropriately adjusted (for example, said distance is 6 to 18 bases). More particularly, there are pKYP10 [EP-A 0083069], pLSA1 [Miyaji et. al: Agric. Biol. Chem., 53, 277 (1989)], pGEL1 [Sekine at. al, Proc. Natl. Acad. Sci., USA, 82, 4306 (1985)] and the like.

As general procedures of recombinant DNA techniques used in the present invention, there can be used those described in EP-A 0370205 or those described by Sambrook, Fritsch, Maniatis et al. [Molecular Cloning, A laboratory manual, 2nd edition, Cold Spring Harbor Laboratory Press, 1989]. Isolation of mRNA and synthesis of cDNA library can be effected using the above-described methods and many kits on the market. For introducing DNA in an animal cell, there can be used any currently known methods. For example, electroporation method [Miyaji et al.: Cytotechnology, 3, 133 (1990)], calcium phosphate method [EP-A 0370205], lipofection method [Philip L. Felgner et al.: Proc. Natl. Acad. Sci., USA, 84, 7413 (1987)] and the like can be used. Obtaining of transfected cells and culturing them can be performed according to the method described in EP-A 0370205 or JP-A 2-257891.

As a process for producing cloned α2→3 sialyltransferase, there are a method for expressing it in a host cell, a method for secreting it from a host cell, and a method for expressing it on cell surface of a host cell. The place where expression is effected varies depending upon the kind of host cell to be used and upon the form of glycosyltransferase to be produced. When glycosyltransferase is produced as it is, using an animal cell as a host cell, it is generally produced in a host cell or on cell surface of a host cell, and a part of it is extracellularly excreted upon cleavage by protease. To secrete glycosyltransferase intentionally, it is produced in a form where a signal peptide is added to a part containing an active site of glycosyltransferase using recombination DNA techniques according to a method by Paulson et al. [C. Paulson et al.: J. Biol. Chem., 264, 17619 (1989)] and a method by Lowe et al [John B. Lowe et al.: Proc. Natl. Acad. Sci., USA, 86, 8227 (1989), John B. Lowe et al.: Genes Develop., 4, 1288 (1990)].

Alternatively, the production yield can be increased using gene amplification system using dihydrofolate reductase gene and the like according to a method described in EP-A 0370205.

α2→3 Sialyltransferase of the present invention thus produced can be purified by a conventional purifying method for glycosyltransferase [J. Evan. Sadler et al.: Methods of Enzymology, 83, 458]. When the enzyme is produced in *Escherichia coli*, it can be effectively purified in combination of the above method and the method described in EP-A 0272703. Alternatively, purification can be carried out by producing the enzyme of the present invention as a fused protein with other protein and subjecting it to affinity chromatography using substance having the affinity with the fused protein. For example, the enzyme of the present invention can be produced as a fused protein with protein A and purified by affinity chromatography using immunoglobulin G according to the method by Lowe et al. [John. B. Lowe et al.: Proc. Natl. Acad. Sci., USA, 86, 8227 (1989), John. B. Lowe et al.: Genes Develop., 4, 1288 (1990)]. Alternatively, the enzyme can be purified by affinity chromatography using an antibody reacting with the enzyme itself.

The activity of sialyltransferase is determined by the known method [J. Evan. Sadler et al.: Methods in Enzymology, 83, 458, Naoyuki Taniguti et al.: Methods in Enzymology, 179, 397].

A sugar chain can be synthesized in vitro using α2→3 sialyltransferase of the present invention. For example, sialic acid can be added in α2→3 linkage to non-reducing endgroup of lactosamine structure (Gal β1→4GlcNAc structure) contained in glycoprotein, glycolipid or oligosaccharide. The structure of sugar chain at non-reducing terminus can also be converted to Sialyl-Le$^x$ structure by acting α2→3 sialyltransferase of the present invention to glycoprotein, glycolipid or oligosaccharide as a substrate. An oligosaccharide having Sialyl-Le$^x$ and modification thereof at non-reducing terminus can be synthesized using known α1→3 fucosyltransferase [Lowe et al.: Genes Develop., 4, 1288 (1990), Goelz et al.: Cell, 63, 1349 (1990)] after acting α2→3 sialyltransferase of the present invention to an oligosaccharide having lactosamine structure at non-reducing terminus.

DNA encoding α2→3 sialyltransferase of the present invention can be used to be expressed together with DNAs encoding glycoprotein, glycolipid or oligosaccharide having the useful physiological activity in an animal cell or insect cell producing a sugar chain substrate to the α2→3 sialyltransferase, and the produced α2→3 sialyltransferase can be acted on glycoprotein, glycolipid or oligosaccharide to obtain glycoprotein, glycolipid or oligosaccharide having the altered sugar chain structure.

Further, a part of oligosaccharide can be excised from the resulting glycoprotein, glycolipid or oligosaccharide having the altered sugar chain structure by using the known enzymatic or chemical method.

DNA encoding α2→3 sialyltransferase of the present invention can be used not only in modification of sugar chain of glycoproteins, glycolipids or oligosaccharides and efficient production of the particular sugar chain but also in therapy for diseases such as inflammation or cancer metastasis using antisense RNA/DNA techniques and diagnosis on those diseases using Northern hybridization method or PCR method.

Expression of the activity of α2→3 sialyltransferase of the present invention can be inhibited using, for example, DNA encoding the α2→3 sialyltransferase by antisense RNA/DNA techniques [Tokuhisa: Bioscience and Industry, 50, 322 (1992), Murakami: Kagaku, 46, 681 (1991), Miller: Biotechnology, 9, 358 (1992), Cohen: Trends in Biotechnology, 10, 87 (1992), Agrawal: Trends in Biotechnology, 10, 152 (1992)] or triple helix technique [Chubb and Hogan: Trends in Biotechnology, 10, 132 (1992)]. More particularly, expression of the α2→3 sialyltransferase can be inhibited by administering in the living body an oligonucleotide which is designed and prepared based on nucleotide sequence of a part of α2→3 sialyltransferase gene, preferably, 10–50 bases sequence in the initiation region. As nucleotide sequence of synthetic oligonucleotide, there can be used the completely same sequence as that of a part of antisense strand disclosed herein or a sequence which is modified so that α2→3 sialyltransferase expression inhibiting activiy is not lost. When triple helix technique is used, nucleotide sequence of synthetic oligonucleotide is designed based on the information about nucleotide sequence of both sense strand and antisense strand.

In addition, expression of cDNA encoding α2→3 sialyltransferase of the present invention can be detected by hybridizaiton method or PCR as follows.

For detecting expression of cDNA encoding α2→3 sialyltransferase of the present invention using Northern hybridization method or PCR method, probe DNA or synthetic oligonucleotide is prepared based on cDNA encoding α2→3 sialyltransferase of the present invention or nucleotide sequence thereof. Northern hybridization method and PCR method are performed according to Molecular Cloning, A laboratory manual, 2nd edition [Cold Spring Harbor Laboratory Press, 1989] and PCR Protocols [Academic Press, 1990].

The following Examples further illustrate the present invention in detail but are not be construed to limit the scope thereof.

In the following Examples, T4 polynucleotide kinase and T4 DNA ligase used were those manufactured by Takarashuzo K.K.

EXAMPLE 1

1. Construction of direct expression cloning vector pAMoERC3Sc (1) Construction of pAGEL106 (see FIG. 1)

According to the method described below, plasmid pAGEL106 having promoter in which simian virus 40 (SV40) early gene promoter and a part of R region and U5 region of long terminal repeat of human T-cell leukemia virus type-1 (HTLV-1) are fused was constructed. That is, DNA fragment containing a part of R region and U5 region [BanII-Sau3AI fragment (0.27 kb)] was isolated from pATK03 and inserted between BglI site and BamHI site of pAGE106 via synthetic linker.

pAGE106 (1 μg) obtained by the method described in EP-A 0370205 was dissolved in a buffer (abbreviated as Y-100 buffer hereinafter) containing 10 mM Tris-HCl (pH 7.5), 6 mM magnesium chloride, 100 mM sodium chloride and 6 mM 2-mercaptoethanol, and digested with 10 units of BglI (manufactured by Takarashuzo, restriction enzymes were used those manufactured by Takarashuzo hereinafter unless others indicated) and 10 units of BamHI at 37° C. for two hours. The reaction solution was subjected to agarose gel electrophoresis to obtain about 4.9 kb of DNA fragment.

Separately, 1μ of pATK03 [Shimizu at al.: Proc. Natl. Acad. Sci., USA, 80, 3618 (1983)] was dissolved in 30 μl of Y-100 buffer, and 10 units of BanII was added thereto. The mixture was subjected to digestion reaction at 37° C. for two hours, and subjected to agarose gel electrophoresis to give about 0.4 kb of DNA fragment. The resulting DNA fragment was dissolved in Y-100 buffer (30 μl) and 10 units of Sau3AI was added thereto. The mixture was subjected to digestion reaction at 37° C. for two hours, and subjected to agarose gel elctrophoresis to give about 0.27 kb of DNA fragment.

Separately, for linking BglI cleavage site and BanII cleavage site, the following DNA liker was synthesized.

5'CGGGCT3' (6 mer)

3'GGAGC5' (5 mer)

The 5 mer and 6 mer single-stranded DNAs of the DNA linker were synthesized using a DNA synthesizer model 380A (Applied Biosystems). Each 0.2 μg of the synthesized DNAs was dissolved in 40 μl of a buffer (abbreviated as T4 kinase buffer hereinafter) containing 50 mM Tris-HCl (pH 7.5), 10 mM magnesium chloride, 5 mM dithiothreitol (abbreviated as DTT hereinafter), 0.1 nM EDTA and 1 mM adenosine triphosphate (abbreviated as ATP hereinafter) and phosphorylated with 30 units of T4 polynucleotide kinase at 7° C. for two hours.

The DNA fragments thus obtained, i.e., 0.2 μg of BglI-BamHI fragment (4.9 kb) derived from pAGE106 and 0.01 μg of BanII-Sau3AI fragment (0.27 kb) derived from pATK03 were dissolved in 30 μl of buffer (abbreviated as T4 ligase buffer hereinafter) containing 66 mM Tris-HCl (pH 7.5), 6.6 mM magnesium chloride, 10 mM DTT and 0.1 mM ATP. 0.01 μg of the above DNA linker was added to the solution and both the DNA fragments and DNA linker were ligated together with 175 units of T4 DNA ligase at 12° C. for 16 hours.

*Escherichia coli* HB101 strain [Bolivar et al.: Gene, 2, 75 (1977)] was transformed using the above reaction mixture according to the method by Cohen et al. [S. N. Cohen et al.: Proc. Natl. Acad. Sci., USA, 69, 2110 (1972)] to obtain kanamycin resistant strains. From these transformants, a plasmid was isolated according to the known method [H. C. Birnboim et al.: Nucleic Acids Res., 7, 1513 (1979)]. This plasmid was designated as pAGEL106, and its structure was confirmed by restriction enzyme digestion.

Figure 2:
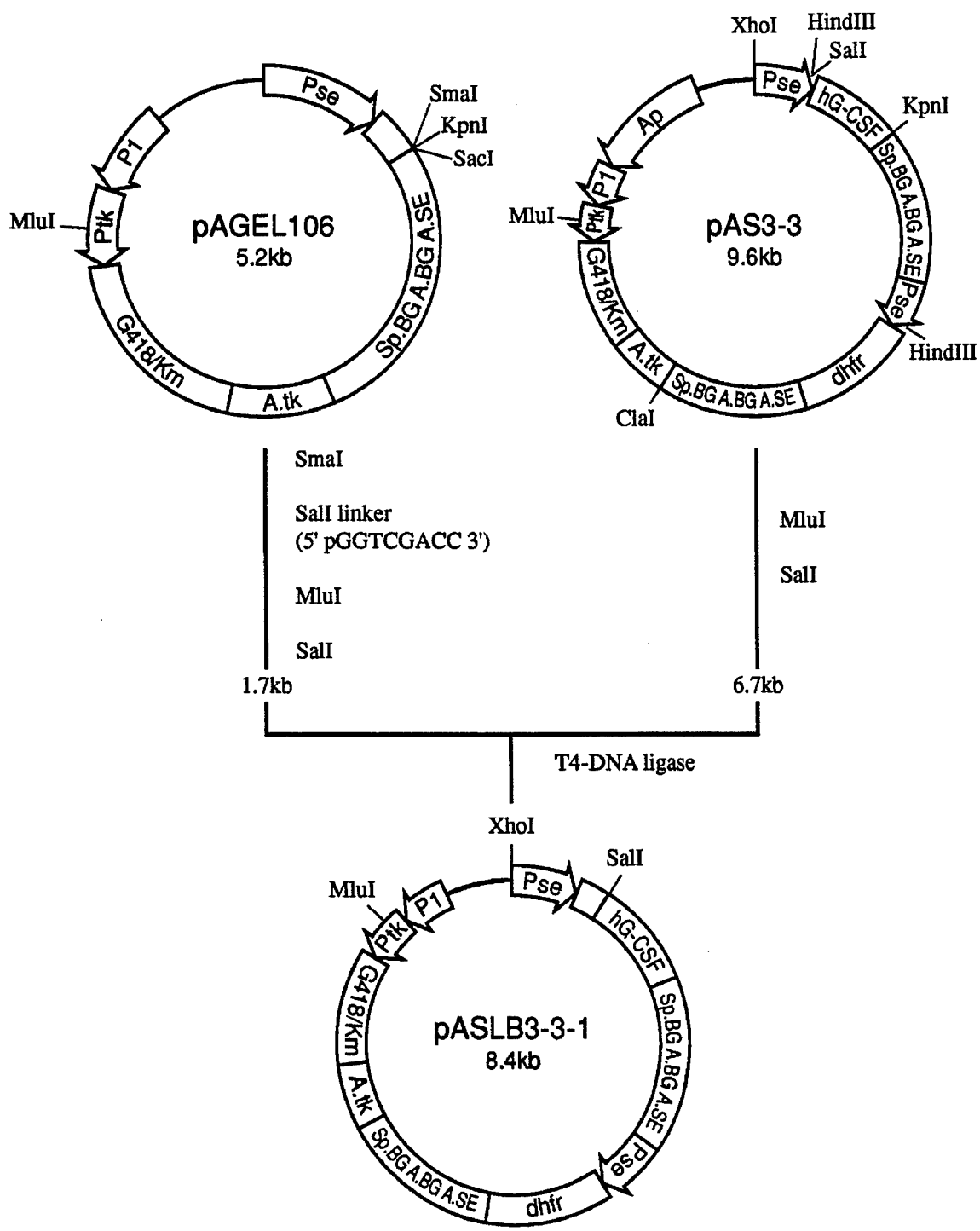
FIG. 2 is a flow sheet showing construction of plasmid pASLB3-3-1.

(2) Construction of pASLB3-3-1 (see FIG. 2)

According to the method described below, expression plasmid pASLB3-3-1 of human granulocyte colony stimulating factor (hG-CSF) having promoter in which SV40 early gene promoter and a part of R region and U5 region of long terminal repeat (LTR) of HTLV-1 are fused was constructed.

0.5 µg of pAGEL106 obtained in Sec. 1(1) of this Example was dissolved in 30 µl of a buffer (abbreviated as K-20 buffer hereinafter) containing 10 mM Tris-HCl (pH 7.5), 6 mM magnesium chloride, 20 mM potassium chloride and 6 mM 2-mercaptoethanol, and digested with 10 units of SmaI at 37° C. for two hours. After precipitation with ethanol, the precipitate was dissolved in 30 µl of T4 ligase buffer, and the digested DNA and 0.01 µl of SalI linker (5'pGGTCGACC3': manufactured by Takarashuzo) were ligated together with 175 units of T4 DNA ligase at 12° C. for 16 hours. After precipitation with ethanol, the precipitate was dissolved in 30 µl of a buffer (abbreviated as Y-175 buffer hereinafter) containing 10 mM Tris-HCl (pH 7.5), 6 mM magnesium chloride, 175 mM sodium chloride and 6 mM 2-mercaptoethanol, and digested with 10 units of SalI and 10 units of MluI at 37° C. for two hours. The reaction solution was subjected to agarose gel electrophoresis to give about 1.7 kb of DNA fragment.

On the ther hand, 1 µg of pAS3-3 obtained by the method described in EP-A 0370205 was dissolved in 30 µl of Y-175 buffer, and digested with 10 units of SalI and 10 units of MluI at 37° C. for 2 hours. The reaction solution was subjected to agarose gel electrophoresis to give about 6.7 kb of DNA fragment.

DNA fragments thus obtained, i.e., 0.1 µg of MluI-SalI fragment (1.7 kb) derived from pAGEL106 and 0.2 µg of MluI-SalI fragment (6.7 kb) derived from pAS3-3 were dissolved in 30 µl of T4 ligase buffer and ligated together with 175 units of T4 DNA ligase at 12° C. for 16 hours.

*Escherichia coli* HB101 strain was transformed using the above reaction solution according to the method by Cohen et al. to obtain a kanamycin resistant strain. From this transformant, a plasmid was isolated according to the known method. This plasmid was designated as pASLB3-3-1, and its structure was confirmed by restriction enzyme digestion.

Figure 3:
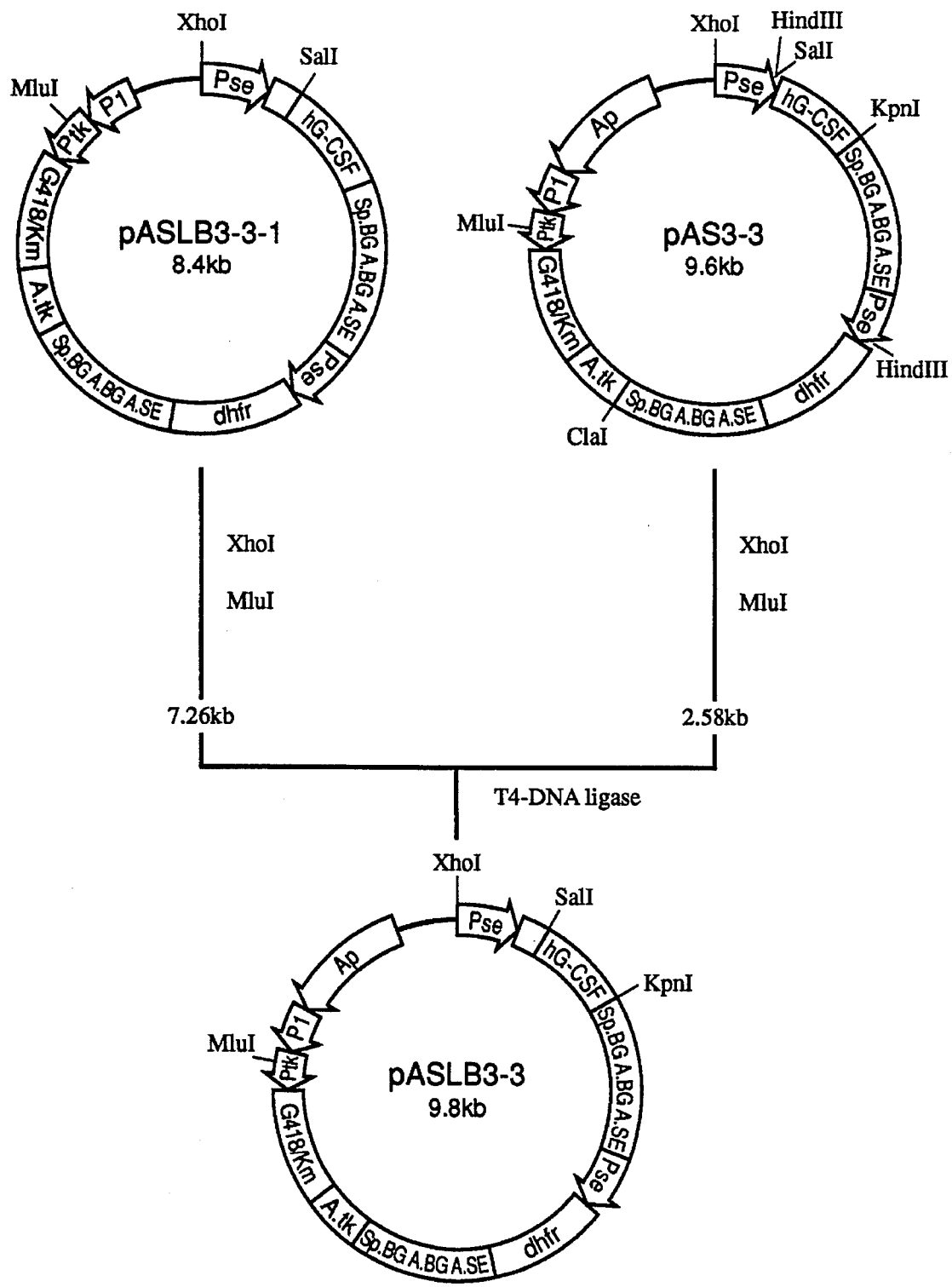
FIG. 3 is a flow sheet showing construction of plasmid pASLB3-3.

(3) Construction of pASLB3-3 (see FIG. 3)

According to the method described below, in order to construct plasmid pASLB3-3 wherein ampicillin resistance gene is introduced in pASLB3-3-1, DNA fragment [XhoI-MluI fragment (2.58 kb)] containing ampicillin resistance gene of pAS3-3 was introduced between XhoI site and MluI site of pASLB3-3-1.

1 µg of pASLB3-3-1 obtained in Sec. 1(2) of this Example was dissolved in 30 µl of a buffer (abbreviated as Y-150 buffer) containing 10 mM Tris-HCl (pH 7.5), 6 mM magnesium chloride, 150 mM sodium chloride and 6 mM 2-mercaptoethanol and digested with 10 units of XhoI and 10 units of MluI at 37° C. for two hours. The reaction solution was subjected to agarose gel electrophoresis to give about 7.26 kb of DNA fragment.

Separately, 1 µg of pAS3-3 was dissolved in Y-150 buffer (30 µl) and digested with 10 units of XhoI and 10 units of MluI at 37° C. for two hours. The reaction solution was subjected to agarose gel electrophoresis to give about 2.58 kb of DNA fragment.

DNA fragments thus obtained, i.e., 0.2 µg of XhoI-MluI fragment (7.26 kb) derived from pASLB3-3-1 and 0.1 µg of XhoI-MluI fragment (2.58 kb) derived from pAS3-3 were dissolved in T4 ligase buffer (30 µl) and ligated together with 175 units of T4 DNA ligase at 12° C. for 16 hours.

*Escherichia coli* HB101 strain was transformed using the above reaction mixture according to the method by Cohen et al. to obtain an ampicillin resistant strain. From this transformant, a plasmid was isolated according to the known method. This plasmid was designated as pASLB3-3, and its structure was confirmed by restriction enzyme digestion.

Figure 4:
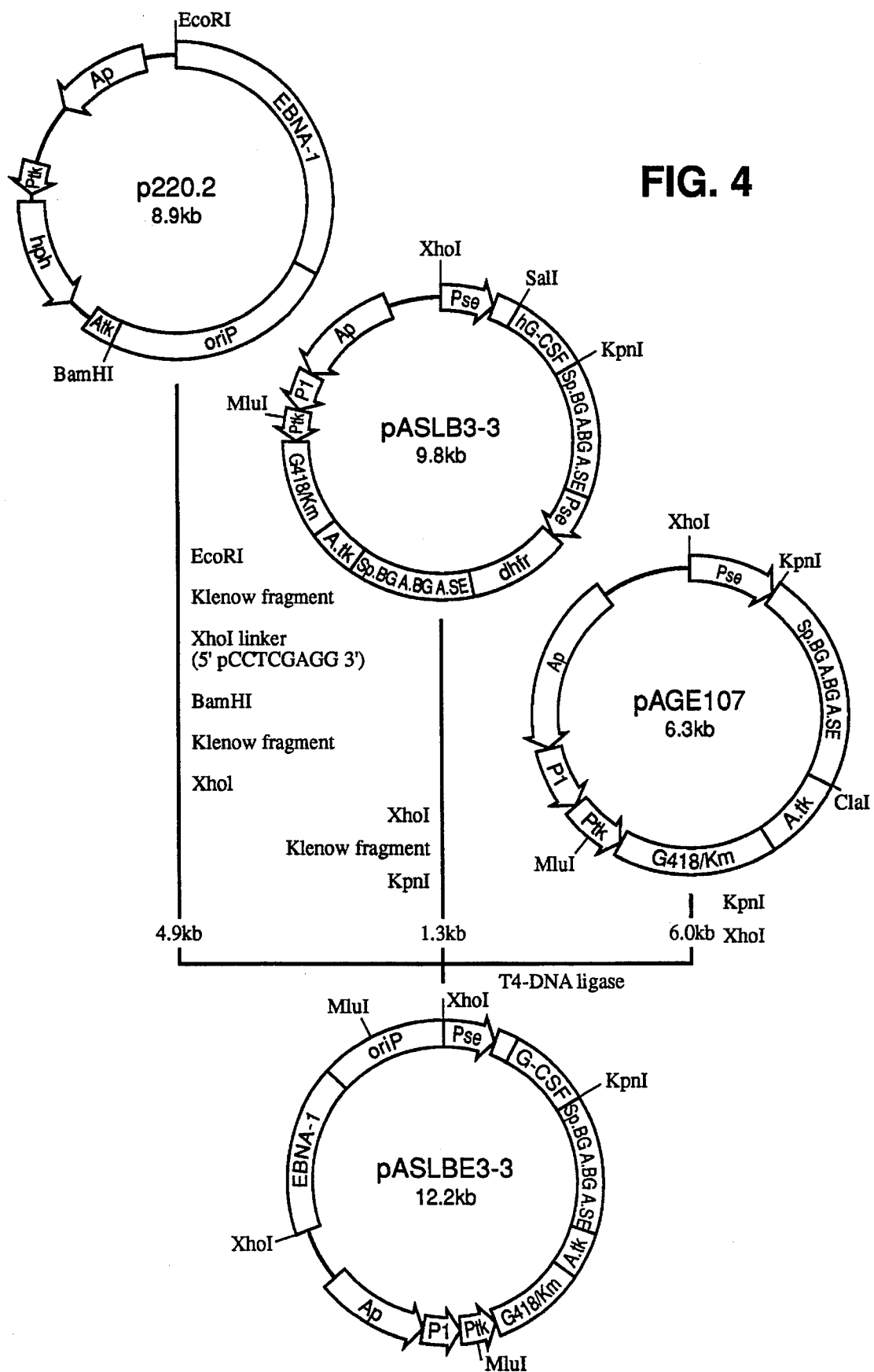
FIG. 4 is a flow sheet showing construction of plasmid pSALBE3-3.

(4) Construction of pASLBE3-3 (see FIG. 4)

According to the method described below, dihydrofolate reductase (dhfr) expression unit was removed from pASLB3-3 to obtain plasmid pASLBE3-3 wherein replication origin (oriP) of Epstein-Barr virus and EBNA-1 gene are introduced. EBNA-1 gene encodes a factor which causes replication by trans-acting to oriP. For that use, oriP and EBNA-1 gene were isolated from plasmid p220.2 wherein SmaI-HaeIII fragment containing multicloning sites derived from pUC12 [Messing et al.: Methods in Enzymology, 101, 20 (1983)] is incorporated at NarI site of p201 [Bill Sugden et al., Nature, 313, 812 (1985)]

1 µg of Plasmid p220.2 was dissolved in Y-100 buffer (30 µl) and digested with 20 units of EcoRI at 37° C. for two hours. After precipitation with ethanol, the precipitate was dissolved in 30 µl of DNA polymerase I buffer containing 50 mM Tris-HCl (pH 7.5), 10 mM magnesium chloride, 0.1 mM dATP (deoxyadenosine triphosphate), 0.1 mM dCTP (deoxycytidine triphosphate), 0.1 mM dGTP (deoxyguanosine triphosphate), and 0.1 mM dTTP (deoxythymidine triphosphate), and 6 units of *Escherichia coli* DNA polymerase I Klenow fragment was added to react at 37° C. for 60 minutes, which resulted in conversion of 5' protruding cohesive end produced by EcoRI digestion into blunt end. The reaction was stopped by extraction with phenol, extracted with chloroform, and precipitated with ethanol. The precipitate was dissolved in 20 µl of T4 ligase buffer, and XhoI linker (5'pCCTCGAGG3', manufactured by Takarashuzo) (0.05 µg) and 175 units of T4 DNA ligase were added to react at 12° C. for 16 hours. After precipitation with ethanol, the precipitate was dissolved in 30 µl of Y-100 buffer, and digested with 10 units of BamHI at 37° C. for two hours. After precipitation with ethanol, the precipitate was dissolved in 30 µl of DNA polymerase I buffer, and 6 units of *Escherichia coli* DNA polymerase I Klenow fragment was added to react at 37° C. for 60 minutes, which resulted in conversion of 5' protruding cohesive end into blunt end. The reaction was stopped by extraction with phenol, extracted with chloroform, and precipitated with ethanol. The precipitate was dissolved in 30 µl of-Y-100 buffer, and digested with 10 units of XhoI at 37° C. for two hours. The reaction solution was subjected to agarose gel electrophoresis to give about 4.9 kb of DNA fragment.

Separately, 1 µg of pASLB3-3 was dissolved in 30 µl of Y-100 buffer, and 20 units of XhoI was added to perform digestion reaction at 37° C. for tow hours. After precipitation with ethanol, the precipitate was dissolved in 30 µl of DNA polymerase I buffer, and 6 units of *Escherichia coli* DNA polymerase I Klenow fragment was added to react 37° C. for 60 minutes, which resulted in conversion of 5' protruding cohesive end produced by XhoI digestion into blunt end. The reaction was stopped by extraction with phenol, extracted with chloroform, precipitated with ethanol, the precipitate was dissolved in a buffer (abbreviated as Y-0 buffer hereinafter) containing 10 mM Tris-HCl (pH 7.5), 6 mM magnesium chloride and 6 mM 2-mercaptoethanol, and 20 units of KpnI was added to perform digestion reaction at 37° C. for two hours. The reaction solution was subjected to agarose gel electrophoresis to give about 1.3 kb of DNA fragment.

Separately, 1 µl of pAGE107 [JP-A 3-22979, Miyaji et al.: Cytotechnology, 3, 133 (1990)] was dissolved in 30 µl of Y-0 buffer, and 20 units of KpnI was added to perform digestion reaction at 37° C. for two hours. Thereafter, sodium chloride was added to give NaCl concentration of 100 mM, and 20 units of XhoI was added to perform digestion reaction at 37° C. for two hours. The reaction solution was subjected to agarose gel electrophoresis to give about 6.0 kb of DNA fragment.

The DNA fragments thus obtained, i.e., 0.2 μg of XhoI-BamHI (blunt end) fragment (4.9 kb) derived from p220.2, 0.1 μg of XhoI (blunt end)-KpnI fragment (1.3 kb) derived from pASLB3-3 and 0.2 μg of KpnI-XhoI fragment (6.0 kb) derived from pAGE107 were dissolved in 30 μl of T4 ligase buffer and ligated with 175 units of T4 DNA ligase at 12° C. for 16 hours.

*Escherichia coli* HB101 strain was transformed using the reaction mixture according to the method by Cohen et al. to obtain an ampicillin resistant strain. From this transformant, a plasmid was isolated according to the known method. This plasmid was designated as pASLBE3-3, and its structure was confirmed by restriction enzyme digestion.

Figure 5:
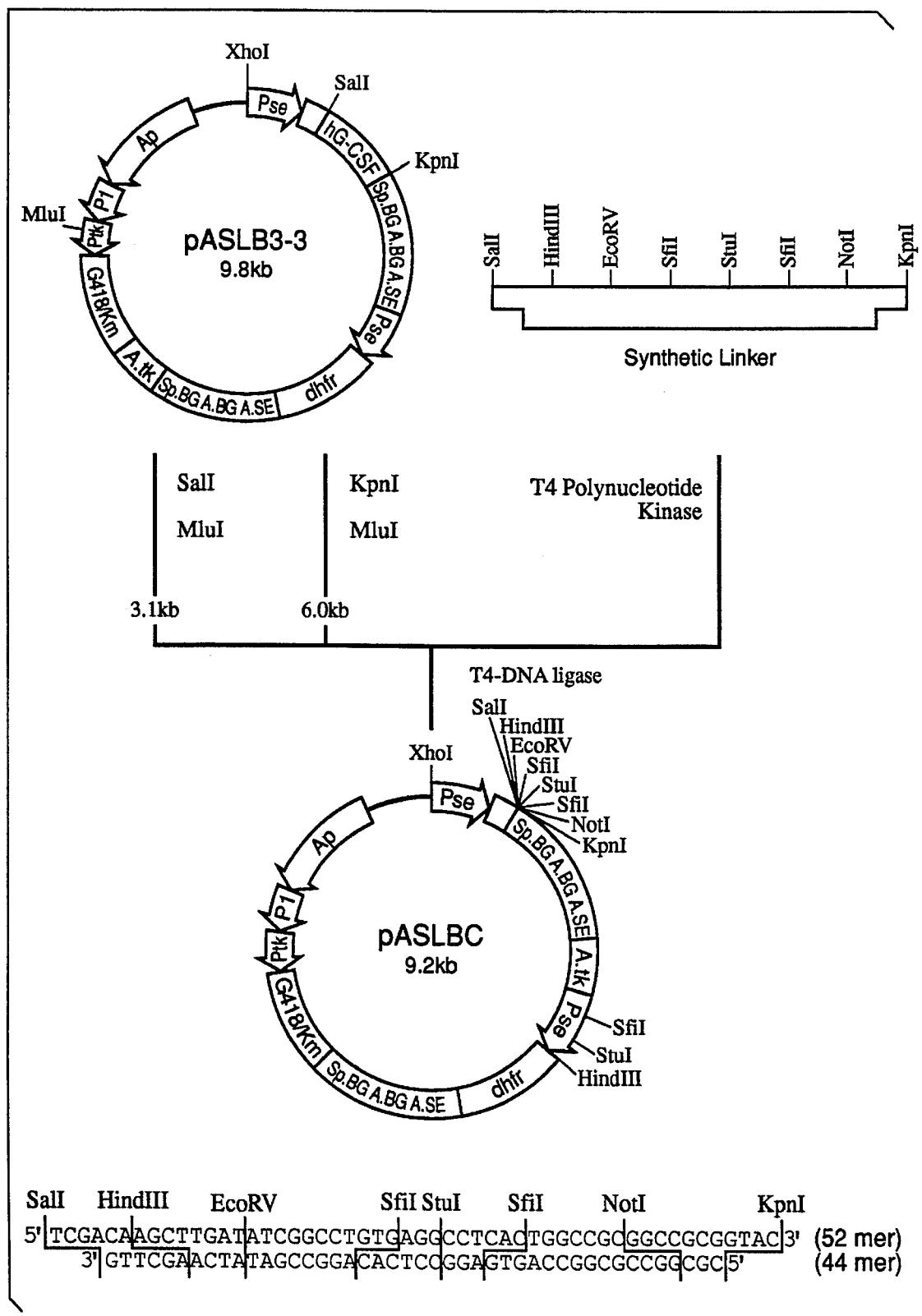
FIG. 5 is a flow sheet showing construction of plasmid pASLBC.

(5) Construction of pASLBC (see FIG. 5)

According to the method described below, plasmid pASLBC was constructed wherein hG-CSF cDNA was removed from pASLB3-3 and multicloning sites were introduced. Multicloning sites were produced using synthetic DNA.

1 μg of pASLB3-3 obtained in Sec. 1(4) of this Example was dissolved in 30 μl of Y-175 buffer and digested with 20 units of SalI and 20 units of MluI at 37° C. for two hours. The reaction solution was subjected to agarose gel electrophoresis to give about 3.1 kb of DNA fragment.

Separately, 1 μg of pASLB3-3 was dissolved in 30 μl of Y-0 buffer and digested with 20 units of KpnI at 37° C. for two hours. Then, sodium chloride was added to this reaction mixture to give NaCl concentration of 150 mM, and this plasmid was digested with 20 units of MluI at 37° C. for another two hours. The reaction mixture was subjected to agarose gel electrophoresis to give about 6.0 kb of DNA fragment.

Separately, as a liker for linking SalI cleavage site and KpnI cleavage site, the following DNA linker was synthesized. Restriction enzyme cleavage sites HindIII, EcoRV, SfiI, StuI and NotI are incorporated in the linker.

| SalI | HindIII | EcoRV | | SfiI | StuI | SfiI | NotI | | KpnI | | |
|------|---------|-------|---|------|------|------|------|---|------|---|---|
| 5'|TCGACA|AGCTTGAT|ATCGGCCTGTG|AGG|CCTCAC|TGGCCGC|GGCCGCGGTAC|3' | (52 mer) |
| 3'|GTTCGA|ACTA|TAGCCGGA|CACTCC|GGA|GTGACCGGCGCCGG|CGC|5' | (44 mer) |

The 52 mer and 44 mer single-stranded DNAs of the DNA linker were synthesized using a DNA synthesizer model 380A (Applied Biosystems). Each 0.2 μg of the synthesized DNAs was dissolved in 20 μl of T4 kinase buffer and phosphorylated with 30 units of T4 polynucleotide kinase at 37° C. for two hours.

The DNA fragments thus obtained, i.e., 0.1 μg of SalI-MluI fragment (3.1 kb) and 0.2 μg of KpnI-MluI fragment (6.0 kb) derived from pASLB3-3 were dissolved in T4 ligase buffer (30 μl). 0.01 μg of the above DNA linker and both DNA fragments were ligated with 175 units of T4 DNA ligase at 12° C. for 16 hours.

*Escherichia coli* HB101 strain was transformed using the reaction mixture according to the method by Cohen et al. to obtain an ampicillin resistant strain. From this transformant, a plasmid was isolated according to the known method. This plasmid was designated as pASLBC, and its structure was confirmed by restriction enzyme digestion.

Figure 6:
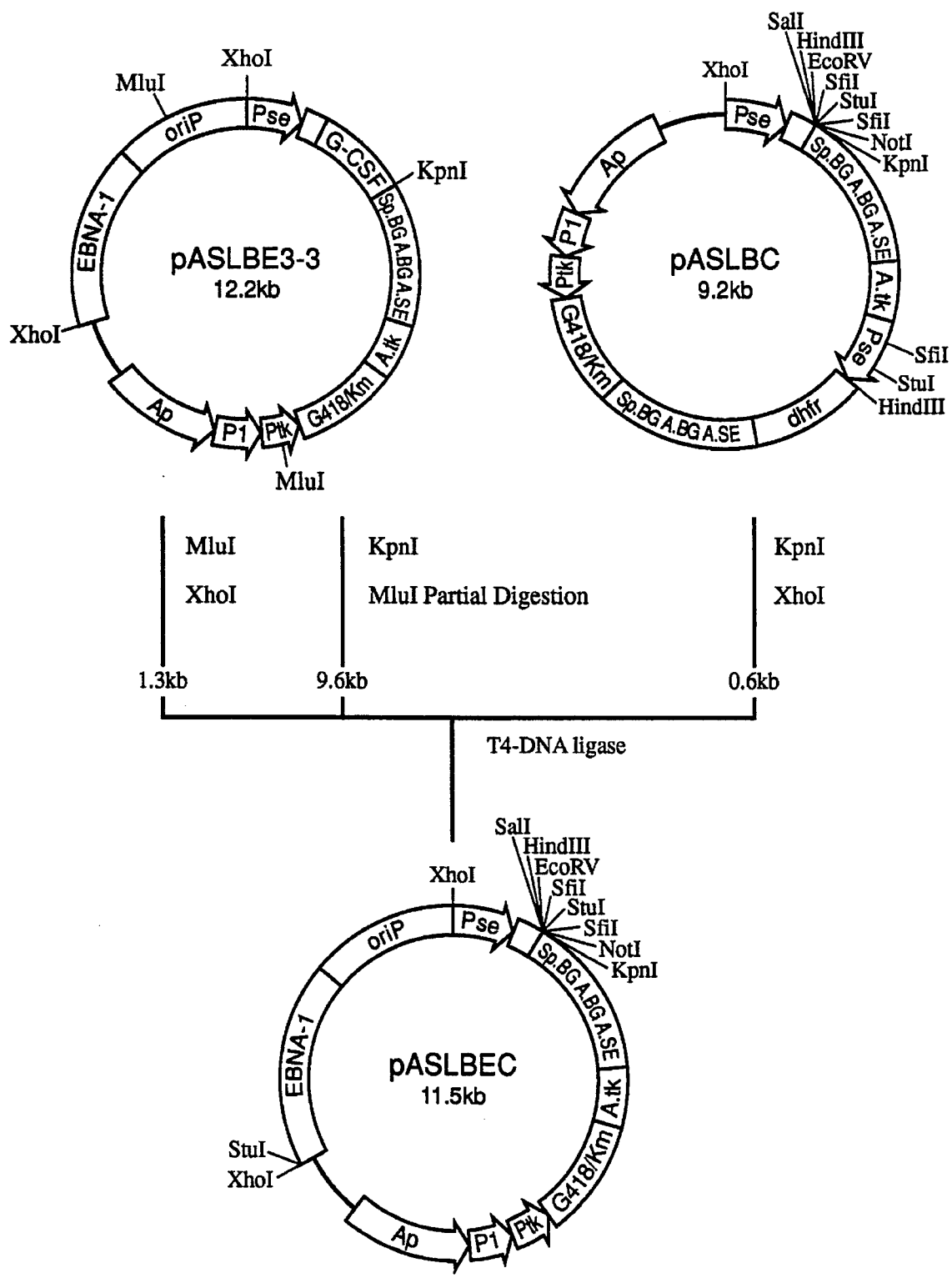
FIG. 6 is a flow sheet showing construction of plasmid pASLBEC.

(6) Construction of pASLBEC (see FIG. 6)

According to the method described below, plasmid pASLBEC was constructed by removing dihydrofolate reductase (dhfr) expression unit from pASLBC and introducing oriP and EBNA-1 genes therein.

1 μg of pASLBE3-3 obtained in Sec. 1(4) of this Example was dissolved in 30 μl of Y-150 buffer and digested with 20 units of MluI and 20 units of XhoI at 37° C. for two hours. The reaction solution was subjected to agarose gel electrophoresis to give about 1.3 kb of DNA fragment.

Separately, 1 μg of pASLBE3-3 was dissolved in 30 μl of Y-0 buffer and digested with 20 units of KpnI at 37° C. for two hours. Thereafter, sodium chloride was added to this reaction mixture to give NaCl concentration of 150 mM and this plasmid was partially digested with 5 units of MluI at 37° C. for 20 minutes. The reaction solution was subjected to agarose gel electrophoresis to give about 9.6 kb of DNA fragment.

Then, 1 μg of pASLBC obtained in Sec. 1(5) of this Example was dissolved in 30 μl of Y-0 buffer and digested with 20 units of KpnI at 37° C. for two hours. Thereafter, sodium chloride was added to this reaction mixture to give NaCl concentration of 100 mM and digested with 20 units of XhoI at 37° C. for another two hours. The reaction solution was subjected to agarose gel electrophoresis to give about 0.6 kb of DNA fragment.

The DNA fragments thus obtained, i.e., 0.2 μg of MluI-XhoI fragment (1.3 kb) and 0.2 μg of KpnI-MluI fragment (9.6 kb) derived from pASLBE3-3 and 0.05 μg of KpnI-XhoI fragment (0.6 kb) derived from pASLBC were dissolved in 30 μl of T4 ligase buffer and ligated together with 175 units of T4 DNA ligase at 12° C. for 16 hours.

*Escherichia coli* HB101 strain was transformed using the reaction mixture according to the method by Cohen et al. to obtain an ampicillin resistant strain. From this transformant, a plasmid was isolated according to the known method. This plasmid was designated as pASLBEC, and its structure was confirmed by restriction enzyme digestion.

Figure 7:
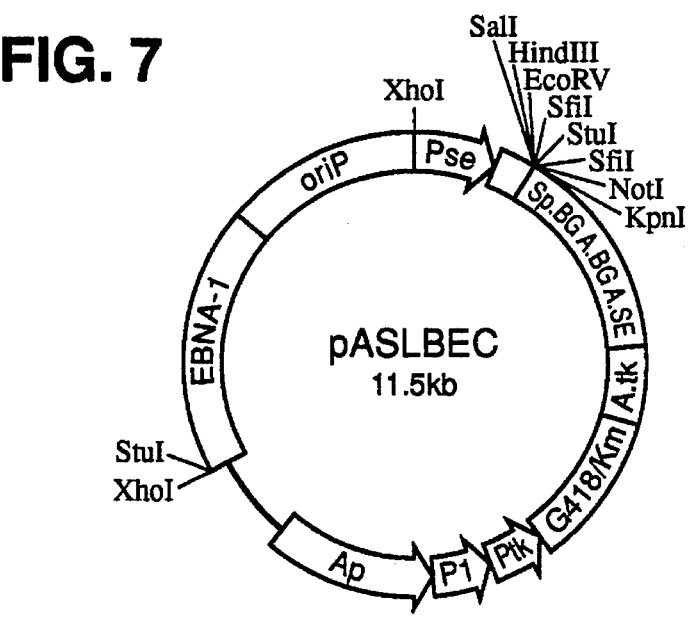
FIG. 7 is a flow sheet showing construction of plasmid pASLBEC2.
Figure 7:
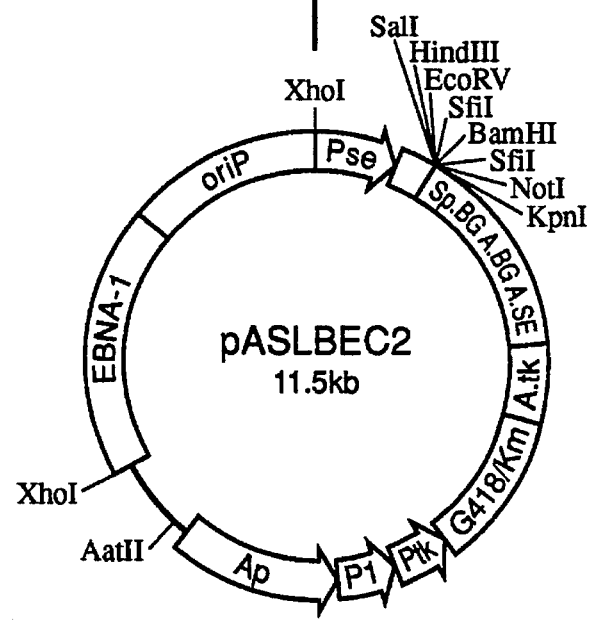

(7) Construction of pASLBEC2 (see FIG. 7)

According to the method described below, BamHI linker was introduced in StuI site in multicloning site of pASLBEC to obtain plasmid pASLBEC2. In pASLBEC2, StuI site in multicloning sites is lost.

1 μg of pASLBEC obtained in Sec. 1(6) of this Example was dissolved in 30 μl of Y-100 buffer and partially digested with 5 units of StuI at 37° C. for 20 minutes. The reaction solution was subjected to agarose gel electrophoresis to give about 11.5 kb of DNA fragment. The resulting DNA fragment was dissolved in 30 μl of T4 ligase buffer. The DNA fragment and 0.01 μg of BamHI linker (5'pCCGGATC-CGG3': manufacture by Takarashuzo) were ligated together with 175 units of T4 DNA ligase at 12° C. for 16 hours. After precipitation with ethanol, the precipitate was dissolved in 30 μl of Y-100 buffer and digested with 20 units of BamHI at 37° C. for two hours. The reaction solution was subjected to agarose gel electrophoresis to give about 11.5 kb of DNA fragment. The resulting DNA fragment was dissolved in T4 ligase buffer (20 μl) and ligated together with 175 units of T4 DNA ligase at 12° C. for 16 hours.

*Escherichia coli* HB101 strain was transformed using the reaction mixture according to the method by Cohen et al. to obtain an ampicillin resistant strain. From this transformant, a plasmid was isolated according to the known method. This plasmnid was designated as pASLBEC2, and its structure was confirmed by restriction enzyme digestion.

Figure 8:
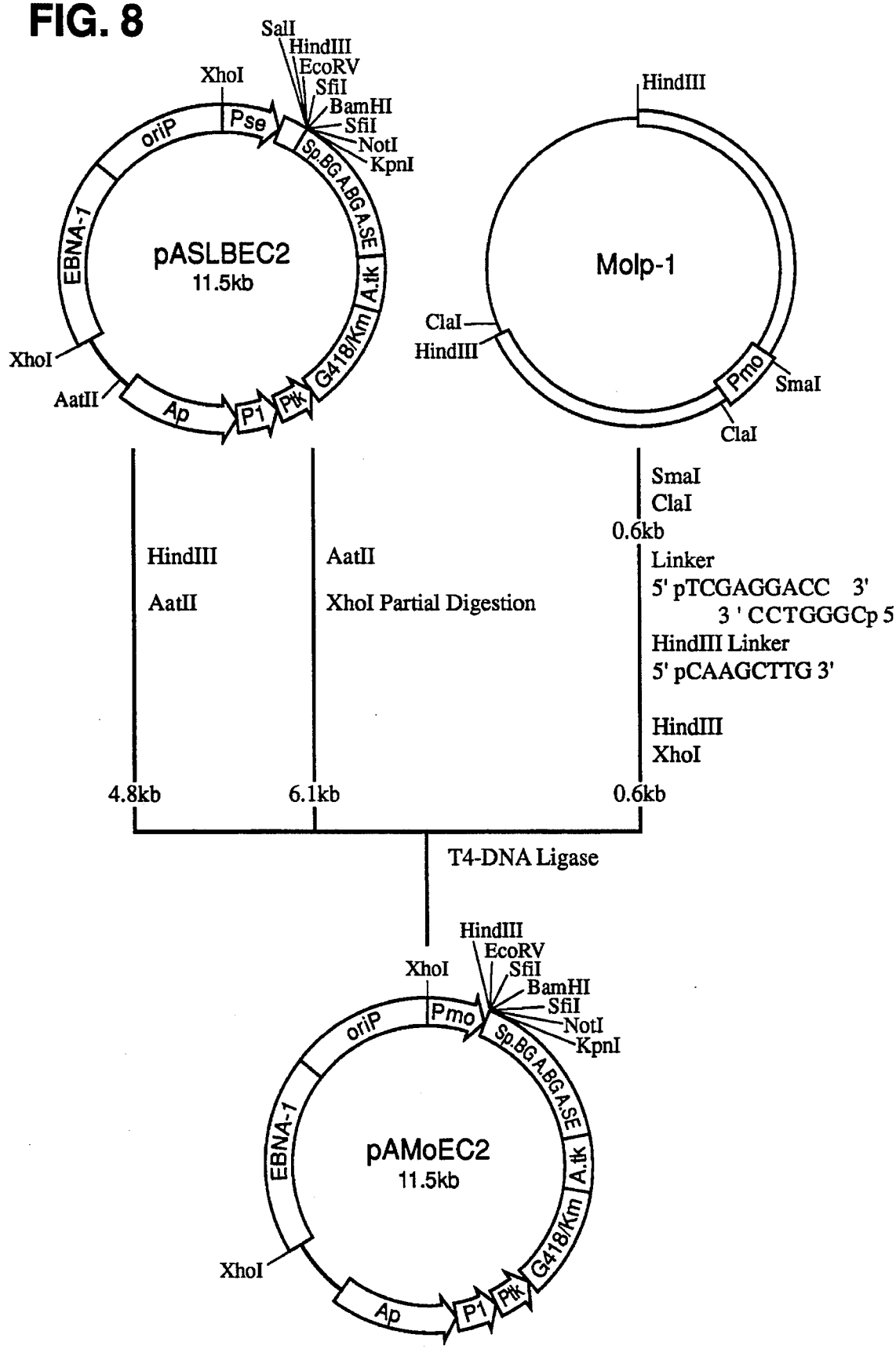
FIG. 8 is a flow sheet showing construction of plasmid pAMoEC2.

(8) Construction of pAMoEC2 (see FIG. 8)

According to the method described below, plasmid pAMoEC2 was constructed wherein promoter in pASL-BEC2 [promoter in which SV40 early gene promoter and a part of R region and U5 region of long terminal repeat (LTR) of HTLV-1 are fused] was replaced by promoter of long terminal repeat (LTR) of Moloney murine leukemia virus. For that use, Moloney murine leukemia virus LTR promoter was isolated from plasmid Molp-1 [Akinori Ishimoto et al.: Virology, 141, 30 (1985)].

1 µg of pASLBEC2 obtained in Sec. 1(7) of this Example was dissolved in a buffer (abbreviated as K-50 buffer hereinafter) containing 10 mM Tris-HCl (pH 7.5), 6 mM magnesium chloride, 50 mM potassium chloride and 6 mM 2-mercaptoethanol and digested with 20 units of HindIII and 20 units of AatII (manufactured by Toyoboseki) at 37° C. for two hours. The reaction solution was subjected to agarose gel electrophoresis to give about 4.8 kb of DNA fragment.

Separately, 1 µg of pASLBEC2 was dissolved in 30 µl of K-50 buffer and digested with 20 units of AatII at 37° C. for two hours. Thereafter, this plasmid was partially digested with 5 units of XhoI at 37° C. for 20 minutes. The reaction solution was subjected to agarose gel electrophoresis to give about 6.1 kb of DNA fragment.

Then, as a linker for linking XhoI cleavage site and ClaI cleavage site, the following linker was synthesized.

5'TCGAGGACC3' (9 mer)

3'CTGGGC5' (7 mer)

The 9 mer and 7 mer single-stranded DNAs of the above DNA liker were synthesized using a DNA synthesizer model 380A (Applied Biosystems). Each 0.2 µg of the synthesized DNAs was dissolved in 40 µl of T4 kinase buffer and phosphorylated with 30 units of T4 polynucleotide kinase at 37° C. for two hours.

Separately, 1 µl of Molp-1 [Akinori Ishimoto et al.: Virology, 141, 30 (1985)] was dissolved in 30 µl of K-20 buffer and digested with 20 units of SmaI at 37° C. for two hours. Thereafter, sodium chloride was added to this reaction mixture to give NaCl concentration of 50 mM and digested with 20 units of ClaI at 37° C. for two hours. The reaction solution was subjected to agarose gel electrophoresis to give about 0.6 kb of DNA fragment. The resulting DNA fragment was dissolved in 30 µl of T4 ligase buffer. The DNA fragment, 0.01 µg of the above DNA linker and 0.03 µg of HindIII linker (5'pCAAGCTTG3': manufactured by Takarashuzo) were ligated together with 175 units of T4 DNA ligase at 12° C. for 16 hours. After precipitation with ethanol, the precipitate was dissolved in 30 µl of a buffer (abbreviated as Y-50 buffer hereinafter) containing 10 mM Tris-HCl (pH 7.5), 6 mM magnesium chloride, 50 mM sodium chloride and 6 mM 2-mercaptoethanol and digested with 10 units of HindIII at 37° C. for two hours. Thereafter, sodium chloride was added to this reaction mixture to give NaCl concentration of 100 mM and digested with 10 units of XhoI at 37° C. for another two hours. The reaction solution was subjected to agarose gel electrophoresis to give about 0.6 kb of DNA fragment.

The DNA fragments thus obtained, i.e., 0.2 µg of HindIII-AatII fragment (4.8 kb) and 0.2 µg of AatII-XhoI fragment (6.1 kb) derived from pASLBEC2 and 0.05 µg of HindIII-XhoI fragment (0.6 kb) derived from Molp-1 were dissolved in 30 µl of T4 ligase buffer and ligated together with 175 units of T4 DNA ligase at 12° C. for 16 hours.

Escherichia coli HB101 strain was transformed using the reaction mixture according to the method by Cohen et al. to obtain an ampicillin resistant strain. From this transformant, a plasmid was-isolated-according to the known method. This plasmid was designated as pAMoEC2, and its structure was confirmed by restriction enzyme digestion.

Figure 9:
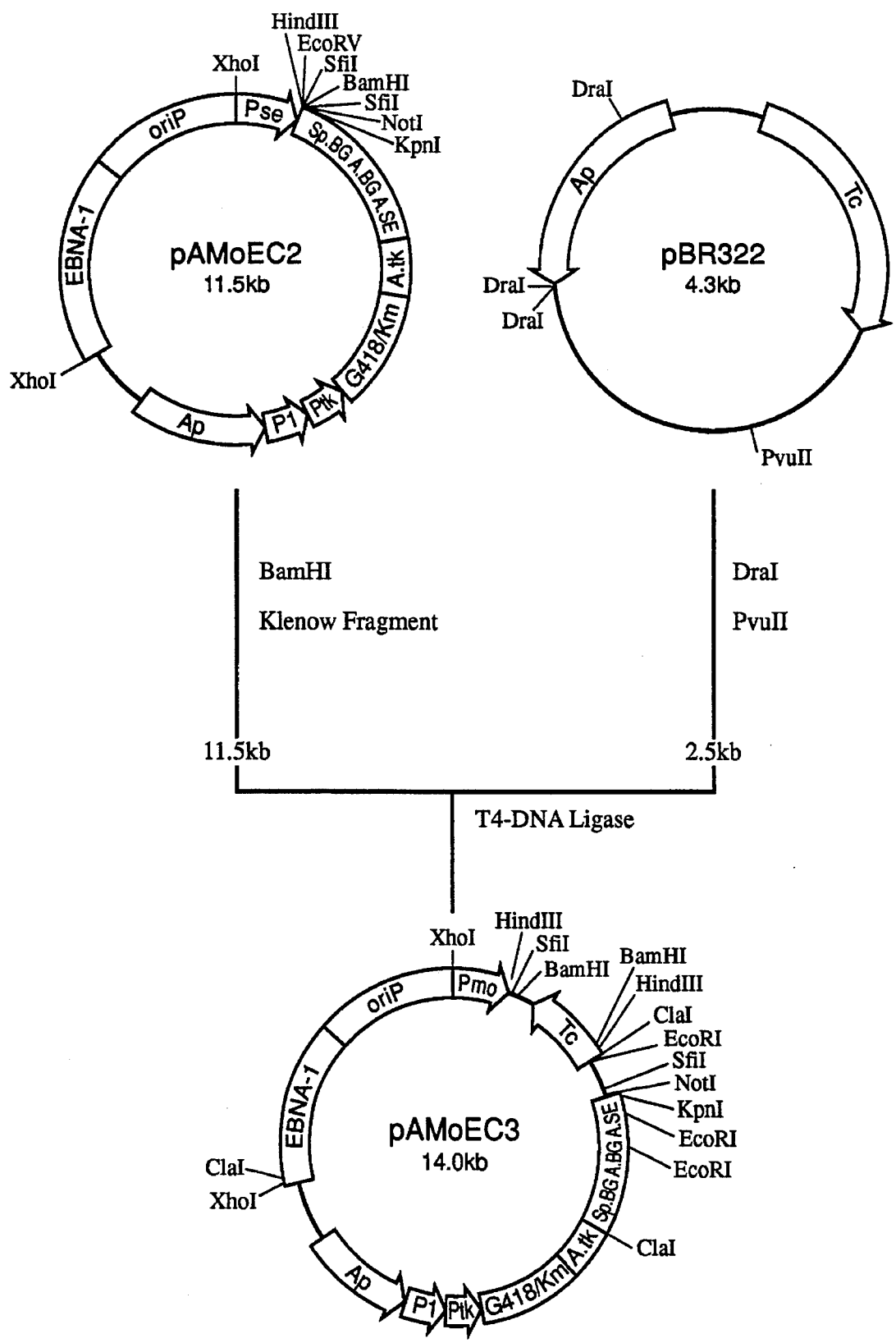
FIG. 9 is a flow sheet showing construction of plasmid pAMoEC3.

(9) Construction of pAMoEC3 (see FIG. 9)

According to the method described below, plasmid pAMoEC3 was constructed by inserting, as stuffer DNA, DNA fragment [DraI-PvuII fragment (2.5 kb)] containing tetracycline resistant gene of pBR322 into BamHI site in multicloning sites of pAMoEC2.

1 µg of pAMoEC2 obtained in Sec. 1(8) of this Example was dissolved in 30 µl of Y-100 buffer and digested with 20 units of BamHI at 37° C. for two hours. After precipitation with ethanol, the precipitate was dissolved in 30 µl of DNA polymerase I buffer, and 6 units of *Escherichia coli* DNA polymerase I Klenow fragment was added to react at 37° C. for 60 minutes, which resulted in conversion of 5' protruding cohensive end produced by BamHI into blunt end. The reaction solution was subjected to agarose gel electrophoresis to give about 11.5 kb of DNA fragment.

Separately, 1 µg of pBR322 [Bolivar et al.: Gene, 2, 95 (1977)] was dissolved in 30 µl of Y-50 buffer and digested with 20 units of DraI and 20 units of PvuII at 37° C. for two hours. The reaction solution was subjected to agarose gel electrophoresis to give about 2.5 kb of DNA fragment.

The DNA fragments thus obtained, i.e., 0.1 µg of BamHI (blunt end) fragment (11.5 kb) derived from pAMoEC2 and 0.2 µg of DraI-PvuII fragment (2.5 kb) derived from pBR322 were dissolved in 30 µl of T4 ligase buffer and ligated together with 175 units of T4 DNA ligase at 12° C. for 16 hours.

*Escherichia coli* HB101 strain was transformed using the reaction mixture according to the method by Cohen et al. to obtain an ampicillin and tetracycline resistant strain. From this transformant, a plasmid was isolated according to the known method. This plasmid was designated as pAMoEC3, and its structure was confirmed by restriction enzyme digestion.

Figure 10:
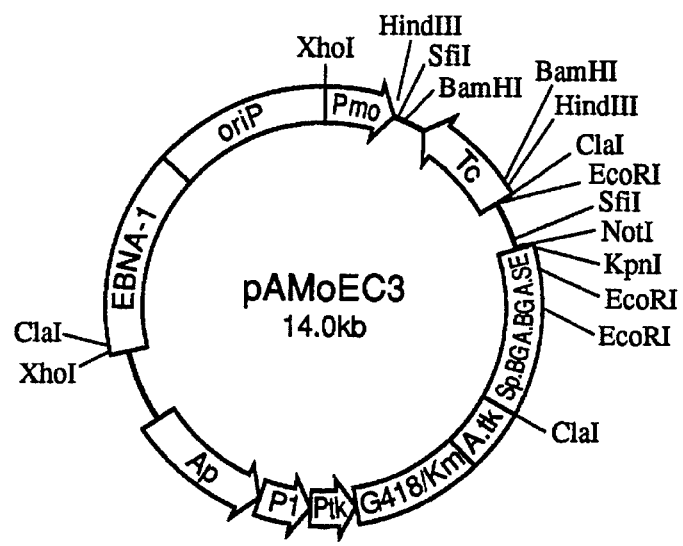
FIG. 10 is a flow sheet showing construction of plasmid pAMoERC3.
Figure 10:
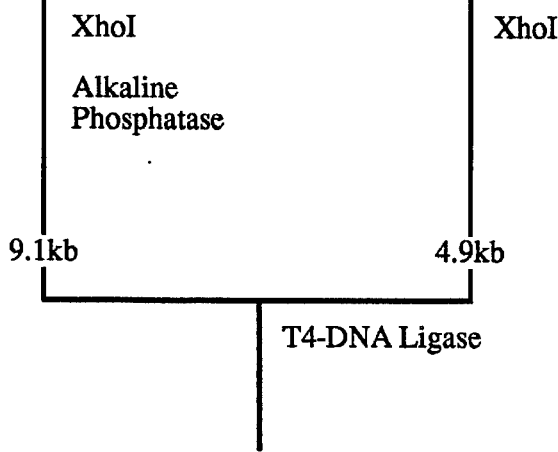
Figure 10:
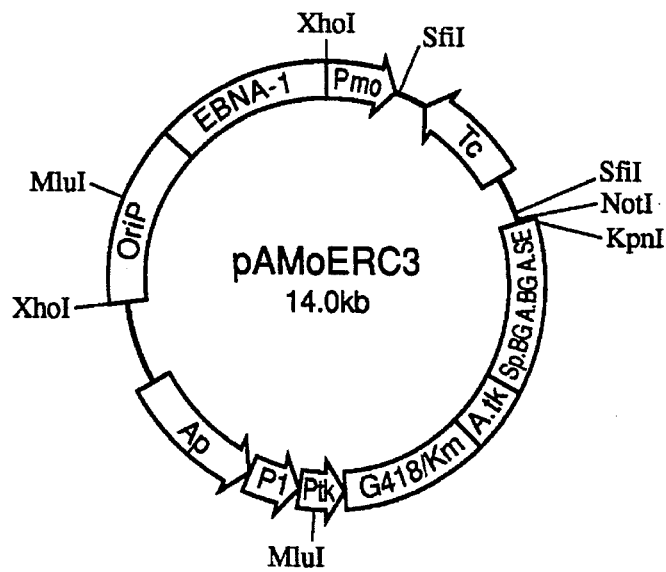

(10) Construction of pAMoERC3 (see FIG. 10)

According to the method described below, plasmid pAMoERC3 was constructed by inverting the orientation of oriP and EBNA-1 gene in plasmid pAMoEC3.

1 µg of pAMoEC3 obtained in Sec. 1(9) of this Example was dissolved in 30 µl of Y-100 buffer and digested with 20 units of XhoI at 37° C. for two hours. Thereafter, this plasmid was added to 30 µl of 1M Tris-HCl (pH 8.0) and dephosphorylated with one unit of *Escherichia coli* alkaline phosphatase (manufactured by Takarashuzo) at 37° C. for two hours. After precipitation with ethanol, the precipitate was dissolved in 30 µl of a buffer (abbreviated as TE buffer hereinafter) containing 10 mM Tris-HCl (pH 8.0) and 1 mM EDTA, and the mixture was subjected to agarose gel electrophoresis to give about 9.1 kb of DNA-fragment.

Separately, 1 µg of pAMoEC3 was dissolved in Y-100 buffer (30 µl) and digested with 20 units of XhoI at 37° C. for two hours. The reaction solution was subjected to agarose gel electrophoresis to give about 4.9 kb of DNA fragment.

The DNA fragments thus obtained, i.e., 0.1 µg of XhoI fragment (9.1 kb) and 0.2 µg of XhoI fragment (4.9 kb) derived from pAMoEC3 were dissolved in 30 µl of T4 ligase buffer and ligated together with 175 units of T4 DNA ligase at 12° C. for 16 hours.

*Escherichia coli* HB101 strain was transformed using the reaction mixture according to the method by Cohen et al. to obtain an ampicillin resistant strain. From this transformant, a plasmid was isolated according to the known method. This plasmid was designated as pAMoERC3, and its structure was confirmed by restriction enzyme digestion.

Figure 11:
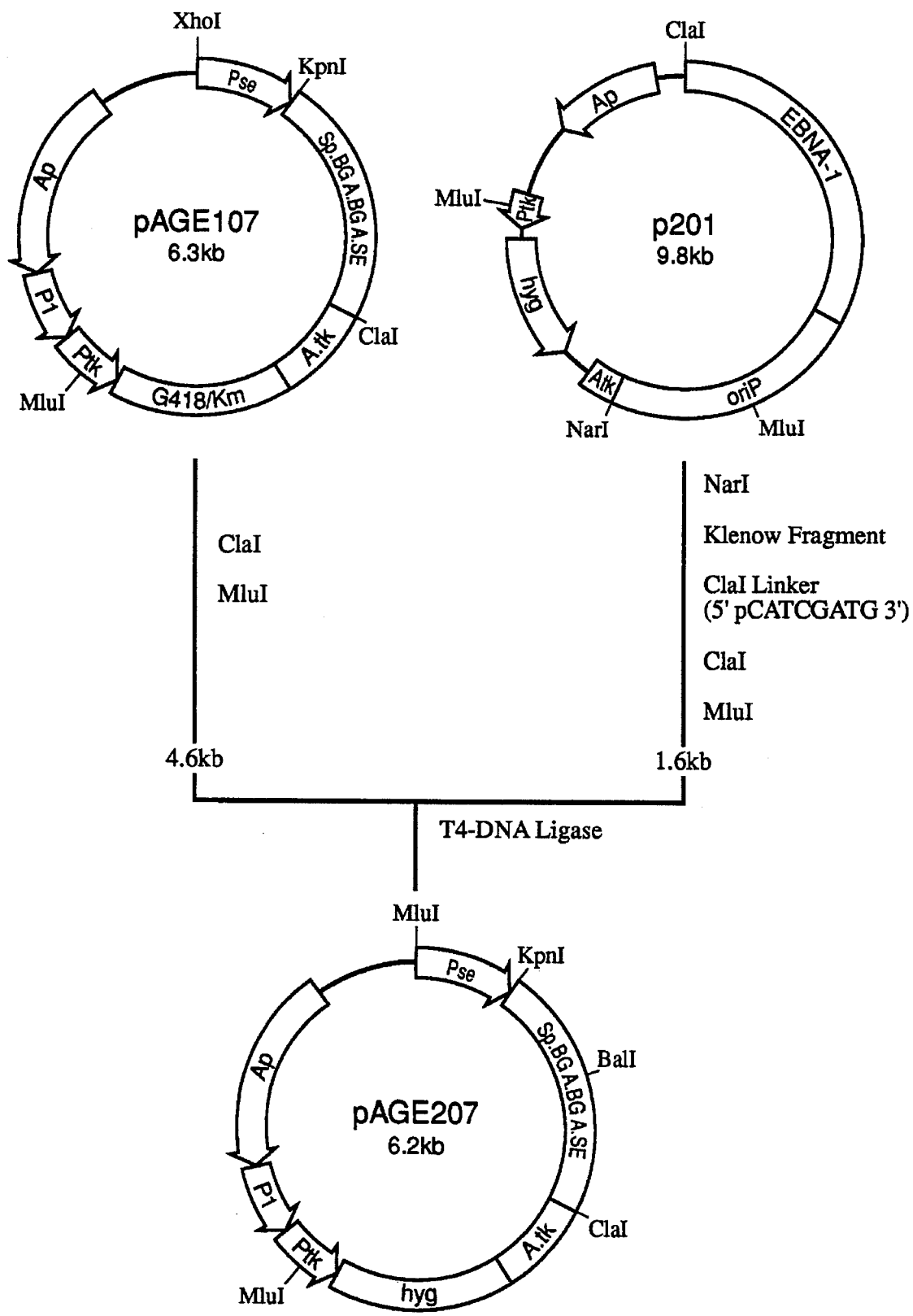
FIG. 11 is a flow sheet showing construction of plasmid pAGE207.

(11) Construction of pAGE207 (see FIG. 11)

According to the method described below, plasmid pAGE207 wherein G418 resistance gene in pAGE107 is replaced by hygromycin (hyg) resistance gene was constructed. For that use, hyg resistance gene was isolated from p201 [Bill Sugden et al., Nature, 313, 812 (1985)].

1 µg of pAGE107 obtained by the method described in JP-A 3-22979 was dissolved in 30 µl of Y-50 buffer and digested with 20 units of claI at 37° C. for two hours. Thereafter, sodium chloride was added to this reaction mixture to give NaCl concentration of 150 mM and digested with 20 units of MluI at 37° C. for another two hours. The reaction solution was subjected to agarose gel electrophoresis to give about 4.6 kb of DNA fragment.

Separately, 0.5 µg of p201 [Bill Sugden et al.: Nature, 313, 812 (1985)] was dissolved in 30 µl of Y-50 buffer and digested with 20 units of NarI [manufactured by New England Biolab] at 37° C. for two hours. After precipitation with ethanol, the precipitate was dissolved in DNA polymerase I buffer (30 µl), and 6 unites of *Escherichia coli* DNA polymerase I Klenow fragment was added to react at 37° C. for 60 minutes, which resulted in conversion of 5' protruding cohensive end produced by NarI digestion into blunt end. The reaction was stopped by extraction with phenol, extracted with chloroform, precipitated with ethanol, the precipitate was dissolved in 20 µl of T4 ligase buffer. The DNA and 0.05 µg of ClaI linker (5'pCATCGATG3': manufactured by Takarashuzo) were ligated together with 175 units of T4 DNA ligase at 12° C. for 16 hours. After precipitaiton with ethanol, the precipitate was dissolved in 30 µl of Y-50 buffer and digested with 10 units of ClaI at 37° C. for two hours. Thereafter, sodium chloride was added to this reaction mixture to give NaCl concentration of 150 mM and digested with 10 units of MluI at 37° C. for another two hours. The reaction solution was subjected to agarose gel electrophoresis to give about 1.6 kb of DNA fragment.

The DNA fragments thus obtained, i.e., 0.2 µg of ClaI-MluI fragment (4.6 kb) derived from pAGE107 and 0.1 µg of ClaI-MluI fragment (1.6 kg) derived from p201 were dissolved in 30 µl of T4 ligase buffer and ligated together with 175 units of T4 DNA ligase at 12° C. for 16 hours.

*Escherichia coli* HB101 strain was transformed using the reaction mixture according to the method by Cohen et al. to obtain an ampicillin resistant strain. From this transformant, a plasmid was isolated according to the known method. This plasmid was designated as pAGE207, and its structure was confirmed by restriciton enzyme digestion.

Figure 12:
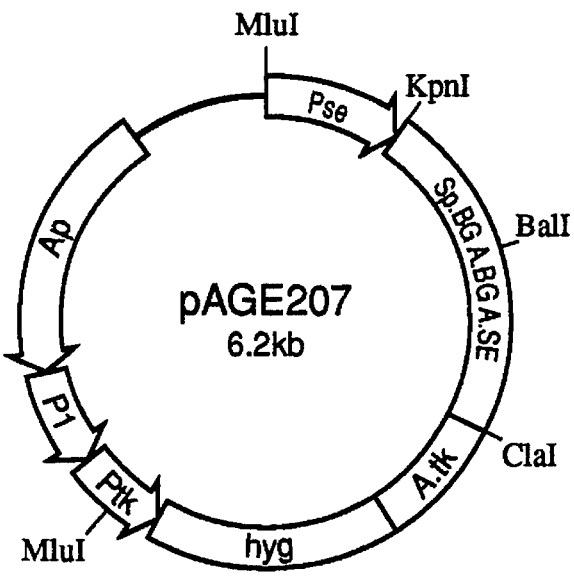
FIG. 12 is a flow sheet showing construction of plasmid pAGE207ScN.
Figure 12:
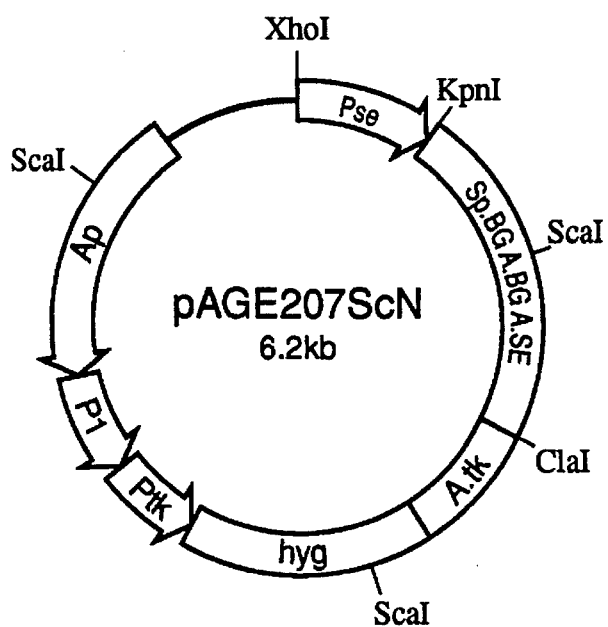

(12) Construction of pAGE207ScN (see FIG. 12)

According to the method described below, in order to remove the similar sequence with SfiI site present in rabbit βglobin gene, plasmid pAGE207ScN in which ScaI linker is inserted at Bali site of pAGE207 was constructed. In pAGE207ScN, the number of inserted ScaI linkers is indefinite.

0.5 µg of pAGE207 obtained in Sec. 1(11) of this Example was dissolved in 30 µl of Y-0 buffer and digested with 10 units of BaII at 37° C. for two hours. After precipitation with ethanol, the precipitate was dissolved in 20 µl of T4 ligase buffer. The DNA and 0.01 µg of ScaI linker (5'pAAGTACTT3: manufactured-by Takarashuzo) were ligated together with 175 units of T4 DNA ligase at 12° C. for 16 hours.

*Escherichia coli* HB101 strain was transformed using the reaction mixture according to the method by Cohen et al. to obtain an ampicillin resistant strain. From this transformant, a plasmid was isolated according to the known method. This plasmid was designated as pAGE207ScN, and its structure was confirmed by restriction enzyme digestion.

Figure 13:
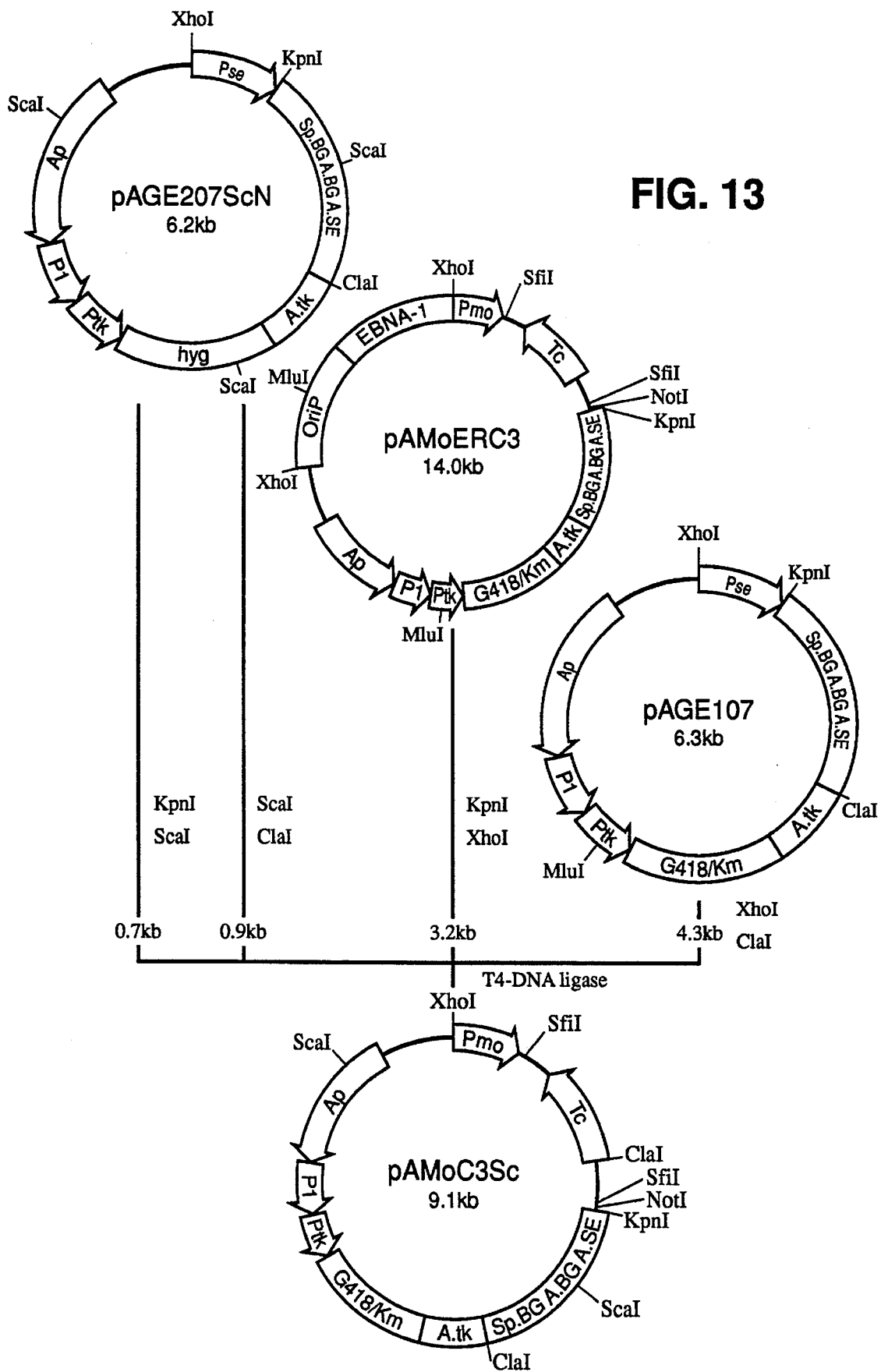
FIG. 13 is a flow sheet showing construction of plasmid pAMoC3Sc.

(13) Construction of Plasmid pAMoC3Sc (see FIG. 13)

According to the method as described below, plasmid pAMoERC3Sc was constructed, in which case for the purpose of removing a similar sequence with SfiI site of rabbit βglobin gene in the plasmid pAMoERC3, the rabbit βglobin gene in the plasmid pAMoERC3 was replaced with the rabbit βglobin gene in the plasmid pAGE207ScN from which that similar sequence had already been removed. For convenience, plasmid pAMoC3Sc was first constructed, and then the plasmid pAMoERC3Sc was constructed. The number of ScaI linkers inserted into the plasmid pAGE207ScN to remove the similar sequence with SfiI site is unknown. In the case of pAMoERC3Sc, however, from the fact that the pAGE207ScN was once digested with ScaI at the time of its construction, it is deduced that the number of ScaI sites inserted thereinto is only one.

First, 1 µg of the pAGE207ScN obtained in Sec. 1(12) of this Example was dissolved in 30 µl of Y-0 buffer and digested with 20 units of KpnI at 37° C. for 2 hours. Then, sodium chloride was added to give an NaCl concentration of 100 mM, and this plasmid was further digested with 20 units of ScaI at 37° C. for 2 hours. The reaction mixture was subjected to agarose gel electrophoresis to give an about 0.7 kb DNA fragment.

Also, 1 µg of the pAGE207ScN was dissolved in 30 µl of Y-100 buffer and digested with 20 units of ScaI and 20 units of ClaI at 37° C. for 2 hours. The reaction mixture was subjected to agarose gel electrophoresis to give an about 0.9 kb DNA fragment.

Separately, 1 µg of the pAMoERC3 obtained in Sec. 1(10) of this Example was dissolved in 30 µl of Y-0 buffer and digested with 20 units of KpnI at 37° C. for 2 hours. Then, sodium chloride was added to give an NaCl concentration of 100 mM, and this plasmid was further digested with 20 units of XhoI at 37° C. for 2 hours. The reaction mixture was subjected to agarose gel electrophoresis to give an about 3.2 kb DNA fragment.

Next, 1 µg of the pAGE107 obtained by the method described in the EP-A 0370205 was dissloved in 30 µl of Y-100 buffer and digested with 20 units of XhoI and 20 units of ClaI at 37° C. for 2 hours. The reaction mixture was subjected to agarose gel electrophoresis to give an about 4.3 kb DNA fragment.

The DNA fragments thus obtained, i.e., 0.1 µg of the KpnI-ScaI fragment (0.7 kb) derived from the pAGE207ScN, 0.1 µg of the scaI-ClaI fragment (0.9 kb) derived from the same plasmid, 0.3 µg of the KpnI-XhoI fragment (3.2 kb) derived from the pAMoERC3, and 0.3 µg of the XhoI-ClaI fragment (4.3 kb) derived from the pAGE107 were dissolved in 30 µl of T4 ligase buffer and ligated together with 175 units of T4 DNA ligase at 12° C. for 16 hours.

*Escherichia coli* HB101 strain was transformed using the reaction mixture according to the method of Cohen et al. to obtain an ampicillin resistant strain. From this transformant, a plasmid was isolated according to the known method. This plasmid was designated as pAMoC3Sc, and its structure was confirmed by restriction enzyme digestion.

Figure 14:
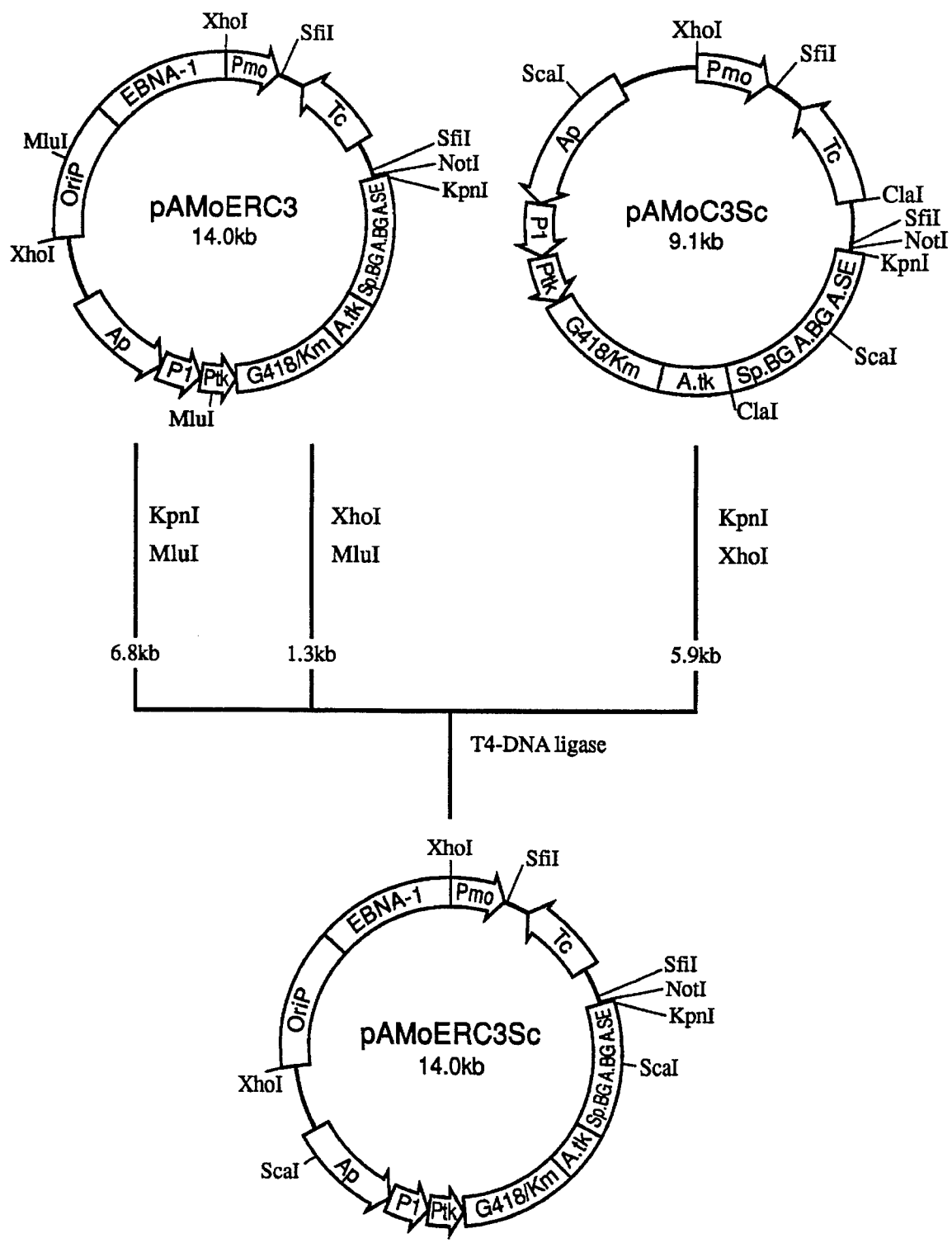
FIG. 14 is a flow sheet showing construction of plasmid pAMoERC3Sc.

(14) Construction of Plasmid pAMoERC3Sc (see FIG. 14)

First, 1 µg of the pAMoERC3 obtained in Sec. 1(10) of this Example was dissloved in 30 µl of Y-0 buffer and digested with 20 units of KpnI at 37° C. for 2 hours. Then, sodium chloride was added to give an NaCl concentration of 150 mM, and this plasmid was further digested with 20 units of MluI at 37° C. for 2 hours. The reaction mixture was subjected to agarose gel electrophoresis to give an about 6.8 kb DNA fragment.

Also, 1 μg of the pAMoERC3 was dissolved in 30 μl of Y-150 buffer and digested with 20 units of XhoI and 20 units of MluI at 37° C. for 2 hours. The reaction mixture was subjected to agarose gel electrophoresis to give an about 1.3 kb of DNA fragment.

Separately, 1 μg of the pAMoC3Sc was dissloved in 30 1 of Y-0 buffer and digested with 20 units of KpnI at 37° C. for 2 hours. Then, sodium chloride was added to this reaction mixture to give an NaCl concentration of 100 mM, and this plasmid was digested with 20 units of XhoI at 37° C. for 2 hours. The reaction mixture was subjected to agarose gel electrophoresis to give an about 5.9 kb DNA fragment.

The DNA fragments thus obtained, i.e., 0.2 μg of the KpnI-MluI fragment (6.8 kb) derived from the pAMoERC3, 0.05 μg of the XhoI-MluI fragment (1.3 kb) derived from the same plasmid, and 0.2 μg of the KpnI-XhoI fragment (5.9 kb) derived from the pAMoC3Sc Were dissloved in 30 μl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAMoERC3Sc, and its structure was confirmed by restriction enzyme digestion.

The plasmid pAMoERC3Sc has a long terminal repeat of Moloney murine leukemia virus as a promoter for expression of heterogeneous genes. For the purpose of attaining high efficiency in the expression of heterogeneous genes, this plasmid is desighed to have a rabbit βglobin gene splicing signal, a rabbit βglobin gene poly A addition signal, and an SV40 early gene poly A addition signal after the position of a heterogeneous genes to be inserted. Moreover, this plasmid has a G418 resistance gene as a drug resistance marker for animal cells and a kanamycin resistance gene (the same as the G418 resistance gene) and an ampicillin resistance gene as drug resistant markers for *Escherichia coli* cells, respectively. Further, this plasmid has a replication origin (oriP) of Epstein-Barr viruses and an EBNA-1 gene which is a trans-acting factor on the oriP to cause replication, so that it can be present in many kinds of cells, including Namalwa cells other than rodent cells, in the form of a plasmid without being incorporated into their chromosomes.

2. Resistance of Namalwa cells to *Ricinus communis* 120 lectin

Namalwa cells conditioned for serum-free media (KJM-1 strain) (Hosoi et al., Cytotechnology, 1, 151 (1988)) were cultured in the presence of *Ricinus communis* 120 lectin at various concentrations, and the resistance of the KJM-1 strain to *Ricinus communis* 120 lectin was examined. The KJM-1 strain was suspended in RPMI1640.ITPSGF medium (RPMI1640 medium (Nissui Seiyaku) containing a 1/40 volume of 7.5% $NaHCO_3$, 200 mM L-glutamine solution (GIBCO) of 3% in volume, penicillin-streptomycin solution (GIBCO; 5000 units/ml penicillin and 5000 μg/ml streptomycin) of 0.5% in volume, 10 mM HEPES, 3 μg/ml insulin, 5 μg/ml transferrin, 5 mM sodium pyruvate, 125 nM sodium selenate, 1 mg/ml galactose, and 0.1% (w/v) prulonic F68) to give a concentration of $5 \times 10^4$ cells/ml, and the suspension was distributed in 200-μl portions into wells of a 96-well microtiter plate. Various concentrations of *Ricinus communis* 120 lectin (Seikagaku Kogyo) were added thereto in 1/100 volumes, and the plate was incubated in a $CO_2$ incubator at 37° C. for 1 to 2 weeks. As the result, it was found that the minimum concentration of *Ricinus communis* 120 lectin to cause complete inhibition of the KJM-1 strain growth was 50 ng/ml. Four million cells of the KJM-1 strain were examined, and the natural occurrence of *Ricinus communis* 120 lectin resistant strain was not observed.

3. Cloning of α2→3 sialyltransferase cDNA (LEC) from human histiocytic leukemia cell line TYH (1) Isolation of mRNA from TYH cells From $1 \times 10^8$ TYH cells (Haranaka et al., Int. J. Cancer, 36, 313 (1985)), about 40 μg of mRNA was isolated using the mRNA extraction kit "Fast Track" (Invitrogen; trade No. K1593-02).

Figure 15:
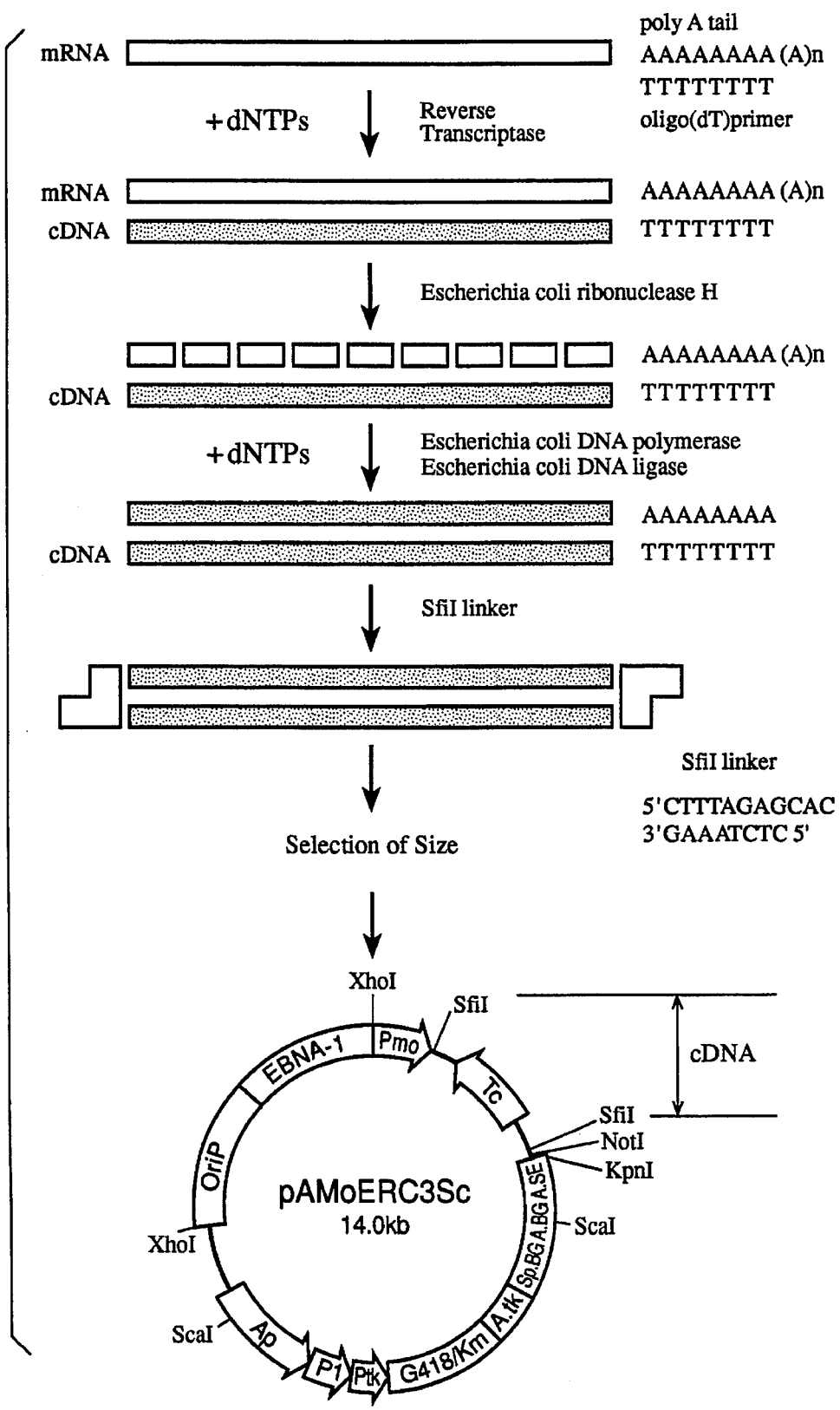
FIG. 15 is s flow sheet showing construction of cDNA library.

(2) Preparation of cDNA library (see FIG. 15)

From 8 μg of mRNA obtained above, double-stranded cDNA was prepared using the cDNA synthesis kit "The Librarian I" (Invitrogen) with a random primer as a primer. Then, each of the SfiI linkers (Seq. ID: 5) as shown below was provided, instead of BstXI linkers, at either terminus of the cDNA. The cDNA-was fractioned in size by agarose gel electrophoresis and cDNA fragments larger than about 1.2 kb were isolated.

SfiI Linkers:

5'-CTTTAGAGCAC-3' (11 mer)

3'-GAAATCTC-5' (8 mer)

The 11 mer and 8 mer single-stranded DNAs of SfiI linkers were synthesized using a DNA synthesizer model 380A (Applied Biosystems). Then, 50 μg of each of the synthesized DNAs was dissloved in 50 μl of T4 kinase buffer and phosphorylated with 30 units of T4 polynucleotide kinase (Takara Shuzo) at 37° C. for 16 hours. The specific reagents and procedures were as described in the manufacturer's instructions accompanying the kit used, except that the above SfiI linkers were used in place of BstXI linkers.

Also, 24 μg of pAMoERC3Sc, which is a direct expression cloning vector, was dissloved in 590 μl of Y-50 buffer and digested with 80 units of SfiI at 37° C. for 16 hours. Then, 5 μl of this solution was subjected to agarose gel electrophoresis, and after the completion of digestion was confirmed, for the purpose of decreasing the amount of clones having no cDNA insert-incorporated at the time of cDNA library construction, this plasmid was further digested with 40 units of BamHI at 37° C. for 2 hours. The reaction mixture was subjected to electrophoresis to give about 11.5 kb DNA fragment.

Next, 2 μg of the SfiI fragment (11.5 kb) derived from the pAMoERC3Sc, together with the cDNA obtained above, was dissolved in 250 μl of T4 ligase buffer and ligated together with 2000 units of T4 DNA ligase at 12° C. for 16 hours. Then, 5 μg of transfer RNA (tRNA) was added thereto, followed by ethanol precipitation, and the resulting precipitate was dissolved in 20 μl of TE buffer. With this reaction mixture, *Escherichia coli* strain LE392 (Maniatis et al., ed., Molecular Cloning, 2.58, Cold Spring Harbor, 1989) was tranformed by electroporation (William J. Dower et al., Nucleic Acids Res., 16, 6127 (1988)) to give about 200,000 ampicillin resistant transformants.

(3) Cloning of α2→3 sialyltransferase cDNA (LEC)

About 200,000 ampicillin-resistant transformants (cDNA library) obtained in Sec. 3(2) of this Example were mixed, after which a plasmid was prepared using >plasmid<maxi kit (trade No. 41031; Qiagen) which is a plasmid preparation kit. The obtained plasmid was ethanol precipitated, and the resulting precipitate was dissolved in TE buffer to give a concentration of 1 μg/μl.

The above plasmid was introduced into the KJM-1 strain by electroporation (Miyaji et al., Cytotechnology, 3, 133 (1990)) at a proportion of 4 μg per 1.6×10⁶ cells. After the introduction of plasmid, these cells were suspended in 8 ml of RPMI1640.ITPSGF medium, and the cells were incubated in a $CO_2$ incubator at 37° C. for 24 hours. Then, the cells were supplemented with G418 (GIBCO) to give a concentration of 0.5 mg/ml and further cultured for 5 to 7 days to give transformants. The obtained transformants were suspended in RPMI1640.ITPSGF medium containing *Ricinus communis* 120 lectin (50 ng/ml) to give a concentration of $5\times10^4$ cells/ml, and the cells were distributed in 200-μl portions into wells of a 96-well microtiter plate. The cells were cultured in a $CO_2$ incubator at 37° C. for 2 to 3 weeks, and 7 strains were obtained which had become resistant to a *Ricinus communis* 120 lectin. From this resistant strain, a plasmid was isolated according to the Hirt method (Robert F. Margolskee et al., Mol. Cell. Biol., 8, 2837 (1988)), and *Escherichia coli* strain LE392 was transformed with this plasmid by electroporation (Willium J. Dower et al., Nucleic Acids Res., 16, 6127 (1988)). From this transformant, a plasmid was prepared using >plasmid<maxi kit (trade No. 41031; Qiagen), and its structure was examined by restriction enzyme digestion to find that it contained about 1.9 kb cDNA. The cDNA containing plasmid was designated as pAMoERL. When this plamid was also introduced into the KJM-1 strain by the above method, this strain became resistant to *Ricinus communis* 120 lectin; it was therefore found that this cDNA is a gene responsible for lectin resistance. The KJM-1 strain containing the plasmid pAMoERL was able to grow even in the presence of 200 ng/ml of *Ricinus communis* 120 lectin.

4. Sequensing of α2→3 sialyltransferase cDNA (LEC)

(1) Introduction of α2→3 sialyltransferase cDNA (LEC) into pUCl19 (see FIG. 16)

First, 1 μg of pAMoERL obtained in Sec. 3(3) of this Example was dissloved in 30 μl of Y-100 buffer and digested with 20 units of ECoRV and 20 units of Asp718 (Boehringer Mannheim) at 37° C. for 2 hours. The reaction mixture was subjected to electrophoresis to give an about 1.97 kb DNA fragment.

Separately, 1 μg of pUCl19 (Messing et al., Methods in Enzymology, 153, 3 (1987)) was dissloved in 30 μl of K-20 buffer and digested with 20 units of SmaI at 37° C. for 2 hours. Then, sodium chloride was added to give an NaCl concentration of 100 mM, and this plasmid was further digested with 20 units of Asp718 at 37° C. for 2 hours. The reaction mixture was subjected to electrophoresis to give an about 3.16 kb DNA fragment.

The DNA fragments thus obtained, i.e., 0.2 μg of the ECoRV-Asp718 fragment (1.97 kb) derived from the pAMoERL and 0.1 μg of the SmaI-Asp718 fragment (3.16 kb) derived from the pUCl19 were dissloved in 30 μl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pUCl19-LEC, and its structure was confirmed by restriction enzyme digestion.

(2) Construction of deletion plasmids for sequencing

First, 2 μg of pUCl19-LEC obtained in Sec. 4(1) of this Example was dissloved in 30 μl of Y-150 buffer and digested with 20 units of BamHI and 20 units of SphI at 37° C. for 2 hours. After ethanol precipitation, the resulting precipitate was dissolved in 100 μl of ExoIII buffer (deletion kit for kilo-sequence; Takara Shuzo). Also, 2 μg of pUCl19-LEC was dissloved in 30 μl of Y-0 buffer and digested with 20 units of SacI at 37° C. for 2 hours. Then, sodium chloride was added to give an NaCl concentration of 150 mM, and this plasmid was further digested with 20 units of NotI at 37° C. for 2 hours. After ethanol precipitation, the resulting precipitate was dissloved in 100 μl of ExoIII buffer.

From the BamHI-SphI fragment and the SacI-NotI fragment thus obtained from the pUCl19-LEC, several tens of deletion plasmids were prepared, respectively, using the deletion kit for kilo-sequence (Takara Shuzo).

The nucleotide sequence of the deletion plasmid obtained above was determined using the Taq DyeDeoxy terminator cycle sequencing kit (trade No. 401113; Applied Biosystems). The determined nucleotide sequence is shown in the Sequence Listing (Seq. ID: 1). Also, it was found from the corresponding-amino acid sequence that this protein has a common structure to glycosyltransferase (hereinafter abbreviated to GT). That is, this protein seems to have a structure where 8 amino acids in the N-terminal portion are put out at the cytoplasm side, a highly hydrophobic region consisting of the subsequent 18 amino acids is used for binding to the membrane, and most of the remaining C-terminal portion including -the catalytic site is exposed to the internal cavity of the Golgi's apparatus. The comparison of amino acid sequence between this protein and other GTs made clear that this protein has a certain homology with rat α2→6 sialyltransferase. For these reasons, it is considered that *Ricinus communis* 120 lectin resistance gene encodes GT.

5. Measurement of α2→3 sialyltrasferase activity of the KJM-1 strain having expression plasmid for *Ricinus communis* 120 lectin resistance gene The KJM-1 strain having the plasmid pAMoERL obtained in Sec. 3 of this Example was suspended in 30 ml of RPMI1640.ITPSGF medium containing 0.5 mg/ml of G418 to give a concentration of $5\times10^5$ cells/ml, and the cells were cultured in a $CO_2$ incubator at 37° C. for 3 days. After the culturing, the cells were collected by centrifugation at 160×g for 10 minutes and washed with 10 ml of PBS (8 g/l NaCl, 0.2 g/l KCl, 1.15 g/l anhydrous sodium monohydrogenphosphate, 0.2 g/l potassium dihydrgenphosphate), followed by further centrifugation to collect the cells.

About $1.4\times10^7$ cells obtained above were suspended in 100 μl of homogenization buffer (250 mM saccarose, 10 mM Tris-HCl (pH 7.4)), and lysed by sonication. The lysate was cetrifuged at 550×g for 10 minutes to obtain a supernatant.

Also, as a control, the KJM-1 strain having the vector plasmid pAMoERC3Sc was prepared, and the above procedures were followed to obtain a supernatant.

Then, 20 μl of each of the two supernatants obtained above was allowed to react in an assay solution (0.1M cacodylic acid-HCl (pH 6.5), 0.01M $MnCl_2$, 0.45% Triton X-100, 0.08 mM substrate, 5 mM CMP-sialic acid (added or not added)) having the final volume of 50 μl at 37° C. for 2 hours, and the products were identifed by high performance liquid chromatography (HPLC) to determine the α2→3 sialyltransferase activity in the respective supernatants. The activity determinations were carried out using 200 μg of proteins in the supernatant, and protein quantitation was achieved using BCA protein assay reagent (PIERCE). As the substrate, a sugar chain fluorescence-labeled with aminopyridine (Galβ1→4GlcNAcβ1→3Galβ1→4Glc-aminopyridine) was used, The fluorescence labeling of the substrate was carried out using lacto-N-neotetraose (BioCarb Chemicals) by the conventional method (Akimoto Kondo, et al., Agric. Biol. Chem., 54, 2169 (1990)). Each of the supernatants was allowed to react with an assay solution containing or not containing CMP-sialic acid as a sugar donor. The reaction mixture was separated by HPLC, and the peaks appearing only with the assay solution containing CMP-sialic acid were considered as the products. After completion of the reaction, the assay solution was treated at 100° C. for 5 minutes, and centrifuged at 10,000×g for 10 minutes. The resulting supernatant was Subjected to HPLC which was carried out on the TSKgel ODS-80T$_M$ column (4.6 mm×30 cm; Tosoh) eluting with 0.02M ammonium acetate buffer (pH 4.0) at a temperature of 50° C. at a rate of 1 ml/min. The products were detected using the fluorescence HPLC monitor model RF-535T (Shimazu Seisakusho) with an excitation wavelength of 320 nm and an emission wavelength of 400 nm. As the result, peaks 1 and 2 were detected as the products, as shown in FIG. 17. From the facts that the elution time was identical with that of the standard and that the substrate was regenerated by sialidase treatment of the products, it was found that the peak 1 corresponds to NeuAcα2→6Galβ1→4GlcNAcβ1→3Galβ1→4Glc-aminopyridine and the peak 2 corresponds to NeuAcα2→3Galβ1→4GlcNAcβ1→3Galβ1→4 Glc-aminopyridine.

The sialidase treatment of the products was carried out as follows. First, 10 µl of the supernatant was subjected to HPLC, and the peaks 1 and 2 were fractioned and freeze-dried, independently, followed by dissolution in 50 µl of buffer containing 20 mM Tris-maleic acid (pH 6.0) and 1 mM calcium citrate. Then, 20 µl of the solution was treated with 2 µl of 400 mU/ml sialidase (neuraminidase; Sigma, N-2133) at 37° C. for 16 hours. Also, as a control, the same reaction was conducted using 2 µl of water in place of sialidase. After completion of the reaction, the solution was treated at 100° C. for 5 minutes, and centrifuged at 10,000×g for 10 minutes. Then, 10 µl of the supernatant was subjected to the above HPLC. The results are shown in FIG. 18. Both from the peak 1 and from the peak 2, peak 3 was detected as the product by sialidase treatment. In view of its elution time, the peak 3 is considered to be Galβ1→4GlcNAcβ1→3Galβ1→4Glc-aminopyridine as the substrate.

The comparison of HPLC pattern between the KJM-1 strain having the plasmid pAMoERL and the KJM-1 strain having the plasmid pAMoERC3Sc made clear that both the strains gave approximately the same peak 1 but the strain having the pAMoERL strain gave a significantly higher peak 2 than that of the strain having the pMoERC3Sc. The ratio of peak 2 to peak 1 for the KJM-1 strain having the pAMoERL was 6 to 7 times greater than that for the KJM-1 strain having the pAMoERC3Sc as the vector (see FIG. 17). From these results, it was shown that this *Ricinus communis* 120 lectin resistance gene is an α2→3 sialyltransferase gene and that oligosaccharides with sialic acid added can be produced using α2→3 sialyltransferase encoded in the said gene.

EXAMPLE 2

Synthesis of sialyl-Le$^x$ in the strain KJM-1 having the expression plasmid for α2→3 sialyltransferase:

The KJM-1 strain having the plasmid pAMoERL obtained in Sec. 3(3) of Example 1 and the strain KJM-1 having the direct expression cloning vector pAMoERC3Sc obtained in Sec. 1(14) of Example 1 were independently cultured in the RPMI1640.ITPSGF medium containing 0.5 mg/ml of G418. Then, about 1×10$^6$ cells of each strain were taken in a microtube (1.5 ml; Eppendorf) and centrifuged at 550×g for 7 minutes. The collected cells were washed with 1 ml of PBS containing 0.1% sodium azide (hereinafter abbreviated as A-PBS), and the expression of sialyl-Le$^x$ in the cells of each strain was examined by indirect fluorescent antibody staining with KM93 (Shitara et al., Anticancer Res., 9, 999 (1989)) which is a monoclonal antibody reacting with sialyl-Le$^x$, as described below.

Figure 19A:
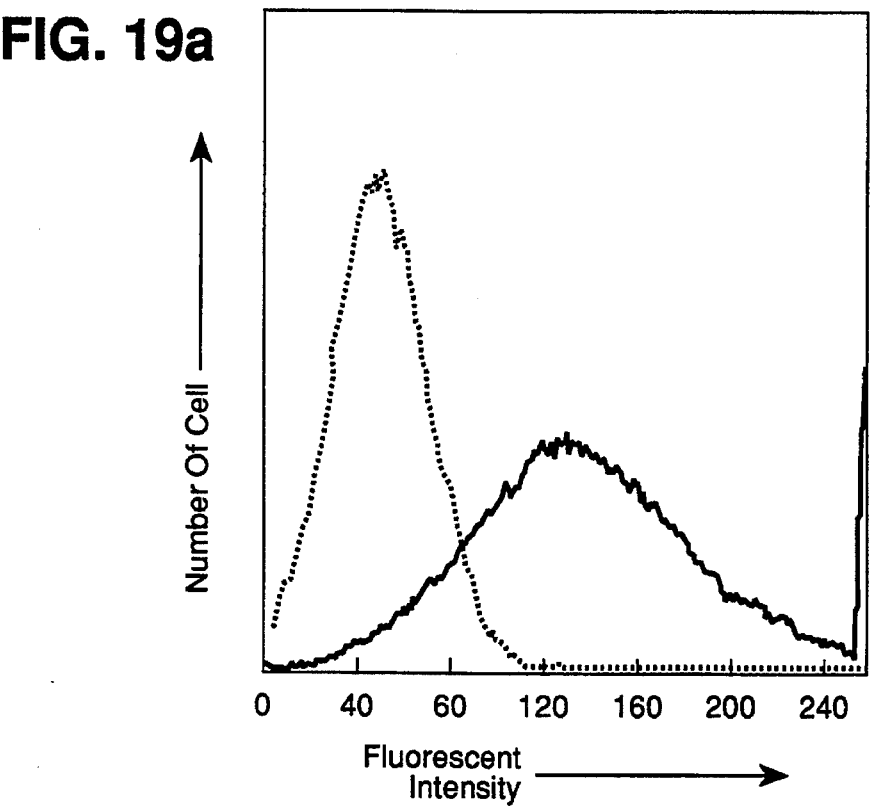
FIG. 19 is a view showing the results of analysis by a flow cell sorter FCS-1 (manufactured by Nihonbunko) after indirect fluorescent antibody staining. Pannel a shows the results of indirect fluorescent antibody staining using KM93 or serum of normal mouse on KJM-1 in which pAMoERC3Sc is introduced. Dotted line shows the pattern when normal mouse serum is used, and solid line shows the pattern when KM93 is used. Pannel b shows the results of indirect fluorescent antibody staining using KM93 on KJM-1 strain in which pAMoERL is introduced. Dotted line is the same one shown in Pannel a., and solid line shows the pattern when KM93 is used.
Figure 19B:
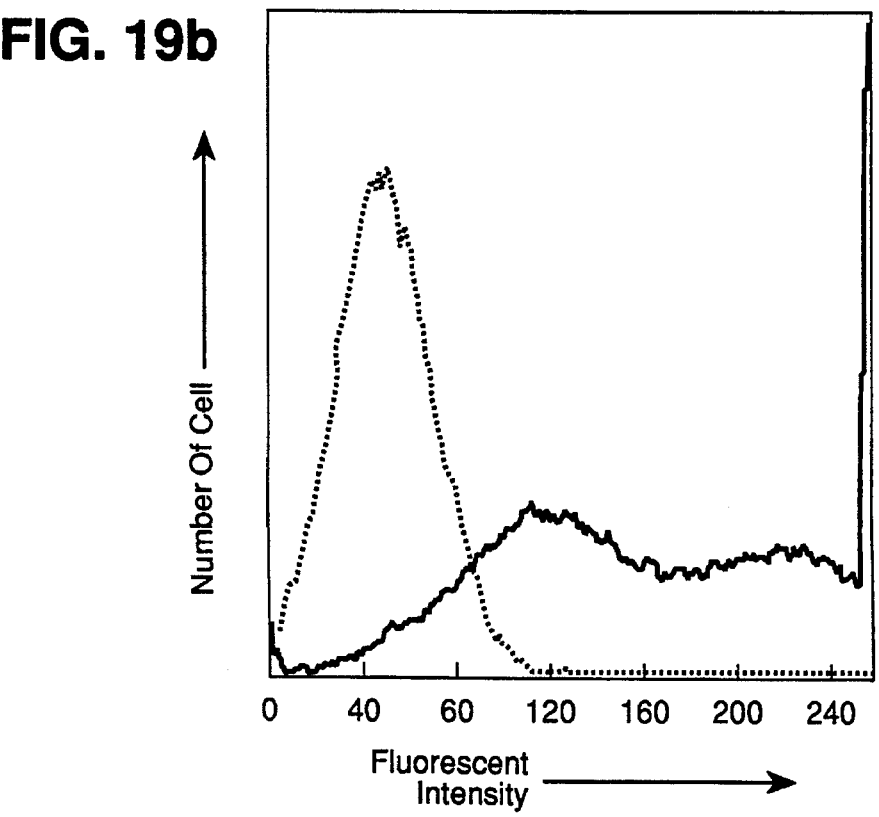

The cells of each strain were suspended in 50 µl of A-PBS solution containing 10 µg/ml KM93 and allowed to react at 4° C. for 1 hour. After washing three times with A-PBS, these cells were suspended in 20 µl of A-PBS containing the anti-mouse antibodies IgG and IgM (Cappel) diluted 20-fold with A-PBS which had been fluorescence-labeled with fluorescein isothiocyanate (FITC), and allowed to react at 4° C. for 30 minutes. After washing three times with A-PBS, these cells were again suspended in A-PBS, and analysis was carried out with the flow cell sorter FCS-1 (Nihon Bunko). As a control, the same analysis was carried out using the normal mouse serum diluted 500-fold with A-PBS in place of KM93. The results are shown in FIG. 19. The fluorescence intensity of the cells stained with KM93 for the KJM-1 strain having the direct expression cloning vector pAMoERC3Sc was stronger than that of the control (see FIG. 19(a)). This indicates that sialyl-Le$^x$ is also expressed in the original KJM-1 strain. The fluorescence intensity of the cells stained with KM93 for the KJM-1 strain having the plasmid pAMoERL capable of expressing cDNA encoding α2→3 sialyltrasferase of the present invention was further stronger than that of the strain KJM-1 containing the pAMoERC3Sc (see FIG. 19(b)). This indicates that sialyl-Le$^x$ is synthesized in cells by α2→3 sialyltransferase of the present invention.

EXAMPLE 3

Production by animal cells of α2→3 sialyltransferase derived from TYH cells:
1. Construction of plasmid pAMoPRSAL-35F for expression of cDNA encoding α2→3 sialyltransferase
   (1) Construction of pAGE147 (see FIG. 20)
   According to the method as described below, the plasmid pAGE147 was constructed by replacing the SV40 early gene promoter of the plasmid pAGE107 with a long terminal repeat (LTR) of Moloney murine leukemia virus as a promoter.

First, 2 µg of the plasmid pPMOL1 obtained by the method as described in JP-A 1-63394 was dissloved in 30 µl of Y-0 buffer and digested with 20 units of SmaI at 30° C. for 3 hours. Then, sodium chloride was added to give an NaCl concentration of 50 mM, and this plasmid was further digested with 20 units of ClaI at 37° C. for 2 hours. The reaction mixture was subjected to agarose gel electrophoresis to give an about 0.6 kb DNA fragment containing the LTR promoter of Moloney murine leukemia virus.

Next, 25 pmoles of each of the two synthetic DNA fragments as shown below, which had been synthesized in Sec. 1(8) of Example 1, were dissloved in 10 µl of T4 kinase buffer and phospholylated at their 5'-termini with 5 units T4 DNA kinase at 37° C. for 30 minutes.

5'-TCGAGGACC-3' (9 mer)

3'-CCTGGGC-5' (7 mer)

The DNA fragments thus obtained, i.e., 0.05 µg of the ClaI-SmaI fragment (0.6 kb) derived from the pPMOL1, two 5'-phospholylated synthetic DNA fragments (each 1 pmol), and HindIII linker (5'-pCAAGCTTG-3'; Takara Shuzo) (1 pmol) were dissloved in 30 µl of T4 ligase buffer and ligated together with 200 units of T4 DNA ligase at 12° C. for 16 hours. After recovery by ethanol precipitation, the DNA fragments were dissloved in Y-100 buffer and digested with 10 units of HindIII and 10 units of XhoI at 37° C. for 2 hours. The reaction was stopped by phenol/chloroform extraction and the DNA fragments were recovered by ethanol precipitation.

Independently, 1 µg of pAGE107 (JP-A 3-22979; Miyaji et al., Cytotechnology, 3, 133 (1990)) was dissloved in 30 µl of Y-100 buffer and digested with 10 units of HindIII and 10 units of XhoI at 37° C. for 2 hours. The reaction mixture was subjected to agarose gel electrophoresis to give an about 6.0 kb DNA fragment containing the G418 resistance gene and ampicillin resistance gene.

The DNA fragments thus obtained, i.e., 0.3 µg of the HindIII-XhoI fragment (6.0 kb) derived from the pAGE107 and 0.01 µg of the HindIII-XhoI fragment (0.6 kb) derived from the pPMOL1 were dissloved in 20 µl of T4 ligase buffer and ligated together with 200 units of T4 DNA ligase at 12° C. for 16 hours.

*Escherichia coli* HB101 strain was trasformed using this reaction mixture according to the method of Cohen et al. to obtain an ampicillin resistant strain. From this transformant, a plasmid was isolated according to the known method. This plasmid was designated as pAGE147, and its structure was confirmed by restriction enzyme digestion.

Figure 21:
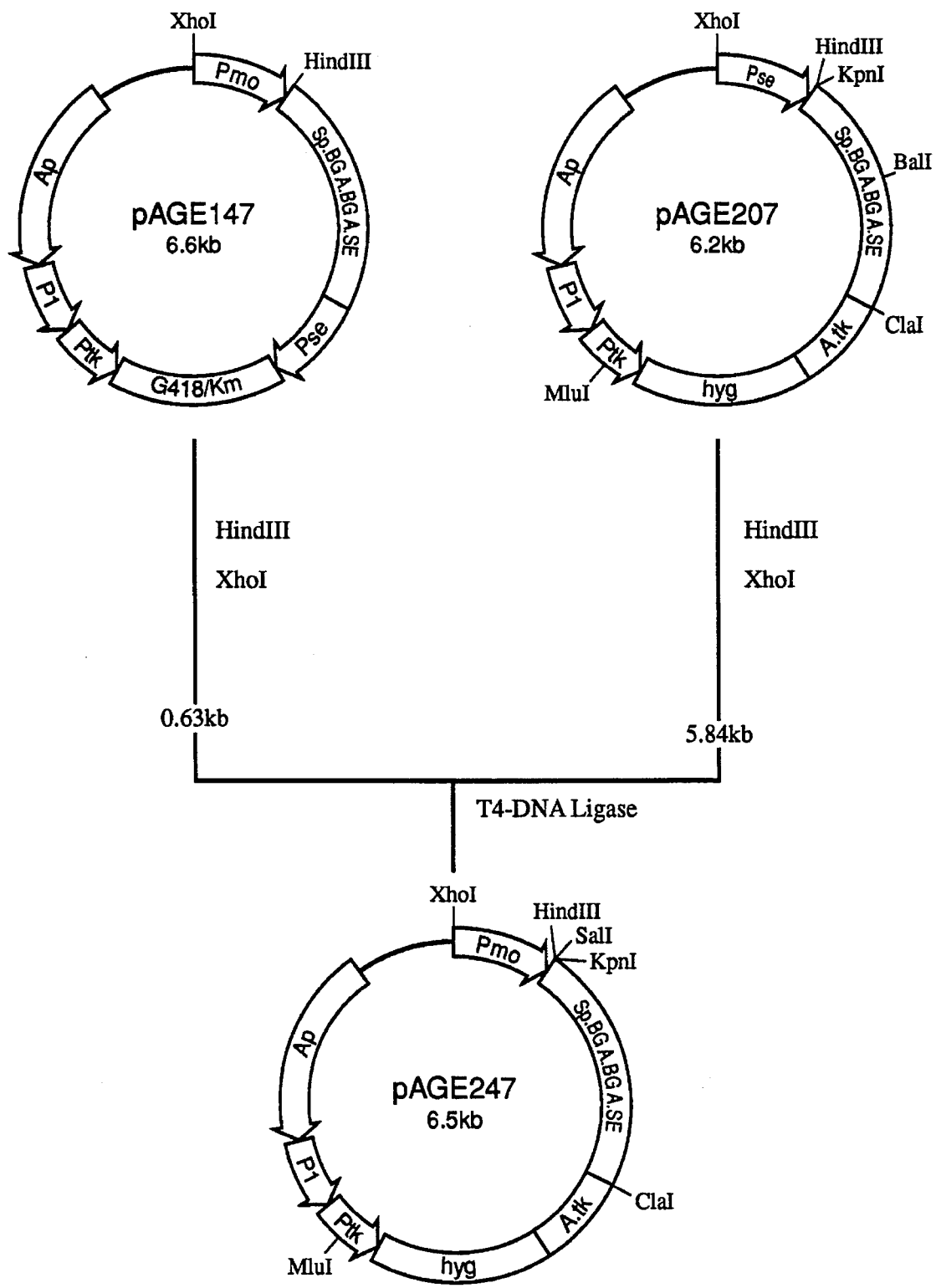
FIG. 21 is a flow sheets showing construction of plasmid pAGE247.

(2) Construction of pAGE247 (see FIG. 21)

According to the method as described below, the plasmid pAGE247 was constructed by replacing the SV40 early gene promoter of the plasmid pAGE207 with a long terminal repeat (LTR) of Moloney murine leukemia virus as a promoter.

First, 2 µg of the plasmid pAGE147 obtained in Sec. 1(1) of this Example was dissolved in 30 µl of Y-100 buffer and digested with 10 units of HindIII and 10 units of XhoI at 37° C. for 2 hours. The reaction mixture was subjected to agarose gel electrophoresis to give an about 0.63 kb DNA fragment containing the LTR promoter of Moloney murine leukemia virus.

Independently, 2 µg of the plasmid pAGE207 obtained in Sec. 1(11) of Example 1 was dissloved in 30 µl of Y-100 buffer and digested with 10 units of HindIII and 10 units of XhoI at 37° C. for 2 hours. The reaction mixture was subjected to agarose gel electrophoresis to give an about 5.84 kb DNA fragment containing the hyg resistance gene and the ampicillin resistance gene.

The DNA fragments thus obtained, i.e., 0.05 µg of the HindIII-XhoI fragment (0.63 kb) derived from the pAGE147 and 0.1 µg of the HindIII-XhoI fragment (5.84 kb) derived from the pAGE207 were dissloved in 30 µl of T4 ligase buffer and ligated together with 100 units of T4 DNA ligase at 12° C. for 16 hours.

*Escherichia coli* HB101 strain was trasformed using this reaction mixture according to the method of Cohen et al. to obtain an ampicillin resistant strain. From this transformant, a plasmid was isolated according to the known method. This plasmid was designated as pAGE247, and its structure was confirmed by restriction enzyme digestion.

Figure 22:
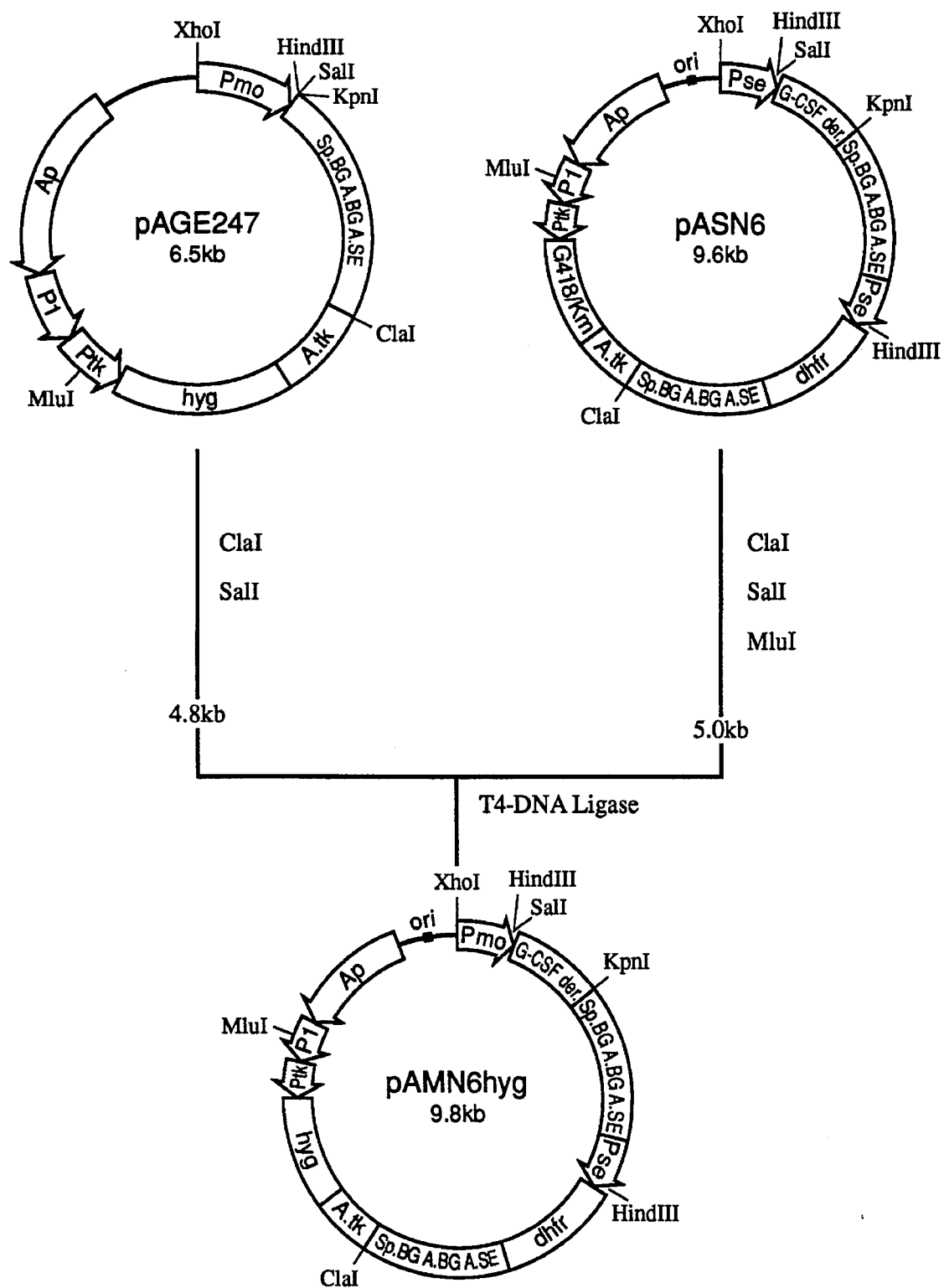
FIG. 22 is a flow sheet showing construction of plasmid pAMN6hyg.

(3) Construction of pAMN6hyg (see FIG. 22)

According to the method as described below, the plasmid pAMN6hyg for expression of human granulocyte colony stimulating factor derivative was constructed which contains the LTR of Moloney murine leukemia virus as a promoter and the hyg resistance gene as a marker.

First, 2 µg of the plasmid pAGE247 obtained in Sec. 1(2) of this Example was dissloved in 30 µl of Y-50 buffer and digested with 20 units of ClaI at 37° C. for 2 hours. Then, sodium chloride was added to give an NaCl concentration of 175 mM, and this plasmid was further digested with 20 units of SalI at 37° C. for 2 hours. The reaction mixture was subjected to agarose gel electrophoresis to give an about 4.8 kb DNA fragment containing the LTR promotor of Moloney murine leukemia virus, the ampicillin resistance gene and the hyg resistance gene.

Separately, 2 µg of the plasmid pASN6 obtained by the method as described in EP-A 0370205 was dissolved in 30 µl of Y-50 buffer and digested with 20 units of ClaI at 37° C. for 2 hours. Then, sodium chloride was added to give an NaCl concentration of 175 mM, and this plasmid was further digested with 20 units of SalI and 20 units of MluI at 37° C. for 2 hours. The reaction mixutre was subjected to agarose gel electrophoresis to give an about 5.0 kb DNA fragment containing the human granulocyte colony stimulating factor derivative gene.

The DNA fragments thus obtained, i.e., 0.1 µg of the ClaI-SalI fragment (4.8 kb) derived from the pAGE247 and 0.1 µg of the CalI-SalI fragment (5.0 kb) derived from the pASN6 were dissloved in 20.7µl of T4 ligase buffer and ligated together with 200 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAMN6hyg and its structure was confirmed by restriction enzyme digestion.

Figure 23:
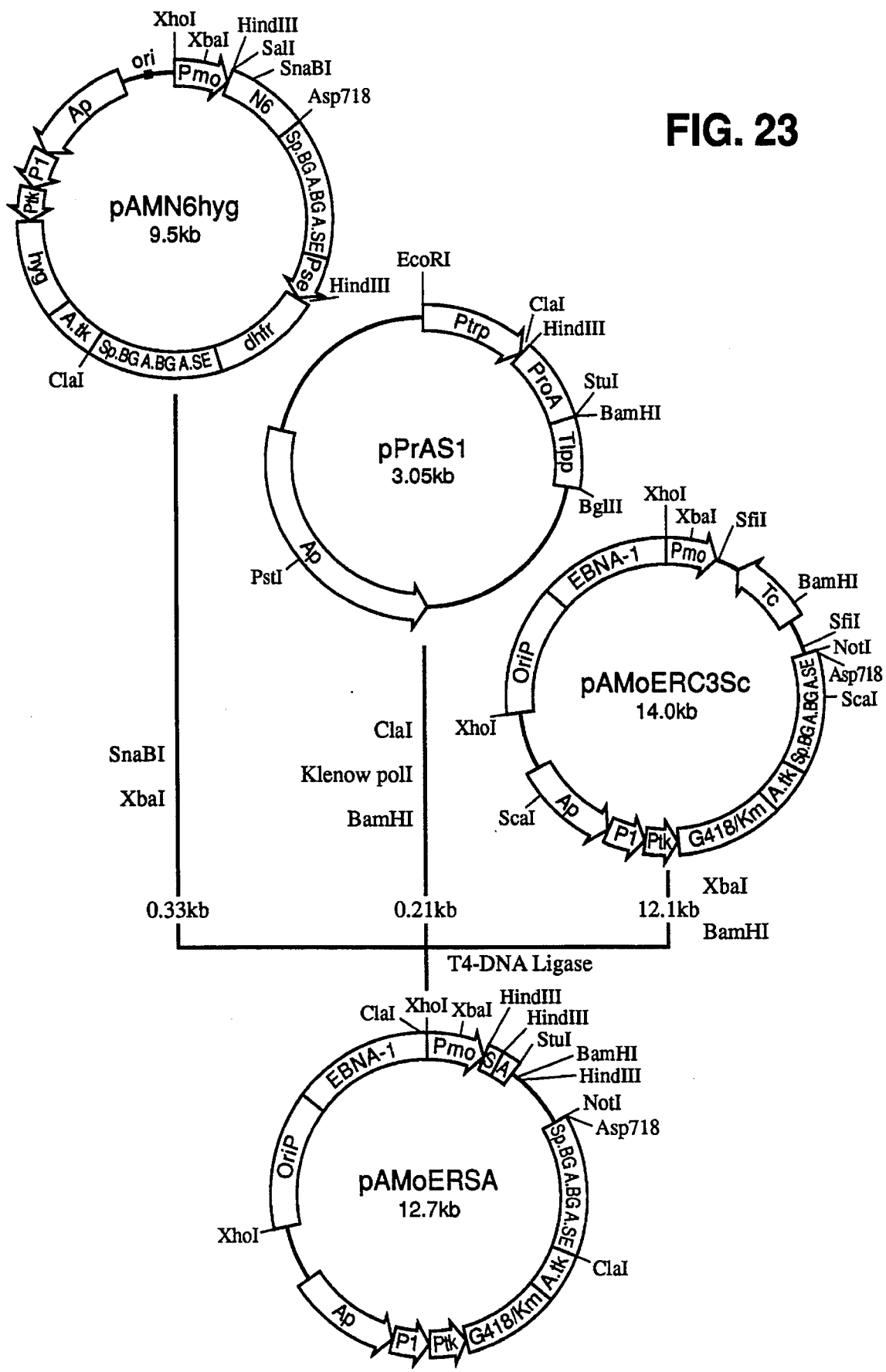
FIG. 23 is a flow sheet showing construction of plasmid pAMoERSA.

(4) Construction of secretory expression vector pAMoERSA (see FIG. 23)

According to the methods as described below, the secretory expression vector pAMoERSA for secretory expression of an arbitrary protein as a fused protein with the binding region of *Staphylococcus* aureus protein A to immunoglobulin G (IgG) was constructed, First, 2 µg of the plasmid pAMN6hyg obtained in Sec. 1(3) of this Example was dissloved in 30 µl of Y-50 buffer and digested with 20 units of SnaBI at 37° C. for 2 hours. Then, sodium chloride was added to give an NaCl concentration of 100 mM, and this plasmid was further digested with 20 units of XbaI at 37° C. for 2 hours. The reaction mixture was subjected to agarose gel electrophoresis to give an about 0.33 kb DNA fragment containing the signal sequence of human granulocyte colony stimulating factor.

Also, 2 µg of the pPrAS1 (Saito et al., Protein Engineering, 2, 481 (1989)) was dissloved in 30 µl of Y-50 buffer and digested with 20 units of ClaI at 37° C. for 2 hours. After ethanol precipitation, the precipitate was dissloved in 30 µl of DNA polymerase I buffer, and the 5'-cohesive end produced by the ClaI digestion was converted into a blunt end with 6 units of the Klenow fragment of *Escherichia coli* DNA polymerase I at 37° C. for 60 minutes. The reaction was stopped by phenol extraction, and after chloroform extraction and ethanol precipitation, the resulting precipitate was dissloved in 30 µl of Y-100 buffer and digested with 20 units of BamHI at 37° C. for 2 hours. The reaction mixture was subjected to agarose gel electrophoresis to give an about 0.21 kb DNA fragment containing the IgG-binding region of *Staphylococcus aureus* protein A.

Separately, 2 µg of the plasmid pAMoERC3Sc obtained in 1(14) of Example 1 was dissloved in 30 µl of Y-100 buffer and digested with 20 units of XbaI and 20 units of BamHI at 37° C. for 2 hours. The reaction mixture was subjetced to agarose gel electrophoresis to give an about 12.1 kb DNA fragment.

The DNA fragments thus obtained, i.e., 0.05 μg of the SnaBI-XbaI fragment (0.33 kb) derived from the pAMN6hyg, 0.05 μg of the ClaI(blunt)-BamHI fragment (0.21 kb) derived from the pPrAS1, and 0.1 μg of the XbaI-BamHI fragment (12.1 kb) derived from the pAMoERC3Sc were dissloved in 30 μl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the hnown method. This plasmid was designated as pAMoERSA, and its structure was confirmed by restriction enzyme digestion.

Figure 24:
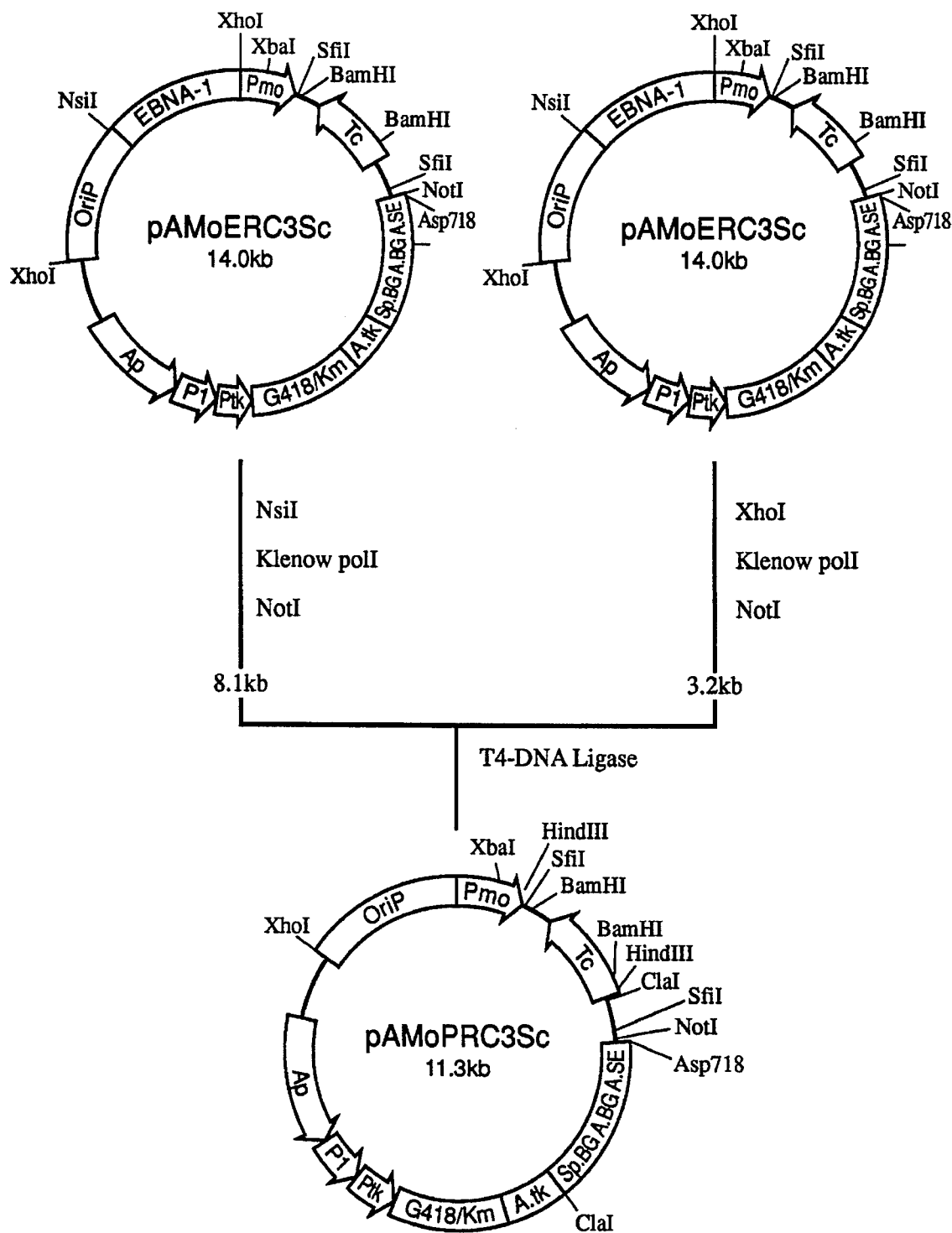
FIG. 24 is a flow sheet showing construction of plasmid pAMoPRC3Sc.

(5) Construction of pAMoPRC3Sc (see FIG. 24)

In cases where certain cells capable of expressing EBNA-1, such as Namalwa cells, are used as a host, the plasmid introduced into the host can be present as it is, without being integrated into the chromosome, even if it has no EBNA-1 gene in the plasmid pAMoERC3Sc. According to the methods as described below, therefore, the plasmid pAMoPRC3Sc was constructed by removing the EBNA-1 gene in the plasmid pAMoERC3Sc. The plasmid pAMoPRC3Sc can be used as a direct expression cloning vector similarily to the case of the plasmid pAMoERC3Sc.

First, 2 μg of the plasmid pAMoERC3Sc obtained in Sec. 1(14) of Example 1 was dissolved in 30 μl of Y-50 buffer and digested with 20 units of NsiI (New England Biolabs) at 37° C. for 2 hours. After ethanol precipitation, the resulting precipitate was dissolved in 30 μl of DNA polymerase I buffer, and the 3'-cohesive end produced by the NsiI digestion was converted into a blunt end with 6 units of the Klenow fragment of *Escherichia coli* DNA polymerase I at 37° C. for 60 minutes. The reaction was stopped by phenol extraction, and after chloroform extraction and ethanol precipitation, the resulting precipitate was dissloved in 30 μl of Y-100 buffer and digested with 20 units of NotI at 37° C. for 2 hours. The reaction mixture was subjected to agarose gel electrophoresis to give an about 8.1 kb DNA fragment.

Separately, 2 μg of the same plasmid as above was dissloved in 30 μl of Y-100 buffer and digested with 20 units of XhoI at 37° C. for 2 hours. After ethanol precipitation, the resulting precipitate was dissloved in 30 μl of DNA polymerase I buffer, and the 5'-cohesive end produced by the XhoI digestion was converted into a blunt end with 6 units of the Klenow fragment of *Escherichia coli* DNA polymerase I at 37° C. for 60 minutes. The reaction was stopped by phenol extraction, and after chloroform extraction and ethanol precipitation, the resulting precipitate was dissloved in 30 μl of Y-100 buffer and digested with 20 units of NotI at 37° C. for 2 hours. The reaction mixture was subjected to agarose gel electrophoresis to give an about 3.2 kb DNA fragment.

The DNA fragments thus obtained, i.e., 0.1 μg of the NsiI(blunt)-NotI fragment (8.1 kb) derived from the plasmid pAMoERC3Sc and 0.1 μg of the XhoI(blunt)-NotI fragment (3.2 kb) derived from the same plasmid were dissloved in 30 μl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAMoPRC3Sc and its structure was confirmed by restriction enzyme digestion.

Figure 25:
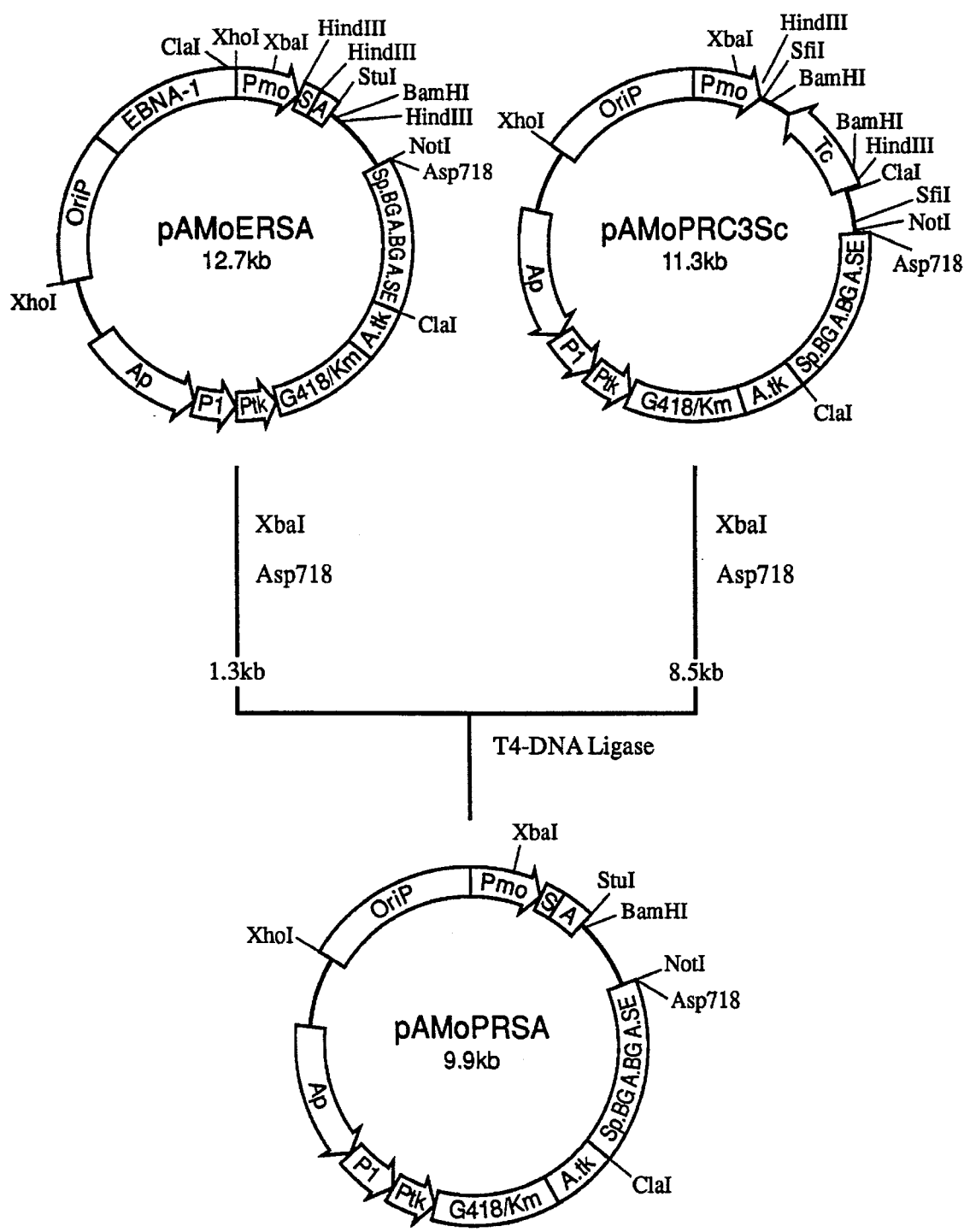
FIG. 25 is a flow sheet showing construction of plasmid pAMoPRSA.

(6) Construction of pAMoPRSA (see FIG. 25)

According to the methods as described below, the plsamid pAMoPRSA was constructed by removing the EBNA-1 gene in the pAMoERSA. The plasmid pAMoPRSA can be used as a secretory expression vector similarily-to the case of the plasmid pAMoERSA.

First, 2 μg of the plasmid pAMoERSA obtained in Sec. 1(4) of this Example was dissloved in 30 μl of a buffer containing 10 mM Tris-HCl (pH 7.5), 6 mM MgCl$_2$, 80 mM NaCl, and 6 mM 2-mercaptoethanol (hereinafter abbreviated as Y-80 buffer) and digested with 20 units of XbaI and 20 units of ASp718 (Boehringer Mannheim) at 37° C. for 2 hours. The reaction mixture was subjected to agarose gel electrophoresis to give an about 1.3 kb DNA fragment.

Separately, 2 μg of the plasmid pAMoPRC3Sc was dissolved in 30 μl of Y-100 buffer and digested with 20 units of XbaI and 20 units;of Asp718 at 37° C. for 2 hours. The reaction mixture was subjected to agarose gel electrophoresis to give an about 8.5 kb DNA fragment.

The DNA fragments thus obtained, i.e., 0.05 μg of the XbaI-Asp718 fragment (1.3 kb) derived from the pAMoERSA and 0.1 μg of the XbaI-Asp718 fragment (8.5 kb) derived from the pAMoPRC3Sc were dissolved in 30 μl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAMoPRSA, and its structure was confirmed by restriction enzyme digestion.

Figure 26:
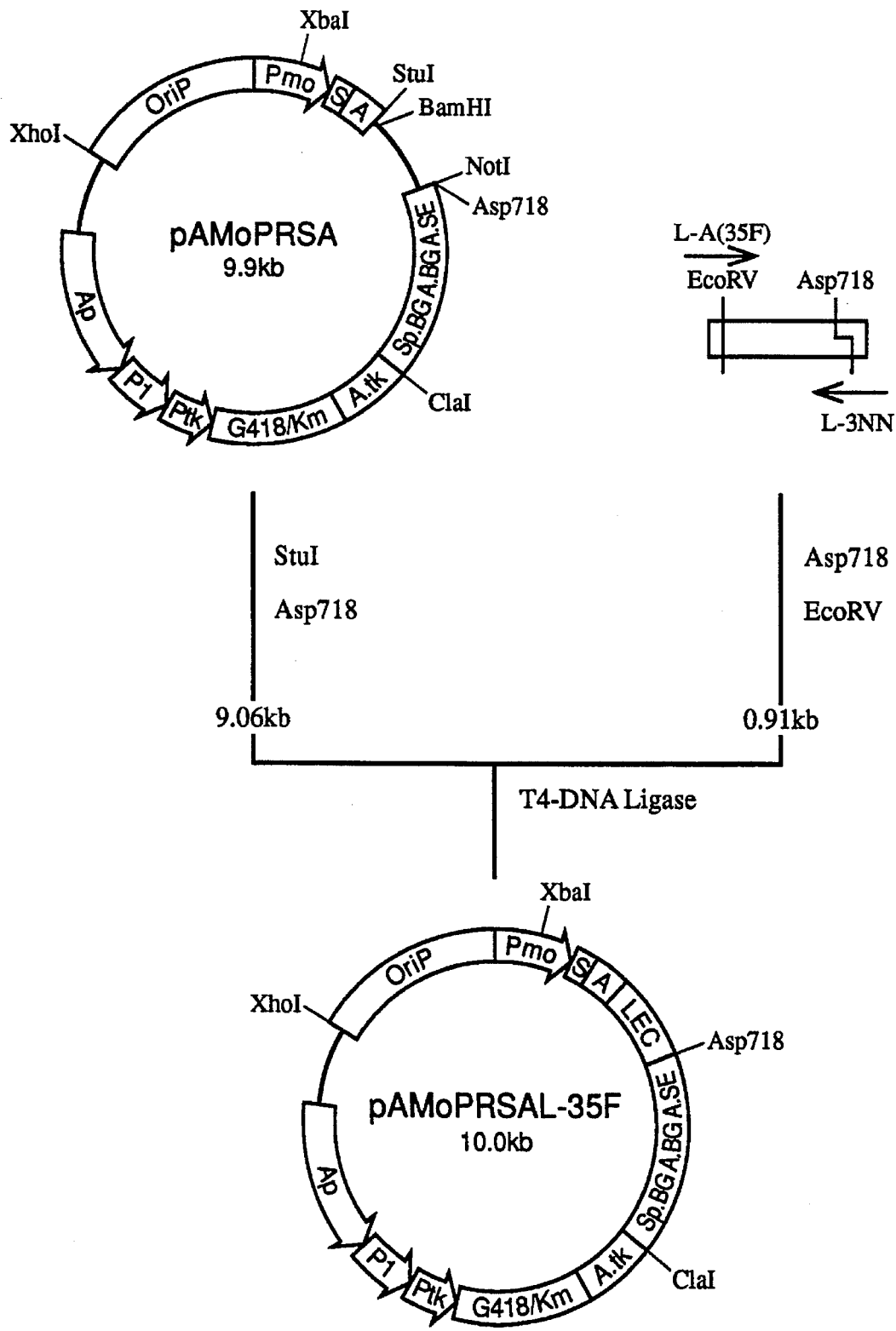
FIG. 26 is a flow sheet showing construction of plasmid pAMoPRSAL-35F.

(7) Construction of pAMoPRSAL-35F (see FIG. 26)

The cloned α2→3 sialyltransferase seems to have a structure where 8 amino acids at the N-terminal portion are put out at the cytoplasm side, the highly hydrophobic region consisting of the subsequent 18 amino acids is used for binding to the membrane, and most of the remaining C-terminal portion including the catalytic site is exposed to the internal cavity of Golgi's apparatus. According to the methods as described below, therefore, the secretory expression of α2→3 sialyltransferase was achieved by removing the membrane-binding region from α2→3 sialyltransferase and adding instead the signal sequence of granulocyte colony stimulating factor and the IgG-binding region of *Staphylococcus aureus* protein A.

The cDNA portion encoding a certain region on and after the membrane-binding region of α2→3 sialyltransferase (from 35th Phe to 333rd Phe) was prepared by the polymerase chain reaction (PCR) method and inserted into the secretory expression vector pAMoPRSA obtained in Sec. 1(6) of this Example.

As a set of primers using PCR, the following two synthetic DNA fragments, i.e., L-A(35F) (44 mer) and L-3NN (36 mer), were synthesized by DNA synthesizer model 380A (Applied Biosystems).

L-A(35F) (44 mer): 5'-CTCTCCGATATCTGTTTTATTTTC-CCATCTCAGAGAAGAAAGAG-3'

L-3NN (36 mer): 5'-GATTAAGGTACCAAGTCAGAAGTATGT-GAGGTTCTT-3'

The primers using PCR L-A(35F) and L-3NN are designed to have an EcoRV site and an Asp718 site, respectively, so that DNA fragments amplified by PCR can be incorporated between the StuI site and the Asp718 site of the plasmid pAMoPRSA after digestion with EcoRV and Asp718. The PCR was carried out using a GeneAmp™ DNA amplification reagent kit with AmpliTaq™ recombinant Taq DNA polymerase (Takara Shuzo). The reaction mixture was prepared accodring to the methods as described in the kit, and Perkin Elmer Cetus DNA thermal cycler (Takara Shuzo)

was used for incubation. Thirty cycles of amplification were carried out according to the following scheme: 94° C. for 1 minute, 55° C. for 1 minute and 72° C. for 3 minutes. Then, further incubation was carried out at 72° C. for 7 minutes. As a template, 1 ng of the plasmid pUC119-LEC obtained in Example 1 was used. After completion of the reaction, chloroform extraction and ethanol precipitation were successively carried out. The resulting precipitate was then dissloved in 30 μl of Y-100 buffer and digested with 20 units of EcoRV and 20 units of Asp718 at 37° C. for 2 hours. The reaction micture was subjected to agarose gel electrophoresis to give an about 0.9 kb DNA fragment.

Separately, 2 μg of the plasmid pAMoPRSA was dissloved in 30 μl of Y-100 buffer and digested with 20 units of StuI and 20 units of Asp718 at 37° C. for 2 hours. The reaction mixture was subjected to agarose gel electrophoresis to give an about 9.06 kb DNA fragment.

The DNA fragments thus obtained. i.e., 0.1 g of the EcoRV-Asp718 fragment (0.9 kb) derived from the DNA fragments amplified by PCR and 0.1 μg of the StuI-Asp718 fragment (9.06 kb) derived from the pAMoPRSA were dissloved in 30 μl of T4 ligase buffer and ligated together with 175 units of T4 DNA ligase at 12° C. for 16 hours.

Escherichia coliHB101 strain was transformed using this reaction mixture according to the method of Cohen et al. to obtain an ampicillin resistant strain. From this transformant, a plasmid was isolated according to the known method. This plasmid was designated as pAMoPRSAL-35F, and its structure was confirmed by restriction enzyme digestion.

2. Secretory expression of cDNA encoding α2→3 sialyltransferase using Namalwa KJM-1 cell as host The plasmid pAMoPRSA (secretory expression vector; control) obtained in Sec. 1(6) of this Example and the plasmid pAMoPRSAL-35F (plasmid for secretory expression of α2→3 sialyltransferase) obtained in Sec. 1(7) of this Example were prepared using the plasmid preparation kit >plasmid<maxi kit (trade No. 41031; Qiagen). Each of the plasmids thus obtained was ethanol precipitated and dissolved in TE buffer to give a concentration of 1 μg/μl. Then, both plasmids were independently introduced into the Namalwa KJM-1 cells at a proportion of 4 μg per 1×10$^6$ cells by electroporation (Miyaji et al., Cytotechnology, 3, 133 (1990)). The cells were suspended in 8 ml of RPMI1640.ITPSGF medium, and the cells were cultured in a $CO_2$ incubator at 37° C. for 24 hours. Then, the cells were supplemented with G418 (GIBCO) to give a concentration of 0.5 mg/ml and further cultured for 7 to 14 days to obtain transformants. Each of the transformants was suspended in 30 ml of RPMI1640.ITPSGF medium containing 0.5 mg/ml of G418 at 1×10$^5$ cells/ml, and the cells were cultured in a $CO_2$ incubator at 37° C. for 8 days. Then, centrifugation at 160×g for 10 minutes gave the separation of a supernatant from the cells, and the supernatant was further centrifuged at 1500×g for 10 minutes. The culture supernatant thus obtained was stored at −80° C. until it was used.

α2→3 Sialyltransferase encoded in the plasmid pAMoPRSAL-35F can readily be purified using IgG Sepharose because of its secretory expression as a fused protein with the IgG-binding region of *Staphylococcus aureus* protein A. To the culture supernatant obtained above, sodium azide was added to give a final concentraion of 0.1%. Then, 100 μl of IgG Sepharose (Pharmacia) which had been pre-treated according to the accompanying instructions was added, and the mixture was gently stirred at 4° C. overnight. The IgG Sepharose was recovered by centrifugation at 160×g for 10 minutes, and washed three times with 1 ml of RPMI1640.ITPSGF medium. The sialyltranseferase activity was measured by directly using 5 μl of this IgG Sepharose. The activity measurement was carried out by reacting in 30 μl of the assay solution (0.1M cacodylate buffer (pH 6.5), 0.01M $MnCl_2$, 0.45% Triton X-100, 0.1 mM substrate, the above IgG Sepharose (5 μl), 5 mM CMP-sialic acid (added or not added)) at 37° C. for 2 hours, and then identifying the products by high performance liquid chromatography (HPLC). As the substrate, various sugar chains (lacto-N-neotetraose (LNnT), lacto-N-tetraose (LNT), lacto-N-fucopentaose III (LNFP-III) and lacto-N-fucopentaose V (LNFP-V); all are available from Oxford GlycoSystems, and the respective structures are shown in FIG. 1) fluorescence-labeled with aminopyridine were used. The fluorescence labeling of the substrate was carried out according to the conventional method (Akihiro Kondo et al., Agric. Biol. Chem., 54, 2169 (1990)). The IgG Sepharose was allowed to react with an assay solution containing or not contaning CMP-sialic acid as a sugar donor. The reaction mixture was separated by HPLC, and the peaks appearing only with the assay solution containing CMP-sialic acid were considered as the products. After completion of the reaction, the assay solution was treated with at 100° C. for for 5 minutes, and centrifuged at 10,000×g for 10 minutes. The resulting supernatant was subjected to HPLC which was carried out on the TSKgel ODS-80T$_M$ column (4.6 mm×30 cm; Tosoh) eluting with 0.02M ammonium acetate buffer (pH 4.0) at a temperature of 50° C. at a rate of 1 ml/min. The products were detected using the fluorescence HPLC monitor model RF-535T (Shimazu Seisakusho) with an excitation wavelength of 320 nm and an emission wavelength of 400 nm. The products was identified from the facts that the elution time was coincided with that of the standard and that the substrate was regenerated by sialidase treatment of the products. The quantitative analysis of the products was carried out with the use of pyridylaminated lactose as the standard for comparison of fluorescence intensity. The results of this assay are shown in Table 1. The activity to various sugar chain substrates is also shown in terms of a relative activity when the activity to the substrate LNnT is taken as 100.

TABLE 1

| | α2→3 Sialyltransferase activity | | | |
| --- | --- | --- | --- | --- |
| | | pAMoPRSAL-35F | | Known α2→3 ST |
| Substrate sugar chain | pAMoPRSA pmol | pmol | Relative activity | Relative activity |
| Galβ1-4GlcNAcβ1-3Galβ1-4Glc (LNnT) | 0 | 51.3 | 100 | 6 |

TABLE 1-continued

|  |  | α2→3 Sialyltransferase activity | | | |
|---|---|---|---|---|---|
|  |  |  | pAMoPRSAL-35F | | Known α2→3 ST |
| Substrate sugar chain | | pAMoPRSA pmol | pmol | Relative activity | Relative activity |
| Galβ1-4GlcNAcβ1-3Galβ1-4Glc (LNFP-III)<br>3<br>\|<br>Fucα1 | | 0 | 8.1 | 16 |  |
| Galβ1-3GlcNAcβ1-3Galβ1-4Glc (LNT) | | 0 | 23.8 | 46 | 100 |
| Galβ1-3GlcNAcβ1-3Galβ1-4Glc (LNFP-V)<br>3<br>\|<br>Fucα1 | | 0 | 28.8 | 56 |  |

In cases where the IgG Sepharose derived from the culture supernatant of Namalwa cells having the plasmid pAMoPRSAL-35F was used, α2→3 sialyltransferase activity was detected when any of the sugar chains was used as the substrate. On the other hand, in cases where the IgG Sepharose derived from the culture supernatant of Namalwa cells containing the vector pAMoPRSA, no activity was detected when any of the sugar chains was used as the substrate. These results indicates that α2→3 sialyltransferase undergo secretory production into the culture supernatant as a fused protein with the IgG-binding region of *Staphylococcus aureus* protein A and that it can readily be recovered and purified using IgG Sepharose.

Also shown in Table 1 are the relative activities of a known α2→3 sialyltransferase, for which purification has been reported so far (Wienstein et al., J. Biol. Chem., 257, 13845 (1982)), to various sugar chain substrates when its activity to the substrate LNT is taken as 100. The known α2→3 sialyltransferase exhibits a higher specificity to LNT than LNnT, whereas the α2→3 sialyltransferase of the present invention exhibits a higher specificity to LNnT than LNT. This indicates that the α2→3 sialyltransferase of the present invention is a novel enzyme having a different substrate specificity from that of the known enzyme.

It was also found that the α2→3 sialyltransferase of the present invention can take LNFP-III as the substrate. No report has been made so far on such α2→3 sialyltransferase having an enzymatic activity to LNFP-III. This indicates that the use of this enzyme can make possible the direct in vitro synthesis of sialyl-Le$^x$ sugar chains from Le$^x$ sugar chains.

Because the α2→3 sialyltransferase of the present invention can take not only LNnT but also LNT as the substrate, it is possible to synthesize sialyl-Le$^x$ sugar chains, as well as sialyl-Le$^a$ sugar chains. That is, with the use of the α2→3 sialyltransferase of the present invention, the terminal structure of a sugar chain can be converted into NeuAcα2-3Galβ1-4GlcNAc or NeuAcα2-3Galβ1 -3GlcNAc, which are then made into a sialyl-Le$^x$ sugar chain or a sialyl-Le$^a$ sugar chain, using α1→3 fucosyltransferase or α1→4 fucosyltransferase, respectively. Moreover, the α2→3 sialyltransferase of the present invention exhibits a higher substrate specificity to LNnT than that attained by the known α2→3 sialyltransferase, and is therefore superior to the known α2→3 sialyltransferase with respect to the capability for synthesis of sialyl-Le$^x$ sugar chains.

EXAMPLE 4

Production by animal cells of α2→3 sialyltransferase derived from human melanoma cell strain WM266-4:

1. Cloning of α2→3 sialyltransferase cDNA (WM17) derived from human melanoma cell line WM266-4

(1) Isolation of mRNA from human melanoma WM266-4 cell line

From $1 \times 10^8$ WM266-4 cells (ATCC CRL1676), about 30 μg of mRNA was isolated using the mRNA extraction kit "Fast Track" (trade No. K1593-02; Invitrogen), according to the manufacturer's instructions accompanying the kit used.

(2) Preparation of cDNA library

From 8 μg of mRNA obatined above, double-stranded cDNA was prepared using the cDNA synthesis kit "The Librarian I" (Invitrogen) with a random primer as a primer. Then, each of the following SfiI linkers (Seq. ID: 5) as prepared in Example 1 was added, instead of BstXI linker, at either terminus of the cDNA. The cDNA was fractioned in size by agarose gel electrophoresis and cDNA fragments larger than about 1.2 kb were isolated.

SfiI Linkers:

5'-CTTTAGAGCAC-3' (11 mer)

3'-GAAATCTC-5' (8 mer)

Before use, these SfiI linkers (11 mer and 8 mer) had been independently dissloved at 100 nM in 50 μl of T4 kinase buffer and phosphorylated with 30 units of T4 polynucleotide kinase (Takara Shuzo) at 37° C. for 16 hour. The specific reagents and procedures were as described in the manufacturer's instructions accompanying the kit used, except that the above SfiI linkers were used in place of BstXI linkers. As the direct expression cloning vector, the vector pAMoPRC3Sc obtained in Sec. 1(5) of Example 3 was used.

First, 24 μg of the vector pAMoPRC3Sc was dissloved in 590 μl of Y-50 buffer and digested with 80 units of SfiI at 37° C. for 16 hours. Then, the reaction mixture was taken at a volume of 5 μl for agarose gel electrophoresis, and after the completion of digestion was confirmed, this vector was further digested with 40 units of BamHI at 37° C. for 2 hours. The digestion with BamHI was done for the purpose of decreasing the amount of background (i.e., clones containing no cDNA insert) at the time of cDNA library construction. The reaction mixture was subjected to agarose gel electrophoresis to give an about 8.8 kb DNA fragment.

Then, 2 μg of the SfiI fragment (8.8 kb) derived from the pAMoPRC3Sc, together with the cDNA obtained above, was dissolved in 250 μl of T4 ligase buffer and ligated together with 2000 units of T4 DNA ligase at 12° C. for 16 hours. Thereafter, 5 μg of transfer RNA (tRNA) was added, and after ethanol precipitation, the resulting precipitate was dissloved in 20 μl of TE buffer. The reaction mixture was used to transform *Escherichia coli* LE392 strain (Maniatis et al., Molecular Cloning, 2.58, Cold Spring Harbor, 1989) by electroporation (William J. Dower et al., Nucleic Acids Res., 16, 6127 (1988)) to give about 200,000 ampicillin resistant transformants.

(3) Cloning of α2→3 sialyltransferase cDNA (WM17)

About 200,000 ampicillin resistant transformants (cDNA library) obtained in Sec. 1(2) of this Example were mixed, after which a plasmid was prepared using >plasmid<maxi kit (trade No. 41031; Qiagen) which is a plasmid preparation kit. The obtained plasmid was ethanol precipitated and the resulting precipitate was dissloved in TE buffer to give a concentration of 1 μg/μl.

The above plasmid was introduced into the KJM-1 strain by electroporation (Miyaji et al., Cytotechnology, 3, 133 (1990)) at a proportion of 4 μg per $1.6 \times 10^6$ cells. After the introduction of plasmid, these cells were suspended in 8 ml of RPMI1640.ITPSGF medium, and the cells were cultured in a $CO_2$ incubator at 37° C. for 24 hours. Then, the cells were supplemented with G418 (GIBCO) to give a concentration of 0.5 mg/ml and further cultured for 5 to 7 days to obtain transformants. The obatined transformant was suspended in RPMI1640.ITPSGF medium containing *Ricinus communis* 120 lectin (50 ng/ml) to give a concentration of $5 \times 10^4$ cells/ml, and the suspension was distributed in 200 -μl portions into wells of a 96-well microtiter plate. The cells were cultured in a $CO_2$ incubator at 37° C. for 4 weeks, and a certain strain was obtained which had become resistant to *Ricinus communis* 120 lectin. After culturing of this resistant cell, a plasmid was isolated from about $5 \times 10^6$ cells according to the Hirt method (Robert F. Margolskee et al., Mol. Cell. Biol., 8, 2837 (1988)). The isolated plasmid was introduced into *Escherichia coli* strain LE392 by electroporation (William J. Dower et al., Nucleic Acids Res., 16, 6127 (1988)) to give an ampicillin resistant transformant. From this transformant, a plasmid was prepared using >plasmid<maxi kit (Qiagen), and its structure was examined by restriction enzyme digestion to find that it contained about 1.9 kb cDNA. The cDNA containing plasmid was designated as pAMoPRWM17. When this plasmid was also introduced into the KJM-1 strain by the above method, the transformant became resistant to *Ricinus communis* 120 lectin; it was therefore found that this cDNA is a gene responsible for lectin resistance. The KJM-1 strain containing the plasmid DAMoPRWM17 was able to grow even in the presence of 200 ng/ml *Ricinus communes* 220 lectin.

2. Sequencing of α2→3 sialyltransferase cDNA (WM17)

Figure 27:
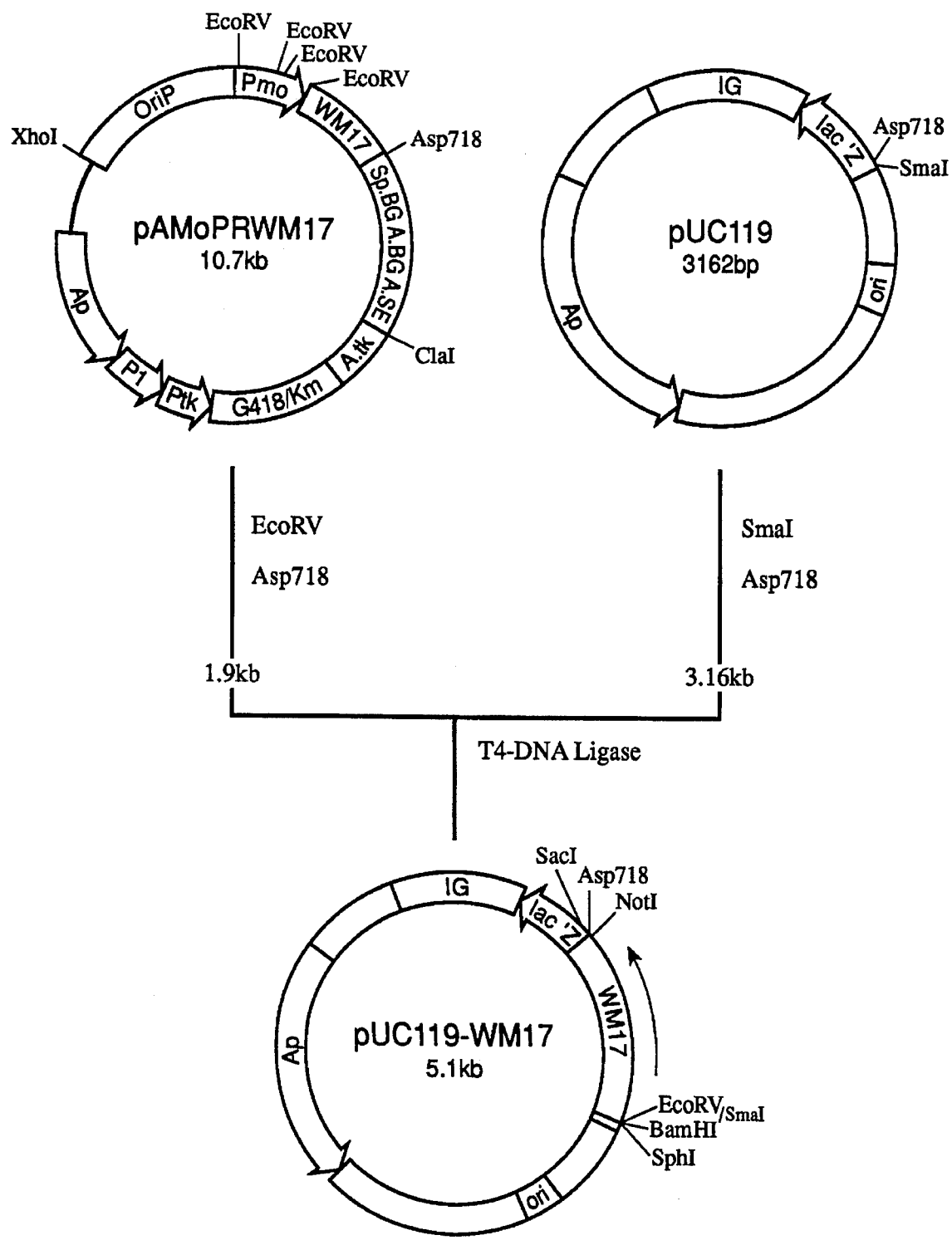
FIG. 27 is a flow sheet showing construction of plasmid pUCl19-WM17.

(1) Incorporation of α2→3 sialyltransferase cDNA (WM17) into plasmid pUCl19 (see FIG. 27)

First, 1 μg of the plasmid pAMoPRWM17 was dissloved in 30 μl of Y-100 buffer and digested with 20 units of EcoRV and 20 units of Asp718 (Boehringer Mannheim) at 37° C. for 2 hours. The reaction mixture was subjected to agarose gel electrophoresis to give an about 1.9 kb DNA fragment.

Separately, 1 μg of the plasmid pUCl19 (Messing et al., Methods in Enzymology, 153, 3 (1987)) was dissloved in 30 μl of K-20 buffer and digested with 20 units of SmaI at 37° C. for 2 hours. Then, sodium chloride was added to give an NaCl concentration of 100 mM, and this plasmid was further digested with 20 units of Asp718 at 37° C. for 2 hours. The reaction mixture was subjected to agarose gel electrophoresis to give an about 3.16 kb DNA fragment.

The DNA fragments thus obtained, i.e., 0.2 μg of the EcoRV-Asp718 fragment (1.9 kb) derived from the pAMoPRWM17 and 0.1 μg of the SmaI-Asp718 fragment (3.16 kb) derived from the pUCl19 were dissolved in 30 μl of T4 ligase buffer and ligated together with 175 units of T4 DNA ligase at 12° C. for 16 hours. *Escherichia coli* HB101 strain was transformed using this reaction mixture according to the method of Cohen et al. to obtain an ampicillin resistant strain. From this transformant, a plasmid was isolated according to the known method. This plasmid was designated as pUCl19-WM17, and its structure was confirmed by restriction enzyme digestion.

(2) Construction of deletion plasmids for sequencing

First, 2 μg of the plasmid PUCl19-WM17 was dissloved in 30 μl of Y-150 buffer and digested with 20 units of BamHI and 20 units of SphI at 37° C. for 2 hours. After ethanol precipitation, the resuling precipitate was dissloved in 100 μl of ExoIII buffer (accompanying the deletion kit for kilosequence; Takara Shuzo). Independently, 2 μg of the same plasmid was dissloved in 30 μl of Y-0 buffer and digested with 20 units of SacI at 37° C. for 2 hours. Then, sodium chloride was added to give an NaCl concentration of 150 mM and digested with 20 units of NotI at 37° C. for 2 hours. After ethanol precipitation, the resulting precipitate was dissloved in 100 μl of ExoIII buffer.

From the BamHI-SphI fragment derived from the plasmid pUCt19-WM17 and the SacI-NotI fragment derived from the same plasmid, several tens of deletion plasmids were respectively prepared using the deletion kit for kilo-sequence (Takara Shuzo). Specific reagents and procedures were as described in the manufacturer's instructions accompanying the kit used.

The nucleotide sequence of the deletion plasmid obtained above was determined using the Taq DyeDeoxy terminator cycle sequencing kit (trade No. 401113; Applied Biosystems). The determined nucleotide sequence is shown in the sequence listing (Seq. ID: 6). A poly A tail follows 1742 base pairs (bp) nucleotide. From this nucleotide sequence, it was found that this gene encodes a protein consisting of 329 amino acids. The amino acid sequence of this protein is also shown in the sequence listing (Seq. ID: 7). It was also found that the amino acid sequence has about 91% homology with that encoded by α2→3 sialyltransferase cDNA cloned from TYH cells in Example 4. From these results, it is considered that the gene (WM17) isolated in terms of resistance to *Ricinus communis* 120 lectin encodes α2→3 sialyltransferase.

3. Measurement of α2→3 sialyltransferage activity of KJM-1 strain containing WM17 expression plasmid In the same manner as described in Sec. 5 of Example 5, comparison of α2→3 sialyltransferase activity was made between the KJM-1 strain containing the WM17 expression plasmid (pAMoPRWM17) and the KJM-1 strain containing the plasmid pAMoPRC3Sc as a control. As the result, the α2→3 sialyltransferase activity of the KJM-1 strain containing the plasmid pAMoPRWM17 was 6 to 7 times higher than that of the KJM-1 strain containing the plasmid pAMoPRC3Sc.

4. Synthesis of sialyl-Le$^x$ sugar chain in KJM-1 strain having expression plasmid for α2→3 sialyltransferase The KJM-1 strain containing the pAMoPRWM17 (expression plasmid for α2→3 sialyltransferase) obatined in Sec. 1 of Example 4 and the KJM-1 strain containing the pAMoPRC3Sc (control plasmid) were independently cultured in the RPMI1640.ITPSGF medium containing 0.5 mg/ml of G418, after which about $1 \times 10^6$. cells of each strain were taken in a microtube (1.5 ml; Eppendorf) and collected by centrifugation at 550×g for 7 minutes. Then, these cells were washed with 1 ml of A-PBS and subjected to indirect fluorescent antibody staining with KM93 (Shitara et al., Anticancer Res., 9, 999 (1989)) which is an antibody reacting with the sialyl-Le$^x$ sugar chain, thereby examining the production of sialyl-Le$^x$ sugar chain in these cells. The collected cells of each strain were suspended in 50 μl (10 μg/ml) of KM93 and allowed to react at 4° C. for 1 hour. Then, these cells were washed three times with A-PBS and suspended in 20 μl of fluorescence-labeled anti-mouse IgG and IgM antibodies (Cappel, used after 20-fold dilution with A-PBS), followed by reaction at 4° C. for 30 minutes. After washing three times with A-PBS, these cells were again suspended in A-PBS and subjected to anlysis using EPICS elite flow cytometer (Coulter).

As a control, the same analysis was carried out using the normal mouse serum diluted 500-fold with A-PBS in place of KM93.

Figure 28:
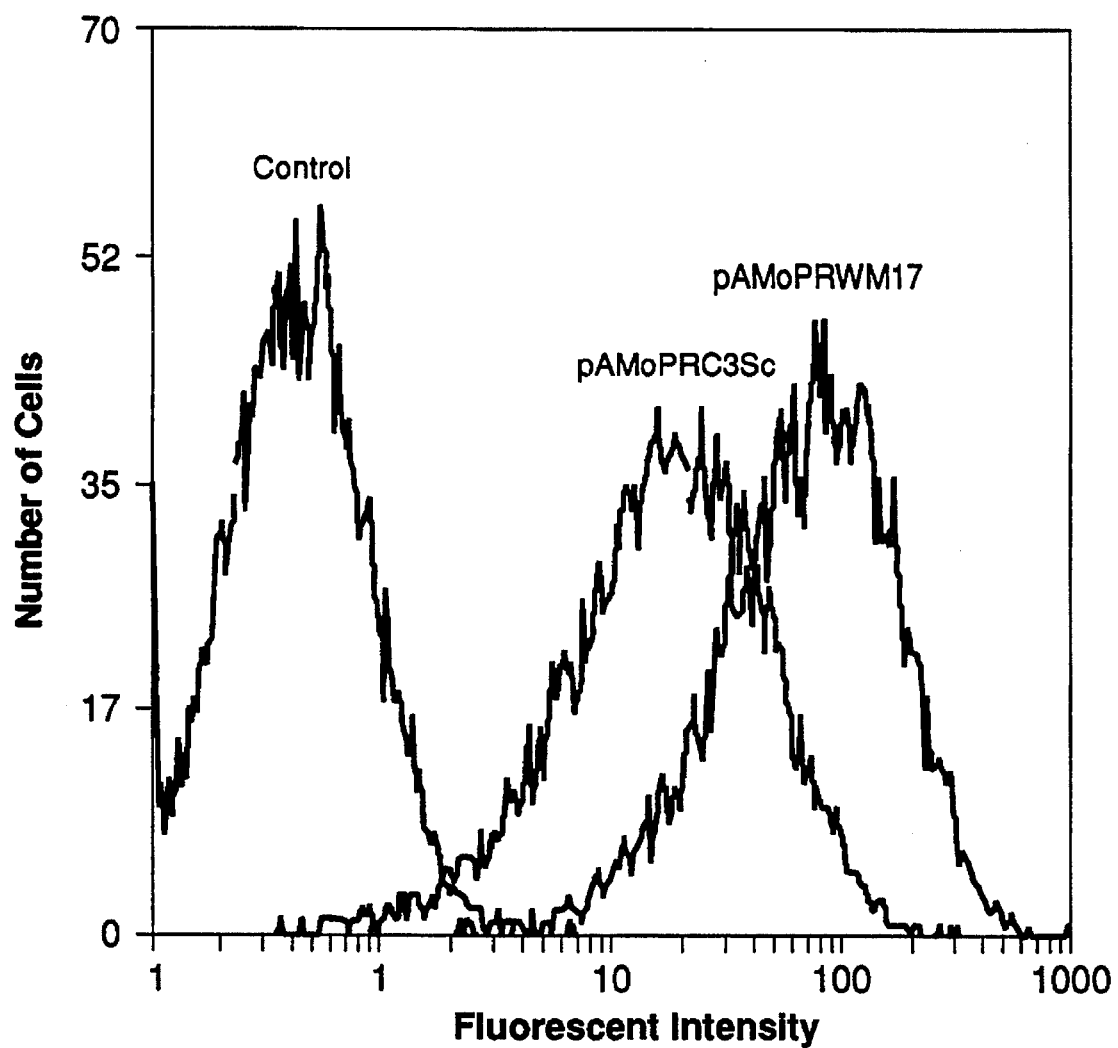
FIG. 28 is a view showing the results of analysis by EPICS Elite Flow Cytometer (manufactured by COULTER) after indirect fluorescent antibody staining. As a control, the results of indirect fluorescent antibody staining using normal mouse serum on KJM-1 strain in which pAMoPRC3Sc (control plasmid) is introduced are also shown. In addition, the results of indirect fluorescent antibody staining using KM93 on KJM-1 strain in which pAMoPRC3Sc (control plasmid) or pAMoPRWM17 ($\alpha 2 \rightarrow 3$ sialyltransferase expression plasmid) is introduced are also shown as pAMoPRC3Sc or pAMoPRWM17, rescpectively.

The results are shown in FIG. 28. It is found that for the KJM-1 strain containing the direct expression cloning vector pAMoPRC3Sc (control plasmid), the cells stained with KM93 exhibit a higher fluorescence intensity than that of the control. This indicates that the KJM-1 strain is originally able to express the sialy-Le$^x$ sugar chains. Also found is that the fluorescence intensity obtained when the cells of the KJM-1 strain containing the pAMoPRWM17 (α2→3 sialyltransferase expression plasmid) were stained with KM93 is further higher than that obatined when the cells of the KJM-1 strain having the pAMoPRC3Sc (control plasmid) were stained with KM93. This indicates that α2→3 sialyltransferase encoded in the gene WM17 can synthesize sialyl-Le$^x$ sugar chains in cells.

5. Secretory production by animal cells of α2→3 sialyltransferase derived from WM266-4 cell line (1) Construction of plasmid pAMoPRSAW17-31F for secretory expression of cDNA encoding α2→3 sialyltransferase (see FIG. 29)

In view of the amino acid sequence, α2→3 sialyltransferase encoded in the cloned gene WM17 seems to have a structure where 8 amino acids in the N-terminal portion are put out at the cytoplasma side, the highly hydrophobic region consisting of the subsequent 18 amino acids is used for binding the membrane, and most of the remaining C-terminal portion (including the catalytic site) is exposed to the internal cavity of Golgi's apparatus. According to the method as described below, therefore, the secretory production of α2→3 sialyltransferase was achieved by removing the membrane-binding region from α2→3 sialyltransferase and-adding-instead the signal sequence of granulocyte colony stimulating factor and the IgG-binding region of *Staphylococcus aureus* protein A. The gene portion encoding a certain region following the membrane-binding region of α2→3 sialyltransferase (from 31st Phe to 329th Phe) was prepared by PCR method and inserted into the secretory expression vector pAMoPRSA obtained in Sec. 1(6) of Example 3.

As a set of primers using PCR, the following two synthetic DNA fragments, i.e., W17-A(31F) (44 mer) and W17-C (36 mer), were synthesized by DNA synthesizer model 380A (Applied Biosystems).

W17-A(31F) (44 mer): 5'-CTCTCCGATATCTGTTTTATTTTC-CCATCCAGAGAAGAAGGAG-3'

W17-C (36 mer) 5'-GATTAAGGTACCAGGTCAGAAGGACGT-GAGGTTCTT-3'

The primers using PCR W17-A (31F) and W17-C are designed to have an EcoRV site and an Asp718 site, respectively, so that DNA fragments amplified by PCR can be incorporated between the S tuI site and the Asp718 site of the plasmid pAMoPRSA after digestion with EcoRV and Asp718. The PCR was carried out using a GeneAmp™ DNA amplification reagent kit with AmpliTaq™ recombinant Taq DNA polymerase (Takara Shuzo). The reaction mixture was prepared according to the method as described in the kit, and Perkin Elmer Cetus DNA thermal cycler (Takara Shuzo) was used for incubation. Thirty cycles of amplification were carried out according to the following scheme: 94° C. for 1 minute, 55° C. for 1 minute and 72° C. for 3 minutes Then, further incubation was carried out at 72° C. for 7 minutes. As a templete, 1 ng of the plasmid pUCl19-WM17 obtained in Sec. 2(1) of this Example was used. After completion of the reaction, chloroform extraction and ethanol precipitation were successively carried out. The resulting precipitate was then dissloved in 30 μl of Y-100 buffer and digested with 20 units of EcoRV and 20 units of Asp718 at 37° C. for 2 hours. The reaction mixture was subjected to agarose gel electrophoresis to give an about 0.91 kb DNA fragment.

Separately, 2 μg of the plasmid pAMoPRSA was dissloved in 30 μl of Y-100 buffer and digested with 20 units of StuI and 20 units of Asp718 at 37° C. for 2 hours. The reaction mixture was subjected to agarose gel electrophoresis to give an about 9.06 kb DNA fragment.

Then, 0.1 μg of the EcoRV-ASp718 fragment (0.91 kb) derived from the amplified DNA by PCR and 0.1 μg of the StuI-ASp718 fragment (9.06 kb) derived from the plasmid pAMoPRSA were dissloved in 30 μl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAMoPRSAW17-31F, and its structure was confirmed by restriction enzyme digestion.

(2) Secretory expression of cDNA encoding α2→3 sialyltransferase with Namalwa KJM-1 cells used as a host The plasmid pAMoPRSA (secretory expression vector; control) obtained in Sec. 1(6) of Example 3 and the plasmid pAMoPRSAW17-31F (secretory expression plasmid for α2→3 sialyltransferase) obtained in Sec. 5' (1) of this Example were prepared using the plasmid preparation kit, >plasmid<maxi kit (trade No. 41031; Qiagen). Each of the plasmids thus obtained was precipitated by ethanol and dissloved in TE buffer to give a concentration of 1μg/μl. Then, both plasmids were independently introduced into the Namalwa KJM-1 cells at a proportion of 4 μg per 1.6×10$^6$ cells by electroporation (Miyaji et al., Cytotechnology, 3, 133 (1990)). The cells were suspended in 8 ml of RPMI1640.ITPSGF medium, and the cells were cultured in a CO$_2$ incubator at 37° C. for 24 hours. Then, the cells were supplemented with G418 (GIBCO) at a concentration of 0.5 mg/ml and further cultured for 7 to 14 days, resulting in transformants. Each of the transformants was suspended in 30 ml of RPMI1640.ITPSGF medium containing 0.5 mg/ml of G418 to give a concentration of 1×10$^5$ cells/ml, and the cells were cultured in a CO$_2$ incubator at 37° C. for 8 days. Then, centrifugation at 160×g for 10 minutes gave the separation of a supernatant from the cells, and the supernatant was further centrifuged-at 1500×g for 10 minutes. The culture supernatant thus obtained was stored at −80° C. until it was used.

α2→3 sialyltransferase encoded in the plasmid pAMo-PRSAW17-31F can readily be purified using IgG Sepharose because of its secretory production as a fused protein with the IgG-binding region of *Staphylococcus aureus* protein A. To the culture supernatant obtained above, sodium azide was added to give a final concentration of 0.1%. Then, 100 μl of IgG Sepharose (Pharmacia) which had been pre-treated according to the accompanying instructions was added, and the mixture was gently stirred at 4° C. overnight. The IgG Sepharose was recovered by centrifugation at 160×g for 10 minutes, and washed three times with 1 ml of RPMI1640.ITPSGF medium. The sialyltransferase activity was measured by directly using 5 µl of this IgG Sepharose. The activity measurement was carried out by reacting in 30 µl of the assay solution (0.1M cacodylate buffer (pH 6.5), 0.01M $MnCl_2$, 0.45% Triton X-100, 0.1 mM substrate, the above IgG Sepharose (5 µl), 5 mM CMP-sialic acid (added or not added)) at 37° C. for 2 hours, and then identifying the products by high performance liquid chromatography (HPLC). As the substrate, various sugar chains (lacto-N-neotetraose (LNnT), lacto-N-tetraose (LNT), lacto-N-fucopentaose III (LNFP-III) and lacto-N-fucopentaose V (LNFP-V); all are available from Oxford GlycoSystems, and the respective structures are shown in FIG. 1) fluorescence-labeled with aminopyridine were used. The fluorescence labeling of the substrate was carried out according to the conventional method (Akihiro Kondo et al., Agric. Biol. Chem., 54, 2169 (1990)). The IgG Sepharose was allowed to react with an assay solution containing or not containing CMP-sialic acid as a sugar donor. The reaction mixture was analysed by HPLC, and the peaks appearing only with the assay solution containing CMP-sialic acid were considered as the products. After completion of the reaction, the assay solution was treated at 100° C. for 5 minutes, and centrifuged at 10,000×g for 10 minutes. Then, 10 µl of the resulting supernatant was subjected to HPLC which was carried out on the TSKgel ODS-80$T_M$ column (4.6 mm×30 cm; Tosoh) eluting with 0.02M ammonium acetate buffer (pH 4.0) at a temperature of 50° C. at a rate of 1 ml/min. The products were detected using the fluorescence HPLC monitor model RF-535T (Shimazu Seisakusho) with an excitation wavelength of 320 nm and an emission wavelength of 400 nm. The products were identified from the facts that the elution time was coincided with that of the standard and that the substrate was regenerated by sialidase treatment of the products. The quantitative analysis of the products was carried out with the use of pyridylaminated lactose as the standard for comparison of fluorescence intensity. The results of this assay are shown in Table 2. The activity to various sugar chain substrates is also shown in terms of a relative activity when the activity to the substrate LNnT is taken as 100.

In cases where the IgG Sepharose derived from the culture supernatant of Namalwa cells having the plasmid pAMoPRSAW17-31F was used, α2→3 sialyltransferase activity was detected when any of the sugar chains was used as the substrate. On the other hand, in cases where the IgG Sepharose derived from the culture supernatant of Namalwa cells having the vector pAMoPRSA, no activity was detected when any of the sugar chains was used as the substrate. These results indicate that α2→3 sialyltransferase undergo secretory production into the culture suprnatant as a fused protein with the IgG-binding region of *Staphylococcus aureus* protein A and that it can readily be recovered and purified using IgG Sepharose.

Also shown in Table 2 are the relative activities of a known α2→3 sialyltransferase, for which purification has been reported so far (Wienstein et al., J. Biol. Chem., 257, 13845 (1982)), to various sugar chain substrates when its activity to the substrate LNT is taken as 100. The known α2→3 sialyltransferase exhibits a higher specificity to LNT than LNnT, whereas the α2→3 sialyltransferase of the present invention exhibits a higher specificity to LNnT than LNT. This indicates that the α2→3 sialyltransferase of the present invention is a novel enzyme having a different susbtrate specificity from that of the known enzyme.

It was also shown that the α2→3 sialyltransferase of the present invention can take LNFP-III as the substrate. No report has been made so far on such α2→3 sialyltransferase having an enzymatic activity to LNFP-III. This indicates that the use of this enzyme can make possible the direct in vitro synthesis of sialyl-$Le^x$ sugar chains from $Le^x$ sugar chains.

Because the α2→3 sialyltransferase of the present invention can take not only LNnT but also LNT as the substrate, it is possible to synthesize sialyl-$Le^a$ sugar chains, as well as sialyl-$Le^x$ sugar chains. That is, with the use of the α2→3 sialyltransferase of the present invention, the terminal structure of a sugar chain can be converted into NeuAcα2-3Galβ1-4GlcNAc or NeuAcα2-3Galβ1 -3GlcNAc, which are then made into a sialyl-$Le^x$ sugar chain or a sialyl-$Le^a$ sugar chain, using α1→3 fucosyltransferase or α1→4 fucosyltransferase, respectively. Moreover, the α2→3 sialyltransferase of the present invention exhibits a higher substrate specificity to LNnT than that attained by the known α2→3 sialyltransferase, and is therefore supeior to the known α2→3 sialyltransferase with respect to the capability for synthesis of sialyl-$Le^x$ sugar chains.

TABLE 2

| | α2→3 Sialyltransferase activity | | | |
| | | pAMoPRSAW17-31F | | Known α2→3 ST |
| Substrate sugar chain | pAMoPRSA pmol | pmol | Relative activity | Relative activity |
| --- | --- | --- | --- | --- |
| Galβ1-4GlcNAcβ1-3Galβ1-4Glc (LNnT) | 0 | 113.8 | 100 | 6 |
| Galβ1-4GlcNAcβ1-3Galβ1-4Glc (LNFP-III)<br>　　　3<br>　　　\|<br>　　Fucα1 | 0 | 9.4 | 8 | |
| Galβ1-3GlcNAcβ1-3Galβ1-4Glc (LNT) | 0 | 47.5 | 42 | 100 |
| Galβ1-3GlcNAcβ1-3Galβ1-4Glc (LNFP-V)<br>　　　3<br>　　　\|<br>　　Fucα1 | 0 | 36.3 | 32 | |

What is claimed is:

1. A cDNA encoding an α2→3 sialyltransferase having an amino acid sequence as designated by Seq. ID: 2 or 7 or a DNA having homology with said cDNA.

2. A cDNA having a nucleotide sequence as designated by Seq. ID: 1 or 6.

3. A recombinant vector containing a cDNA which encodes α2→3 sialyltransferase having an amino acid sequence as designated by Seq. ID: 2 or 7.

4. A recombinant vector containing a cDNA which encodes an amino acid sequence as designated by Seq. ID: 1 or 6.

5. A process of preparing a cDNA according to claim 1 or 2, which comprises the steps of:

constructing a cDNA library by incorporating into a vector, a cDNA synthesized using as an template an mRNA extracted from an animal cell;

introducing said cDNA library into a cell and preparing a culture of the obtained cell in the presence of a lectin having an activity to inhibit the growth of said cell; and separating the grown cell from said culture and isolating from said cell, a DNA which encodes $\alpha 2 \rightarrow 3$ sialyltransferase.

6. A process of preparing a recombinant vector according to claim 3 or 4, which comprises the steps of:

constructing a cDNA library by incorporating into a vector, a cDNA synthesized using as an template an mRNA extracted from an animal cell;

introducing said cDNA library into a cell and preparing a culture of the obtained cell in the presence of a lectin having an activity to inhibit the growth of said cell;

separating the grown cell from said culture and isolating from said cell, a DNA which encodes $\alpha 2 \rightarrow 3$ sialyltransferase; and introducing said DNA into a vector downstream the position of a promoter therein.

7. A process for production of an $\alpha 2 \rightarrow 3$ sialyltransferase having an amino acid sequence as designated by Seq. ID: 2 or 7, which comprises the steps of:

preparing a culture of a cell containing a recombinant vector according to claim 3 or 4 in a medium and allowing $\alpha 2 \rightarrow 3$ sialyltransferase produced by said cell to accumulate in said culture; and isolating $\alpha 2 \rightarrow 3$ sialyltransferase from said culture.

8. A process according to claim 5, wherein said animal cell is a TYH cell or a human melanoma WM266-4 cell.

9. A process according to claim 6, wherein said animal cell is a TYH cell or a human melanoma WM266-4 cell.

10. A process according to claim 5, wherein said lectin is *Ricinus communis* 120 lectin.

11. A process according to claim 6, wherein said lectin is *Ricinus communis* 120 lectin.

12. Plasmid pUCl19-LEC.

13. Plasmid pUCl19-WM17.

14. A cell containing a recombinant vector according to claim 3 or 4.

15. A method for adding sialic acid at non-reducing terminus in the lactosamine structure of a glycoprotein or a glycolipid in $\alpha 2 \rightarrow 3$ linkage by use of a cell according to claim 14.

16. A method for converting non-reducing terminus of sugar chains on glycoproteins or glycolipids into sialyl-Le$^x$ structure by use of a cell according to claim 14.

17. A method for detecting the expression of an $\alpha 2 \rightarrow 3$ sialyltransferase having an amino acid sequence as designated by Seq. ID: 2 or 7 by hybridization using a cDNA according to claim 1 or 2.

18. A method for detecting the expression of an $\alpha 2 \rightarrow 3$ sialyltransferase having an amino acid sequence as designated by Seq. ID: 2 or 7 by polymerase chain reaction using synthesized oligonucleotides as probes which are designed based on the nucleotide sequence of cDNA according to claim 1 or 2.

19. A method for suppressing the expression of an $\alpha 2 \rightarrow 3$ sialyltransferase having an amino acid sequence as designated by Seq. ID: 2 or 7 by use of an oligonucleotide which contains part or all of the nucleotide sequence of a cDNA according to claim 1 or 2.

20. An *Escherichia coli* strain containing a recombinant vector according to claim 3 or 4.

21. *Escherichia coli* strain HB101/pUCl19-LEC (FERM BP-3625).

22. *Escherichia coli* strain HB101/pUCl19-WM17 (FERM BP-4013).

* * * * *

UNITED STATES PATENT AND TRADEMARK OFFICE
CERTIFICATE OF CORRECTION

PATENT NO. : 5,494,790
DATED : Feb. 27, 1996
INVENTOR(S) : Sasaki, et al.

Page 1 of 24

It is certified that error appears in the above-identified patent and that said Letters Patent is hereby corrected as shown below:

The Title Page should be deleted to appear as per attached

Please delete columns 1 - 54 and substitute columns 1- 44 as per attached.

Signed and Sealed this

Twenty-second Day of April, 1997

Attest:

BRUCE LEHMAN

Attesting Officer

Commissioner of Patents and Trademarks

United States Patent [19]

Sasaki et al.

[11] Patent Number: 5,494,790

[45] Date of Patent: Feb. 27, 1996

[54] α2→3 SIALYLTRANSFERASE

[75] Inventors: Katsutoshi Sasaki, Machida; Etsuyo Watanabe, Kawasaki; Tatsunari Nishi, Machida; Susumu Sekine; Nobuo Hanai, both of Sagimihara; Mamoru Hasegawa, Kawasaki, all of Japan

[73] Assignee: Kyowa Hakko Kogyo Co., Ltd., Tokyo, Japan

[21] Appl. No.: 309,985

[22] Filed: Sep. 20, 1994

Related U.S. Application Data

[62] Division of Ser. No. 991,587, Dec. 16, 1992, Pat. No. 5,384,249.

Foreign Application Priority Data

| Dec. 17, 1991 | [JP] | Japan | 3-333661 |
| Apr. 10, 1992 | [JP] | Japan | 4-091044 |

[51] Int. Cl.$^6$ .................. C12Q 1/68; C12N 9/10; C12N 15/54

[52] U.S. Cl. .................. 435/6; 435/85; 435/193; 435/252.33; 435/320.1; 536/23.2

[58] Field of Search .................. 536/23.2; 435/320.1, 435/193, 252.33, 85, 6

[56] References Cited

U.S. PATENT DOCUMENTS 5,047,335  9/1991  Paulson et al. .................. 435/69.1

FOREIGN PATENT DOCUMENTS

| 475354 | 3/1992 | European Pat. Off. |
| WO91-12340 | 2/1991 | WIPO |
| WO91-06635 | 8/1991 | WIPO |
| 12340 | 8/1991 | WIPO |

OTHER PUBLICATIONS

Ripka, et al, Biochem. Biophys. Acfa., vol. 159, No. 2 (1989) 554–60.
Paulson, et al., FASEB J., vol. 4, No. 7 (1990) A1862.
Gillespie, et al., FASEB J., vol. 4, No. 7 (1990) A2068.
Joziasse, et al., J. Biol. Chem., vol. 260, No. 8 (1985) 4941–51.
Weinstein et al., J. Biol. Chem. vol. 262, No. 36 pp. 17735–17743 (1987).
Weinstein et al., J. Biol. Chem. vol. 257, No. 22 pp. 13835–13844 (1982).
Wen et al., J. Biol. Chem., vol. 267 (Oct. 1992) pp. 21011–21019.
Kanani et al., Cancer Research, vol. 50 (Aug. 1990) pp. 5003–5007.
Sadler et al., J. Biol. Chem., vol. 254, No. 11 (Jun. 1979) pp. 4434–4443.
Saitoh et al., Cancer Research, vol. 51 (Jun. 1991) 2854–2862.
Phillips et al., Science, vol. 250 (Nov. 1990) pp. 1130–1132.
Sabesan et al. J. Am. Chem. Soc., vol. 108, No. 8 (1986) pp. 2068–2080.

*Primary Examiner*—Charles L. Patterson, Jr.
*Attorney, Agent, or Firm*—Fitzpatrick, Cella, Harper & Scinto

[57] ABSTRACT

There are provided a novel α2→3 sialyltransferase expressed by a cloned gene from animal cells, a cDNA encoding the α2→3 sialyltransferase, a method for detecting or supporting the expression of an α2→3 sialyltransferase by use of said cDNA, a recombinant vector containing said cDNA, a cell containing said vector, and their production processes.

22 Claims, 29 Drawing Sheets

α2→3 SIALYLTRANSFERASE

BACKGROUND OF THE INVENTION

Field of the Invention

The present invention relates to a novel α2→3 sialyltransferase, DNA encoding the α2→3 sialyltransferase, a recombinant vector in which the DNA is incorporated and a cell containing the recombinant vector as well as a process for producing them. Further, the present invention relates to processes for synthesizing a sugar chain and attaching sialic acid to a sugar chain using the α2→3 sialyltransferase of the present invention and processes for synthesizing a sugar chain and attaching sialic acid to a sugar chain by expressing the α2→3 sialyltransferase of the present invention in a transformed cell. Further, the present invention relates to a method for detecting or inhibiting the expression of the α2→3 sialyltransferase of the present invention by using cDNA encoding the α2→3 sialyltransferase of the present invention. The α2→3 sialyltransferase of the present invention is useful for attaching sialic acid to a sugar chain and thereby obtaining useful physiological activity, and modifying a sugar chain which is attached to a useful physiologically active protein.

BACKGROUND OF THE INVENTION

While protein produced by procaryotes such as *Escherichia coli* and the like have no sugar chain, the proteins and lipids produced by eucaryotes such as yeast, fungi, plant cells, animal cells and the like have an attached sugar chain in many cases.

Examples of sugar chains found in animal cells are the N-linked sugar chain (also called N-glycan) which binds to asparagine (Asn) residue in proteins, and the O-linked sugar chain (also called O-glycan) which binds to serine (Ser) or threonine (Thr) residues that are known to be part of glycoproteins. It has been recently revealed that certain lipids containing sugar chains are covalently bonded to a number of proteins and that the proteins attach to cell membranes via those lipids. Those lipids containing such a sugar chain are known as glycosyl phosphatidylinositol anchors.

Another example of a sugar chain found in animal cells is glycosaminoglycan. A compound wherein a protein and a glycosaminoglycan are covalently bonded is called a proteoglycan. Although the glycosaminoglycan which is a component of a proteoglycan has a similar structure to that of O-glycan, which is a glycoprotein sugar chain, glycosaminoglycan has chemical properties that differ from those of O-glycan. Glycosaminoglycan has a characteristic structure composed of disaccharide unit repeats containing glucosamine or galactosamine and uronic acid (except that keratan sulfate has no uronic acid), wherein the sulfate groups are covalently bonded thereto (except that hyaluronic acid has no sulfate groups).

Another example of a sugar chain found in animal cells is the sugar chain contained in glycolipids. Glycolipids in animal cells can be further characterized as sphingoglycolipids in which a sugar, a long chain fatty acid and sphingosine, which is a long chain base are covalently bonded, and glyceroglycolipids in which a sugar chain is covalently bonded to glycerol.

Elucidation of the function of sugar chains has rapidly advanced together with the advances in molecular biology and cell biology. Consequently, a variety of the functions of sugar chains have been revealed. Firstly, sugar chains play an important roll in the clearance of glycoproteins in blood. Erythropoietin obtained by transferring a gene in *Escherichia coli* manifests its activity in vitro, but is known to be rapidly cleared in vivo [Dordal et al.: Endocrinology, 116, 2293 (1985) and Browne et al.: Cold Spr. Harb. Symp. Quant. Biol., 51, 693, 1986]. Human granulocytemacrophage colony stimulating factor (hGM-CSF) naturally has two N-linked sugar chains, but it is known that, as the number of sugar chains is decreased, the clearance rate in rat plasma is raised proportionally thereto [Donahue et al.: Cold Spr. Harb. Symp. Quant. Biol., 51, 685 (1986)]. The clearance rate and clearance sites vary depending upon the structure of the sugar chain. It is known that, while hGM-CSF to which sialic acid is added is cleared in the kidney, hGM-CSF from which sialic acid is removed has a higher clearance rate and is cleared in the liver. Additionally, the clearance rates in rat plasma and rat perfusion liquid were studied with respect to α1-acid glycoproteins having different sugar chains, which were biosynthesized by rat liver primary culture in the presence of various N-linked sugar chain biosynthesis inhibitors. In both cases, the clearance rates were slower in descending order of high mannose type, sugar chain deficient type, hybrid type and complex type (natural type). It is also known that the clearance in blood of tissue-type plasminogen activator (t-PA), used as a fibrinolytic agent, is significantly influenced by the structure of its sugar chain.

It is also known that a sugar chain endows a protein with protease resistance. For example, when formation of the sugar chain of fibronectin is inhibited by zunicamycin, the resulting sugar chain deficient fibronectin is promoted in the intracellular degradation rate. It is also known that addition of a sugar chain to a protein increases heat stability and anti-freezing properties. And it is known that sugar chains contribute to the increased solubility of certain proteins.

Sugar chains also help proteins maintain their correct steric structure. It is known that removal of two N-linked sugar chains naturally present in membrane-bound glycoproteins of the vesicular stomatitis virus inhibits the transport of proteins to the cell surface, and a new addition of sugar chains to said proteins restores the transport. In this case, it has been revealed that the removal of sugar chains induces association between protein molecules via disulfide bonding and, as a result, the transport of proteins is inhibited. Since the correct steric structure is restored due to inhibition of this association by a new addition of sugar chains, the transport of proteins again becomes possible. It is shown that the position to which a new sugar chain is added is considerably flexible. To the contrary, it has been revealed that the transport of proteins having natural sugar chains is completely inhibited, in some cases, depending upon the introduction site of the additional sugar chain.

It is also known that a sugar chain can mask an antigen site on a polypeptide. From experiments using polyclonal antibody or monoclonal antibody reacting with a particular region on a polypeptide in hGM-CSF, prolactin, interferon-γ, Rauscher leukemia virus gp70 and influenza hemagglutinin, it is considered that a sugar chain of the above proteins inhibits a reaction with the antibody. There is also known the case where a sugar chain itself has a direct relationship with the manifestation of the activity of a glycoprotein. For example, a sugar chain is considered to participate in the manifestation of activity of glycoprotein hormones such as luteinizing hormone, follicle stimulating hormone, chorionic gonadotropin and the like.

In addition, EP-A 0370205 discloses that granulocyte colony-stimulating factor (G-CSF), pro-urokinase (pro-UK) and the like can be improved in their properties by artificially and intentionally introducing a sugar chain into the proteins using recombinant DNA techniques.

Furthermore, an important function of sugar chains is participation in recognition phenomena between cells, between proteins and between cells and proteins. For example, it is known that the site where a sugar chain is cleared in the living body varies depending upon the structure of the sugar chain. In addition, it has been found that a ligand of ELAM-1, which is inflammatory response-specifically expressed on blood vessel endothelial cells and promotes adhesion to neutrophils, is a sugar chain called Sialyl-Le$^x$ [NeuAc $\alpha 2 \rightarrow 3$Gal $\beta 1 \rightarrow 4$ (Fuc $\alpha 1 \rightarrow 3$)GlcNAc:NeuAc, sialic acid; Gal, galactose; Fuc, fucose; GlcNAc, N-acetylglucosamine]. As a result, there is the possibility that this sugar chain itself or a modification thereof may be useful in pharmaceuticals and the like [Phillips et al.: Science 250, 1130 (1990), Goelz et al.: Trends in Glycoscience and Glycotechnology 4, 14 (1992)].

Further, it is suggested that L-selectin, which is expressed in a part of T lymphocytes and neutrophils, and GMP-140 (also called P-selectin), which is expressed in the membrane surface of platelets and blood vessel endothelial cells participate in inflammatory response in the same manner as ELAM-1, and ligands thereof are also sugar chains similar to the Sialyl-Le$^x$ sugar chain which is a ligand of ELAM-1 [Rosen et al.: Trends in Glycoscience and Glycotechnology 4, 1 (1992), Larsen et al.: Trends in Glycoscience and Glycotechnology 4, 25 (1992), Aruffo et al.: Trends in Glycoscience and Glycotechnology 4, 146 (1992)].

In metastasis of cancer, as in inflammatory response, it is suggested that ELAM-1 and GMP-140 promote metastasis of cancer by causing the adhesion of cancer cells to the inner wall of blood vessels or an aggregation between cancer cells and platelets [Goelz et al.: Trends in Glycoscience and Glycotechnology) 4, 14 (1992), Larsen et al.: Trends in Glycoscience and Glycotechnology 4, 25 (1992)]. These suggestions are consistent with the findings that expression of the Sialyl-Le$^x$ sugar chain is high in cancer cells having high metastasis ability [Irimura et al.: Experimental Medicine 6, 33 (1988)].

From these findings, it is expected that the Sialyl-Le$^x$ sugar chain or derivatives thereof may manifest excellent anti-inflammatory effects and anti-metastatic effects by binding to ELAM-1, L-selectin or GMP-140.

Additionally, in view of the mechanisms of the above-described inflammatory response and metastasis of cancer, inflammatory response could be inhibited and metastasis of cancer could be prevented by inhibiting the expression of the glycosyltransferase which controls the synthesis of the ligand sugar chain recognized by ELAM-1, L-selectin or GMP-140. Antisense RNA/antisense DNA techniques [Tokuhisa: Bioscience and Industry 50, 322 (1992), Murakami: Chemistry 4, 681 (1991)] or Triple helix techniques [Chubb and Hogan: Trends in Biotechnology 10, 132 (1992)] could be useful in inhibiting the expression of the particular genes which code for these glycosyltransferases. Since information on the gene or the nucleotide sequence of the gene coding for the glycosyltransferase to be inhibited is necessary in order to inhibit its expression using antisense RNA/DNA techniques, the cloning of this gene and analysis of the information on its nucleotide sequence are important.

Further, diagnosis of malignancy in inflammatory diseases or cancer could be made by investigating the expression of the particular glycosyltransferase in inflammatory lymphocytes and cancer cells. As techniques for investigating the expression of the desired glycosyltransferase, the Northern hybridization method, which uses as a probe the relevant gene labelled with radioactivity and the like [Sambrook, Fritsch, Maniatis, Molecular Cloning, a laboratory manual, 2nd edition, Cold Spring Harbor Laboratory Press, 1989], and the Polymerase Chain Reaction method (abbreviated as PCR method hereinafter) [Innis et al.: PCR Protocols, Academic Press, 1990] are useful. To apply these methods, however, information on the desired glycosyltransferase gene, or nucleotide sequence thereof, is necessary. As a consequence, the cloning of the desired glycosyltransferase gene and analysis of information on its nucleotide sequence are important to the diagnosis of malignancy in inflammatory diseases or cancer in this manner.

As described above, alteration in the structure of the glycoprotein and mass production of the particular sugar chain or modification thereof are industrially important themes.

The means by which the structure of a sugar chain can be altered have recently advanced remarkably. In particular, the structure of a sugar chain can be altered by a high specific enzyme (exoglycosidase) which successively dissociates a sugar chain or glycopeptidase and endo-type glycosidase which cleaves a bond between a peptide chain and a sugar chain without changing either the peptide chain or the sugar chain. As the result, the biological role of a sugar chain can be studied in detail. Further, endoglycoceramidase, which cleaves between a sugar chain of a glycolipid and ceramide has been recently found [Ito and Yamagata: J. Biol. Chem. 261, 14278 (1986)]. This finding has not only facilitated the preparation of sugar chains of glycolipids but has also advanced the study of the function of cell surface glycolipids.

In addition, a new addition to a sugar chain has been possible by using a glycosyltransferase. For example, sialic acid can be newly added to the end of a sugar chain by using a sialyltransferase [Sabesan and Paulson: J. Am. Chem. Soc. 108, 2068 (1986)]. The sugar chain to be added can be varied by using other various glycosyltransferases or glycosidase inhibitors [Alan et al.: Annu. Rev. Biochem. 56, 497 (1097)]. However, mass production of the glycosyltransferases used in the synthesis of sugar chains is extremely difficult. For that reason, it is desirable to produce glycosyltransferases in large quantities by cloning the glycosyltransferases using recombinant DNA techniques and effectively expressing the glycosyltransferases in host cells.

Methods for cloning a glycosyltransferase include: purifying a protein, producing an antibody reacting with it and performing immunoscreening using the antibody [Weinstein et al.: J. Biol. Chem. 252, 17735 (1987)], and purifying a protein, determining the amino acid sequence thereof, producing synthetic DNA which corresponds thereto and performing hybridization using the DNA as a probe [Narimatsu et al.: Proc. Natl. Acad. Sci., USA, 83, 4720 (1986)]. A method is also known where hybridization is performed using a cloned glycosyltransferase gene as a probe and thereby a glycosyltransferase gene having homology with the glycosyltransferase is cloned [John B. Lowe et al.: J. Biol. Chem. 266, 17467 (1991)]. In addition, there is also a direct expression cloning method using the panning method as the screening method, in which an antibody or lectin reacting with a sugar chain is employed [John B. Lowe et al.: Proc. Natl. Acad. Sci. USA, 86, 8227 (1989); John B. Lowe et al.: Genes Develop., 4, 1288 (1990)].

There is no case in which a glycosyltransferase has been cloned using lectin-resistance as an index. However, from the studies on various lectin-resistant mutants of CHO cell, it has been revealed that there are cases in which a new glycosyltransferase is expressed, where the activity of a certain glycosyltransferase disappears, and where the synthesis of sugar nucleotide or its transfer to Golgi body is inhibited [Pamela Stanley et al.: Methods in Enzymology, 96, 157]. Therefore, it is considered that cloning of a glycosyltransferase can be performed using lectin-resistance as an index by introducing a gene derived from a cell expressing the glycosyltransferase to be cloned into CHO cell or lectin-resistant mutants of CHO cell [Ravindra Kumar et al.: Mol. Cell. Biol., 9, 5713 (1989)].

James Ripka et al. have tried to clone N-acetyl-glucosaminyltransferase I by introducing human genomic DNA derived from A431 cell into lectin-resistant mutants of CHO cell (Lec1) using resistance to lectin concanavalin A as an index. However, they could not clone a glycosyltransferase by the screening method using lectin-resistance as an index [James Ripka et al.: Biochem. Biophys. Res. Commun., 159, 554 (1989)]. Heffernan et al. have cloned mouse sialic acid hydroxylase using resistance to lectin WGA (wheat germ agglutinin) as an index by introducing a cDNA library into CHO cell [Michael Heffernan et al.: Nucleic Acids Res., 19, 85 (1991)] which was made to produce large T antigen of polyoma [Michael Heffernan et al.: Glycoconjugate J., 8, 154 (1991)]. However, there is no report in which a glycosyltransferase was cloned in a screening system using lectin-resistance as an index. In addition, with respect to hosts, Stanley, Ripka, Heffernan et al. all used CHO cell or lectin-resistant mutants of CHO cell as a host.

With respect to sialyltransferase, a cDNA encoding an enzyme having βgalactoside α2→6 sialyltranferase activity has been isolated and the nucleotide sequence thereof has been revealed [Weinstein et al.: J. Biol. Chem., 262, 17735 (1987)]. With respect to an enzyme having βgalactoside α2→3 sialyltransferase activity, Gillespie et al. have reported cloning a gene encoding an enzyme which adds sialic acid to galactose in O-linked sugar chain of glycoproteins (the sugar chain which is added to serine or threonine residue), but the base sequence thereof has not been revealed [Gillespie et al.: Glycoconjugate J., 7, 469 (1990)]. In addition, Weinstein et al. have reported a method for purifying an enzyme having βgalactoside α2→3 sialyltransferase activity from rat liver [Weinstein et al.: J. Biol. Chem., 257, 13835 (1982)]. However, the desired enzyme can only be obtained in an extremely small amount. Hitherto, there have been no reports in which sialic acid has been added in α2→3 linkage to a desired position on sugar chains of glycoproteins, glycolipids, oligosaccharides and the like using recombinant DNA techniques.

OBJECTS OF THE INVENTION

The main objects of the present invention are to provide a novel α2→3 sialyltransferase which effectively alters a sugar chain of a protein and produces a particular sugar chain, cDNA encoding said α2→3 sialyltranferase and a vector containing said cDNA.

These objects, as well as other objects and advantages of the present invention, will become apparent to those skilled in the art from the following description with reference to the accompanying drawings.

SUMMARY OF THE INVENTION

The present inventors constructed a cDNA library by incorporating cDNA which was synthesized using mRNA extracted from animal cells as a template into an expression cloning vector, introduced said cDNA library into a cell, the resultant cell was cultured in the presence of lectin having activity which inhibits the growth of said cell, and the growing cells were isolated to obtain a cloned gene which was introduced in a host cell to express. As the result, we found that a novel α2→3 sialyltransferase was expressed, resulting in completion of the present invention.

According to the present invention, there is provided novel α2→3 sialyltransferase having the amino acid sequence shown by SEQUENCE IDENTIFIER NUMBER (Seq.ID:) 2 or 7, cDNA encoding said α2→3 sialyltransferase, and a recombinant vector containing said DNA. α2→3 sialyltransferase of the present invention is a glycosyltransferase having βgalactoside α2→3 sialyltransferase activity and functioning to add sialic acid to the end of a substrate sugar chain in α2→3 linkage.

BRIEF EXPLANATION OF THE DRAWINGS

FIG. 1 is a flow sheet showing construction of plasmid pAGEL106.

FIG. 2 is a flow sheet showing construction of plasmid pASLB3-3-1.

FIG. 3 is a flow sheet showing construction of plasmid pASLB3-3.

FIG. 4 is a flow sheet showing construction of plasmid pSALBE3-3.

FIG. 5 is a flow sheet showing construction of plasmid pASLBC.

FIG. 6 is a flow sheet showing construction of plasmid pASLBEC.

FIG. 7 is a flow sheet showing construction of plasmid pASLBEC2.

FIG. 8 is a flow sheet showing construction of plasmid pAMoEC2.

FIG. 9 is a flow sheet showing construction of plasmid pAMoEC3.

FIG. 10 is a flow sheet showing construction of plasmid pAMoERC3.

FIG. 11 is a flow sheet showing construction of plasmid pAGE207.

FIG. 12 is a flow sheet showing construction of plasmid pAGE207ScN.

FIG. 13 is a flow sheet showing construction of plasmid pAMoC3Sc.

FIG. 14 is a flow sheet showing construction of plasmid pAMoERC3Sc.

FIG. 15 is a flow sheet showing construction of cDNA library.

Figure 16:
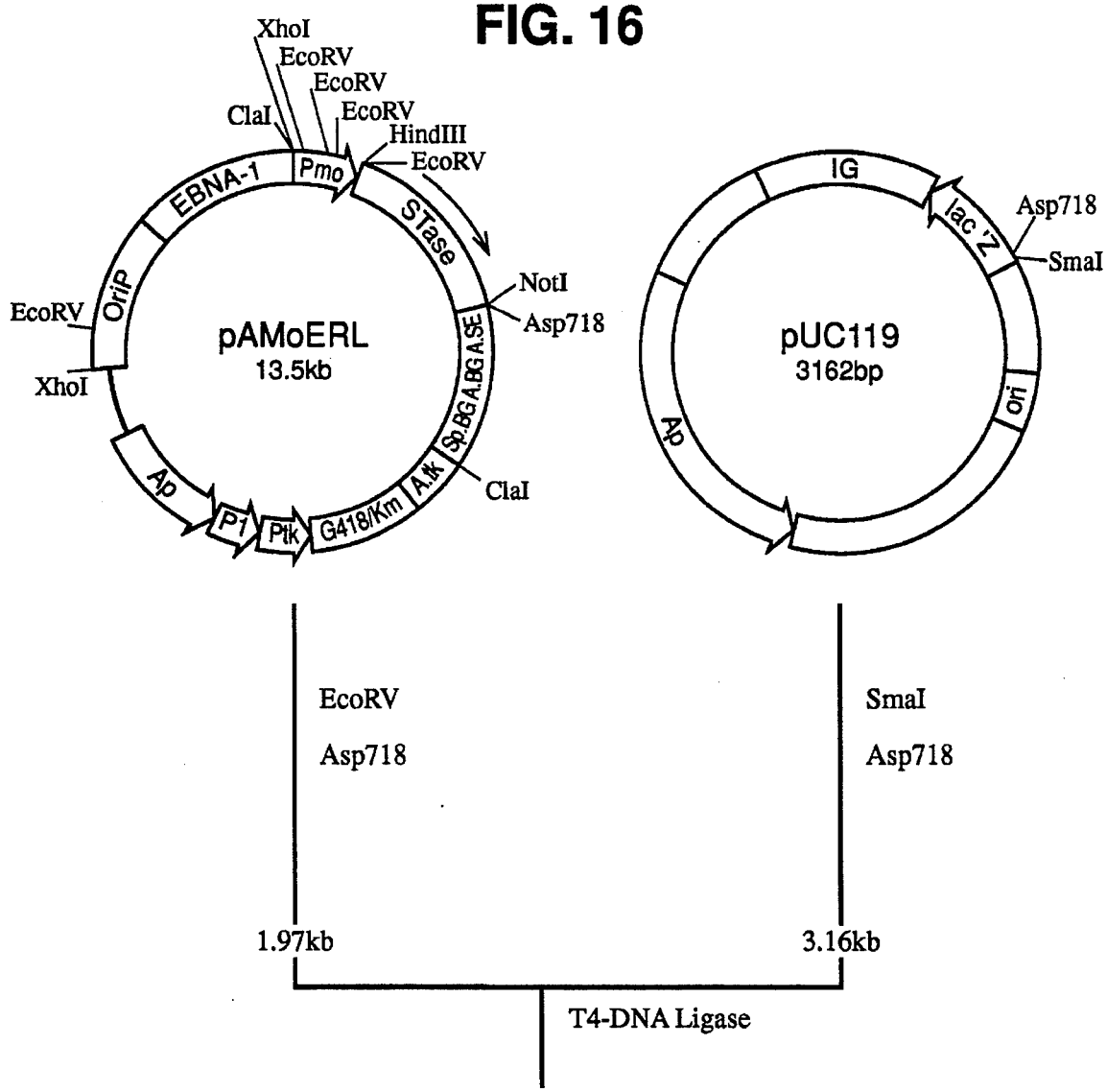
FIG. 16 is a flow sheet showing construction of plasmid pUC119-LEC.
Figure 16:
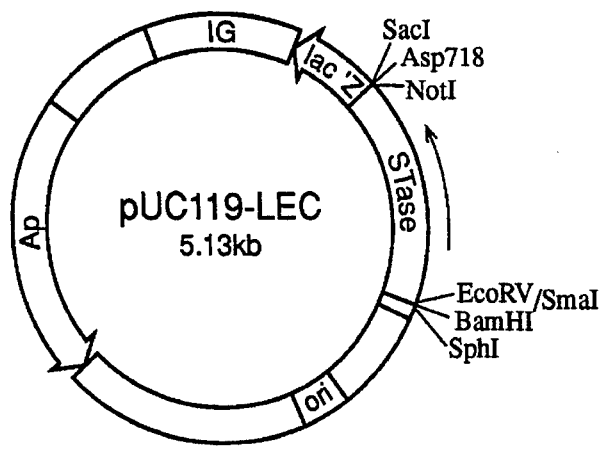
Figure 17A:
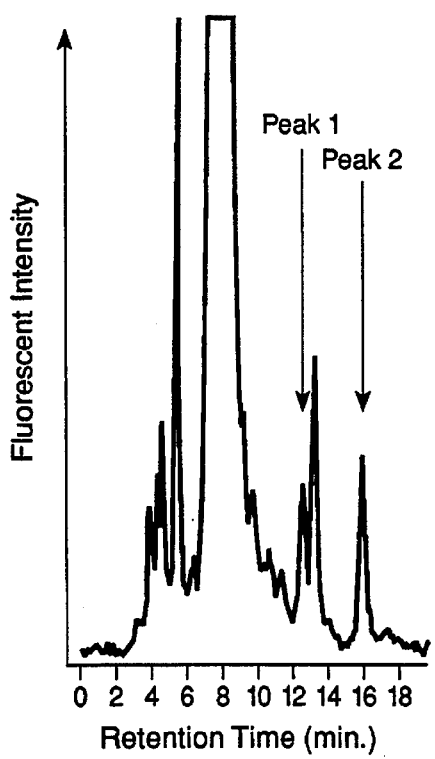
FIG. 17 is a view showing the results of the sialyltransferase activity measured by HPLC. Pannels a. and b. show HPLC pattern on KJM-1 strain in which pAMoERL is introduced and Pannels c. and d. show HPLC pattern on KJM-1 strain in which vector pAMoERC3Sc is introduced, respectively. Pannels a. and c. show HPLC pattern where an assay solution containing CMP-sialic acid as sugar donor is used and Pannels b. and d. show HPLC pattern where an assay solution not containing CMP-sialic acid is used, respectively.
Figure 17B:
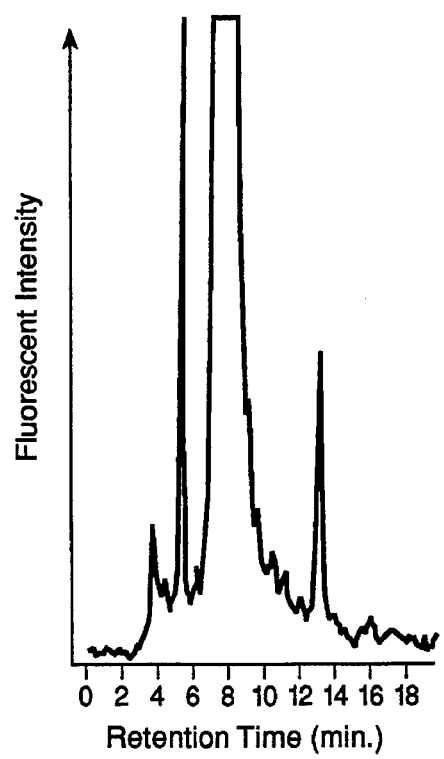
Figure 17C:
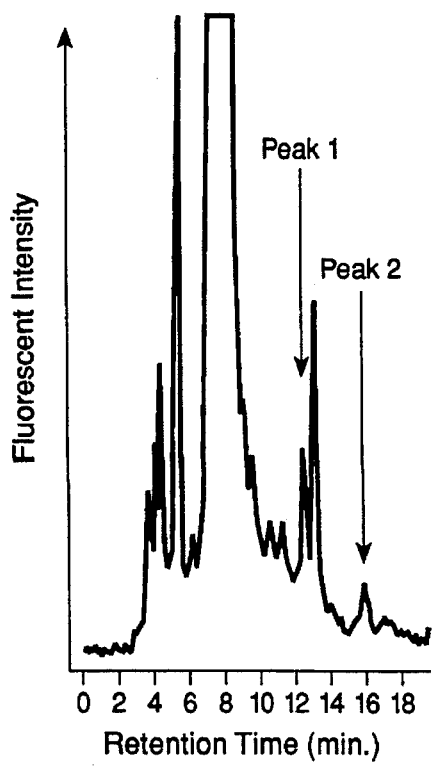
Figure 17D:
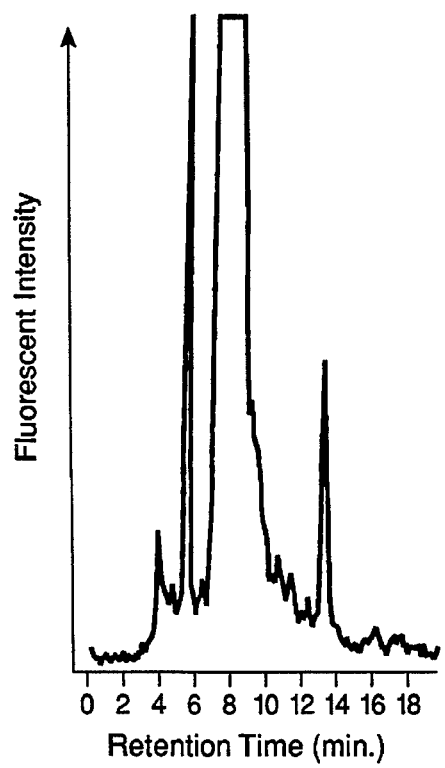
Figure 18C:
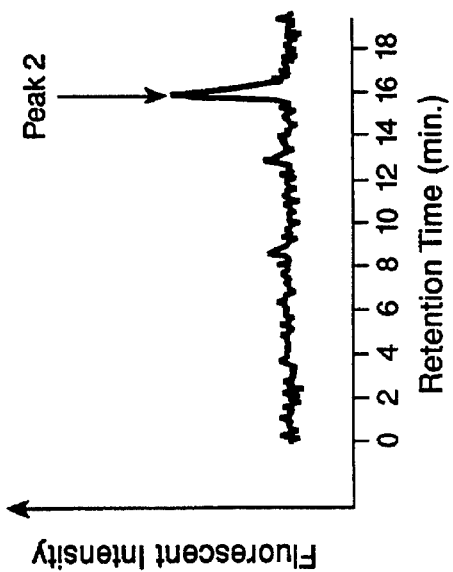
FIG. 18 is a view showing the results of analysis by HPLC after peak 1 and peak 2 are treated with sialidase. Pannels a. and c. show HPLC pattern on peak 1 and peak 2 without sialidase treatment, respectively. Pannels b. and d. show HPLC pattern on peak 1 and peak 2 after sialidase treatment, respectively. Peak 3 shows the product obtained by treating peak 1 and peak 2 with sialidase.
Figure 18D:
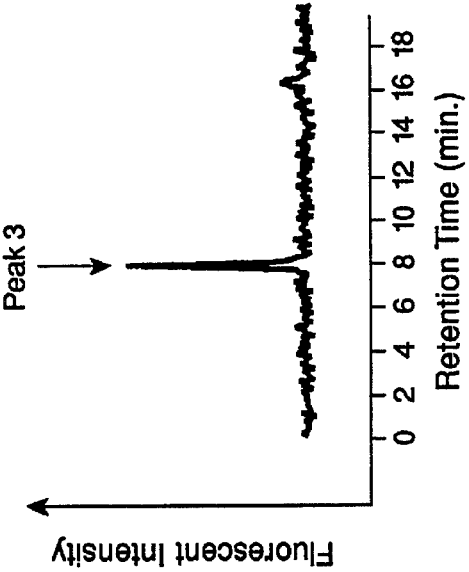
Figure 18A:
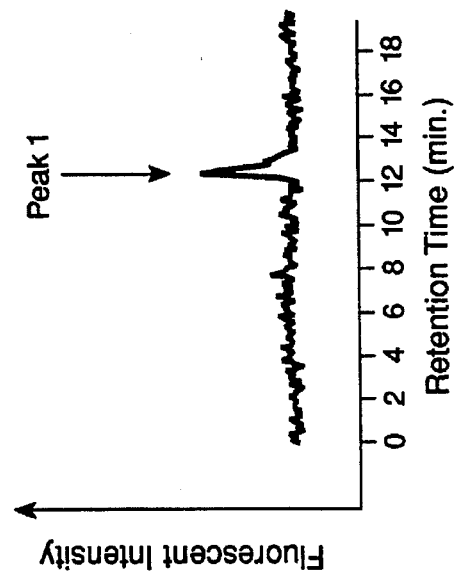
Figure 18B:
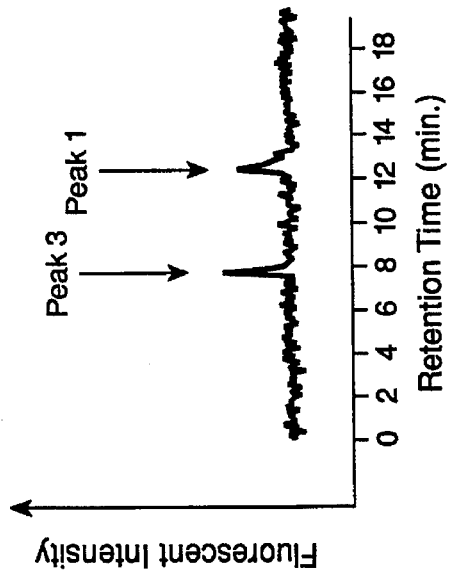

FIG. 16 is a flow sheet showing construction of plasmid pUC119-LEC.

FIG. 17 is a view showing the results of the sialyltransferase activity measured by HPLC. Panels a. and b. show HPLC pattern on KJM-1 strain in which pAMoERL is introduced and Panels c. and d. show HPLC pattern on KJM-1 strain in which vector pAMoERC3Sc is introduced, respectively. Panels a. and c. show HPLC pattern where an assay solution containing CMP-sialic acid as sugar donor is used and Panels b. and d. show HPLC pattern where an assay solution not containing CMP-sialic acid is used, respectively.

FIG. 18 is a view showing the results of analysis by HPLC after peak 1 and peak 2 are treated with sialidase. Panels a. and c. show HPLC pattern on peak 1 and peak 2 without sialidase treatment, respectively. Panels b. and d. show HPLC pattern on peak 1 and peak 2 after sialidase treatment, respectively. Peak 3 shows the product obtained by treating peak 1 and peak 2 with sialidase.

FIG. 19 is a view showing the results of analysis by a flow cell sorter FCS-1 (manufactured by Nihonbunko) after indirect fluorescent antibody staining. Panel a. shows the results of indirect fluorescent antibody staining using KM93 or serum of normal mouse on KJM-1 in which pAMoERC3Sc is introduced. Dotted line shows the pattern when normal mouse serum is used, and solid line shows the pattern when KM93 is used. Panel b. shows the results of indirect fluorescent antibody staining using KM93 on KJM-1 strain in which pAMoERL is introduced. Dotted line is the same one shown in Panel a., and solid line shows the pattern when KM93 is used.

Figure 20:
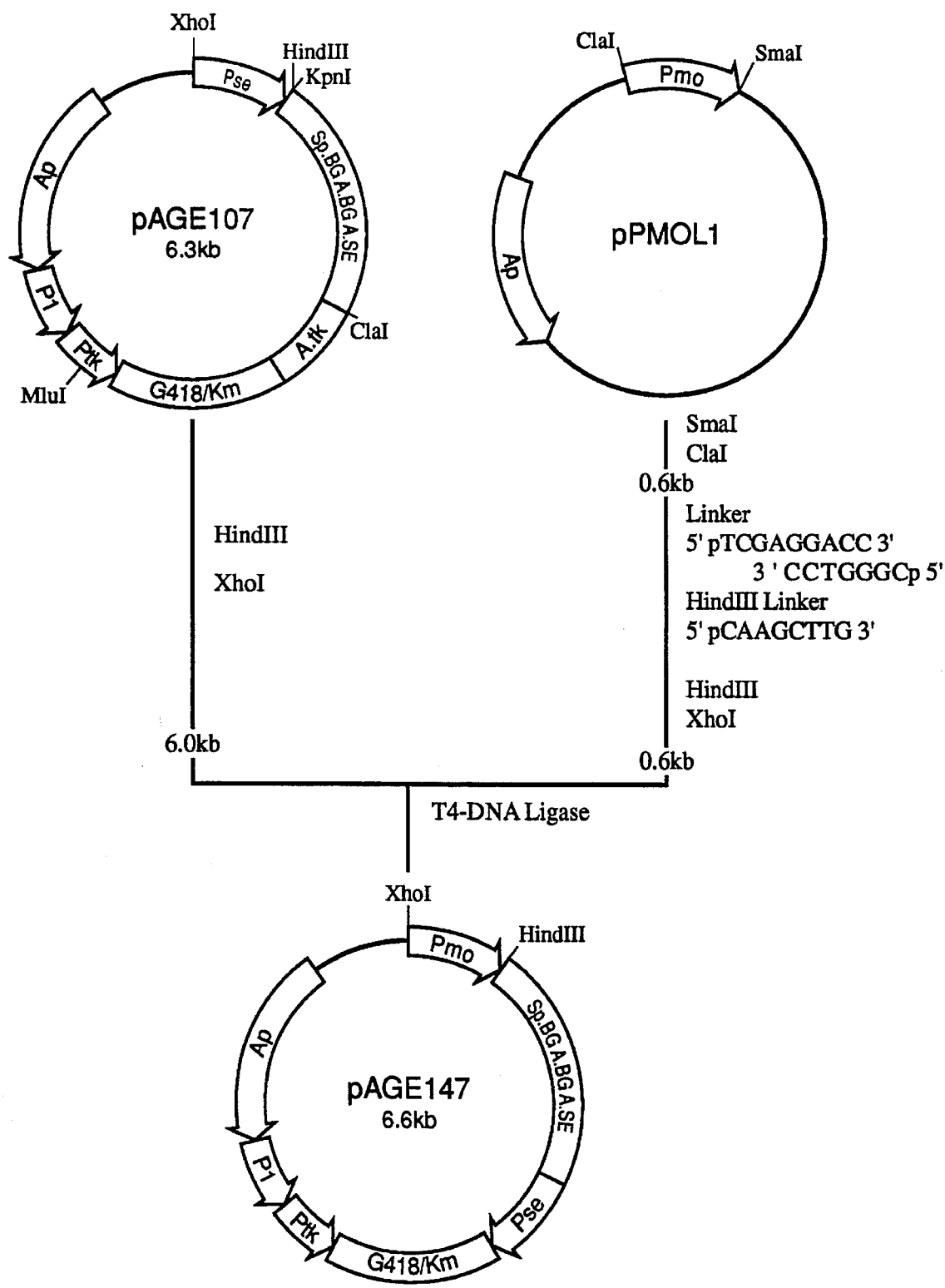
FIG. 20 is a flow sheet showing construction of plasmid pAGE147.

FIG. 20 is a flow sheet showing construction of plasmid pAGE147.

FIG. 21 is a flow sheet showing construction of plasmid pAGE247.

FIG. 22 is a flow sheet showing construction of plasmid pAMN6hyg.

FIG. 23 is a flow sheet showing construction of plasmid pAMoERSA.

FIG. 24 is a flow sheet showing construction of plasmid pAMoPRC3Sc.

FIG. 25 is a flow sheet showing construction of plasmid pAMoPRSA.

FIG. 26 is a flow sheet showing construction of plasmid pAMoPRSAL-35F.

FIG. 27 is a flow sheet showing construction of plasmid pUC119-WM17.

FIG. 28 is a view showing the results of analysis by EPICS Elite Flow Cytometer (manufactured by COULTER) after indirect fluorescent antibody staining. As a control, the results of indirect fluorescent antibody staining using normal mouse serum on KJM-1 strain in which pAMoPRC3Sc (control plasmid) is introduced are also shown. In addition, the results of indirect fluorescent antibody staining using KM93 on KJM-1 strain in which pAMoPRC3Sc (control plasmid) or pAMoPRWM17 (α2→3 sialyltransferase expression plasmid) is introduced are also shown as pAMoPRC3Sc or pAMoPRWM17, respectively.

Figure 29:
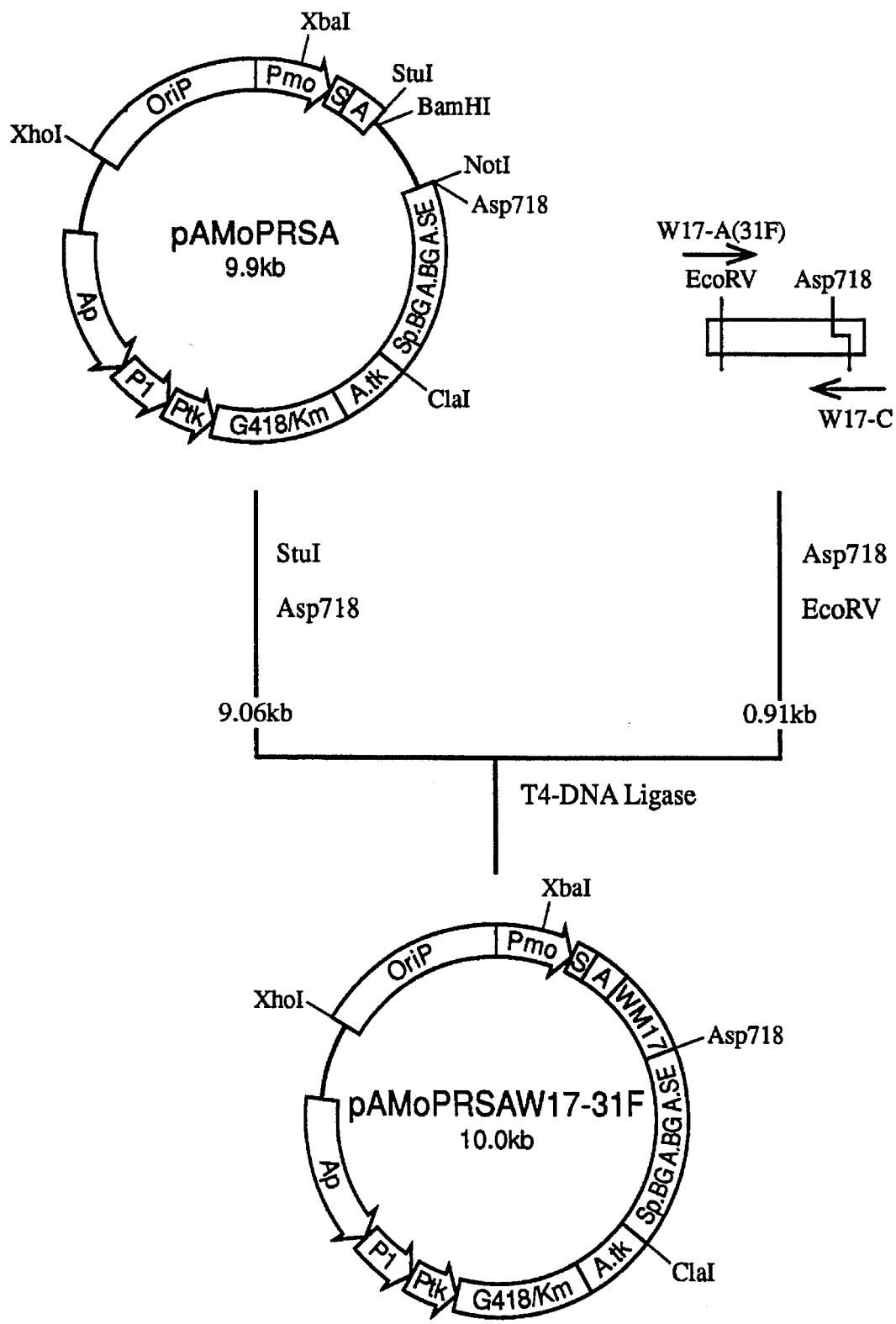
FIG. 29 is a flow sheet showing construction of plasmid pAMoPRSAW17-31F.

FIG. 29 is a flow sheet showing construction of plasmid pAMoPRSAW17-31F.

The abbreviations used herein have the following meanings.

dhfr: dihydrofolate reductase gene
hg-CSF: human granulocyte colony stimulating factor gene
bp: base pairs
kb: kilobase pairs
G418/Km: G418 and kanamycin resistance gene derived from transposon 5 (Tn5)
hyg: hygromycin resistance gene
Ap: ampicillin resistance gene derived from pBR322
Tc: tetracycline resistance gene derived from pBR322
Pl: Pl promoter derived from pBR322
Ptk: Herpes simplex virus (HSV) thymidine kinase (tk gene promoter)
Sp. βG: rabbit βglobin gene splicing signal
A. βG: rabbit βglobin gene poly A addition signal
A. SE: simian virus 40 (SV40) early gene poly A addition signal
Atk: Herpes simplex virus (HSV) thymidine kinase (tk) gene poly A addition signal
Pse: simian virus 40 (SV40) early gene promoter
Pmo: Moloney murine leukemia virus long terminal repeat (LTR) promoter
HTLV-1: human T-cell leukemia virus type-1 (HTLV-1) gene
EBNA-1: Epstein-Barr virus EBNA-1 gene
oriP: Epstein-Barr virus replication gene
ori: pUC119 replication gene
lac'Z: a part of *Escherichia coli* βgalactosidase gene
IG: intergenic region of M13 phage DNA

DETAILED DESCRIPTION OF THE INVENTION cDNA encoding the α2→3 sialyltransferase of the present invention include (a) DNA having the nucleotide sequence shown in Seq. ID:1 or 6, (b) DNA having a nucleotide sequence different from that shown in Seq. ID: 1 or 6 due to the presence of a plurality of genetic codes relative to one amino acid, or due to natural mutation which occurs in individual animals including human beings, (c) DNA in which mutations such as substitution, deletion, insertion and the like are introduced in the DNA defined by (a) or (b) without losing the activity of α2→3 sialyltransferase activity of the present invention, for example, DNA having such homology with α2→3 sialyltransferase encoded by DNA defined by (a) or (b) as can be isolated by the hybridization method. The α2→3 sialyltransferase of the present invention includes all α2→3 sialyltransferases encoded by DNA defined in the above (a), (b) or (c).

A process for producing cDNA which encodes the α2→3 sialyltransferase of the present invention is explained below by exemplifying a process for producing cDNA defined in the above (a).

A cDNA library is constructed by incorporating cDNA synthesized using mRNA extracted from animal cells as a template into an expression cloning vector. This cDNA library is introduced into animal or insect cells, and the cells are cultured in the presence of lectin which inhibits the growth of the cells. A cell transfected with cDNA encoding glycosyltransferases which change the structure of the sugar chain recognized by lectin grows in the presence of lectin. This cell is isolated, and cDNA encoding the desired α2→3 sialyltransferase is obtained from the cell.

As the animal cell used in the above method, any animal cell can be used so long as the cDNA encoding the α2→3 sialyltransferase of the present invention can be expressed in that animal cell. For example, human histiocytic leukemia cell line TYH [Haranaka et al.: Int. J. Cancer, 36, 313 (1985)], human melanoma cell line WM266-4 (ATCC CRL1676) and the like can be used. As the vector in which the cDNA, synthesized usign mRNA extracted from these cells as a template, is incorporated, any vector can be used in which said cDNA can be incorporated and expressed. For example, pAMoERC3Sc and the like can be used. As an animal or insect cell into which the cDNA library constructed using said vector is introduced, any cell can be used in which said cDNA library can be introduced and expressed. For example, human Namalwa cell [Hosoi et al.: Cytotechnology, 1, 151 (1988)] and the like can be used. As the lectin to be used in the present invention, any lectin can be used which can inhibit growth of the cell into which the cDNA is introduced. For example, Ricinus communis 120 lectin and the like can be used. After the resistance of the host cell to lectin is determined, the lectin is used in such a concentration as can inhibit the growth of the host cell. The plasmid having cDNA encoding the α2→3 sialyltransferase of the present invention, or the DNA fragment containing the cDNA part, is recovered from the cells which grow in the presence of lectin by known methods, including the Hirt method [Robert F. Margolskee et al.: Mol. Cell. Biol., 8, 2837 (1988)]. As a plasmid having cDNA encoding the enzyme of the present invention, there are, for example, pUC119-LEC, pUC119-WM17 and the like. Escherichia coli HB101/pUC119-LEC containing pUC119-LEC and Escherichia coli HB101/pUC119-WM17 were deposited with the Fermentation Research Institute, Agency of Industrial Science and Technology, 1-3, Higashi 1 chome Tsukubashi Ibaraki-ken 305, Japan on Oct. 29, 1991 and on Sep. 22, 1992 under the Budapest Treaty, and have been assigned the accession numbers FERM BP-3625 and FERM BP-4013, respectively.

DNA defined by the above (b) and (c) can be prepared by well known recombinant DNA techniques such as the hybridization method, and a method introducing mutations in DNA and the like, based on cDNA encoding α2→3 sialyltransferase obtained by the above process. Alternatively, cDNA encoding α2→3 sialyltransferase of the present invention can be prepared using the chemosynthetic method.

DNA encoding α2→3 sialyltransferase of the present invention, obtained in the above process, is inserted downstream of an appropriate promoter to construct a recombinant vector which is introduced into a host cell, and the resulting cell is cultured to obtain the α2→3 sialyltransferase of the present invention. As a host cell, any host cell can be used to which recombinant DNA techniques have been applied such as procaryotic cells, animal cells, yeasts, fungi, insect cells and the like. For example, there are Escherichia coli cell as a procaryotic cell, CHO cell which is Chinese hamster ovary cell, COS cell which is monkey cell, Namalwa cell which is human cell and the like as animal cells. In particular, a direct expression system using a Namalwa cell as a host cell is suitably used introduces cDNA of the library into this cell is extremely efficient, the introduced plasmid (cDNA library) can exist extrachromosomally, and the plasmid is easily recovered from the resultant lectin-resistant strain.

As a vector for introducing DNA encoding the present α2→3 sialyltransferase therein, there can be used any vector into which DNA encoding the α2→3 sialyltransferase of the present invention can be incorporated and which can be expressed in a host cell. For example, there are pAGE107 [JP-A 3-22979, Miyaji et al.: Cytotechnology, 3, 133 1990)], pAS3-3 [EP-A 0370205], pAMoERC3Sc, CDM8 [Brian Seed et al.: Nature, 329, 840 (1987)] and the like. For expressing the cDNA encoding the enzyme of the present invention in Escherichia coli, it is preferable to use a plasmid in which foreign DNA can be inserted downstream of a promoter having strong transcription activity such as the trp promoter and the like and the distance between the Shine-Dalgarno sequence (abbreviated as SD sequence hereinafter) and the initiation codon is appropriately adjusted (for example, said distance is 6 to 18 bases). More particularly, there are pKYP10 [EP-A 0083069], pLSA1 [Miyaji et. al: Agric. Biol. Chem., 53, 277 (1989)] pGEL1 [Sekine et al, Proc. Natl. Acad. Sci., USA, 82, 4306 (1985)] and the like.

As general procedures of recombinant DNA techniques used in the present invention, those described in EP-A 0370205 or those described by Sambrook, Fritsch, Maniatis et al. [Molecular Cloning, A laboratory manual, 2nd edition, Cold Spring Harbor Laboratory Press, 1989] can be used. Isolation of mRNA and synthesis of the cDNA library can be effected by using the above-described methods and many kits on the market. For introducing DNA into an animal cell, there can be used any currently known method. For example, the electroporation method [Miyaji et al.: Cytotechnology, 3, 133 (1990)], the calcium phosphate method [EP-A 0370205], the lipofection method [Philip L. Felgner et al.: Proc. Natl. Acad. Sci., USA, 84, 7413 (1987)] and the like can be used. Obtaining transfected cells and culturing them can be performed according to the method described in EP-A 0370205 or JP-A 2-257891.

As a process for producing cloned α2→3 sialyltransferase, there is a method for expressing it in a host cell, a method for secreting it from a host cell, and a method for pressing it on the cell surface of a host cell. The place where expression is effected varies depending upon the kind of host cell used and upon the from of glycosyltransferase to be produced.

When glycosyltransferase is produced in its normal form, using an animal cell as a host cell, it is generally produced in the host cell or on the cell surface of the host cell, and a part of it is extracellularly excreted upon cleavage by a protease. To secrete glycosyltransferase intentionally, it is produced in a form where a signal peptide is added to a part containing an active site of the glycosyltransferase by using recombination DNA techniques according to a method by Paulson et al. [C. Paulson et al.: J. Biol. Chem., 264, 17610 (1989)] and a method by Lowe et al. [John B. Lowe et al.: Proc. Natl. Acad. Sci., USA, 86, 8227 (1989); John B. Lowe et al.: Genes Develop., 4, 1288 (1990)].

Alternatively, the production yield can be increased by using a gene amplification system using dihydrofolate reductase gene and the like according to a method described in EP-A 0370205.

The α2→3 sialyltransferase of the present invention thus produced can be purified by a conventional purifying method for glycosyltransferases [J. Evan. Sadler et al.: Methods of Enzymology, 83, 458]. When the enzyme is produced in Escherichia coli, it can be effectively purified by combining the above method and the method described in EP-A 0272703. Alternatively, purification can be carried out by producing the enzyme of the present invention as a fused protein and subjecting it to affinity chromatography using a substance have an affinity for the fused protein. For example, the enzyme of the present invention can be produced as a fused protein with protein A and purified by affinity chromatography using immunoglobulin G according to the method described by Lowe et al. [John B. Lowe et al.: Proc. Natl. Acad. Sci., USA, 86, 8227 (1989); John B. Lowe et al.: Genes Develop., 4, 1288 (1990)]. Alternatively, the enzyme can be purified by affinity chromatography using an antibody reacting with the enzyme itself.

The activity of the sialyltransferase is determined by the known method [J. Evan. Sadler et al.: Methods in Enzymology, 83, 458; Naoyuki Taniguti et al.: Methods in Enzymology, 179, 397].

A sugar chain can be synthesized in vitro using the α2→3 sialyltransferase of the present invention. For example, sialic acid can be added in a α2→3 linkage to non-reducing end-group of the lactosamine structure (Gal β1→4GlcNAc structure) contained in a glycoprotein, glycolipid or oligosaccharide. The structure of a sugar chain at the non-reducing terminus can also be converted to the Sialyl-Le$^x$ structure by acting α2→3 sialyltransferase of the present invention on a glycoprotein, glycolipid or oligosaccharide as a substrate. An oligosaccharide having Sialyl-Le$^x$ and modification thereof at the non-reducing terminus can be synthesized using a known α1→3 fucosyltransferase [Lowe et al.: Genes Develop., 4, 1288 (1990); Goelz et al.: Cell, 63, 1349 (1990)] after acting α2→3 sialyltransferase of the present invention on an oligosaccharide having the lactosamine structure at the non-reducing terminus.

DNA encoding α2→3 sialyltransferase of the present invention can be used together with DNAs encoding glycoproteins, glycolipids or oligosaccharides having useful physiological activity in an animal cell or insect cell and providing a sugar chain substrate for the α2→3 sialyltransferase. The produced α2→3 sialyltransferase can be acted on glycoproteins, glycolipids or oligosaccharides to obtain glycoproteins, glycolipids or oligosaccharides having the altered sugar chain structure.

Further, a part of the oligosaccharide can be excised from the resulting glycoprotein, glycolipid or oligosaccharide having the altered sugar chain structure by using the know enzymatic or chemical method.

DNA encoding the α2→3 sialyltransferase of the present invention can be used not only to modify the sugar chain of glycoproteins, glycolipids or oligosaccharides and to efficiently produce the particular sugar chain but also in therapy for diseases such as inflammation or cancer metastasis using antisense RNA/DNA techniques and diagnosis on those diseases using the Northern hybridization method or the PCR method.

Expression of the activity of the α2→3 sialyltransferase of the present invention can be inhibited using, for example, antisense RNA/DNA techniques [Tokuhisa: Bioscience and Industry, 50, 322 (1992), Murakami: Kagaku, 46, 681 (1991); Miller: Biotechnology, 9, 358 (1992); Cohen: Trends in Biotechnology, 10, 87 (1992); Agrawal: Trends in Biotechnology, 10, 152 (1992)] or the triple helix technique [Chubb and Hogan: Trends in Biotechnology, 10, 132 (1992)]. More particularly, expression of the α2→3 sialyltransferase can be inhibited by administering in the living body an oligonucleotide which is designed and prepared based on the nucleotide sequence of a part of the α2→3 sialyltransferase gene, preferably a 10–50 base sequence in the initiation region. As the nucleotide sequence of the synthetic oligonucleotide, there can be used the completely same sequence as that of a part of the antisense strand disclosed herein or a sequence which is modified so that the α2→3 sialyltransferase expression inhibiting activity is not lost. When the triple helix technique is used, the nucleotide sequence of the synthetic oligonucleotide is designed based on information about the nucleotide sequences of both the sense and antisense strands.

In addition, expression of the cDNA encoding the α2→3 sialyltransferase of the present invention can be detected by the hybridization method or the PCR method as follows.

For detecting expression of the cDNA encoding the α2→3 sialyltransferase of the present invention using the Northern hybridization method or the PCR method, probe DNA or a synthetic oligonucleotide is prepared based on the cDNA encoding the α2→3 sialyltransferase of the present invention or a nucleotide sequence thereof. The Northern hybridization method and the PCR method are performed according to Molecular Cloning, a Laboratory Manual, 2nd edition [Cold Spring Harbor Laboratory Press, 1989] and PCR Protocols [Academic Press 1990].

The following Examples further illustrate the present invention in detail but are not to be construed as limiting the scope thereof.

In the following Examples, the T4 polynucleotide kinase and the T4 DNA ligase used were those manufactured by Takarashuzo K.K.

EXAMPLE 1

1. Construction of direct expression cloning vector pAMoERC3Sc (1) Construction of pAGEL106 (see FIG. 1)

According to the method described below, plasmid pAGEL106 having promoter in which simian virus 40 (SV40) early gene promoter and a part of R region and U5 region of long terminal repeat of human T-cell leukemia virus type-1 (HTLV-1) are fused was constructed. That is, a DNA fragment containing a part of R region and U5 region [BanII-Sau3AI fragment (0.27 kb)] was isolated from pATK03 and inserted between BglI site and BamHI site of pAGE106 via synthetic linker.

pAGE106 (1 μg) obtained by the method described in EP-A 0370205 was dissolved in a buffer (abbreviated as Y-100 buffer hereinafter) containing 10 mM Tris-HCl (pH 7.5), 6 mM magnesium chloride, 100 mM sodium chloride and 6 mM 2-mercaptoethanol, and digested with 10 units of BglI (manufactured by Takarashuzo; the restriction enzymes used were those manufactured by Takarashuzo hereinafter, unless otherwise indicated) and 10 units of BamHI at 37° C. for two hours. The reaction solution was subjected to agarose gel electrophoresis to obtain about 4.9 kb of the DNA fragment.

Separately, 1μ of pATK03 [Shimizu et al.: Proc. Natl. Acad. Sci., USA, 80, 3618 (1983)] was dissolved in 30 μl of Y-100 buffer, and 10 units of BanII was added thereto. The mixture was subjected to digestion reaction at 37° C. for two hours, and subjected to agarose gel electrophoresis to give about 0.4kb of DNA fragment. The resulting DNA fragment was dissolved in Y-100 buffer (30 μl) and 10 units of Sau3AI was added thereto. The mixture was subjected to digestion reaction at 37° C. for two hours, and subjected to agarose gel electrophoresis to give about 0.27 kb of DNA fragment.

Separately, for linking BglI cleavage site and BanII cleavage site, the following DNA linker was synthesized.

5'CGGGCT3' (6mer)
3'GGAGC5' (5mer)

The 5 mer and 6 mer single-stranded DNAs of the DNA linker were synthesized using a DNA synthesizer model 380A (Applied Biosystems). Each 0.2 μg of the synthesized DNAs was dissolved in 40 μl of a buffer (abbreviated as T4 kinase buffer hereinafter) containing 50 mM Tris-HCl (pH 7.5), 10 mM magnesium chloride, 5 mM dithiothreitol (abbreviated as DTT hereinafter), 0.1 nM EDTA and 1mM adenosine triphosphate (abbreviated as ATP hereinafter) and phosphorylated with 30 units of T4 polynucleotide kinase at 37° C. for two hours.

The DNA fragments thus obtained, i.e., 0.2 μg of BglI-BamHI fragment (4.9 kb) derived from pAGE106 and 0.01 μg of BanII-Sau3AI fragment (0.27 kb) derived from pATKo73 were dissolved in 30 μl of buffer (abbreviated as T4 ligase buffer hereinafter) containing 66 mM Tris-HCl (pH 7.5), 6.6 mM magnesium chloride, 10 mM DTT and 0.1 mM ATP. 0.01 μg of the above DNA linker was added to the solution and both the DNA fragments and DNA linker were ligated together with 175 units of T4 DNA ligase at 12° C. for 16 hours.

Escherichia coli HB101 strain [Bolivar et al.: Gene, 2, 75 (1977)] was transformed using the above reaction mixture according to the method described by Cohen et al. [S. N. Cohen et al.: Proc. Natl. Acad. Sci., USA, 69, 2110 (1972)] to obtain kanamycin resistant strains. From these transformants, a plasmid was isolated according to the known method [H. C. Birnboim et al.: Nucleic Acids Res., 7, 1513 (1979)]. This plasmid was designated as pAGEL106, and its structure was confirmed by restriction enzyme digestion.

(2) Construction of pASLB3-3-1 (see FIG. 2)

According to the method described below, expression plasmid pASLB3-3-1 of human granulocyte colony stimulating factor (hG-CSF) having promoter in which SV40 early gene promoter and a part of R region and U5 region of long terminal repeat (LTR) of HTLV-1 are fused was constructed.

0.5 μg of pAGEL106 obtained in Sec. 1(1) of this Example was dissolved in 30 μl of a buffer (abbreviated as K-20 buffer hereinafter) containing 10 mM Tris-HCl (pH 7.5), 6 mM magnesium chloride, 20 mM potassium chloride and 6 mM 2-mercaptoethanol, and digested with 10 units of SmaI at 37° C. for two hours. After precipitation with ethanol, the precipitate was dissolved in 30 μl of T4 ligase buffer, and the digested DNA and 0.01 μl of SalI linker (5'pGGTCGACC3': manufactured by Takarashuzo) were ligated together with 175 units of T4 DNA ligase at 12° C. for 16 hours. After precipitation with ethanol, the precipitate was dissolved in 30 μl of a buffer (abbreviated as Y-175 buffer hereinafter) containing 10 mM Tris-HCl (pH 7.5), 6 mM magnesium chloride, 175 mM sodium chloride and 6 mM 2-mercaptoethanol, and digested with 10 units of SalI and 10 units of MluI at 37° C. for two hours. The reaction solution was subjected to agarose gel electrophoresis to give about 1.7kb of DNA fragment.

On the other hand, 1 μg of pAS3-3 obtained by the method described in EP-A 0370205 was dissolved in 30 μl of Y-175 buffer, and digested with 10 units of SalI and 10 units of MluI at 37° C. for 2 hours. The reaction solution was subjected to agarose gel electrophoresis to give about 6.7 kb of DNA fragment.

DNA fragments thus obtained, i.e., 0.1 μg of MluI-SalI fragment (1.7 kb) derived from pAGEL106 and 0.2 μg of MluI-SalI fragment (6.7 kb) derived from pAS3-3 were dissolved in 30 μl of T4 ligase buffer and ligated together with 175 units of T4 DNA ligase at 12° C. for 16 hours.

Escherichia Coli HB101 strain was transformed using the above reaction solution according to the method described by Cohen et al. to obtain a kanamycin resistant strain. From this transformant, a plasmid was isolated according to the known method. This plasmid was designated as pASLB3-3-1, and its structure was confirmed by restriction enzyme digestion.

(3) Construction of pASLB3-3 (see FIG. 3)

According to the method described below, in order to construct plasmid pASLB3-3 wherein ampicillin resistance gene is introduced in pASLB3-3-1, DNA fragment [XhoI-MluI fragment (2.58 kb)] containing ampicillin resistance gene of pAS3-3 was introduced between XhoI site and MluI site of pASLB3-3-1.

1 μg of pASLB3-3-1 obtained in Sec. 1(2) of this Example was dissolved in 30 μl of a buffer (abbreviated as Y-150 buffer) containing 10 mM Tris-HCl (pH 7.5), 6 mM magnesium chloride, 150 mM sodium chloride and 6 mM 2-mercaptoethanol and digested with 10 units of XhoI and 10 units of MluI at 37° C. for two hours. The reaction solution was subjected to agarose gel electrophoresis to give about 7.26 kb of DNA fragment.

Separately, 1 μg of pAS3-3 was dissolved in Y-150 buffer (30 μl) and digested with 10 units of XhoI and 10 units of MluI at 37° C. for two hours. The reaction solution was subjected to agarose gel electrophoresis to give about 2.58 kb of DNA fragment.

DNA fragments thus obtained, i.e., 0.2 μg of XhoI-MluI fragment (7.26 kb) derived from pASLB3-3-1 and 0.1 μg of XhoI-MluI fragment (2.58 kb) derived from pAS3-3 were dissolved in T4 ligase buffer (30 μl) and ligated together with 175 units of T4 DNA ligase at 12° C. for 16 hours.

Escherichia coli HB101 strain was transformed using the above reaction mixture according to the method described by Cohen et al. to obtain an ampicillin resistant strain. From this transformant, a plasmid was isolated according to the known method. This plasmid was designated as pASLB3-3, and its structure was confirmed by restriction enzyme digestion.

(4) Construction of pASLBE3-3 (see FIG. 4)

According to the method described below, dihydrofolate reductase (dhfr) expression unit was removed from pASLB3-3 to obtain plasmid pASLBE3-3 wherein replicaiton origin (oriP) of Epstein-Barr virus and EB-NA-1 gene are introduced. EBNA-1 gene encodes a factor which causes replication by trans-acting to oriP. For that use, oriP and EBNA-1 gene were isolated from plasmid p220.2 wherein SmaI-HaeIII fragment containing multicloning sites derived from pUC12 [Messing et al.: Methods in Enzymology, 101, 20 (1983)] is incorporated at NarI site of p201 [Bill Sugden et al., Nature, 313, 812 (1985)].

1 μg of Plasmid p220.2 was dissolved in Y-100 buffer (30 μl) and digested with 20 units of EcoRI at 37° C. for two hours. After precipitation with ethanol, the precipitate was dissolved in 30 μl of DNA polymerase I buffer containing 50 mM Tris-HCl (pH 7.5), 10 mM magnesium chloride, 0.1 mM dATP (deoxyadenosine triphosphate), 0.1 mM dCTP (deoxycytidine triphosphate), 0.1 mM dGTP (deoxyguanosine triphosphate), and 0.1 mM dTTP (deoxythymidine triphosphate), and 6 units of Escherichia coli DNA polymerase I Klenow fragment was added to react at 37° C. for 60 minutes, which resulted in conversion of 5' protruding cohesive end produced by EcoRI digestion into blunt end. The reaction was stopped by extraction with phenol, extracted with chloroform, and precipitated with ethanol. The precipitate was dissolved in 20 µl of T4 ligase buffer, and XhoI linker (5'pCCTCGAGG3', manufactured by Takarashuzo) (0.05 µg) and 175 units of T4 DNA ligase were added to react at 12° C. for 16 hours. After precipitation with ethanol, the precipitate was dissolved in 30 µl of Y-100 buffer, and digested with 10 units of BamHI at 37° C. for two hours. After precipitation with ethanol, the precipitate was dissolved in 30 µl of DNA polymerase I buffer, and 6 units of Escherichia coli DNA polymerase I Klenow fragment were added to react at 37° C. for 60 minutes, which resulted in conversion of 5' protruding cohesive end into blunt end. The reaction wa stopped by extraction with phenol, extracted with chloroform, and precipitated with ethanol. The precipitate was dissolved in 30 µl of Y-100 buffer, and digested with 10 units of XhoI at 37° C. for two hours. The reaction solution was subjected to agarose gel electrophoresis to give about 4.9 kb of DNA fragment.

Separately, 1 µg of pASLB3-3 was dissolved in 30 µl of Y-100 buffer, and 20 units of XhoI was added to perform digestion reaction at 37° C for two hours. After precipitation with ethanol, the precipitate was dissolved in 30 µl of DNA polymerase I buffer, and 6 units of Escherichia coli DNA polymerase I Klenow fragment were added to react at 37° C. for 60 minutes, which resulted in conversion of 5' protruding cohesive end produced by XhoI digestion into blunt end. The reaction was stopped by extraction with phenol, extracted with chloroform, precipitated with ethanol, the precipitate was dissolved in a buffer (abbreviated as Y-0 buffer hereinafter) containing 10 mM Tris-HCl (pH 7.5), 6 mM magnesium chloride and 6 mM 2-mercaptoethanol, and 20 units of KpnI were added to perform digestion reaction at 37° C. for two hours. The reaction solution was subjected to agarose gel electrophoresis to give about 1.3 kb of DNA fragment.

Separately, 1 µl of pAGE107 [JP-A 3-22979, Miyaji et al.: Cytotechnology, 3, 133 (1990)] was dissolved in 30 µl of Y-0 buffer, and 20 units of KpnI were added to perform digestion reaction at 37° C. for two hours. Thereafter, sodium chloride was added to give a NaCl concentration of 100 mM, and 20 units of XhoI were added to perform digestion reaction at 37° C. for two hours. The reaction solution was subjected to agarose gel electrophoresis to give about 6.0 kb of DNA fragment.

The DNA fragments thus obtained, i.e., 0.2 µg of XhoI-BamHI (blunt end) fragment (4.9 kb) derived from p220.2, 0.1 µg of XhoI (blunt end)-KpnI fragment (1.3 kb) derived from pASLB3-3 and 0.2 µg of KpnI-XhoI fragment (6.0 kb) derived from pAGE107 were dissolved in 30 µl of T4 ligase buffer and ligated with 175 units of T4 DNA ligase at 12° C. for 16 hours.

Escherichia coli HB101 strain was transformed using the reaction mixture according to the method described by Cohen et al. to obtain an ampicillin resistant strain. From this transformant, a plasmid was isolated according to the known method. This plasmid was designated as pASLB3E3-3, and its structure was confirmed by restriction enzyme digestion.

(5) Construction of pASLBC (see FIG. 5)

According to the method described below, plasmid pASLBC was constructed wherein hG-CSF cDNA was removed from pASLB3-3 and multicloning sites were introduced. Multicloning sites were produced using synthetic DNA.

1 µg of pASLB3-3 obtained in Sec. 1(4) of this Example was dissolved in 30 µl of Y-175 buffer and digested with 20 units of SalI and 20 units of MluI at 37° C. for two hours. The reaction solution was subjected to agarose gel electrophoresis to give about 3.1 kb of DNA fragment.

Separately, 1 µg of pASLB3-3 was dissolved in 30 µl of Y-0 buffer and digested with 20 units of KpnI at 37° C. for two hours. Then, sodium chloride was added to this reaction mixture to give NaCl concentration of 150 mM, and this plasmid was digested with 20 units of MluI at 37° C. for another two hours. The reaction mixture was subjected to agarose gel electrophoresis to give about 6.0 kb of DNA fragment.

Separately, as a linker for linking SalI cleavage site and KpnI cleavage site, the following DNA linker was synthesized. Restriction enzyme cleavage sites HindIII, EcoRV, SfiI, StuI and NotI are incorporated in the linker.

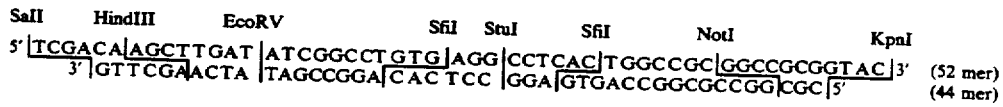

The 52 mer and 44 mer single-stranded DNAs of the DNA linker were synthesized using a DNA synthesizer model 380A (Applied Biosystems). Each 0.2 µg of the synthesized DNAs was dissolved in 20 µl of T4 kinase buffer and phosphorylated with 30 units of T4 polynucleotide kinase at 37° C. for two hours.

The DNA fragments thus obtained, i.e., 0.1 µg of SalI-MluI fragment (3.1 kb) and 0.2 µg of KpnI-MluI fragment (6.0 kb) derived from pASLB3-3 were dissolved in T4 ligase buffer (30 µl). 0.01 µg of the above DNA linker and both DNA fragments were ligated with 175 units of T4 DNA ligase at 12° C. for 16 hours.

Escherichia coli HB101 strain was transformed using the reaction mixture according to the method described by Cohen et al. to obtain an ampicillin resistant strain. From this transformant, a plasmid was isolated according to the known method. This plasmid was designated as pASLBC, and its structure was confirmed by restriction enzyme digestion.

(6) Construction of pASLBEC (see FIG. 6)

According to the method described below, plasmid pASLBEC was constructed by removing dihydrofolate reductase (dhfr) expression unit from pASLBC and introducing oriP and EBNA-1 genes therein.

1 µg of pASLBE3-3 obtained in Sec. 1(4) of this Example was dissolved in 30 µl of Y-150 buffer and digested with 20 units of MluI and 20 units of XhoI at 37° C. for two hours. The reaction solution was subjected to agarose gel electrophoresis to give about 1.3 kb of DNA fragment.

Separately, 1 µg of pASLBE3-3 was dissolved in 30 µl of Y-0 buffer and digested with 20 units of KpnI at 37° C. for two hours. Thereafter, sodium chloride was added to this reaction mixture to give a NaCl concentration of 150 mM and this plasmid was partially digested with 5 units of MluI at 37° C. for 20 minutes. The reaction solution was subjected to agarose gel electrophoresis to give about 9.6 kb of DNA fragment.

Then, 1 µg of pASLBC obtained in Sec. 1(5) of this Example was dissolved in 30 µl of Y-0 buffer and digested with 20 units of KpnI at 37° C. for two hours. Thereafter, sodium chloride was added to this reaction mixture to give a NaCl concentration of 100 mM and digested with 20 units of XhoI at 37° C. for another two hours. The reaction solution was subjected to agarose gel electrophoresis to give about 0.6 kb of DNA fragment.

The DNA fragments thus obtained, i.e., 0.2 μg of MluI-XhoI fragment (1.3 kb) and 0.2 μg of KpnI-MluI fragment (9.6 kb) derived from pASLBE3-3 and 0.05 μg of KpnI-XhoI fragment (0.6 kb) derived from pASLBC were dissolved in 30 μl of T4 ligase buffer and ligated together with 175 units of T4 DNA ligase at 12° C. for 16 hours.

*Escherichia coli* HB101 strain was transformed using the reaction mixture according to the method described by Cohen et al. to obtain an ampicillin resistant strain. From this transformant, a plasmid was isolated according to the known method. This plasmid was designated as pASLBEC, and its structure was confirmed by restriction enzyme digestion.

(7) Construction of pASLBEC2 (see FIG. 7)

According to the method described below, BamHI linker was introduced in StuI site in multicloning site of pASLBEC to obtain plasmid pASLBEC2. In pASLBEC2, StuI site in multicloning sites is lost.

1 μg of pASLBEC obtained in Sec. 1(6) of this Example was dissolved in 30 μl of Y-100 buffer and partially digested with 5 units of StuI at 37° C. for 20 minutes. The reaction solution was subjected to agarose gel electrophoresis to give about 11.5 kb of DNA fragment. The resulting DNA fragment was dissolved in 30 μl of T4 ligase buffer. The DNA fragment and 0.01 μg of BamHI linker (5'pCCGGATCCGG3': manufactured by Takarashuzo) were ligated together with 175 units of T4 DNA ligase at 12° C. for 16 hours. After precipitation with ethanol, the precipitate was dissolved in 30 μl of Y100 buffer and digested with 20 units of BamHI at 37° C. for two hours. The reaction solution was subjected to agarose gel electrophoresis to give about 11.5 kb of DNA fragment. The resulting DNA fragment was dissolved in T4 ligase buffer (20 μl) and ligated together with 175 units of T4 DNA ligase at 12° C. for 16 hours.

*Escherichia coli* HB 101 strain was transformed using the reaction mixture according to the method described by Cohen et al. to obtain an ampicillin resistant strain. From this transformant, a plasmid was isolated according to the known method. This plasmid was designated as pASLBEC2, and its structure was confirmed by restriction enzyme digestion.

(8) Construction of pAMoEC3 (see FIG. 8)

According to the method described below, plasmid pAMoEC2 was constructed wherein promoter in pASLBEC2 [promoter in which SV40 early gene promoter and a part of R region and U5 region of long terminal repeat (LTR) of HTLV-1 are fused] was replaced by promoter of long terminal repeat (LTR) of Moloney murine leukemia virus. For that use, Moloney murine leukemia virus LTR promoter was isolated from plasmid Molp-1 [Akinori Ishimoto et al.: Virology, 141, 30 (1985)].

1 μg of pASLBEC2 obtained in Sec. 1(7) of this Example was dissolved in a buffer (abbreviated as K-50 buffer hereinafter) containing 10 mM Tris-HCl (pH 7.5), 6 mM magnesium chloride, 50 mM potassium chloride and 6 mM 2-mercaptoethanol and digested with 20 units of HindIII and 20 units of AatII (manufactured by Toyoboseki) at 37° C. for two hours. The reaction solution was subjected to agarose gel electrophoresis to give about 4.8 kb of DNA fragment.

Separately, 1 μg of pASLBEC2 was dissolved in 30 μl of K-50 buffer and digested with 20 units of AatII at 37° C. for two hours. Thereafter, this plasmid was partially digested with 5 units of XhoI at 37° C. for 20 minutes. The reaction solution was subjected to agarose gel electrophoresis to give about 6.1 kb of DNA fragment.

Then, as a linker for linking XhoI cleavage site and ClaI cleavage site, the following linker was synthesized.

5'TCGAGGACC3' (9 mer)
3'CCTGGGC5' (7 mer)

The 9 mer and 7 mer single-stranded DNAs of the above DNA linker were synthesized using a DNA synthesizer model 380A (Applied Biosystems). Each 0.2 μg of the synthesized DNAs was dissolved in 40 μl of T4 kinase buffer and phosphorylated with 30 units of T4 polynucleotide kinase at 37° C. for two hours.

Separately, 1 μl of Molp-1 [Akinori Ishimoto et al.: Virology, 141, 30 (1985)] was dissolved in 30 μl of K-20 buffer and digested with 20 units of SmaI at 37° C. for two hours. Thereafter, sodium chloride was added to this reaction mixture to give a NaCl concentration of 50 mM and digested with 20 units of ClaI at 37° C. for two hours. The reaction solution was subjected to agarose gel electrophoresis to give about 0.6 kb of DNA fragment. The resulting DNA fragment was dissolved in 30 μl of T4 ligase buffer. The DNA fragment, 0.01 μg of the above DNA linker and 0.03 μg of HindIII linker (5'pCAAGCTTG3': manufactured by Takarashuzo) were ligated together with 175 units of T4 DNA ligase at 12° C. for 16 hours. After precipitation with ethanol, the precipitate was dissolved in 30 μl of a buffer (abbreviated as Y-50 buffer hereinafter) containing 10 mM Tris-HCl (pH 7.5), 6mM magnesium chloride, 50 mM sodium chloride and 6 mM 2-mercaptoethanol and digested with 10 units of HindIII at 37° C. for two hours. Thereafter, sodium chloride was added to this reaction mixture to give a NaCl concentration of 100 mM and digested with 10 units of XhoI at 37° C. for another two hours. The reaction solution was subjected to agarose gel electrophoresis to give about 0.6 kb of DNA fragment.

The DNA fragments thus obtained, i.e., 0.2 μg of HindIII-AatII fragment (4.8 kb) and 0.2 μg of AatII-XhoI fragment (6.1 kb) derived from pASLBEC2 and 0.05 μg of HindIII-XhoI fragment (0.6 kb) derived from Molp-1 were dissolved in 30 μl of T4 ligase buffer and ligated together with 175 units of T4 DNA ligase at 12° C. for 16 hours.

*Escherichia coli* HB101 strain was transformed using the reaction mixture according to the method described by Cohen et al. to obtain an ampicillin resistant strain. From this transformant, a plasmid was isolated according to the known method. This plasmid was designated as pAMoEC2, and its structure was confirmed by restriction enzyme digestion.

(9) Construction of pAMoEC3 (see FIG. 9)

According to the method described below, plasmid pAMoEC3 was constructed by inserting, as stuffer DNA, DNA fragment [DraI-PvuII fragment (2.5 kb)] containing tetracycline resistant gene of pBR322 into BamHI site in multicloning sites of pAMoEC2.

1 μg of pAMoEC2 obtained in Sec. 1(8) of this Example was dissolved in 30 μl of Y-100 buffer and digested with 20 units of BamHI at 37° C. for two hours. After precipitation with ethanol, the precipitate was dissolved in 30 μl of DNA polymerase I buffer, and 6 units of Escherichia coli DNA polymerase I Klenow fragment were added to react at 37° C. for 60 minutes, which resulted in conversion of 5' protruding cohesive end produced by BamHI into blunt end. The reaction solution was subjected to agarose gel electrophoresis to give about 11.5 kb of DNA fragment.

Separately, 1 μg of pBR322 [Bolivar et al.: Gene, 2, 95 (1977)] was dissolved in 30 μl of Y-50 buffer and digested with 20 units of DraI and 20 units of PvuII at 37° C. for two hours. The reaction solution was subjected to agarose gel electrophoresis to give about 2.5 kb of DNA fragment.

The DNA fragments thus obtained, i.e., 0.1 μg of BamHI (blunt end) fragment (11.5 kb) derived from pAMoEC2 and 0.2 μg Of DraI-PvuII fragment (2.5 kb) derived from pBR322 were dissolved in 30 μl of T4 ligase buffer and ligated together with 175 units of T4 DNA ligase at 12° C. for 16 hours.

Escherichia coli HB101 strain was transformed using the reaction mixture according to the method described by Cohen et al. to obtain an ampicillin and tetracycline resistant strain. From this transformant, a plasmid was isolated according to the known method. This plasmid was designated as pAMoEC3, and its structure was confirmed by restriction enzyme digestion.

(10) Construction of pAMoERC3 (see FIG. 10)

According to the method described below, plasmid pAMoERC3 was constructed by inverting the orientation of oriP and EBNA-1 gene in plasmid pAMoEC3.

1 μg of pAMoEC3 obtained in Sec. 1(9) of this Example was dissolved in 30 μl of Y-100 buffer and digested with 20 units of XhoI at 37° C. for two hours. Thereafter, this plasmid was added to 30 μl of 1M Tris-HCl (pH 8.0) and dephosphorylated with one unit of Escherichia coli alkaline phosphatase (manufactured by Takarashuzo) at 37° C. for two hours. After precipitation with ethanol, the precipitate was dissolved in 30 μl of a buffer (abbreviated as TE buffer hereinafter) containing 10 mM Tris-HCl (pH 8.0) and 1 mM EDTA, and the mixture was subjected to agarose gel electrophoresis to give about 9.1 kb of DNA fragment.

Separately, 1 μg of pAMoEC3 was dissolved in Y-100 buffer (30 μl) and digested with 20 units of XohI at 37° C. for two hours. The reaction solution was subjected to agarose gel electrophoresis to give about 4.9 kb of DNA fragment.

The DNA fragments thus obtained, i.e., 0.1 μg of XhoI fragment (9.1 kb) and 0.2 μg of XhoI fragment (4.9 kb) derived from pAMoEC3 were dissolved in 30 μl of T4 ligase buffer and ligated together with 175 units of T4 DNA ligase at 12° C. for 16 hours.

Escherichia coli HB101 strain was transformed using the reaction mixture according to the method described by Cohen et al. to obtain an ampicillin resistant strain. From this transformant, a plasmid was isolated according to the known method. This plasmid was designated as pAMoERC3, and its structure was confirmed by restriction enzyme digestion.

(11) Construction of pAGE207 (see FIG. 11)

According to the method described below, plasmid pAGE207 wherein G418 resistance gene in pAGE107 is replaced by hygromycin (hyg) resistance gene was constructed. For that use, hyg resistance gene was isolated from p201 [Bill Sugden et al, Nature, 313, 812 (1985)].

1 μg of pAGE107 obtained by the method described in JP-A 3-22979 was dissolved in 30 μl of Y-50 buffer and digested with 20 units of ClaI at 37° C. for two hours. Thereafter, sodium chloride was added to this reaction mixture of give a NaCl concentration of 150 mM and digested with 20 units of MluI at 37° C. for another two hours. The reaction solution was subjected to agarose gel electrophoresis to give about 4.6 kb of DNA fragment.

Separately, 0.5 μg of p201 [Bill Sudgen et al.: Nature, 313, 812 (1985)] was dissolved in 30 μl of Y-50 buffer and digested with 20 units of NarI [manufactured by New England Biolab] at 37° C. for two hours. After precipitation with ethanol, the precipitate was dissolved in DNA polymerase I buffer (30 μl), and 6 units of Escherichia coli DNA polymerase I Klenow fragment were added to react at 37° C. for 60 minutes, which results in conversion of 5' protruding cohesive end produced by NarI digestion into blunt end. The reaction was stopped by extraction with phenol, extracted with chloroform, precipitated with ethanol, the precipitate was dissolved in 20 μl of T4 ligase buffer. The DNA and 0.05 μg of ClaI linker (5'pCATCGATG3': manufactured by Takarashuzo) were ligated together with 175 units of T4 DNA ligase at 12° C. for 16 hours. After precipitation with ethanol, the precipitate was dissolved in 30 μl of Y-50 buffer and digested with 10 units of ClaI at 37° C. for two hours. Thereafter, sodium chloride was added to this reaction mixture to give a NaCl concentration of 150 mM and digested with 10 units of MluI at 37° C. for another two hours. The reaction solution was subjected to agarose gel electrophoresis to give about 1.6 kb of DNA fragment.

The DNA fragments thus obtained, i.e., 0.2 μg of ClaI-MluI fragment (4.6 kb) derived from pAGE107 and 0.1 μg of CalI-MluI fragment (1.6) kg derived from p201 were dissolved in 30 μl of T4 ligase buffer and ligated together with 175 units of T4 DNA ligase at 12° C. for 16 hours. Escherichia coli HB101 strain was transformed using the reaction mixture according to the method described by Cohen et al. to obtain an ampicillin resistant strain. From this transformant, a plasmid was isolated according to the known method. This plasmid was designated as pAGE207, and its structure was confirmed by restriction enzyme digestion.

(12) Construction of pAGE207ScN (see FIG. 12)

According to the method described below, in order to remove the similar sequence with SfiI site present in rabbit βglobin gene, plasmid pAGE207ScN in which ScaI linker is inserted at BalI site of pAGE207 was constructed. In pAGE207ScN, the number of inserted ScaI linkers is indefinite.

0.5 μg of pAGE207 obtained in Sec. 1(11) of this Example was dissolved in 30 μl of Y-0 buffer and digested with 10 units of BalI at 30° C. for two hours. After precipitation with ethanol, the precipitate was dissolved in 20 μl of T4 ligase buffer. The DNA and 0.001 μg of ScaI linker (5'pAAGTACTT3': manufactured by Takarashuzo) were ligated together with 175 units of T4 DNA ligase at 12° C. for 16 hours.

Escherichia coli HB101 strain was transformed using the reaction mixture according to the method described by Cohen et al. to obtain an ampicillin resistant strain. From this transformant, a plasmid was isolated according to the known method. This plasmid was designated as pAGE207ScN, and its structure was confirmed by restriction enzyme digestion.

(13) Construction of Plasmid pAMoC3Sc (see FIG. 13)

According to the method as described below, plasmid pAMoERC3Sc was constructed, in which case for the purpose of removing a similar sequence with SfiI site of rabbit βglobin gene in the plasmid pAMoERC3, the rabbit βglobin gene in the plasmid pAMoERC3 was replaced with the rabbit βglobin gene in the plasmid pAGE207ScN from which that similar sequence had already been removed. For convenience, plasmid pAMoC3Sc was first constructed, and then the plasmid pAMoERC3Sc was constructed. The number of ScaI linkers inserted into the plasmid pAGE207ScN to remove the similar sequence with SfiI site is unknown. In the case of pAMoERC3Sc, however, from the fact that the pAGE207ScN was once digested with ScaI at the time of its construction, it is deduced that the number of ScaI sites inserted thereinto is only one.

First, 1 μg of the pAGE207ScN obtained in Sec. 1(12) of this Example was dissolved in 30 μl of Y-0 buffer and digested with 208 units of KpnI at 37° C. for 2 hours. Then, sodium chloride was added to give a NaCl concentration of 100 mM, and this plasmid was further digested with 20 units of ScaI at 37° C. for 2 hours. The reaction mixture was subjected to agarose gel electrophoresis to give an about 0.7 kb DNA fragment.

Also, 1 μg of the pAGE207ScN was dissolved in 30 μl of Y-100 buffer and digested with 20 units of ScaI and 20 units of ClaI at 37° C. for 2 hours. The reaction mixture was subjected to agarose gel electrophoresis to give an about 0.9 kb DNA fragment.

Separately, 1 μg of the pAMoERC3 obtained in Sec. 1(10) of this Example was dissolved in 30 ml of Y-0 buffer and digested with 20 units of KpnI at 37° C. for 2 hours. Then, sodium chloride was added to give a NaCl concentration of 100 mM, and this plasmid was further digested with 20 units of XhoI at 37° C. for 2 yours. The reaction mixture was subjected to agarose gel electrophoresis to give an about 3.2 kb DNA fragment.

Next, 1 μg of the pAGE107 obtained by the method described in the EP-A 0370205 was dissolved in 30 μl of Y-100 buffer and digested with 20 units of XhoI and 20 units of ClaI at 37° C. for 2 hours. The reaction mixture was subjected to agarose gel electrophoresis to give an about 4.3 kb DNA fragment.

The DNA fragments thus obtained, i.e., 0.1 μg of the KpnI-ScaI fragment (0.7 kb) derived from the pAGE207ScN, 0.1 μg of the ScaI-ClaI fragment (0.9 kb) derived from the same plasmid, 0.3 μg of the KpnI-XhoI fragment (3.2 kb) derived form the pAMoERC3, and 0.3 μg of the XhoI-ClaI fragment (4.3 kb) derived from the pAGE107 were dissolved in 30 μl of T4 ligase buffer and ligated together with 175 units of T4 DNA ligase at 12° C. for 16 hours.

Escherichia coli HB101 strain was transformed using the reaction mixture according to the method of Cohen et al. to obtain an ampicillin resistant strain. From this transformant, a plasmid was isolated according to the known method. This plasmid was designated as pAMoC3Sc, and its structure was confirmed by restriction enzyme digestion.

(14) Construction of Plasmid pAMoERC3Sc (see FIG. 14)

First, 1 μg of the pAMoERC3 obtained in Sec. 1(10) of this Example was dissolved in 30 μl of Y-0 buffer and digested with 20 units of KpnI at 37° C. for 2 hours. Then, sodium chloride was added to give a NaCl concentration of 150 mM, and this plasmid was further digested with 20 units of MluI at 37° C. for 2 hours. The reaction mixture was subjected to agarose gel electrophoresis to give an about 6.8 kb DNA fragment.

Also, 1 μg of the pAMoERC3 was dissolved in 30 μl of Y-150 buffer and digested with 20 units of XhoI and 20 units of MluI at 37° C. for 2 hours. The reaction mixture was subjected to agarose gel electrophoresis to give an about 1.3 kb of DNA fragment.

Separately, 1 μg of the pAMoC3Sc was dissolved in 30 μl of Y-0 buffer and digested with 20 units of KpnI at 37° C. for 2 hours. Then, sodium chloride was added to this reaction mixture to give a NaCl concentration of 100 mM, and this plasmid was further digested with 20 units of XhoI at 37° C. for 2 hours. The reaction mixture was subjected to agarose gel electrophoresis to give an about 5.9 kb DNA fragment.

The DNA fragments thus obtained, i.e., 0.2 μg of the KpnI-MluI fragment (6.8 kb) derived from the pAMoERC3, 0.05 μg of the XhoI-MluI fragment (1.3 kb) derived from the same plasmid, and 0.2 μg of the KpnI-XhoI fragment (5.9 kb) derived from the pAMoC3Sc were dissolved in 30 μl of T4 ligase buffer and ligated together with 175 units of T4 DNA ligase at 12° C. for 16 hours.

Escherichia coli HB101 strain was transformed using this reaction mixture according to the method of Cohen et al. to obtain an ampicillin resistant strain. From this transformant, a plasmid was isolated according to the known method. This plasmid was designated as pAMoERC3Sc, and its structure was confirmed by restriction enzyme digestion.

The plasmid pAMoERC3Sc has a long terminal repeat of Moloney murine leukemia virus as a promoter for expression of heterogeneous genes. For the purpose of attaining high efficiency in the expression of heterogeneous genes, this plasmid is designed to have a rabbit βglobin gene splicing signal, a rabbit βglobin gene poly A addition signal, and an SV40 early gene poly A addition signal after the position of the heterogenous genes to be inserted. Moreover, this plasmid has a G418 resistance gene as a drug resistance marker for animal cells and a kanamycin resistance gene (the same as the G418 resistance gene) and an ampicillin resistance gene as drug resistant markers for Escherichia coli cells, respectively. Further, this plasmid has a replication origin (oriP) of Epstein-Barr viruses and an EBNA-1 gene which is a trans-acting factor on the oriP to cause replication, so that it can be present in many kinds of cells, including Namalwa cells other than rodent cells, in the form of a plasmid without being incorporated into their chromosomes.

2. Resistance of Namalwa cells to Ricinus communis 120 lectin.

Namalwa cells conditioned for serum-free media (KJM-1 strain) [Hosoi et al., Cytotechnology, 1, 151 (1988)] were cultured in the presence of Ricinus commuis 120 lectin at various concentrations, and the resistance of the KJM-1 strain to Ricinus communis 120 lectin was examined. The KJM-1 strain was suspended in RPMI1640•ITPSGF medium (RPMI1640 medium (Nissui Seiyaku) containing a 1/40 volume of 7.5% NaHCO₃, 200 mM L-glutamine solution (GIBCO) of 3% in volume, penicillin-streptomycin solution (GIBCO; 5000 units/ml penicillin and 5000 μg/ml streptomycin) of 0.5% in volume, 10 mM HEPES, 3 μg/ml insulin, 5 mg/ml transferrin, 5mM sodium pyruvate, 125 nM sodium selenate, 1 mg/ml galactose, and 0.1% (w/v) prulonic F68) to give a concentration of $5 \times 10^4$ cells ml, and the suspension was distributed in 200-μl portions into wells of a 96-well microtiter plate. Various concentrations of Ricinus communis 120 lectin (Seikagaku Kogyo) were added thereto in 1/100 volumes, and the plate was incubated in a $CO_2$ incubator at 37° C. for 1 to 2 weeks. As the result, it was found that the minimum concentration of *Ricinus communis* 120 lectin to cause complete inhibition of the KJM-1 strain growth was 50 ng/ml. Four million cells of the KJM-1 strain were examined, and the natural occurrence of *Ricinus communis* 120 lectin resistance strain was not observed.

3. Cloning of α2→3 sialyltransferase cDNA (LEC) from human histiocytic leukemia cell line TYH (1) Isolation of mRNA from TYH cells From $1\times10^8$ TYH cells [Haranaka et al., Int. J. Cancer, 36, 313 (1985)] about 40 μg of mRNA was isolated using the mRNA extraction kit "Fast Track" (Invitrogen; trade No. K1593-02).

(2) Preparation of cDNA library (see FIG. 15)

From 8 μg of mRNA obtained above, double-stranded cDNA was prepared using the cDNA synthesis kit "The Librarian I" (Invitrogen) with a random primer as a primer. Then, each of the SfiI linkers (Seq. ID: 5) as shown below was provided, instead of BstXI linkers, at either terminus of the cDNA. The cDNA was fractioned in size by agarose gel electrophoresis and cDNA fragments larger than about 1.2 kb were isolated.

SfiI Linkers:

5'-CTTTAGAGCAC-3' (11 mer)

3'-GAAATCTC-5' (8 mer)

The 11 mer and 8 mer single-stranded DNAs of SfiI linkers were synthesized using a DNA synthesizer model 380A (Applied Biosystems). Then, 50 μg of each of the synthesized DNAs was dissolved in 50 μl of T4 kinase buffer and phosphorylated with 30 units of T4 polynucleotide kinase (Takarashuzo) at 37° C. for 16 hours. The specific reagents and procedures were as described in the manufacturer's instructions accompanying the kit used, except that the above SfiI linkers were used in place of BstXI linkers.

Also, 24 μg of pAMoERC3Sc, which is a direct expression cloning vector, was dissolved in 590 μl of Y-50 buffer and digested with 80 units of SfiI at 37° C. for 16 hours. Then, 5μl of this solution was subjected to agarose gel electrophoresis, and after the completion of digestion was confirmed, for the purpose of decreasing the amount of clones having no cDNA insert incorporated at the time of cDNA library construction, this plasmid was further digested with 40 units of BamHI at 37° C. for 2 hours. The reaction mixture was subjected to electrophoresis to give about 11.5 kb of DNA fragment.

Next, 2 μg of the SfiI fragment (11.5 kb) derived from the pAMoERC3Sc, together with the cDNA obtained above, were dissolved in 250 μl of T4 ligase buffer and ligated together with 2000 units of T4 DNA ligase at 12° C. for 16 hours. Then, 5 μg of transfer RNA (tRNA) was added thereto, followed by ethanol precipitation, and the resulting precipitate was dissolved in 20 μl of TE buffer. With this reaction mixture, *Escherichia coli* strain LE392 [Maniatis et al., ed., Molecular Cloning, 2.58, Cold Spring Harbor, 1989] was transformed by electroporation [William J. Dower et al., Nucleic Acids Res., 16, 6127 (1988) to give about 200,000 ampicillin resistant transformants.

(3) Cloning of α2→3 sialyltransferase cDNA (LEC)

The approximately 200,000 ampicillin-resistant transformants (cDNA library) obtained in Sec. 3(2) of this Example were mixed, after which a plasmid was prepared using >plasmid<maxi kit (trade No. 41031; Qiagen) which is a plasmid preparation kit. The obtained plasmid was ethanol precipitated, and the resulting precipitate was dissolved in TE buffer to give a concentration of 1 μg/μl.

The above plasmid was introduced into the KJM-1 strain by electroporation [Miyaji et al., Cytotechnology, 3, 133 (1990)] at a proportion of 4 μg per $1.6\times10^6$ cells. After the introduction of the plasmid, these cells were suspended in 8 ml of RPMI1640-ITPSGF medium, and the cells were incubated in a CO2 incubator at 37° C. for 24 hours. Then, the cells were supplemented with G418 (GIBCO) to give a concentration of 0.5 mg/ml and further cultured for 5 to 7 days to give transformants. The obtained transformants were suspended in RPMI1640-ITPSGF medium containing *Ricinus communis* 120 lectin (50 ng/ml) to give a concentration of $5\times10^4$ cells/ml, and the cells were distributed in 200-μl portions into wells of a 96-well microtiter plate. The cells were cultured in a $CO_2$ incubator at 37° C. for 2 to 3 weeks, and 7 strains were obtained which had become resistant to *Ricinus communis* 120 lectin. From this resistant strain, a plasmid was isolated according to the Hirt method [Robert F. Margolskee et al., Mol. Cell. Biol., 8, 2837 (1988)] and *Escherichia coli* strain LE392 was transformed with this plasmid by electroporation [William J. Dower et al., Nucleic Acid Res., 16, 6127 (1988)]. From this transformant, a plasmid was prepared using >plasmid<maxi kit (trade No. 41031; Qiagen), and its structure was examined by restriction enzyme digestion to find that it contained about 1.9 kb cDNA. The cDNA containing plasmid was designated as pAMoERL. When this plasmid was also introduced into the KJM-1 strain by the above method, this strain became resistant to *Ricinus communis* 120 lectin; it was therefore found that this cDNA is a gene responsible for lectin resistance. The KJM-1 strain containing the plasmid pAMoERL was able to grow even in the presence of 200 ng/ml of *Ricinus communis* 120 lectin.

4. Sequencing of α2→3 sialyltransferase cDNA (LEC)

(1) Introduction of α2→3 sialyltransferase cDNA (LEC) into pUC119 (see FIG. 16)

First, 1 μg of pAMoERL obtained in Sec. 3(3) of this Example was dissolved in 30 μl of Y-100 buffer and digested with 20 units of EcoRV and 20 units of Asp718 (Boehringer Mannheim) at 37° C. for 2 hours. The reaction mixture was subjected to electrophoresis to give a roughly 1.97 kb DNA fragment.

Separately, 1 μg of pUC119 [Messing et al., Methods in Enzymology, 153, 3 (1987)] was dissolved in 30 μl of K-20 buffer and digested with 20 units of SmaI at 37° C. for 2 hours. Then, sodium chloride was added to give a NaCl concentration of 100 mM, and this plasmid was further digested with 20 units of Asp718 at 37° C. for 2 hours. The reaction mixture was subjected to electrophoresis to give a roughly 3.16 kb DNA fragment.

The DNA fragments thus obtained, i.e., 0.2 μg of the EcoRV-Asp718 fragment (1.97 kb) derived from the pAMoERL and 0.1 μg of the SmaI-Asp718 fragment (3.16 kb) derived from the pUC119 were dissolved in 30 μl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pUC119-LEC, and its structure was confirmed by restriction enzyme digestion.

(2) Construction of deletion plasmids for sequencing.

First, 2 μg of pUC119-LEC obtained in Sec. 4(1) of this Example was dissolved in 30 μl of Y-150 buffer and digested with 20 units of BamHI and 20 units of SphI at 37° C. for 2 hours. After ethanol precipitation, the resulting precipitate was dissolved in 100 μl of ExoIII buffer (deletion kit for kilo-sequence; Takarashuzo). Also, 2 μg of pUC119-LEC was dissolved in 30 μl of Y-0 buffer and digested with 20 units of SacI at 37° C. for 2 hours. Then, sodium chloride was added to give a NaCl concentration of 150 Mm, and this plasmid was further digested with 20 units of NotI at 37° C. for 2 hours. After ethanol precipitation, the resulting precipitate was dissolved in 100 μl of ExoIII buffer.

From the BamHI-SphI fragment and the SacI-NotI fragment thus obtained from the pUC119-LEC, several tens of deletion plasmids were prepared, respectively, using the deletion kit for kilo-sequence (Takarashuzo).

The nucleotide sequence of the deletion plasmid obtained above was determined using the Taq DyeDeoxy terminator cycle sequencing kit (trade No. 401113; Applied Biosystems). The determined nucleotide sequence is shown in the Sequence Listing (Seq. ID: 1). Also, it was found from the corresponding amino acid sequence that this protein has a common structure to glycosyltransferase (hereinafter abbreviated to GT). That is, this protein seems to have a structure where 8 amino acids in the N-terminal portion are put out at the cytoplasm side, a highly hydrophobic region consisting of the subsequent 18 amino acids is used for binding to the membrane, and most of the remaining C-terminal portion including the catalytic site is exposed to the internal cavity of the Golgi's apparatus. The comparison of amino acid sequences between this protein and other GTs made it clear that this protein has a certain homology with rat α2→3 sialyltransferase. For these reasons, it is considered that *Ricinus communis* 120 lectin resistance gene encodes GT.

5. Measurement of α2→3 sialyltransferase activity of the KJM-1 strain having expression plasmid for *Ricinus communis* 120 lectin resistance gene.

The KJM-1 strain having the plasmid pAMoERL obtained in Sec. 3 of this Example was suspended in 30 ml of RPMI1640-ITPSGF medium containing 0.5 mg/ml of G418 to give a concentration of $5 \times 10^5$ cells/ml, and the cells were cultured in a $CO_2$ incubator at 37° C. for 3 days. After the culturing, the cells were collected by centrifugation at 160×g for 10 minutes and washed with 10 ml of PBS (8 g/l NaCl, 0.2 g/l KCl, 1.15 anhydrous sodium monohydrogenphosphate, 0.2 g/l potassium dihydrogenphosphate), followed by further centrifugation to collect the cells.

About $1.4 \times 10^7$ cells obtained above were suspended in 100 μl of homogenization buffer (250 mM saccharose, 10 mM Tris-HCl (pH 7.4)), and lysed by sonication. The lysate was centrifuged at 550×g for 10 minutes to obtain a supernatant.

Also, as a control, the KJM-1 strain having the vector plasmid pAMoERC3Sc was prepared, and the above procedures were followed to obtain a supernatant.

Then, 20 μl of each of the two supernatants obtained above were allowed to react in an assay solution (0.1 M cacodylic acid-HCl (pH 6.5), 0.01 M $MnCl_2$, 0.45% Triton X-100, 0.08 mM substrate, 5 mM CMP-sialic acid (added or not added)) having the final volume of 50 μl at 37° C. for 2 hours, and the products were identified by high performance liquid chromatography (HPLC) to determine the α2→3 sialyltransferase activity in the respective supernatants. The activity determinations were carried out using 200 μg of proteins in the supernatant, and protein quantitation was achieved using BCA protein assay reagent (PIERCE). As the substrate, a sugar chain fluorescence-labeled with aminopyridine (Galβ1→4GLcNAcβ1→3Galβ→4Glc-aminopyridine) was used. The fluorescence labeling of the substrate was carried out using lacto-N-neotetraose (BioCarb Chemicals) by the conventional method [Akimoto Kondo, et al., Agric. Biol. Chem., 54, 2169 (1990)]. Each of the supernatants was allowed to react with an assay solution containing or not containing CMP-sialic acid as a sugar donor. The reaction mixture was separated by HPLC, and the peaks appearing only with the assay solution containing CMP-sialic acid were considered as the products. After completion of the reaction, the assay solution was treated at 100° C. for 5 minutes, and centrifuged at 10,000×g for 10 minutes. The resulting supernatant was subjected to HPLC which was carried out on a TSKgel ODS-80T$_m$ column (4.6 mm×30 cm; Tosoh) eluting with 0.02 M ammonium acetate buffer (pH 4.0) at a temperature of 50° C. at a rate of 1 ml/min. The products were detected using the fluorescence HPLC monitor model RF-535T (Shimazu Seisakusho) with an excitation wavelength of 320 nm and an emission wavelength of 400 nm. As the result, peaks 1 and 2 were detected as the products, as shown in Fig. 17. From the facts that the elution time was identical with that of the standard and the substrate was regenerated by sialidase treatment of the products, it was found that the peak 1 corresponds to NeuAcα2→6Galβ1→4GlcNAcβ1→3Galβ1→4Glc-aminopyridine and the peak 2 corresponds to NeuAcα2→3Galβ1→4GlcNAcβ1→3Galβ1→4Glc-aminopyridine.

The sialidase treatment of the products was carried out as follows. First, 10 μl of the supernatant was subjected to HPLC, and the peaks 1 and 2 were fractioned and freeze-dried, independently, followed by dissolution in 50 μl of buffer containing 20 mM Trismaleic acid (pH 6.0) and 1 mM calcium citrate. Then, 20 μl of the solution was treated with 2 μl of 400 mU/ml sialidase (neuraminidase; Sigma, N-2133) at 37° C. for 16 hours. Also, as a control, the same reaction was conducted using 2 μl of water in place of sialidase. After completion of the reaction, the solution was treated at 100° C. for 5 minutes, and centrifuged at 10,000×g for 10 minutes. Then, 10 μl of the supernatant was subjected to the above HPLC. The results are shown in FIG. 18. Both from peak 1 and from peak 2, peak 3 was detected as the product of sialidase treatment. In view of its elution time, peak 3 is considered to be Galβ1→4GlcNAcβ1→3Galβ→4Glc-aminopyridine as the substrate.

The comparison of HPLC patten between the KJM-1 strain having the plasmid pAMoERL and the KJUM1 strain having the plasmid pAMoERC3Sc made clear that both the strains gave approximately the same peak 1 but the strain having the pAMoERL strain gave a significantly higher peak 2 than that of the strain having the pAMoERC3Sc. The ratio of peak 2 to peak 1 for the KJM-1 strain having the pAMoERL was 6 to 7 times greater than that for the KJM-1 strain having the pAMoERC3Sc as the vector (see FIG. 17). From these results, it was shown that this *Ricinus communis* 120 lectin resistance gene is an α2→3 sialyltransferase gene and that oligosaccharides with sialic acid added can be produced using α2→3 sialyltransferase encoded in the said gene.

EXAMPLE 2

Synthesis of sialyl-Le$^x$ in the strain KJM-1 having the expression plasmid for α2→3 sialyltransferase:

The KJM-1 strain having the plasmid pAMoERL obtained in Sec. 3(3) of Example 1 and the strain KJM-1 having the direct expression cloning vector pAMoERC3Sc obtained in Sec. 1(14) of Example 1 were independently cultured in the RPMI1640•ITPSGF medium containing 0.5 mg/ml of G418. Then, about $1 \times 10^6$ cells of each strain were taken in a microtube (1.5 ml; Eppendorf) and centrifugated at 550×g for 7 minutes. The collected cells were washed with 1 ml of PBS containing 0.1% sodium azide (hereinafter abbreviated as A-PBS), and the expression of sialyl-Le$^x$ in the cells of each strain was examined by indirect fluorescent antibody staining with KM93 [Shitara et al., Anticancer Res., 9, 999 (1989)] which is a monoclonal antibody reacting with sialyl-Le$^x$, as described below.

The cells of each strain were suspended in 50 μl of A-PBS solution containing 10 μg/ml KM93 and allowed to react at 4° C. for 1 hour. After washing three times with A-PBS, these cells were suspended in 20 μl of A-PBS: containing the anti-mouse antibodies IgG and IgM (Cappel) diluted 20-fold with A-PBS which had been fluorescence-labeled with fluorescein isothiocyanate (FITC), and allowed to react at 4° C. for 30 minutes. After washing three times with A-PBS, these cells were again suspended in A-PBS, and analysis was carried out with the flow cell sorter FCS-1 (Nihon Bunko). As a control, the same analysis was carried out using the normal mouse serum diluted 500-fold with A-PBS in place of KM93. The results are shown in FIG. 19. The fluorescence intensity of the cells stained with KM93 for the KJM-1 strain having the direct expression cloning vector pAMoERC3Sc was greater than that of the control (see FIG. 19(a)). This indicates that sialyl-Le$^x$ is also expressed in the original KJM-1 strain. The fluorescence intensity of the cells stained with KM93 for the KJM-1 strain having the plasmid pAMoER1 capable of expressing cDNA encoding α2→3 sialyltransferase of the present invention was further greater than that of the strain KJM-1 containing the pAMoERC3Sc (see Fig. 19(b)). This indicates that sialyl-Le$^x$ is synthesized in cells by the α2→3 sialyltransferase of the present invention.

EXAMPLE 3

Production by animal cells of α2→3 sialyltransferase derived form TYH cells:

1. Construction of plasmid pAMoPRSAL-35F for expression of cDNA encoding α2→3 sialyltransferase (1) Construction of pAGE147 (see FIG. 20)

According to the method as described below, the plasmid pAGE147 was constructed by replacing the SV40 early gene promoter of the plasmid pAGE107 with a long terminal repeat (LTR) of Moloney murine leukemia virus as a promoter.

First, 2 μg of the plasmid pPMOL1 obtained by the method as described in JP-A 1-63394 was dissolved in 30 μl of Y-o buffer and digested with 20 units of SamI at 30° C. for 3 hours. Then, sodium chloride was added to give a NaCl concentration of 50 mM, and this plasmid was further digested with 20 units of ClaI at 37° C. for 2 hours. The reaction mixture was subjected to agarose gel electrophoresis to give an about 0.6 kb DNA fragment containing the LTR promoter of Moloney murine leukemia virus.

Next, 25 pmoles of each of the two synthetic DNA fragments as shown below, which had been synthesized in Sec. 1(8) of Example 1, were dissolved in 10 μl of T4 kinase buffer and phosphorylated at their 5'-termini with 5 units of T4 DNA kinase at 37° C. for 30 minutes.

5'-TCGAGGACC-3' (9 mer)
3'-CCTGGGC-5' (7 mer)

The DNA fragments thus obtained, i.e., 0.05 μg of the ClaI-SmaI fragment (0.6 kb) derived from the pPMOL1, two 5'-phosphorylated synthetic DNA fragments (each 1 pmol), and HindIII linker (5'-pCAAGCTTG-3'; Takarashuzo) (1 pmol) were dissolved in 30 μl of T4 ligase buffer and ligated together with 200 units of T4 DNA ligase at 12° C. for 16 hours. After recovery by ethanol precipitation, the DNA fragments were dissolved in Y-100 buffer and digested with 10 units of HindIII and 10 units of XhoI at 37° C. for 2 hours. The reaction was stopped by phenol/chloroform extraction and the DNA fragments were recovered by ethanol precipitation.

Independently, 1 μg of pAGE107 [JP-A 3-22979; Miyaji et al., Cytotechnology, 3, 133 (1990)] was dissolved in 30 μl of Y-100 buffer and digested with 10 units of HindIII and 10 units of XhoI at 37° C. for 2 hours. The reaction mixture was subjected to agarose gel electrophoresis to give roughly a 6.0 kb DNA fragment containing the G418 resistance gene and the ampicillin resistance gene.

The DNA fragments thus obtained, i.e., 0.3 μg of the HindIII-XhoI fragment (6.0 kb) derived from the pAGE107 and 0.01 μg of the HindIII-XhoI fragment (0.6 kb) derived from the pPMOL1 were dissolved in 20 μl of T4 ligase buffer and ligated together with 200 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAGE147, and its structure was confirmed by restriction enzyme digestion.

(2) Construction of pAGE247 (see FIG. 21)

According to the method as described below, the plasmid pAGE247 was constructed by replacing the SV40 early gene promoter of the plasmid pAGE207 with a long terminal repeat (LTR) of Moloney murine leukemia virus as a promoter.

First, 2 μg of the plasmid pAGE147 obtained in Sec. 1(1) of this Example was dissolved in 30 μl of Y-100 buffer and digested with 10 units of HindIII and 10 units of XhoI at 37° C. for 2 hours. The reaction mixture was subjected to agarose gel electrophoresis to give an about 0.63 kb DNA fragment containing the LTR promoter of Moloney murine leukemia virus.

Independently, 2 μg of the plasmid pAGE207 obtained in Sec. 1(11) of Example 1 was dissolved in 30 μl of Y-100 buffer and digested with 10 units of HindIII and 10 units of XhoI at 37° C. for 2 hours. The reaction mixture was subjected to agarose gel electrophoresis to give an about 5.84 kb DNA fragment containing the hyg resistance gene and the ampicillin resistance gene.

The DNA fragments thus obtained, i.e., 0.05 µg of the HindIII-XhoI fragment (0.63 kb) derived from the pAGE147 and 0.1 µg of the HindIII-XhoI fragment (5.84 kb) derived from the pAGE207 were dissolved in 30 µl of T4 ligase buffer and ligated together with 100 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAGE247, and its structure was confirmed by restriction enzyme digestion.

(3) Construction of pAMN6hyg (see FIG. 22)

According to the method as described below, the plasmid pAMN6hyg for expression of human granulocyte colony stimulating factor derivative was constructed which contains the LTR of Moloney murine leukemia virus as a promoter and the hyg resistance gene as a marker.

First, 2 µg of the plasmid pAGE247 obtained in Sec. 1(2) of this Example was dissolved in 30 µl of Y-50 buffer and digested with 20 units of ClaI at 37° C. for 2 hours. Then, sodium chloride was added to give a NaCl concentration of 175 mM, and this plasmid was further digested with 20 units of SalI at 37° C. for 2 hours. The reaction mixture was subjected to agarose gel electrophoresis to give an about 4.8 kb DNA fragment containing the LTR promotor of Moloney murine leukemia virus, the ampicillin resistance gene and the hyg resistance gene.

Separately, 2 µg of the plasmid pASN6 obtained by the method as described in EP-A 0370205 was dissolved in 30 µl of Y-50 buffer and digested with 20 units of ClaI at 37° C. for 2 hours. Then, sodium chloride was added to give a NaCl concentration of 175 mM, and this plasmid was further digested with 20 units of SalI and 20 units of MluI at 37° C. for 2 hours. The reaction mixture was subjected to agarose gel electrophoresis to give an about 5.0 kb DNA fragment containing the human granulocyte colony stimulating factor derivative gene.

The DNA fragments thus obtained, i.e., 0.1 µg of the ClaI-SalI fragment (4.8 kb) derived from the pAGE247 and 0.1 µg of the ClaI-SalI fragment (5.0 kb) derived from the pASN6 were dissolved in 20 µl of T4 ligase buffer and ligated together with 200 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAMN6hyg and its structure was confirmed by restriction enzyme digestion.

(4) Construction of secretory expression vector pAMoERSA (see FIG. 23)

According to the methods as described below, the secretory expression vector pAMoERSA for secretory expression of an arbitrary protein as a fused protein with the binding region of *Staphylococcus aureus* protein A to immunoglobulin G (IgG) was constructed.

First, 2 µg of the plasmid pAMN6hgy obtained in Sec. 1(3) of this Example was dissolved in 30 µl of Y-50 buffer and digested with 20 units of SnaBI at 37° C. for 2 hours. Then, sodium chloride was added to give a NaCl concentration of 100 mM, and this plasmid was further digested with 20 units of XbaI at 37° C. for 2 hours. The reaction mixture was subjected to agarose gel electrophoresis to give an about 0.33 kb DNA fragment containing the signal sequence of human granulocyte colony stimulating factor.

Also, 2 µg of the pPrAS1 [Saito et al., Protein Engineering, 2, 481 (1989)] was dissolved in 30 µl of Y-50 buffer and digested with 20 units of ClaI at 37° C. for 2 hours. After ethanol precipitation, the precipitate was dissolved in 30 µl of DNA polymerase I buffer, and the 5'-cohesive end produced by the ClaI digestion was converted into a blunt end with 6 units of the Klenow fragment of *Escherichia coli* DNA polymerase I at 37° C. for 60 minutes. The reaction was stopped by phenol extraction, and after chloroform extraction and ethanol precipitation, the resulting precipitate was dissolved in 30 µl of Y-100 buffer and digested with 20 units of BamHI at 37° C. for 2 hours. The reaction mixture was subjected to agarose gel electrophoresis to give an about 0.21 kb DNA fragment containing the IgG-binding region of *Staphylococcus aureus* protein A.

Separately, 2 µg of the plasmid pAMoERC3Sc obtained in Sec. 1(14) of Example 1 was dissolved in 30 µl of Y-100 buffer and digested with 20 units of XbaI and 20 units of BamHI at 37° C. for 2 hours. The reaction mixture was subjected to agarose gel electrophoresis to give an about 12.1 kb DNA fragment.

The DNA fragments thus obtained, i.e., 0.05 µg of the SnaBI-XbaI fragment (0.33 kb) derived from the pAMN6hyg, 0.05 µg of the ClaI(blunt)-BamHI fragment (0.21 kb) derived from the pPrAS1, and 0.1 µg of the XbaI-BamHI fragment (12.1 kb) derived from the pAMoERC3Sc were dissolved in 30 µl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAMoERSA, and its structure was confirmed by restriction enzyme digestion.

(5) Construction of pAMoPRC3Sc (see FIG. 24)

In cases where certain cells capable of expressing EBNA-1, such as Namalwa cells, are used as a host, the plasmid introduced into the host can be present as it is, without being integrated into the chromosome, even if it has no ENBA-1 gene in the plasmid pAmoERC3Sc. According to the methods as described below, therefore, the plasmid pAMoPRC3Sc was constructed by removing the EBNA-1 gene in the plasmid pAMoERC3Sc. The plasmid pAMoPRC3Sc can be used as a direct expression cloning vector similar to the case of the plasmid pAMoERC3Sc.

First, 2 µg of the plasmid pAMoERC3Sc obtained in Sec. 1(14) of Example 1 was dissolved in 30 µl of Y-50 buffer and digested with 20 units of NsiI (New england Biolabs) at 37° C. for 2 hours. After ethanol precipitation, the resulting precipitate was dissolved in 30 µl of DNA polymerase I buffer, and the 3'-cohesive end produced by the NsiI digestion was converted into a blunt end with 6 units of the Klenow fragment of *Escherichia coli* DNA polymerase I at 37° C. for 60 minutes. The reaction was stopped by phenol extraction, and after chloroform extraction and ethanol precipitation, the resulting precipitate was dissolved in 30 µl of Y-100 buffer and digested with 20 units of NotI at 37° C. for 2 hours. The reaction mixture was subjected to agarose gel electrophoresis to give an about 8.1 kb DNA fragment.

Separately, 2 μg of the same plasmid as above was dissolved in 30 μl of Y-100 buffer and digested with 20 units of XhoI at 37° C. for 2 hours. After ethanol precipitation, the resulting precipitate was dissolved in 30 μl of DNA polymerase I buffer, and the 5'-cohesive end produced by the XhoI digestion was converted into a blunt end with 6 units of the Klenow fragment of *Escherichia coli* DNA polymerase I at 37° C. for 60 minutes. The reaction was stopped by phenol extraction, and after chloroform extraction and ethanol precipitation, the resulting precipitate was dissolved in 30 μl of Y-100 buffer and digested with 20 units of NotI at 37° C. for 2 hours. The reaction mixture was subjected to agarose gel electrophoresis to give an about 3.2 kb DNA fragment.

The DNA fragments thus obtained, i.e., 0.1 μg of the NsiI(blunt)-NotI fragment (8.1 kb) derived from the plasmid pAMoERC3Sc and 0.1 μg of the XhoI(blunt)-NotI fragment (3.2 kb) derived from the same plasmid were dissolved in 30 μl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAMoPRC3Sc and its structure was confirmed by restriction enzyme digestion.

(6) Construction of pAMoPRSA (see FIG. 25)

According to the methods as described below, the plasmid pAMoPRSA was constructed by removing the EBNA-1 gene in the pAMoERSA. The plasmid pAMoPRSA can be used as a secretory expression vector similar to the case of the plasmid pAMoERSA.

First, 2 μg of the plasmid pAMoERSA obtained in Sec. 1(4) of this Example was dissolved in 30 μl of a buffer containing 10 mM Tris-HCl (pH 7.5), 6 mM MgCl$_2$, 80 mM NaCl, and 6 mM 2-mercaptoethanol (hereinafter abbreviated as Y-80 buffer) and digested with 20 units of XbaI and 20 units of Asp718 (Boehringer Mannheim) at 37° C. for 2 hours. The reaction mixture was subjected to agarose gel electrophoresis to give an about 1.3 kb DNA fragment.

Separately, 2 μg of the plasmid pAMoPRC3Sc was dissolved in 30 μl of Y-100 buffer and digested with 20 units of XbaI and 20 units of Asp718 at 37° C. for 2 hours. The reaction mixture was subjected to agarose gel electrophoresis to give an about 8.5 kb DNA fragment.

The DNA fragments thus obtained, i.e., 0.05 μg of the XbaI-Asp718 fragment (1.3 kb) derived from the pAMoERSA and 0.1 μg of the XbaI-Asp718 fragment (8.5 kb) derived from the pAMoPRC3Sc were dissolved in 30 μl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pAMoPRSA, and its structure was confirmed by restriction enzyme digestion.

(7) Construction of pAMoPRSAL-35F (see FIG. 26)

The cloned α2→3 sialyltransferase seems to have a structure where 8 amino acids at the N-terminal portion are put out at the cytoplasm side, the highly hydrophobic region consisting of the subsequent 18 amino acids is used for binding to the membrane, and most of the remaining C-terminal portion including the catalytic site is exposed to the internal cavity of Golgi's apparatus. According to the methods as described below, therefore, the secretory expression of α2→3 sialyltransferase was achieved by removing the membrane-binding region from α2→3 sialyltransferase and adding instead the signal sequence of granulocyte colony stimulating factor and the IgG-binding region of *Staphylococcus aureus* protein A.

The cDNA portion encoding a certain region on and after the membrane-binding region of α2→3 sialyltransferase (from 35th Phe to 333rd Phe) was prepared by the polymerase chain reaction (PCR) method and inserted into the secretory expression vector pAMoPRSA obtained in Sec. 1(6) of this Example.

As a set of primers using PCR, the following two synthetic DNA fragments, i.e., L-A(35F) (44 mer) and L-3NN (36 mer), were synthesized by DNA synthesizer model 380A (Applied Biosystems).

L-A(35F) (44 mer):
5'-CTCTCCGATATCTGTTTTATTTTC-CCATCTCAGAGAAGAAAGAG-3'

L-3NN (36 mer):
5'-GATTAAGGTACCAAGTCAGAAGTATGT-GAGGTTCTT-3'

The primers using PCR L-A(35F) and L-3NN are designed to have an EcoRV site and an Asp718 site, respectively, so that DNA fragments amplified by PCR can be incorporated between the StuI site and the Asp718 site of the plasmid pAMoPRSA after digestion with EcoRV and Asp718. The PCR was carried out using a GeneAmp™ DNA amplification reagent kit with AmpliTaq™ recombinant TaqDNA polymerase (TakaraShuzo). The reaction mixture was prepared according to the methods described in the kit, and a Perkin Elmer Cetus DNA thermal cycler (Takarashuzo) was used for incubation. Thirty cycles of amplification were carried out according to the following scheme: 94° C. for 1 minute, 56° C. for 1 minute and 72° C. for 3 minutes. Then, further incubation was carried out at 72° C. for 7 minutes. As a template, 1 ng of the plasmid pUC119-LEC obtained in Example 1 was used. After completion of the reaction, chloroform extraction and ethanol precipitation were successively carried out. The resulting precipitate was then dissolved in 30 μl of Y-100 buffer and digested with 20 units of EcoRV and 20 units of Asp718 at 37° C. for 2 hours. The reaction mixture was subjected to agarose gel electrophoresis to give an about 0.9 kb DNA fragment.

Separately, 2 μg of the plasmid pAMoPRSA was dissolved in 30 μl of Y-100 buffer and digested with 20 units of StuI and 20 units of Asp718 at 37° C. for 2 hours. The reaction mixture was subjected to agarose gel electrophoresis to give an about 9.06 kb DNA fragment.

The DNA fragments thus obtained, i.e., 0.1 μg of the EcoRV-Asp718 fragment (0.9 kb) derived from the DNA fragments amplified by PCR and 0.1 μg of the StuI-ASP718 fragment (9.06 kb) derived from the pAMoPRSA were dissolved in 30 μl of T4 ligase buffer and ligated together with 175 units of T4 DNA ligase at 12° C. for 16 hours.

*Escherichia coli* HB101 strain was transformed using this reaction mixture according to the method of Cohen et al. to obtain an ampicillin resistant strain. From this transformant, a plasmid was isolated according to the known method. This plasmid was designated as pA- MoPRSAL-35F, and its structure was confirmed by restriction enzyme digestion.

2. Secretory expression of cDNA encoding α2→3 sialyltransferase Namalwa KJM-1 cell as host.

The plasmid pAMoPRSA (secretory expression vector; control) obtained in Sec. 1(6) of this Example and the plasmid pAMoPRSAL-35F (plasmid for secretory expression of α2→3 sialyltransferase) obtained in Sec. 1(7) of this Example were prepared using the plasmid preparation kit >plasmid<maxi kit (trade No. 41031; Qiagen). Each of the plasmids thus obtained was ethanol precipitated and dissolved in TE buffer to give a concentration of 1 μg/μl. Then, both plasmids were independently introduced into the Namalwa KJM-1 cells at a proportion of 4 μg per $1\times10^6$ cells by electroporation [Miyaji et al, Cytotechnology, 3, 133 (1990)]. The cells were suspended in 8 ml of RPMI1640-ITPSGF medium, and the cells were cultured in a $CO_2$ incubator at 37° C. for 24 hours. Then, the cells were supplemented with G418 (GIBCO) to give a concentration of 0.5 mg/ml and further cultured for 7 to 14 days to obtain transformants. Each of the transformants was suspended in 30 ml of RPMI1640-ITPSGF medium containing 0.5 mg/ml of G418 at $1\times10^5$ cells/ml, and the cells were cultured in a $CO_2$ incubator at 37° C. for 8 days. Then, centrifugation at $160\times g$ for 10 minutes separated a supernatant from the cells, and the supernatant was further centrifuged at $1500\times g$ for 10 minutes. The culture supernatant thus obtained was stored at $-80°$ C. until it was used.

α2→3 sialyltransferase encoded in the plasmid pAMoPRSAL-35F can readily be purified using IgG Sepharose because of its secretory expression as a fused protein with the IgG-binding region of *Staphylococcus aureus* protein A. To the culture supernatant obtained above, sodium azide was added to give a final concentration of 0.1%. Then, 100 μl of IgG Sepharose (Pharmacia) which had been pre-treated according to the accompanying instructions was added, and the mixture was gently stirred at 4° C. overnight. The IgG Sepharose was recovered by centrifugation at $160\times g$ for 10 minutes, and washed three times with 1 ml of RPMI1640-ITPSGF medium. The sialyltransferase activity was measured by directly using 5 μl of this IgG Sepharose. The activity measurement was carried out by reacting in 30 μl of the assay solution (0.1 M cacodylate buffer (pH 6.5), 0.01 M $MnCl_2$, 0.45% Triton X-100, 0.1 mM substrate, the above IgG Sepharose (5 μl), 5 mM CMP-sialic acid (added or not added)) at 37° C. for 2 hours, and then identifying the products by high performance liquid chromatography (HPLC). As the substrate, various sugar chains (lacto-N-neotetraose (LNnT), lacto-N-tetraose (LNT), lacto-N-fucopentaose III (LNFP-III) and lacto-N-fucopentaose V (LNFP-V); all are available from Oxford GlycoSystems, and the respective structures are shown in FIG. 1) fluorescence-labeled with aminopyridine were used. The fluorescence labeling of the substrate was carried out according to the conventional method [Akihire Kondo et al., Agric. Biol. Chem., 54, 2169 (1990)]. The IgG Sepharose was allowed to react with an assay solution containing or not containing CMP-sialic acid as a sugar donor. The reaction mixture was separated by HPLC, and the peaks appearing only with the assay solution containing CMP-sialic acid were considered the products. After completion of the reaction, the assay solution was treated at 100° C. for 5 minutes, and centrifuged at $10,000\times g$ for 10 minutes. The resulting supernatant was subjected to HPLC which was carried out on a TSKgel ODS-80T$_M$ column (4.6 mm×30 cm; Tosoh) eluting with 0.02M ammonium acetate buffer (pH 4.0) at a temperature of 50° C. and at a rate of 1 ml/min. The products were detected using a fluorescence HPLC monitor model RF-535T (Shimazu Seisakusho) with an excitation wavelength of 320 nm and an emission wavelength of 400 nm. The products were identified from the fact that the elution time coincided with that of the standard and that the substrate was regenerated by sialidase treatment of the products. The quantitative analysis of the products was carried out with the use of pyridylaminated lactose as the standard for comparison of fluorescence intensity. The results of this assay are shown in Table 1. The activity to various sugar chain substrates is also shown in terms of a relative activity when the activity to the substrate LNnT is taken as 100.

TABLE 1

| | α2→3 Sialyltransferase activity | | | |
|---|---|---|---|---|
| | pAMoPRSA | pAMoPRSAL-35F | | Known α2→3 ST |
| Substrate sugar chain | pmol | pmol | Relative activity | Relative activity |
| Galβ1-4GlcNAcβ1-3Galβ1-4Glc (LNnT) | 0 | 51.3 | 100 | 6 |
| Galβ1-4GlcNAcβ1-3Galβ1-4Glc (LNFP-III)<br>3<br>\|<br>Fucα1 | 0 | 8.1 | 16 | |
| Galβ1-3GlcNAcβ1-3Galβ1-4Glc (LNT) | 0 | 23.8 | 46 | 100 |
| Galβ1-3GlcNAcβ1-3Galβ1-4Glc (LNFP-V)<br>3<br>\|<br>Fucα1 | 0 | 28.8 | 56 | |

In cases where the IgG Sepharose derived from the culture supernatant of Namalwa cells having the plasmid pAMoPRSAL-35F was used, α2→3 sialyltransferase activity was detected when any of the sugar chains was used as the substrate. On the other hand, in cases where the IgG Sepharose derived from the culture supernatant of Namalwa cells containing the vector pAMoPRSA, no activity was detected when any of the sugar chains was used as the substrate. These results indicate that α2→3 sialyltransferase undergoes secretory production into the culture supernatant as a fused protein with the IgG-binding region of *Staphylococcus aureus* protein A and that it can readily be recovered and purified using IgG Sepharose.

Also shown in Table 1 are the relative activities of a known α2→3 sialyltransferase, for which purification has been reported so far [(Wienstein et al., J. Biol. Chem., 257, 13845 (1982)], to various sugar chain substrates when its activity to the substrate LNT is taken as 100. The known α2→3 sialyltransferase exhibits a higher specificity to LNT than LNnT, whereas the α2→3 sialyltransferase of the present invention exhibits a higher specificity to LNnT than LNT. This indicates that the α2→3 sialyltransferase of the present invention is a novel enzyme having a different substrate specificity from that of the known enzyme.

It was also found that the α2→3 sialyltransferase of the present invention can take LNFP-III as the substrate. No report has been made so far on the existence of an α2→3 sialyltransferase having enzymatic activity to LNFP-III. This indicates that the use of this enzyme can make possible the direct in vitro synthesis of sialyl-$Le^x$ sugar chains from $Le^x$ sugar chains.

Because the α2→3 sialyltransferase of the present invention can take not only LNnT but also LNT as the substrate, it is possible to synthesize sialyl-$Le^x$ sugar chains, as well as sialyl-$Le^a$ sugar chains. That is, with the use of the α2→3 sialyltransferase of the present invention, the terminal structure of a sugar chain can be converted into NeuAcα2-3Galβ1-4GlcNAc or NeuAcα2-3Galβ1-3GlcNAc, which are then made into a sialyl-$Le^x$ sugar chain or a sialyl-Le sugar chain, using α1→3 fucosyltransferase or α1→3 fucosyltransferase, respectively. Moreover, the α2→3 sialyltransferase of the present invention exhibits a higher substrate specificity to LNnT than that attained by the known α2→3 sialyltransferase, and is therefore superior to the known α2→3 sialyltransferase with respect to the capability for synthesis of sialyl-$Le^x$ sugar chains.

EXAMPLE 4

Production by animal cells of α2→3 sialyltransferase derived from human melanoma cell strain WM266-4: 1. Cloning of α2→3 sialyltransferase cDNA (WM17) derived from human melanoma cell line WM266-4.

(1) Isolation of mRNA from human melanoma WM266-4 cell line

From $1 \times 10^8$ WM266-4 cells (ATCC CRL1676), about 30 μg of mRNA was isolated using the mRNA extraction kit "Fast Track" (trade NO. K1593-02; Ivitrogen), according to the manufacturer's instructions accompanying the kit used.

(2) Preparation of cDNA library

From 8 μg of mRNA obtained above, double-stranded cDNA was prepared using the cDNA synthesis kit "The Librarian I" (Invitrogen) with a random primer as a primer. Then, each of the following SfiI linkers (Seq. ID: 5) as prepared in Example 1 was added, instead of BstXI linker, at either terminus of the cDNA. The cDNA was fractioned in size by agarose gel electrophoresis and cDNA fragments larger than about 1.2 kb were isolated.

SfiI Linkers:

5'-CTTTAGAGCAC-3' (11 mer)
3'-GAAATCTC-5' (8 mer)

Before use, these SfiI linkers (11 mer and 8 mer) had been independently dissolved at 100 nM in 50 μl of T4 kinase buffer and phosphorylated with 30 units of T4 polynucleotide kinase (Takarashuzo) at 37° C. for 16 hours. The specific reagents and procedures were as described in the manufacturer's instructions accompanying the kit used, except that the above Sfi I linkers were used in place of BstXI linkers. As the direct expression cloning vector, the vector pAMoPRC3Sc obtained in Sec. 1(5) of Example 3 was used.

First, 24 μg of the vector pAMoPRC3Sc was dissolved in 590 μl of Y-50 buffer and digested with 80 units of SfiI at 37° C. for 16 hours. Then, the reaction mixture was taken at a volume of 5 μl for agarose gel electrophoresis, and after the completion of digestion was confirmed, this vector was further digested with 40 units of BamHI at 37° C. for 2 hours. The digestion with BamHI was done for the purpose of decreasing the amount of background (i.e., clones containing no cDNA insert) at the time of cDNA library construction. The reaction mixture was subjected to agarose gel electrophoresis to give an about 8.8 kb DNA fragment.

Then, 2 μg of the SfiI fragment (8.8 kb) derived from the pAMoPRC3Sc, together with the cDNA obtained above, was dissolved in 250 μl of T4 ligase buffer and ligated together with 2000 units of T4 DNA ligase at 12° C. for 16 hours. Thereafter, 5 μg of transfer RNA (tRNA) was added, and after ethanol precipitation, the resulting precipitate was dissolved in 20 μl of T4 buffer. The reaction mixture was used to transform Escherichia coli LE392 strain [Maniatis et al., Molecular Cloning, 2.58, Cold Spring Harbor, 1989] by electroporation [William J. Dower et al., Nucleic Acids Res., 16, 6127 (1988)] to give about 200,000 ampicillin resistant transformants.

(3) Cloning of α2→3 sialyltransferase cDNA (WM17)

About 200,000 ampicillin resistant transformants (cDNA library) obtained in Sec. 1(2) of this Example were mixed, after which a plasmid was prepared using >plasmid<maxi kit (trade No. 41031; Qiagen) which is a plasmid preparation kit. The obtained plasmid was ethanol precipitated and the resulting precipitate was dissolved in TE Buffer to give a concentration of 1 μg/μl.

The above plasmid was introduced into the KJM-1 strain by electroporation [Miyaji et al., Cytotechnology, 3, 133 (1990)] at a proportion of 4 μg per $1.6 \times 10^6$ cells. After the introduction of the plasmid, these cells were suspended in 8 ml of RPMI164-0.ITPSGF medium, and the cells were cultured in a $CO_2$ incubator at 37° C. for 24 hours. Then, the cells were supplemented with G418 (GIBCO) to give a concentration of 0.5 mg/ml and further cultured for 5 to 7 days to obtain transformants. The obtained transformants were suspended in RPMI1640.ITPSGF medium containing Ricinus communis 120 lectin (50 ng/ml) to give a concentration of $5 \times 10^4$ cells/ml, and the suspension was distributed in 200-μl portions into wells of a 96-well microtiter plate. The cells were cultured in a $CO_2$ incubator at 37° C. for 4 weeks, and a certain strain was obtained which had become resistant to Ricinus communis 120 lectin. After culturing of this resistant cell, a plasmid was isolated from about $5 \times 10^6$ cells according to the Hirt method [Robert F. Margolskee et al., Mol. Cell. Biol., 8, 2837 (1988)]. The isolated plasmid was introduced into Escherichia coli strain LE392 by electroporation [William J. Dower et al., Nucleic Acids Res., 16, 6127 (1988)] to give an ampicillin resistant transformant. From this transformant, a plasmid was prepared using >plasmid<maxi kit (Qiagen), and its structure was examined by restriction enzyme digestion to find that it contained about 1.9 kb cDNA. The cDNA containing plasmid was designated as pA-MoPRWM17. When this plasmid was introduced into the KJM-1 strain by the above method, the transformant became resistant to *Ricinus communis* 120 lectin; it was therefore found that this cDNA is a gene responsible for lectin resistance. The KJM-1 strain containing the plasmid pAMoPRWM17 was able to grow even in the presence of 200 ng/ml *Ricinus communis* 120 lectin.

2. Sequencing of α2→3 sialyltransferase cDNA (WM17)

(1) Incorporation of α2→3 sialyltransferase cDNA (WM17) into plasmid pUC119 (see FIG. 27)

First, 1 μg of the plasmid pAMoPRWM17 was dissolved in 30 μl of Y-100 buffer and digested with 20 units of Eco RV and 20 units of Asp718 (Boehringer Mannheim) at 37° C. for 2 hours. The reaction mixture was subjected to agarose gel electrophoresis to give an about 1.9 kb DNA fragment.

Separately, 1 μg of the plasmid pUC119 [Messing et al., Methods in Enzymology, 153, 3 (1987)] was dissolved in 30 μl of K-20 buffer and digested with 20 units of SmaI at 37° C. for 2 hours. Then, sodium chloride was added to give a NaCl concentration of 100 mM, and this plasmid was further digested with 20 units of Asp718 at 37° C. for 2 hours. The reaction mixture was subjected to agarose gel electrophoresis to give an about 3.16 kb DNA fragment.

The DNA fragments thus obtained, i.e., 0.2 μg of the EcoRV-Asp718 fragment (1.9 kb) derived from the pAMoPRWM17 and 0.1 μg of the SmaI-ASP718 fragment (3.16 kb) derived from the pUC119 were dissolved in 30 μl of T4 ligase buffer and ligated together with 175 units of T4 DNA ligase at 12° C. for 16 hours. *Escherichia coli* HB101 strain was transformed using this reaction mixture according to the method of Cohen et al. to obtain an ampicillin resistant strain. From this transformant, a plasmid was isolated according to the known method. This plasmid was designated as pUC119-WM17, and its structure was confirmed by restriction enzyme digestion.

(2) Construction of deletion plasmids for sequencing

First, 2 μg of the plasmid pUC119-WM17 was dissolved in 30 μl of Y-150 buffer and digested with 20 units of BamHI and 20 units of SphI at 37° C. for 2 hours. After ethanol precipitation, the resulting precipitate was dissolved in 100 μl of ExoIII buffer (accompanying the deletion kit for kilo-sequence; Takarashuzo). Independently, 2 μg of the same plasmid was dissolved in 30 μl of Y-0 buffer and digested with 20 units of SacI at 37° C. for 2 hours. Then, sodium chloride was added to give a NaCl concentration of 150 mM and digested with 20 units of NotI at 37° C. for 2 hours. After ethanol precipitation, the resulting precipitate was dissolved in 100 μl of ExoIII buffer.

From the BamHI-SphI fragment derived from the plasmid pUC119-WM17 and the SacI-NotI fragment derived from the same plasmid, several tins of deletion plasmids were respectively prepared using the deletion kit for kilo sequence (Takarashuzo). Specific reagents and procedures were as described in the manufacturer's instructions accompanying the kit used.

The nucleotide sequence of the deletion plasmid obtained above was determined using the Taq DyeDeoxy termintor cycle sequencing kit (trade No. 401113; Applied Biosystems). The determined nucleotide sequence is shown is the sequence listing (Seq. ID: 6). A poly A tail follws a 1742 base pairs (bp) nucleotide. From this nucleotide sequence, it was found that this gene enclodes a protein consisting of 329 amino acids. The amino acid sequence of this protein is also shown in the sequence listing (Seq. ID: 7). It was also found that the amino acid sequence has about 91% homology with that encoded by α2→3 sialyltransferase cDNA cloned from TYH cells in Example 4. From these results, it is considered that the gene (WM17) isolated in terms of resistance to *Ricinus communis* 120 lectin encodes α2→3 sialyltransferase.

3. Measurement of α2→3 sialyltransferase activity of KJM-1 strain containing WM17 expression plasmid.

In the same manner as described in Sec. 5 of Example 5, comparison of α2→3 sialyltransferase activity was made between the KJM-1 strain containing the WM17 expression plasmid (pAMoPRWM17) and the KJM-1 strain containing the plasmid pAMoPRC3Sc as a control. As the result, the α2→3 sialyltransferase activity of the KJM-1 strain containing the plasmid pAMoPRWM17 was 6 to 7 times higher than that the KJM-1 strain containing the plasmid pAMoPRC3Sc.

4. Synthesis of sialyl-Le$^x$ sugar chain in KJM-1 strain having expression plasmid for α2→3 sialyltransferase.

The KJM-1 strain containing the pAMoPRWM17 (expression plasmid for α2→3 sialyltransferase) obtained in Sec. 1 of Example 4 and the KJM-1 strain containing the pAMoPRC3Sc (control plasmid) were independently cultured in the RPMI1640.ITPSGF medium containing 0.5 mg/ml of G418, after which about $1 \times 10^6$ cells of each strain were taken in a microtube (1.5 ml; Eppendorf) and collected by centrifugation at 550×g for 7 minutes. Then, these cells were washed with 1 ml of A-PBS and subjected to indirect fluorescent anitbody staining with KM93 [Shitara et al., Anticancer Res., 9, 999 (1989)] which is an antibody reacting with the sialyl-Le$^x$ sugar chain, therby examining the production of sialyl-Le$^x$ sugar chain in these calls. The collected cells of each strain were suspended in 50 μl (10 μg/ml) of KM93 and allowed to react at 4° C. for 1 hour. Then, these cells were washed three times with A-PBS and suspended in 20 μl of fluorescence-labeled anti-mouse IgG and IgM antibodies (Cappel, used after 20-fold dilution with A-PBS), followed by reaction at 4° C. for 30 minutes. After washing three times with A-PBS, these cells were again suspended in A-PBS and subjected to analysis using an EPICS elite flow cytometer (Coulter).

As a control, the same analysis was carried out using the normal mouse serum diluted 500-fold with A-PBS in place of KM93.

The results are shown in FIG. 28. It is found that for the KJM-1 strain containing the direct expression cloning vector pAMoPRC3Sc (control plasmid), the cells stained with KM93 exhibit a higher fluorescent intensity than that of the control. This indicates that the KJM-1 strain is originally able to express the sialyl-Le$^x$ sugar chains. Also found is that the fluorescent itensity obtained when the cells of the KJM-1 strain containing the pAMoPRWM17 (α2→3 sialyltransferase expession plasmid) were stained with KM93 is even greater than that obtained when the cells of the KJM-1 strain having the pAMoPRC3Sc (control plasmid) were stained with KM93. This indicates that α2→3 sialyltransferase encoded in the gene WM17 can synthesize sialyl-Le$^x$ sugar chains in cells.

5. Secretory production by animal cells of α2→3 sialyltransferase derived from WM266-4 cell line (1) Construction of plasmid pAMoPRSAW17-31F for secretory expression of cDNA encoding α2→3 sialyltransferase (see FIG. 29)

In view of the amino acid sequence, the α2→3 sialyltransferase encoded in the cloned gene WM17 seems to have a structure where 8 amino acids in the N-terminal portion are put out at the cytoplasm side, the highly hydrophobic region consisting of the subsequent 18 amino acids is used for binding the membrane, and most of the remaining C-terminal portion (including the catalytic site) is exposed to the internal cavity of Golgi's apparatus. According to the method as described below, therefore, the secretory production of α2→3 sialyltransferase was achieved by removing the membrane-binding region from α2→3 sialyltransferase and adding instead the signal sequence of granulocyte colony stimulating factor and the IgG-binding region of Staphylococcus aureus protein A. The gene portion encoding a certain region following the membrane-binding region of α2→3 sialyltransferase (from 31st Phe to 329th Phe) was prepared by the PCR method and inserted into the secretory expression vector pAMoPRSA obtained in Sec. 1(6) of Example 3.

As a set of primers using PCR, the following two sythetic DNA fragments, i.e., W17-A(31F) (44 mer) and W17-C (36 mer), were synthesized by DNA synthesizer model 380A (Applied Biosystems).

W17-A(31F) (44 mer):
5'-CTCTCCGATATCTGTTTTATTTTC-
CCATCCCAGAGAAGAAGGAG-3'
W17-C (36 mer)
5'-GATTAAGGTACCAGGTCAGAAGGACGT-
GAGGTTCTT-3'

The primers using PCR W17-A (31F) and W17-C are designed to have an EcoRV site and an Asp718 site, respectively, so that DNA fragments amplified by PCR can be incorporated between the StuI site and the Asp718 site of the plasmid pAMoPRSA after digestion with EcoRV and Asp718. The PCR was carried out using a GeneAmp$^{TM}$ DNA amplification reagent kit with AmpliTaq$^{TM}$recombinant Taq DNA polymerase (Takarashuzo). The reaction mixture was prepared according to the method described in the kit, and a Perkin Elmer Cetus DNA thermal cycler (Takarashuzo) was used for incubation. Thirty cycles of amplification were carried out according to the following scheme: 94° C. for 1 minute, 55° C. for 1 minute and 72° C. for 3 minutes. Then, further incubation was carried out at 72° C. for 7 minutes. As a template, 1 ng of the plasmid pUC119WM17 obtained in Sec. 2(1) of this Example was used. After completion of the reaction, chloroform extraction and ethanol precipitation were successively carried out. The resulting precipitate was then dissolved in 30 μl of Y-100 buffer and digested with 20 units of EcoRV and 20 units of ASp718 at 37° C. for 2 hours. The reaction mixture was subjected to agarose gel electrophoresis to give an about 0.91 kb DNA fragment.

Separately, 2 μg of the plasmid pAMoPRSA was dissolved in 30 μl of Y-100 buffer and digested with 20 units of StuI and 20 units of Asp718 at 37° C. for 2 hours. The reaction mixture was subjected to agarose gel electrophoresis to give an about 0.91 kb DNA fragment.

Separately, 2 μg of the plasmid pAMoPRSA was dissolved in 30 μl of Y-100 buffer and digested with 20 units of StuI and 20 units of Asp718 at 37° C. for 2 hours. The reaction mixture was subjected to agarose gel electrophoresis to give about a 9.06 kb DNA fragment.

Then, 0.1 μg of the EcoRV-Asp718 fragment (0.91 kb) derived from the amplified DNA by PCR and 0.1 μg of the StuI-Asp718 fragment (9.06 kb) derived from the plasmid pAMoPRSA were dissolved in 30 μl of T4 ligase buffer and ligated together with 175 units of T4 DNA ligase at 12° C. for 16 hours.

Escherichia coli HB101 strain was transformed using this reaction mixture according to the method of Cohen et al. to obtain an ampicillin resistant strain. From this transformant, a plasmid was isolated according to the known method. This plasmid was designated as pAMoPRSAW17-31F, and its structure was confirmed by restriction enzyme digestion.

(2) Secretory expression of cDNA encoding α2→3 sialyltransferase with Namalwa KJM cells used as a host.

The plasmid pAMoPRSA (secretory expression vector; control) obtained in Sec. 1(6) of Example 3 and the plasmid pAMoPRSAW17-31F (secretory expression plasmid for α2→3 sialyltransferase) obtained in Sec. 5(1) of this Example were prepared using the plasmid preparation kit, >plasmid<maxi kit (trade No. 41031; Qiagen). Each of the plasmids thus obtained was precipitated by ethanol and dissolved in TE buffer to give a concentration of 1 μg/μl. Then, both plasmids were independently introduced into the Namalwa KJM-1 cells at a proportion of 4 μg per $1.6 \times 10^6$ cells by electroporation [Miyaji et al., Cytotechnology, 3, 133 (1990)]. The cells were suspended in 8 ml of RPMI16-40ITPSGF medium, and the cells were cultured in a $CO_2$ incubator at 37° C. for 24 hours. Then, the cells were supplemented with G418 (GIBCO) at a concentration of 0.5 mg/ml and further cultured for 7 to 14 days, resulting in transformants. Each of the transformants was suspended in 30 ml of RPMI1640ITPSGF medium containing 0.5 mg/ml of G418 to give a concentration of $1 \times 10^5$ cells/ml, and the cells were cultured in a $CO_2$ incubator at 37° C. for 8 days. Then, centrifugation at 160×g for 10 minutes separated a supernatant from the cells, and the supernatant was furher centrifuged at 1500×g for 10 minutes. The culture supernatant thus obtained was stored at −80° C. until it was used.

α2→3 sialyltransferase encoded in the plasmid pAMoPRSAW17-31F can be readily purified using IgG Sepharose because of its secretory production as a fused protein with the IgG-binding region of Staphylococcus aureus protein A. To the culture supernatant obtained above, sodium azide was added to give a final concentration of 0.1%. Then, 100 μl of IgG Sepharose (Pharmacia) which had been pre-treated according to the accompanying instructions was added, and the mixture was gently stirred at 4° C. overnight. The IgG Sepharose was recovered by centrifugation at 160×g for 10 minutes, and washed three times with 1 ml of RPMI1640ITPSGF medium. The sialyltransferase activity was measured by directly using 5 μl of this IgG Sepharose. The activity measurement was carried out by reacting in 30 μl of the assay solution (0.1 M cacodylate buffer (pH 6.5), 0.01 M $MnCl_2$, 0.45% Triton X-100, 0.1 mM substrate, the above IgG Sepharose (5 μl), 5 mM CMP-sialic acid (added or not added) at 37° C. for 2 hours, and then identifying the products by high performance liquid chromatography (HPLC). As the substrate, various sugar chains (lacto-N-neotetraose (LNnT), lacto-N-tetraose (LNT), lacto-N-fucopentaose III (LNFP-III) and lacto-N-fucopentaose V (LNFP-V); all are available from Oxford GlycoSystems, and the respective structures are shown in FIG. 1) fluorescence-labeled with aminopyridine were used. The fluorescence labeling of the substrate was carried out according to the conventional method [Akihiro Kondo et al., Agric, Biol. Chem., 54, 2169 (1990]. The Sepharose was allowed to react with an assay solution containing or not containing CMP-sialic acid as a sugar donor. The reaction mixture was analyzed by HPLC, and the peaks appearing only with the assay solution containing CMP-sialic acid were considered to be the products. After completion of the reaction, the assay solution was treated at 100° C. for 5 minutes, and centrifuged at 10,000×g for 10 minutes. Then, 10 μl of the resulting supernatant was subjected to HPLC which was carried out on a TSKgel ODS-80TM column (4.6 mm×30 cm; Tosoh) eluting with 0.02M ammonium acetate buffer (pH 4.0) at a temperature of 50° C. and at a rate of 1 ml/min. The products were detected using a fluorescence HPLC monitor model RF-535T (Shimazu Seisakusho) with an excitation wavelength of 320 nm and an emission wavelength of 400 nm. The products were identified by comparison of their elution times to that of the standard and the fact that the substrate was regenerated by sialidase treatment of the products. The quantitative analysis of the products was carried out with the use of pyridylaminated lactose as the standard for comparison of fluorescent intensity. The results of this assay are shown in Table 2. The activity to various sugar chain substrates is also shown in terms of a relative activity when the activity to the substrate LNnT is taken as 100.

higher specificity to LNT than LNnT, whereas the α2→3 sialyltransferase of the present invention exhibits a higher specificity to LNnT than LNT. This indicates that the α2→3 sialyltransferase of the present invention is a novel enzyme having a different substrate specificity than that of the known enzyme.

It was also shown that the α2→3 sialyltransferase of the present invention can take LNFP-III as the substrate. No report has been made so far on an α2→3 sialyltransferase having an enzymatic activity on LNFP-III. This indicates that this enzyme makes direct in vitro synthesis of sialyl-Le$^x$ sugar chains from Le$^x$ sugar chains possible.

Because the α2→3 sialyltransferase of the present invention can take not only LNnT but also LNT as the substrate, it is possible to synthesize sialyl-Le$^a$ sugar chains, as well as sialyl-Le$^x$ sugar chains. That is, with the use of the α2→3 sialyltransferase of the present invention, the terminal structure of a sugar chain can be converted into NeuAcα2-3Galβ1-4GlcNAc or NeuAcα2-3Galβ1-3GlcNAc, which are then made into a sialyl-Le$^x$ sugar chain or a sialyl-Le$^a$ sugar chain, using α1→3 fucosyltransferase or α1→4 fucosyltransferase, respectively. Moreover, the α2→3 sialyltransferase of the present invention exhibits a higher substrate specificity to LNnT than that attained by the known α2→3 sialyltransferase, and is therefore superior to the known α2→3 sialyltransferase with respect to capability for synthesis of sialyl-Le$^x$ sugar chains.

What is claimed is:

1. A cDNA encoding an α2→3 sialyltransferase hav-

TABLE 2

| | α2→3 Sialyltransferase activity | | |
|---|---|---|---|
| | pAMoPRSA | pAMoPRSAW17-31F | Known α2→3 ST |
| Substrate sugar chain | pmol | pmol / Relative activity | Relative activity |
| Galβ1-4GlcNAcβ1-3Galβ1-4Glc (LNnT) | 0 | 113.8 / 100 | 6 |
| Galβ1-4GlcNAcβ1-3Galβ1-4Glc (LNFP-III)<br>      3<br>      |<br>      Fucα1 | 0 | 9.4 / 8 | |
| Galβ1-3GlcNAcβ1-3Galβ1-4Glc (LNT) | 0 | 47.5 / 42 | 100 |
| Galβ1-3GlcNAcβ1-3Galβ1-4Glc (LNFP-V)<br>      3<br>      |<br>      Fucα1 | 0 | 36.3 / 32 | |

In cases where the IgG Sepharose derived from the culture supernatant of Namalwa cells having the plasmid pAMoPRSAW17-31F was used, α2→3 sialyltransferase activity was detected when any of the sugar chains was used as the substrate. On the other hand, in cases where the IgG Sepharose derived from the culture supernatant of Namalwa cells having the vector pAMoPRSA, no activity was detected when any of the sugar chains was used as the substrate. These results indicate that α2→3 sialyltransferase undergoes secretory production into the culture supernatant as a fused protein with the IgG-binding region of *Staphylococcus aureus* protein A and that it can readily be recovered and purified using IgG Sepharose.

Also shown in Table 2 are the relative activities of a known α2→3 sialyltransferase, for which purification has been reported so far [Wienstein et al. , J. Biol. Chem., 257, 13845 (1982)], to various sugar chain substrates when its activity to the substrate LNT is taken as 100. The known α2→3 sialyltransferase exhibits a ing an amino acid sequence as designated by Seq. ID: 2 or 7 or a DNA having homology with said cDNA.

2. A cDNA having a nucleotide sequence as designated by Seq. ID: 1 or 6.

3. A recombinant vector containing a cDNA which encodes α2→3 sialyltransferase having an amino acid sequence as designated by Seq. ID: 2 or 7.

4. A recombinant vector containing a cDNA which encodes an amino acid sequence as designated by Seq. ID: 1 or 6.

5. A process of preparing a cDNA according to claim 1 or 2, which comprises the steps of:

constructing a cDNA library by incorporating into a vector, a cDNA synthesized using as an template an mRNA extracted from an animal cell;

introducing said cDNA library into a cell and preparing a culture of the obtained cell in the presence of a lectin having an activity to inhibit the growth of said cell; and separating the grown cells from said culture and isolating from said cell, a DNA which encodes α2→3 sialyltransferase.

6. A process of preparing a recombinant vector according to claim 3 or 4, which comprises the steps of:
constructing a cDNA library by incorporating into a vector, a cDNA synthesized using as an template an mRNA extracted from an animal cell;
introducing said cDNA library into a cell and preparing a culture of the obtained cell in the presence of a lectin having an activity to inhibit the growth of said cell;
separating the grown cell from said culture and isolating from said cell, a DNA which encodes α2→3 sialyltransferase; and
introducing said DNA into a vector downstream the position of a promoter therein.

7. A process for production of an α2→3 sialyltransferase having an amino acid sequence as designated by Seq. ID: 2 or 7, which comprises the steps of:
preparing a culture of a cell containing a recombinant vector according to claim 3 or 4 in a medium and allowing α2→3 sialyltransferase produced by said cell to accumulate in said culture; and isolating α2→3 sialyltransferase from said culture.

8. A process according to claim 5, wherein said animal cell is a TYH cell or a human melanoma WM266-4 l cell.

9. A process according to claim 6, wherein said animal cell is a TYH cell or a human melanoma WM266-4 cell.

10. A process according to claim 5, wherein said lectin is *Ricinus communis* 120 lectin.

11. A process according to claim 6, wherein said lectin is *Ricinus communis* 120 lectin.

12. Plasmid pUC119- LEC.

13. Plasmid pUC119-WM17.

14. A cell containing a recombinant vector according to claim 3 or 4.

15. A method for adding sialic acid at non-reducing terminus in the lactosamine structure of a glycoprotein or a glycolipid in α2→3 linkage by use of a cell according to claim 14.

16. A method for converting non-reducing terminus of sugar chains on glycoproteins or glycolipids into sialyl-Le$^x$ structure by use of a cell according to claim 14.

17. A method for detecting the expression of an α2→3 sialyltransferase having an amino acid sequence as designated by Seq. ID: 2 or 7 by hybridization using a cDNA according to claim 1 or 2.

18. A method for detecting the expression of an α2→3 sialyltransferase having an amino acid sequence as designated by Seq. ID: 2 or 7 by polymerase chain reaction using synthesized oligonucleotides as probes which are designed based on the nucleotide sequence of cDNA according to claim 1 or 2.

19. A method for suppressing the expression of an α2→3 sialyltransferase having an amino acid sequence as designated by Seq. ID: 2 or 7 by use of an oligonucleotide which contains part or all of the nucleotide sequence of a cDNA according to claim 1 or 2.

20. An *Escherichia coli* strain containing recombinant vector according to claim 3 or 4.

21. *Escherichia coli* strain HB101/pUC119-LEC (FERM BP-3625).

22. *Escherichia coli* strain HB101/pUC119-WM17 (FERM BP-4013).

* * * * *